US008455511B2

(12) United States Patent
Nakazato et al.

(10) Patent No.: US 8,455,511 B2
(45) Date of Patent: Jun. 4, 2013

(54) PYRROLOPYRIDINE DERIVATIVES SUBSTITUTED WITH CYCLIC AMINO GROUP

(75) Inventors: Atsuro Nakazato, Tokyo (JP); Taketoshi Okubo, Tokyo (JP); Dai Nozawa, Tokyo (JP); Mikako Yamaguchi, Tokyo (JP); Tomoko Tamita, Tokyo (JP); Ludo E. J. Kennis, Beerse (BE); Marcel F. L. De Bruyn, Beerse (BE); Jean-Pierre A. M. Bongartz, Beerse (BE); Frans M. A. Van Den Keybus, Beerse (BE); Yves E. M. Van Roosbroeck, Beerse (BE); Marcel G. M. Luyckx, Beerse (BE); Robert J. M. Hendrickx, Beerse (BE)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 256 days.

(21) Appl. No.: 12/951,556

(22) Filed: Nov. 22, 2010

(65) Prior Publication Data

US 2011/0130364 A1 Jun. 2, 2011

Related U.S. Application Data

(60) Division of application No. 12/106,873, filed on Apr. 21, 2008, now Pat. No. 7,932,259, which is a continuation of application No. 10/504,981, filed as application No. PCT/JP03/16598 on Dec. 24, 2003, now abandoned.

(30) Foreign Application Priority Data

Dec. 26, 2002 (JP) ................................ 2002-383667

(51) Int. Cl.

| | |
|---|---|
| ***C07D 471/04*** | (2006.01) |
| ***A61K 31/437*** | (2006.01) |
| *C07D 487/04* | (2006.01) |
| *A61K 31/519* | (2006.01) |
| *A61P 25/28* | (2006.01) |
| *A61P 25/24* | (2006.01) |
| *A61P 25/18* | (2006.01) |

(52) U.S. Cl.
USPC .......................................... 514/300; 546/113

(58) Field of Classification Search
USPC .......................................... 546/113; 514/300
See application file for complete search history.

(56) References Cited

U.S. PATENT DOCUMENTS

| | | | |
|---|---|---|---|
| 6,187,781 | B1 | 2/2001 | Nakazato et al. |
| 6,600,038 | B1 | 7/2003 | Nakazato et al. |
| 2007/0060602 | A1 | 3/2007 | Nakazato et al. |

FOREIGN PATENT DOCUMENTS

| | | |
|---|---|---|
| EP | 0691128 | 1/1996 |
| WO | 94/13676 | 6/1994 |
| WO | 95/34563 | 12/1995 |
| WO | 0202549 | 1/2002 |

OTHER PUBLICATIONS

Hsin, et al., "CRHR$_1$ Receptor Binding and Lipophilicity of Pyrrolopyrimidines, Potential Nonpeptide Corticotropin-Releasing Hormone Type 1 Receptor Antagonists", Bioorganic & Medicinal Chemistry, 2001, 10(1): 175-183.

Hsin, et al., "Synthesis and Biological Activity of Fluoro-Substituted Pyrrolo[2,3-*d*]pyrimidines: The Development of Potential Positron Emission Tomography Imaging Agents for the Corticotropin-Releasing Hormone Type 1 Receptor", Bioorganic and Medicinal Chemistry Letters, 2000, 10(8): 707-710.

Vippagunta et al., "Crystalline solids," Advanced Drug Delivery Reviews, 2001, 48, pp. 3-26.

*Primary Examiner* — Susanna Moore
(74) *Attorney, Agent, or Firm* — Sughrue Mion, PLLC

(57) ABSTRACT

An object of the present invention is to provide an antagonist against CRF receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastric diseases, drug dependence, epilepsy, cerebral infarction, cerebral ischemia, cerebral edema, cephalic external wound, inflammation, immunity-related diseases, alopecia, irritable bowel syndrome, sleep disorders, epilepsy, dermatitides, schizophrenia, etc. This problem can be solved with a pyrrolopyrimidine or pyrrolopyridine derivative substituted with a cyclic amino group represented by formula [I] below which has a high affinity for CRF receptors and is effective against diseases in which CRF is considered to be involved.

[I]

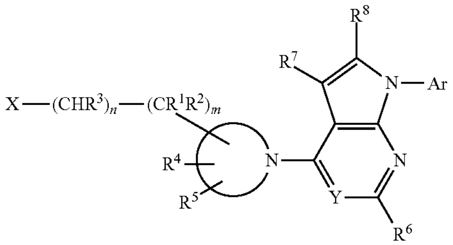

21 Claims, No Drawings

PYRROLOPYRIDINE DERIVATIVES SUBSTITUTED WITH CYCLIC AMINO GROUP

This is a divisional of application Ser. No. 12/106,873 filed Apr. 21, 2008 U.S. Pat. No. 7,932,259, which is a continuation of application Ser. No. 10/504,981 filed May 16, 2005 now abandoned, which is a National Stage Application of International Application No. PCT/JP2003/16598 filed Dec. 24, 2003, which claims priority to Japanese Patent Application No. 2002-383667 filed Dec. 26, 2002. The entire disclosures of the prior applications are considered part of the disclosure of the accompanying divisional application and are hereby incorporated by reference.

DETAILED DESCRIPTION OF THE INVENTION

1. Technical Field

The present invention relates to a therapeutic agent for diseases in which corticotropin releasing factor (CRF) is considered to be involved, such as depression, anxiety, Alzheimer's disease, Parkinson's disease, Huntington's chorea, eating disorder, hypertension, gastral diseases, drug dependence, cerebral infarction, cerebral ischemia, cerebral edema, cephalic external wound, inflammation immunity-related diseases, alpecia, irritable bowel syndrome, sleep disorders, epilepsy, dermatitides, schizophrenia, etc.

2. Description of the Prior Art

CRF is a hormone comprising 41 amino acids (Science, 213, 1394-1397, 1981; and J. Neurosci., 7, 88-100, 1987), and it is suggested that CRF plays a core role in biological reactions against stresses (Cell. Mol. Neurobiol., 14, 579-588, 1994; Endocrinol., 132, 723-728, 1994; and Neuroendocrinol. 61, 445-452, 1995). For CRF, there are the following two paths: a path by which CRF acts on peripheral immune system or sympathetic nervous system through hypothalamus-pituitary-adrenal system, and a path by which CRF functions as a neurotransmitter in central nervous system (in Corticotropin Releasing Factor: Basic and Clinical Studies of a Neuropeptide, pp. 29-52, 1990). Intraventricular administration of CRF to hypophysectomized rats and normal rats causes an anxiety-like symptom in both types of rats (Pharmacol. Rev., 43, 425-473, 1991; and Brain Res. Rev., 15, 71-100, 1990). That is, there are suggested the participation of CRF in hypothalamus-pituitary-adrenal system and the pathway by which CRF functions as a neurotransmitter in central nervous system.

The review by Owens and Nemeroff in 1991 summarizes diseases in which CRF is involved (Pharmacol. Rev., 43, 425-474, 1991). That is, CRF is involved in depression, anxiety, Alzheimer's disease, Parkinson's disease, Huntington's chorea, eating disorder, hypertension, gastrointestinal diseases, drug dependence, inflammation, immunity-related diseases, etc. It has recently been reported that CRF is involved also in epilepsy, cerebral infarction, cerebral ischemia, cerebral edema, and cephalic external wound (Brain Res. 545, 339-342, 1991; Ann. Neurol. 31, 48-498, 1992; Dev. Brain Res. 91, 245-251, 1996; and Brain Res. 744, 166-170, 1997). Accordingly, antagonists against CRF receptors are useful as therapeutic agents for the diseases described above.

WO02/002549 and WO00/053604 disclose pyrrolopyridine and pyrrolopyrimidine derivatives respectively as CRF receptor antagonists. Bioorganic & Medicinal Chemistry 10 (2002) 175-183 also discloses pyrrolopyrimidine derivatives. However, none disclose the compounds provided in the present invention.

Problem(s) to be Solved by Invention

An object of the present invention is to provide an antagonist against CRF receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, irritable bowel syndrome, sleep disorders, epilepsy, dermatitides, schizophrenia, etc.

Means for Solving Problem

The present inventors earnestly investigated pyrrolopyrimidine and pyrrolopyridine derivatives substituted with a cyclic amino group that have a high affinity for CRF receptors, whereby the present invention has been accomplished.

The present invention is pyrrolopyrimidine and pyrrolopyridine derivatives substituted with a cyclic amino group explained below.

A pyrrolopyrimidine or pyrrolopyridine derivative substituted with a cyclic amino group represented by the following formula [I]:

[I]

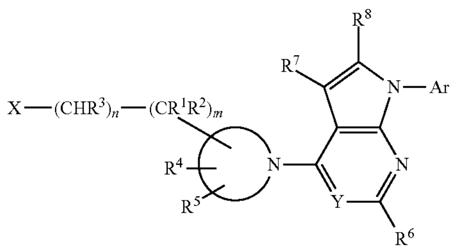

(wherein the cyclic amino group is represented by the following formula [II]:

[II]

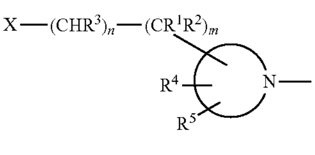

in which the cyclic amino group is a 3- to 8-membered saturated cyclic amine or a 3- to 8-membered saturated cyclic amine bridged with $C_{1-5}$alkylene or $C_{1-4}$alkylene-O—$C_{1-4}$alkylene between any different two carbon atoms of the cyclic amine, which cyclic amine is substituted with a group represented by —$(CR^1R^2)_m$—$(CHR^3)_n$—X, $R^4$ and $R^5$ independently on the same or different carbon atoms of the cyclic amine;

X is cyano, hydroxy or —$OR^9$;

Y is N or $CR^{10}$;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4 and 5;

n is 0 or 1;

with the proviso that when X is hydroxy or $OR^9$, and n is 0, then m is an integer selected from 1, 2, 3, 4 and 5;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy or —$N(R^{11})R^{12}$;

$R^7$ and $R^8$ are the same or different, and independently are hydrogen, halogen, $C_{1-5}$ alkyl, $C_{3-8}$cycloalkyl, $C_{3-8}$cycloalkyl-$C_{1-5}$ alkyl, hydroxy, $C_{1-5}$ alkoxy, $C_{3-8}$cycloalkyloxy, —$N(R^{11a})R^{12a}$, —$CO_2R^{13}$, cyano, nitro, $C_{1-5}$alkylthio, trifluoromethyl or trifluoromethoxy; or $R^7$ and $R^8$ are taken together to form —$CH_2$—$CH_2$—$CH_2$—$CH_2$— or —CH═CH—CH═CH—;

$R^9$ is $C_{1-24}$acyl, $C_{1-10}$alkoxycarbonyl, aryl-$C_{1-5}$alkyloxycarbonyl, —CO—O—$CHR^{14}$—O—CO—$R^{15}$, —P(═O)$(OR^{14a})OR^{15a}$, —CO—$(CH_2)_p$—$(CHR^{16})_q$—$NR^{17}R^{18}$, arylcarbonyl or heteroarylcarbonyl, wherein each said acyl, aryl and heteroaryl is unsubstituted or substituted with $C_{1-5}$alkoxy, and $C_{1-24}$acyl optionally includes one to six double bonds;

$R^{10}$ is hydrogen, $C_{1-5}$alkyl, halogen, cyano or —$CO_2R^{19}$;

Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —$CO_2R^{19a}$; —C(═O)$R^{19a}$; —$CONR^{11b}R^{12b}$, —OC(═O)$R^{19a}$, —$NR^{11b}CO_2R^{19a}$, —$S(O)_rNR^{11b}R^{12b}$, hydroxy-$C_{2-5}$alkylamino-$C_{2-5}$alkoxy, trifluoromethyl, trifluoromethoxy, difluoromethoxy, fluoromethoxy, methylenedioxy, ethylenedioxy and —$N(R^{20})R^{21}$; with the proviso that when X is hydroxy, Y is N, and the cyclic amino group is 5-membered ring, then Ar is aryl or heteroaryl which aryl or heteroaryl is substituted with at least one of substituents which are selected from halogen and trifluoromethyl;

$R^{11}$ and $R^{12}$ are the same or different, and independently are hydrogen, $C_{1-5}$alkyl, $C_{3-8}$cycloalkyl or $C_{3-8}$cycloalkyl-$C_{1-5}$alkyl;

$R^{11a}$ and $R^{12a}$ are the same or different, and independently are hydrogen, $C_{1-5}$alkyl, $C_{3-8}$cycloalkyl or $C_{3-8}$cycloalkyl-$C_{1-5}$alkyl;

$R^{11b}$ and $R^{12b}$ are the same or different, and independently are hydrogen, $C_{1-5}$alkyl, $C_{3-8}$cycloalkyl or $C_{3-8}$cycloalkyl-$C_{1-5}$alkyl;

$R^{13}$ is hydrogen, $C_{1-5}$alkyl, $C_{3-8}$cycloalkyl, $C_{3-8}$cycloalkyl-$C_{1-5}$alkyl, $C_{1-5}$alkoxy-$C_{1-5}$alkyl, $C_{3-8}$cycloalkyloxy-$C_{1-5}$alkyl or phenyl;

$R^{14}$ and $R^{15}$ are the same or different, and independently are hydrogen, $C_{1-5}$alkyl or aryl-$C_{1-5}$alkyl;

$R^{14a}$ and $R^{15a}$ are the same or different, and independently are hydrogen, $C_{1-5}$alkyl or aryl-$C_{1-5}$alkyl;

$R^{16}$ is hydrogen, $C_{1-5}$alkyl, aryl, heteroaryl, aryl-$C_{1-5}$alkyl, heteroaryl-$C_{1-5}$alkyl, hydroxy-$C_{1-5}$alkyl, hydroxycarbonyl-$C_{1-5}$alkyl, hydroxyphenyl-$C_{1-5}$alkyl, $C_{1-5}$alkoxy-$C_{1-5}$alkyl, amino-$C_{1-5}$alkyl, guanidino-$C_{1-5}$alkyl, mercapto-$C_{1-5}$alkyl, $C_{1-5}$alkylthio-$C_{1-5}$alkyl or aminocarbonyl-$C_{1-5}$alkyl;

$R^{17}$ and $R^{18}$ are the same or different, and independently are hydrogen, $C_{1-5}$alkyl, $C_{3-8}$cycloalkyl, $C_{3-8}$cycloalkyl-$C_{1-5}$alkyl, $C_{1-10}$acyl, $C_{1-10}$alkoxycarbonyl or aryl-$C_{1-5}$alkyloxycarbonyl;

or $R^{16}$ and $R^{17}$ are taken together to form —$CH_2$—, —$CH_2CH_2$—, —$CH_2CH_2CH_2$— or —$CH_2CH_2CH_2CH_2$—;

p is an integer selected from 0, 1, 2, 3, 4 and 5;

q is 0 or 1;

$R^{19}$ is hydrogen or $C_{1-5}$alkyl;

$R^{19a}$ is hydrogen or $C_{1-5}$alkyl;

r is 1 or 2;

$R^{20}$ and $R^{21}$ are the same or different, and independently are hydrogen or $C_{1-5}$alkyl), individual isomers thereof, racemic or non-racemic mixtures of isomers thereof or N-oxide thereof, or pharmaceutically acceptable salts and hydrates thereof.

The terms used in the present specification have the following meanings.

The term "a 3- to 8-membered saturated cyclic amine" means aziridine, azetidine, pyrrolidine, piperidine, azepane or azocane.

The term "$C_{1-5}$alkylene" means a straight or branched chain alkylene of 1 to 5 carbon atoms, such as methylene, ethylene, propylene, trimethylene, tetramethylene, pentamethylene or the like.

The term "a 3- to 8-membered saturated cyclic amine bridged with $C_{1-5}$alkylene or $C_{1-4}$alkylene-O—$C_{1-4}$alkylene between any different two carbon atoms of the cyclic amine" includes, for example, 8-azabicyclo[3.2.1]oct-8-yl, 9-azabicyclo[3.3.1]non-9-yl, 7-azabicyclo[2.2.1]hept-7-yl, 3-oxa-7-azabicyclo[3.3.1]non-7-yl and 3-oxa-9-azabicyclo[3.3.1]non-9-yl.

The term "$C_{1-5}$alkyl" means a straight chain or branched chain alkyl group of 1 to 5 carbon atoms, such as methyl, ethyl, propyl, isopropyl, butyl, isobutyl, t-butyl, sec-butyl, pentyl, isopentyl or the like.

The term "$C_{1-5}$alkoxy" means a straight chain or branched chain alkoxy group of 1 to 5 carbon atoms, such as methoxy, ethoxy, propoxy, isopropyloxy, butoxy, isobutyloxy, pentyloxy, isopentyloxy or the like.

The term "$C_{1-5}$alkoxy-$C_{1-5}$alkyl" means a substituted $C_{1-5}$alkyl group having the above-mentioned $C_{1-5}$alkoxy group as the substituent, such as methoxymethyl, 2-methoxyethyl, 2-ethoxyethyl or the like.

The term "hydroxy-$C_{1-5}$alkyl" means a substituted $C_{1-5}$alkyl group having hydroxy group, such as hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl or the like.

The term "cyano-$C_{1-5}$ alkyl" means a substituted $C_{1-5}$alkyl group having cyano group, such as cyanomethyl, 1-cyanoethyl, 2-cyanoethyl, 3-cyanopropyl, 4-cyanobutyl, 5-cyanopentyl or the like.

The term "$C_{3-8}$cycloalkyl" means a cyclic alkyl group of 3 to 8 carbon atoms, such as cyclopropyl, cyclobutyl, cyclopentyl, cyclohexyl, cycloheptyl or the like.

The term "$C_{3-8}$cycloalkyl-$C_{1-5}$alkyl" means a substituted $C_{1-5}$alkyl group having the above-mentioned $C_{3-8}$cycloalkyl as the substituent, such as cyclopropylmethyl, cyclopropylethyl, cyclopentylethyl or the like.

The term "$C_{3-8}$cycloalkyloxy" means a cyclic alkoxy group of 3 to 8 carbon atoms, such as cyclopropyloxy, cyclobutyloxy, cyclopentyloxy or the like.

The term "halogen" means fluorine, chlorine, bromine or iodine atom.

The term "$C_{3-8}$cycloalkyloxy-$C_{1-5}$alkyl" means a substituted $C_{1-5}$alkyl group having the above mentioned $C_{3-8}$cycloalkyloxy as the substituent, such as cyclopropyloxymethyl, 2-cyclopropyloxyethyl or the like.

The term "$C_{1-5}$alkylthio" means a straight chain or branched chain alkylthio group of 1 to 5 carbon atoms, such as methylthio, ethylthio, propylthio or the like.

The term "$C_{1-24}$acyl" means a straight chain or branched chain, and saturated or unsaturated acyl group of 1 to 24 carbon atoms, such as acetyl, propionyl, butyryl, pentanoyl, hexanoyl, heptanoyl, octanoyl, nonanoyl, decanoyl, isobutyryl, 2,2-dimethylpropionyl, octadeca-9,12-dienoyl, eicosa-5,8,11,14-tetraenoyl, docosa-4,7,10,13,16,19-hexaenoyl, eicosa-5,8,11,14,17-pentaenoyl or the like.

The term "$C_{1-10}$alkoxycarbonyl" means a straight chain or branched chain alkoxycarbonyl group of 2 to 11 carbon atoms, such as methoxycarbonyl, ethoxycarbonyl, propoxycarbonyl, butoxycarbonyl, pentyloxycarbonyl, hexyloxycarbonyl, heptyloxycarbonyl, octyloxycarbonyl, nonyloxycarbonyl, decyloxycarbonyl, isopropoxycarbonyl, t-butoxycarbonyl or the like.

The term "aryl" means a monocyclic or bicyclic group of 6 to 12 ring carbon atoms having at least one aromatic ring, such as phenyl, naphthyl or the like.

The term "aryl-$C_{1-5}$alkyloxycarbonyl" means a substituted $C_{1-5}$alkyloxycarbonyl group having the above-mentioned aryl as the substituent, such as benzyloxycarbonyl, phenethyloxycarbonyl or the like.

The term "arylcarbonyl" means a substituted carbonyl group having the above-mentioned aryl as the substituent, such as benzoyl, naphthalene-1-carbonyl, naphthalene-2-carbonyl or the like.

The term "heteroaryl" means a monocyclic or bicyclic group of 5 to 12 ring atoms having at least one aromatic ring having in its ring 1 to 4 atoms which may be the same or different and are selected from nitrogen, oxygen and sulfur, such as pyridyl, pyrimidinyl, imidazolyl, quinolyl, indolyl, benzofuranyl, quinoxalinyl, benzo[1,2,5]thiadiazolyl, benzo[1,2,5]oxadiazolyl or the like.

The term "heteroarylcarbonyl" means a substituted carbonyl group having the above-mentioned heteroaryl as the substituent, such as pyridine-2-carbonyl, pyridine-3-carbonyl, pyridine-4-carbonyl, pyrimidine-2-carbonyl, pyrimidine-4-carbonyl, pyrimidine-5-carbonyl or the like.

The term "$C_{2-5}$alkenyl" means a straight chain or branched chain alkenyl group of 2 to 5 carbon atoms, such as vinyl, isopropenyl, allyl or the like.

The term "$C_{2-5}$alkynyl" means a straight chain or branched chain alkynyl group of 2 to 5 carbon atoms, such as ethynyl, prop-1-ynyl, prop-2-ynyl or the like.

The term "$C_{1-5}$alkysulfinyl" means a straight chain or branched chain alkylsulfinyl group of 1 to 5 carbon atoms, such as methanesulfinyl, ethanesulfinyl or the like.

The term "$C_{1-5}$alkysulfonyl" means a straight chain or branched chain alkylsulfonyl group of 1 to 5 carbon atoms, such as methanesulfonyl, ethanesulfonyl or the like.

The term "hydroxy-$C_{2-5}$alkylamino-$C_{2-5}$alkoxy" means a substituted $C_{2-5}$alkoxy group having a hydroxy-$C_{2-5}$alkylamino group as the substituent such as 2-(2-hydroxyethylamino)ethoxy or the like.

The term "aryl-$C_{1-5}$alkyl" means a substituted $C_{1-5}$alkyl group having the above-mentioned aryl as the substituent, such as benzyl, phenethyl, 3-phenylpropyl, naphthalen-1-ylmethyl, naphthalen-2-ylmethyl or the like.

The term "heteroaryl-$C_{1-5}$alkyl" means a substituted $C_{1-5}$alkyl group having the above-mentioned heteroaryl as the substituent, such as 1H-indol-3-ylmethyl, 1H-imidazol-4-ylmethyl or the like.

The term "hydroxycarbonyl-$C_{1-5}$alkyl" means a substituted $C_{1-5}$alkyl group having a hydroxycarbonyl group as the substituent, such as hydroxycarbonylmethyl, 2-hydroxycarbonylethyl, 3-hydroxycarbonylpropyl, 4-hydroxycarbonylbutyl or the like.

The term "hydroxyphenyl-$C_{1-5}$alkyl" means a substituted $C_{1-5}$alkyl group having a hydroxyphenyl group as the substituent, such as 4-hydroxybenzyl, 3-hydroxybenzyl 2-hydroxybenzyl, 2-(4-hydroxyphenyl)ethyl or the like.

The term "amino-$C_{1-5}$alkyl" means a substituted $C_{1-5}$alkyl group having a amino group as the substituent, such as aminomethyl, 1-aminoethyl, 2-aminoethyl, 3-aminopropyl, 4-aminobutyl, 5-aminopentyl or the like.

The term "guanidino-$C_{1-5}$alkyl" means a substituted $C_{1-5}$alkyl group having a guanidino group as the substituent, such as guanidinomethyl, 1-guanidinoethyl, 2-guanidinoethyl, 3-guanidinopropyl, 4-guanidinobutyl, 5-guanidinopentyl or the like.

The term "mercapto-$C_{1-5}$alkyl" means a substituted $C_{1-5}$alkyl group having a mercapto group as the substituent, such as mercaptomethyl, 1-mercaptoethyl, 2-mercaptoethyl, 3-mercaptopropyl, 4-mercaptobutyl, 5-mercaptopentyl or the like.

The term "$C_{1-5}$alkylthio-$C_{1-5}$alkyl" means a substituted $C_{1-5}$alkyl group having the above-mentioned $C_{1-5}$alkylthio group as the substituent, such as methylthiomethyl, 1-methylthioethyl, 2-methylthioethyl, 3-methylthiopropyl, 4-methylthiobutyl, 5-methylthiopentyl or the like.

The term "aminocarbonyl-$C_{1-5}$alkyl" means a substituted $C_{1-5}$alkyl group having an aminocarbonyl group as the substituent, such as aminocarbonylmethyl, 2-aminocarbonylethyl, 3-aminocarbonylpropyl, 4-aminocarbonylbutyl or the like.

The phrase "aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, $—CO_2R^{19a}$, $C(═O)R^{19a}$, $—CONR^{11b}R^{12b}$, $—C(═O)R^{19a}$, $—S(O)_rNR^{11b}R^{12b}$, hydroxy-$C_{2-5}$alkylamino-$C_{2-5}$alkoxy, trifluoromethyl, trifluoromethoxy, difluoromethoxy, fluoromethoxy, methylenedioxy, ethylenedioxy and $—N(R^{20}R^{21}$" includes, for example, 2,4-dimethylphenyl, 2,6-dimethylphenyl, 2,4-dibromophenyl, 2-bromo-4-isoproylphenyl, 2,4-dichlorophenyl, 2,6-dichlorophenyl, 2-chloro-4-trifluoromethylphenyl, 4-methoxy-2-methylphenyl, 2-chloro-4-trifluoromethoxyphenyl, 4-isopropyl-2-methylthiophenyl, 2,4,6-trimethylphenyl, 4-bromo-2,6-dimethylphenyl, 4-bromo-2,6-diethylphenyl, 4-chloro-2,6-dimethylphenyl, 2,4,6-tribromophenyl, 2,4,5-tribromophenyl, 2,4,6-trichlorophenyl, 2,4,5-trichlorophenyl, 4-bromo-2,6-dichlorophenyl, 6-chloro-2,4-dibromophenyl, 2,4-dibromo-6-fluorophenyl, 2,4-dibromo-6-methylphenyl, 2,4-dibromo-6-methoxyphenyl, 2,4-dibromo-6-methylthiophenyl, 2,6-dibromo-4-isopropylphenyl, 2,6-dibromo-4-trifluoromethylphenyl, 2-bromo-4-trifluoromethylphenyl, 4-bromo-2-chlorophenyl, 2-bromo-4-chlorophenyl, 4-bromo-2-methylphenyl, 4-chloro-2-methylphenyl, 2,4-dimethoxyphenyl, 2,6-dimethyl-4-methoxyphenyl, 4-chloro-2,6-dibromophenyl, 4-bromo-2,6-difluorophenyl, 2,6-dichloro-4-trifluoromethylphenyl, 2,6-dichloro-4-trifluoromethoxyphenyl, 2,6-dibromo-4-trifluoromethoxyphenyl, 2-chloro-4,6-dimethylphenyl, 2-bromo-4,6-dimethoxyphenyl, 2-bromo-4-isopropyl-6-methoxyphenyl, 2,4-dimethoxy-6-methylphenyl, 2,6-dimethyl-4-[2-(2-hydroxyethylamino)ethoxy]phenyl, 6-dimethylamino-4-methylpyridin-3-yl, 2-chloro-6-trifluoromethylpyridin-3-yl, 2-chloro-6-trifluoromethoxypyridin-3-yl, 2-chloro-6-methoxypyridin-3-yl, 6-methoxy-2-trifluoromethylpyridin-3-yl, 2-chloro-6-difluoromethylpyridin-3-yl, 6-methoxy-2-methylpyridin-3-yl, 2,6-dimethoxypyridin-3-yl, 4,6-dimethyl-2-trifluoromethylpyrimidin-5-yl, 2-dimethylamino-6-methylpyridin-3-yl, 6-dimethylamino-2-methylpyridin-3-yl, 2,3-dihydrobenzo[1,4]dioxin-5-yl and benzo[1,3]dioxol-4-yl, 5,7-dimethylbenzo[1,2,5]thiadiazol-4-yl, 5,7-dimethylbenzo[1,2,5]oxadiazol-4-yl, 2-isopropoxy-6-trifluoromethylpyridin-3-yl, 2-methoxy-6-methylpyridin-3-yl, 2,6-dimethylpyridin-3-yl, 2-bromo-6-methoxypyridin-3-yl, 2-chloro-6-dimethylaminopyridin-3-yl, 2,6-dichloropyridin-3-yl, 2,4-dimethyl-6-dimethylaminopyridin-3-yl, 2,4,6-trimethylpyridin-3-yl, 2,4,6-trimethylpyrimidin-5-yl, 4,6-dimethyl-2-dimethylaminopyrimidin-5-yl, 5-iodo-3-methylpyridin-2-yl, 3-methyl-5-methylaminopyridin-2-yl, 3-dimethylamino-5-methylpyridin-2-yl, 5-methyl-3-methylaminopyridin-2-yl, 3-chloro-5-methylpyridin-2-yl, 3-amino-5-methylpyridin-2-yl, 5-methyl-3-nitropyridin-2-yl, 5-diethylamino-3-methylpyridin-2-yl, 5-fluoro-3-methylpyridin-2-yl, 5-chloro-3-methylpyridin-2-yl, 5-dimethylamino-3-methylpyridin-2-yl, 5-amino-3-methylpyridin-2-yl, 3-methyl-5-nitropyridin-2-yl, 3-bromo-5-methylpyridin-2-yl, 4-chloro-2,5-dimethoxyphenyl, 4,5-dimethyl-2-methoxyphenyl, 5-fluoro-2,4-dimethylphenyl, 2,4-dimethoxy-5-methylphenyl, 2-chloro-4-methoxy-5-methylphenyl, 2-chloro-5-fluoro-4-methylphenyl, 2-bromo-4,5-dimethoxyphenyl, 2-bromo-5-fluoro-4-methoxyphenyl, 2-chloro-4,5-dimethoxyphenyl, 2,5-dichloro-4-methoxyphenyl, 2,4-dichloro-5-fluorophenyl, 2-chloro-5-fluoro-4-methoxyphenyl, 2,4,5-trichlorophenyl, 2-chloro-5-fluoro-4-methylphenyl, 5-fluoro-4-methoxy-2-methylphenyl, 4,5-dimethoxy-2-methylphenyl, 5-chloro-4-methoxy-2-methylphenyl, 2,4,5-trimethylphenyl, 6-methoxy-4-methylpyridin-3-yl, 4-methoxy-6-methylpyridin-3-yl, 4,6-dimethylpyridin-3-yl, 2-chloro-4-isopropylphenyl, 2-chloro-4-methylphenyl, 4-amino-2-chlorophenyl, 2-chloro-4-dimethylcarbamoylphenyl, 2-chloro-4-methylcarbamoylphenyl, 4-carbamoyl-2-chlorophenyl, 2-chloro-4-methylsulfonylphenyl, 4-carboxy-2-chlorophenyl, 2-chloro-4-iodophenyl, 2-bromo-4-methylthiophenyl, 2-bromo-4-methylsulfinylphenyl, 2-bromo-4-dimethylaminophenyl, 2-bromo-4-methylsulfonylphenyl, 2-bromo-4-cyclopentylphenyl, 2-bromo-4-tert-butylphenyl, 2-bromo-4-propylphenyl, 2-bromo-4-methylphenyl, 2-bromo-4-trifluoromethoxyphenyl, 2-bromo-4-methoxyphenyl, 2-bromo-4-ethoxyphenyl, 4-isopropyl-2-methylsulfonylphenyl, 4-cyclopentyl-2-methylthiophenyl, 4-butyl-2-methylthiophenyl, 4-methoxy-2-methylthiophenyl, 2-methylthio-4-propylphenyl, 2-dimethylamino-4-isopropylphenyl, 2-iodo-4-isopropylphenyl, 2-fluoro-4-methylphenyl, 2,4-difluorophenyl, 2-chloro-4-methoxyphenyl, 2-chloro-4-hydroxyphenyl, 4-cyano-2-methoxyphenyl, 4-bromo-2-methoxyphenyl, 2-methoxy-4-methylphenyl, 4-chloro-2-methoxyphenyl, 2-hydroxy-4-methylphenyl, 4-fluoro-2-methoxyphenyl, 2-hydroxy-4-methylphenyl, 4-cyano-2-methoxyphenyl, 2-chloro-4-methylthiophenyl, 2-methoxy-4-trifluoromethylphenyl, 4-isopropyl-2-methoxyphenyl, 2-chloro-4-cyanophenyl, 2-chloro-4-ethoxycarbonylphenyl, 2-chloro-4-methylaminophenyl, 4-cyano-2-trifluoromethylphenyl, 4-cyano-2-methylphenyl, 2-methyl-4-trifluoromethoxyphenyl, 2-cyano-4-trifluoromethylphenyl, 4-carboxyamino-2-trifluoromethylphenyl, 4-methoxy-2-trifluoromethylphenyl, 4-fluoro-2-methylphenyl, 4-hydroxy-2-methylphenyl, 4-methoxy-2-methoxycarbonylphenyl, 2-ethyl-4-methoxyphenyl, 2-formyl-4-methoxyphenyl, 4-chloro-2-trifluoromethylphenyl, 4-dimethylamino-2-trifluoromethylphenyl, 4-difluoromethoxy-2-methylphenyl, 2-cyano-4-methoxyphenyl, 4-hydroxy-2-trifluoromethylphenyl, 4-isopropyl-2-trifluoromethylphenyl, 4-diethylamino-2-methylphenyl, 4-fluoro-2-trifluoromethylphenyl, 4-propoxy-2-trifluoromethylphenyl, 4-dimethylamino-2-methylthiophenyl, 4-isopropyl-2-isopropylthiophenyl, 2-ethylthio-4-isopropylphenyl, 4-methylamino-2-methylthiophenyl, 2-methylthio-4-propionylphenyl, 4-acetyl-2-methylthiophenyl, 4-cyano-2-methylthiophenyl, 4-methoxy-2-methylthiophenyl, 4-ethyl-2-methylthiophenyl, 4-bromo-2-methylthiophenyl, 4-isopropyl-2-methylsulfinylphenyl, 2,4-dimethylthiophenyl, 4,6-dimethyl-2-isopropylphenyl, 4,6-dimethyl-2-isopropenylphenyl, 2-acetyl-4,6-dimethylphenyl, 2,6-dimethyl-4-trifluoromethylphenyl, 2,6-dimethyl-4-isopropenylphenyl, 4-acetyl-2,6-dimethylphenyl, 2,4,6-triethylphenyl, 4,6-dimethyl-2-methylthiophenyl, 4,6-dimethyl-2-iodophenyl, 2-fluoromethoxy-4,6-dimethylphenyl, 4,6-dimethyl-2-isopropoxyphenyl, 4,6-dimethyl-2-ethoxyphenyl, 2,6-dichloro-4-ethoxyphenyl, 2-bromo-4,6-dimethoxyphenyl, 2-bromo-6-hydroxy-4-methoxyphenyl, 2,6-dibromo-4-ethoxyphenyl, 4-bromo-2-methoxy-6-methylphenyl, 2,6-dibromo-4-methoxyphenyl, 4,6-dibromo-2-trifluoromethoxyphenyl, 2,4-dibromo-6-trifluoromethylphenyl, 4-bromo-2-chloro-6-methylphenyl, 4-chloro-2,6-dimethoxyphenyl, 2,4-dichloro-6-methoxyphenyl, 4,6-dichloro-2-methylthiophenyl, 4,6-dichloro-2-trifluoromethylphenyl, 2,6-dimethoxy-4-ethylphenyl, 4,6-dimethyl-2-methoxyphenyl, 2,6-dimethoxy-4-methylphenyl, 2-chloro-6-methoxy-4-methylphenyl, 4,6-dimethyl-2-ethoxyphenyl, 6-hydroxy-2,4-dimethylphenyl, 4-cyano-2-methoxy-6-methylphenyl, 6-fluoro-2-methoxy-4-methylphenyl, 4-acetyl-2-methoxy-6-methylphenyl, 2-chloro-4,6-dimethoxyphenyl, 2,6-dimethoxy-4-ethoxyphenyl, 2,4,6-trimethoxyphenyl, 4,6-dibromo-2-trifluoromethoxyphenyl, 2-bromo-4-dimethylamino-6-methoxyphenyl, 4-bromo-2-methoxy-6-methylphenyl, 4,6-dimethoxy-2-propoxyphenyl, 4,6-dichloro-2-propoxyphenyl, 2-bromo-6-hydroxy-4-methoxyphenyl, 2,4,6-trifluorophenyl, 2-bromo-6-fluoro-4-methylphenyl, 4-difluoromethoxy-2,6-dimethylphenyl, 2,6-dimethyl-4-ethoxyphenyl, 2,6-dimethyl-4-isopropoxyphenyl, 2,6-dimethyl-4-methylthiophenyl, 2,6-dimethyl-4-methylsulfonylophenyl, 2,6-dimethyl-4-methylsulfinylophenyl, 2,3-dichlorophenyl, 4-methoxy-2,3-dimethylphenyl, 2-chloro-3-fluoro-4-methoxyphenyl, 2,3,4-trichlorophenyl and 4-methoxy-2,5-dimethylphenyl.

The "pharmaceutically acceptable salts" in the present invention include, for example, salts with an inorganic acid such as sulfuric acid, hydrochloric acid, hydrobromic acid, phosphoric acid, nitric acid or the like; salts with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, naphthalene-2-sulfonic acid or the like; salts with one or more metal ions such as lithium ion, sodium ion, potassium ion, calcium ion, magnesium ion, zinc ion, aluminium ion or the like; salts with amines such as ammonia, arginine, lysine, piperazine, choline, diethylamine, 4-phenylcyclohexylamine, 2-aminoethanol, benzathine or the like.

A compound of the present invention includes any isomers such as diastereomers, enantiomers, geometricisomers and tautomeric forms. In a compound represented by formula [I], if the cyclic amino group has one or more chiral carbons and/or if there is an axial chirality between Ar and pyrrolopyrimidine (or pyrrolopyridine) ring, several stereoisomers (diastereomers or enantiomers) can exist. The compound of the present invention includes the individual isomers and the racemic and non-racemic mixtures of the isomers.

Preferable examples of the compound of the present invention are as follows.

That is, preferable are compounds represented by the following formula [III]

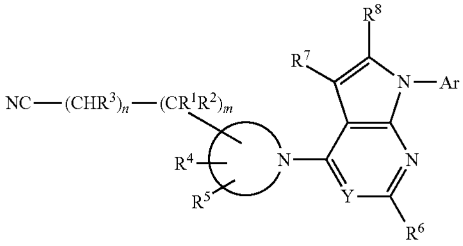

[III]

(wherein the cyclic amino group is represented by the following formula [IV]:

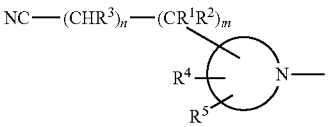

[IV]

in which the cyclic amino group is a 3- to 8-membered saturated cyclic amine or a 3- to 8-membered saturated cyclic amine bridged with $C_{1-5}$alkylene or $C_{1-4}$alkylene-O—$C_{1-4}$ alkylene between any different two carbon atoms of the cyclic amine, which cyclic amine is substituted with a group represented by —$(CR^1R^2)_m$—$(CHR^3)_n$—CN, $R^4$ and $R^5$ independently on the same or different carbon atoms of the cyclic amine;

Y is N or $CR^{10}$;

$R^1$ is hydrogen, hydroxy, $C_{1-5}$alkyl, $C_{1-5}$alkoxy-$C_{1-5}$alkyl or hydroxy-$C_{1-5}$ alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4 and 5;

n is 0 or 1;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-4}$cycloalkyloxy or —$N(R^{11})R^{12}$;

$R^7$ and $R^8$ are the same or different, and independently are hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —$N(R^{11a})R^{12a}$, —$CO_2R^{13}$, cyano, nitro, $C_{1-5}$alkylthio, trifluoromethyl or trifluoromethoxy; or $R^7$ and $R^8$ are taken together to form —$CH_2$—$CH_2$—$CH_2$—$CH_2$— or —CH═CH—CH═CH—;

$R^{10}$ is hydrogen, $C_{1-5}$alkyl, halogen, cyano or —$CO_2R^{19}$;

Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —$CO_2R^{19a}$, —C(═O)$R^{19a}$, —$CONR^{11b}R^{12b}$, —OC(═O)$R^{19a}$, —$NR^{11b}CO_2R^{19a}$, —$S(O)_rNR^{11b}R^{12b}$), hydroxy-$C_{2-5}$alkylamino-$C_{2-5}$alkoxy, trifluoromethyl, trifluoromethoxy, difluoromethoxy, fluoromethoxy, methylenedioxy, ethylenedioxy and —$N(R^{20})R^{21}$;

$R^{11}$ and $R^{12}$ are the same or different, and independently are hydrogen, $C_{1-5}$ alkyl, $C_{3-8}$cycloalkyl or $C_{3-8}$cycloalkyl-$C_{1-5}$alkyl;

$R^{11a}$ and $R^{12a}$ are the same or different, and independently are hydrogen, $C_{1-5}$alkyl, $C_{3-8}$cycloalkyl or $C_{3-8}$cycloalkyl-$C_{1-5}$alkyl;

$R^{11b}$ and $R^{12b}$ are the same or different, and independently are hydrogen, $C_{1-5}$alkyl, $C_{3-8}$cycloalkyl or $C_{3-8}$cycloalkyl-$C_{1-5}$alkyl;

$R^{13}$ is hydrogen, $C_{1-5}$alkyl, $C_{3-8}$cycloalkyl, $C_{3-8}$cycloalkyl-$C_{1-5}$alkyl, $C_{1-5}$alkoxy-$C_{1-5}$ alkyl, $C_{3-8}$cycloalkyloxy-$C_{1-5}$alkyl or phenyl;

$R^{19}$ is hydrogen or $C_{1-5}$alkyl;

$R^{19a}$ is hydrogen or $C_{1-5}$alkyl;

r is 1 or 2;

$R^{20}$ and $R^{21}$ are the same or different, and independently are hydrogen or $C_{1-5}$alkyl). More preferable are compounds represented by the formula [III] in which Y is N. More preferable are compounds represented by the formula [III] in which Y is N; n is 0; $R^1$, $R^2$, $R^4$ and $R^5$ are hydrogen. More preferable are compounds represented by the formula [III] in which Y is N; the cyclic amino group is a 4- to 7-membered saturated cyclic amine; m is an integer selected from 0, 1, 2 and 3; n is 0; $R^1$, $R^2$, $R^4$ and $R^5$ are hydrogen; $R^6$ is methyl; $R^7$ and $R^8$ are the same or different, and independently are hydrogen or $C_{1-5}$alkyl; Ar is phenyl or pyridyl which phenyl or pyridyl is substituted with two or three substituents, which are the same or different, selected from the group consisting of halogen, $C_{1-3}$alkyl, $C_{1-3}$alkoxy, trifluoromethyl, trifluoromethoxy and —$N(R^{20})R^{21}$ (wherein $R^{20}$ and $R^{21}$ are the same or different, and independently are hydrogen or $C_{1-3}$alkyl). More preferable are compounds represented by the formula [III] in which wherein Y is N; the cyclic amino group is a 6-membered saturated cyclic amine; m is 0 or 1; n is 0; $R^1$, $R^2$, $R^4$ and $R^5$ are hydrogen; $R^6$ is methyl; $R^7$ and $R^8$ are the same or different, and independently are hydrogen or methyl; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino.

Other preferable are compounds represented by the formula [III] in which Y is $CR^{10}$. More preferable are compounds represented by the formula [III] in which Y is $CR^{10}$; n is 0; $R^1$, $R^2$, $R^4$ and $R^5$ are hydrogen; $R^{10}$ is hydrogen or halogen. More preferable are compounds represented by the formula [III] in which Y is $CR^{10}$; the cyclic amino group is a 4- to 7-membered saturated cyclic amine; m is an integer selected from 0, 1, 2 and 3; n is 0; $R^1$, $R^2$, $R^4$ and $R^5$ are hydrogen; $R^6$ is methyl; $R^7$ and $R^8$ are the same or different, and independently are hydrogen or $C_{1-5}$alkyl; $R^{10}$ is hydrogen or halogen; Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl. More preferable are compounds represented by the formula [III] in which Y is $CR^{10}$; the cyclic amino group is a 6-membered saturated cyclic amine; m is 0 or 1; n is 0; $R^1$, $R^2$, $R^4$ and $R^5$ are hydrogen; $R^6$ is methyl; $R^7$ and $R^8$ are the same or different, and independently are hydrogen or methyl; $R^{10}$ is hydrogen; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino.

Other preferable are compounds represented by the following formula [V]:

[V]

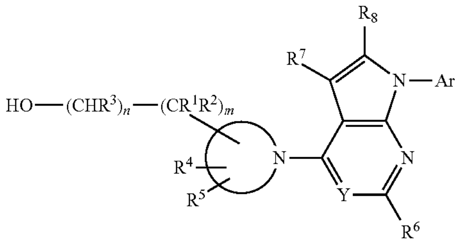

(wherein the cyclic amino group is represented by the following formula [VI]:

[VI]

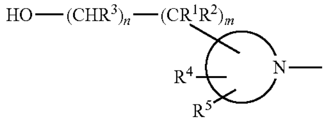

in which the cyclic amino group is a 3- to 8-membered saturated cyclic amine or a 3- to 8-membered saturated cyclic amine bridged with $C_{1-5}$alkylene or $C_{1-4}$alkylene-O—$C_{1-4}$ alkylene between any different two carbon atoms of the cyclic amine, which cyclic amine is substituted with a group represented by —$(CR^1R^2)_m$—$(CHR^3)_n$—OH, $R^4$ and $R^5$ independently on the same or different carbon atoms of the cyclic amine;

Y is N or $CR^{10}$;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4 and 5;

n is 0 or 1;

with the proviso that when n is 0, m is an integer selected from 1, 2, 3, 4 and 5;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy or —$N(R^{11})R^{12}$;

$R^7$ and $R^8$ are the same or different, and independently are hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —$N(R^{11a})R^{12a}$, —$CO_2R^{13}$; cyano, nitro, $C_{1-5}$alkylthio, trifluoromethyl or trifluoromethoxy; or $R^7$ and $R^8$ are taken together to form —$CH_2$—$CH_2$—$CH_2$—$CH_2$— or —CH═CH—CH═CH—;

$R^{10}$ is hydrogen, $C_{1-5}$alkyl, halogen, cyano or —$CO_2R^{19-}$,

Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —$CO_2R^{19a}$, —C(═O)$R^{19a}$, —$CONR^{11b}R^{12b}$, —OC(═O)$R^{19a}$, —$NR^{11b}CO_2R^{19a}$, —$S(O)_rNR^{11b}R^{12b}$, hydroxy-$C_{2-5}$alkylamino-$C_{2-5}$alkoxy, trifluoromethyl, trifluoromethoxy, difluoromethoxy, fluoromethoxy, methylenedioxy, ethylenedioxy and —$N(R^{20})R^{21}$; the proviso that when Y is N, and the cyclic amino group is 5-membered ring, then Ar is aryl or heteroaryl which aryl or heteroaryl is substituted with at least one of substituents which are selected from halogen and trifluoromethyl;

$R^{11}$ and $R^{12}$ are the same or different, and independently are hydrogen, $C_{1-5}$alkyl, $C_{3-8}$cycloalkyl or $C_{3-8}$cycloalkyl-$C_{1-5}$alkyl;

$R^{11a}$ and $R^{12a}$ are the same or different, and independently are hydrogen, $C_{1-5}$alkyl, $C_{3-8}$cycloalkyl or $C_{3-8}$cycloalkyl-$C_{1-5}$alkyl;

$R^{11b}$ and $R^{12b}$ are the same or different, and independently are hydrogen, $C_{1-5}$alkyl, $C_{3-8}$cycloalkyl or $C_{3-8}$cycloalkyl-$C_{1-5}$alkyl;

$R^{13}$ is hydrogen, $C_{1-5}$alkyl, $C_{3-8}$cycloalkyl, $C_{3-8}$cycloalkyl-$C_{1-5}$alkyl, $C_{1-5}$alkoxy-$C_{1-5}$alkyl, $C_{3-8}$cycloalkyloxy-$C_{1-5}$alkyl or phenyl;

$R^{19}$ is hydrogen or $C_{1-5}$alkyl;

$R^{19a}$ is hydrogen or $C_{1-5}$alkyl;

r is 1 or 2;

$R^{20}$ and $R^{21}$ are the same or different, and independently are hydrogen or $C_{1-5}$alkyl). More preferable are compounds represented by the formula [V] in which Y is N. More preferable are compounds represented by the formula [V] in which Y is N; m is an integer selected from 1, 2, 3, 4 and 5; n is 0; $R^1$, $R^2$, $R^4$ and $R^5$ are hydrogen. More preferable are compounds represented by the formula [V] in which Y is N; the cyclic amino group is a 4- to 7-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or $C_{1-5}$alkyl; Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl); with the proviso that when the cyclic amino group is 5-membered ring, Ar is phenyl or pyridyl which phenyl or pyridyl is substituted with at least one of substituents which are selected from halogen and trifluoromethyl. More preferable are compounds represented by the formula [V] in which Y is N; the cyclic amino group is a 6-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or methyl; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino.

Other preferable are compounds represented by the formula [V] in which Y is N; m is 1; n is 0; $R^1$ is $C_{1-5}$alkyl or hydroxy-$C_{1-5}$alkyl; $R^2$, $R^4$ and $R^5$ are hydrogen. More preferable are compounds represented by the formula [V] in which Y is N; m is 1; n is 0; the cyclic amino group is a 4- to 7-membered saturated cyclic amine; $R^1$ is $C_{1-5}$alkyl or hydroxy-$C_{1-5}$alkyl; $R^2$, $R^4$ and $R^5$ are hydrogen; $R^6$ is methyl; $R^7$ and $R^8$ are the same or different, and independently are hydrogen or $C_{1-5}$alkyl; Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl). More preferable are compounds represented by the formula [V] in which Y is N; m is 1; n is 0; the cyclic amino group is a 6-membered saturated cyclic amine; $R^1$ is $C_{1-5}$alkyl or hydroxy-$C_{1-5}$alkyl; $R^2$, $R^4$ and $R^5$ are hydrogen; $R^6$ is methyl; $R^7$ and $R^8$ are the same or different, and independently are hydrogen or methyl; Ar is phenyl which phenyl is substituted with two or three substituents, which are the same or different, selected from the group consisting of chloro, bromo, $C_{1-3}$alkyl, $C_{1-3}$alkylthio, trifluoromethyl, trifluoromethoxy and dimethylamino.

Other preferable are compounds represented by the formula [V] in which Y is N; m is an integer selected from 1, 2, 3, 4 and 5; n is 0; $R^1$, $R^2$ and $R^5$ are hydrogen; $R^4$ is cyano, wherein a group represented by —$(CR^1R^2)_m$—$(CHR^3)_n$—OH and $R^4$ are substituted on the same carbon atom of the cyclic amine. More preferable are compounds represented by the formula [V] in which Y is N; the cyclic amino group is a 4- to 7-membered saturated cyclic amine; m is an integer selected from 1, 2 and 3; n is 0; $R^1$, $R^2$ and $R^5$ are hydrogen; $R^4$ is cyano; $R^6$ is methyl; $R^7$ and $R^8$ are the same or different, and independently are hydrogen or $C_{1-5}$alkyl; Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl), wherein a group represented by —$(CR^1R^2)_m$—$(CHR^3)_n$—OH and $R^4$ are substituted on the same carbon atom of the cyclic amine. More preferable are compounds represented by the formula [V] in which Y is N; the cyclic amino group is a 6-membered saturated cyclic amine; m is an integer selected from 1, 2 and 3; n is 0; $R^1$, $R^2$ and $R^5$ are hydrogen; $R^4$ is cyano; $R^6$ is methyl; $R^7$ and $R^8$ are the same or different, and independently are hydrogen or methyl; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino, wherein a group represented by —$(CR^1R^2)_m$—$(CHR^3)_n$—OH and $R^4$ are substituted on the same carbon atom of the cyclic amine.

Other preferable are compounds represented by the formula [V] in which wherein Y is $CR^{10}$. More preferable are compounds represented by the formula [V] in which Y is $CR^{10}$; m is an integer selected from 1, 2, 3, 4 and 5; n is 0; $R^1$, $R^2$, $R^4$ and $R^5$ are hydrogen; $R^{10}$ is hydrogen or halogen. More preferable are compounds represented by the formula [V] in which Y is $CR^{10}$; the cyclic amino group is a 4- to 7-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or $C_{1-5}$alkyl; $R^{10}$ is hydrogen or halogen; Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl). More preferable are compounds represented by the formula [V] in which Y is $CR^{10}$; the cyclic amino group is a 6-membered saturated cyclic amine; m is an integer selected from 1, 2 and 3; n is 0; independently are hydrogen or methyl; $R^{10}$ is hydrogen; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino.

Other preferable are compounds represented by the formula [V] in which Y is $CR^{10}$; m is 1; n is 0; $R^1$ is $C_{1-5}$alkyl or hydroxy-$C_{1-5}$alkyl; $R^2$, $R^4$ and $R^5$ are hydrogen; $R^{10}$ is hydrogen or halogen. More preferable are compounds represented by the formula [V] in which Y is $CR^{10}$; m is 1; n is 0; the cyclic amino group is a 4- to 7-membered saturated cyclic amine; $R^1$ is $C_{1-5}$alkyl or hydroxy-$C_{1-5}$alkyl; $R^2$, $R^4$ and $R^5$ are hydrogen; $R^6$ is methyl; $R^7$ and $R^8$ are the same or different, and independently are hydrogen or $C_{1-5}$alkyl; $R^{10}$ is hydrogen or halogen; Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl). More preferable are compounds represented by the formula [V] in which Y is $CR^{10}$; m is 1; n is 0; the cyclic amino group is a 6-membered saturated cyclic amine; $R^1$ is $C_{1-5}$alkyl or hydroxy-$C_{1-5}$alkyl; $R^2$, $R^4$ and $R^5$ are hydrogen; $R^6$ is methyl; $R^7$ and $R^8$ are the same or different, and independently are hydrogen or methyl; $R^{10}$ is hydrogen; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino.

Other preferable are compounds represented by the formula [V] in which Y is $CR^{10}$; m is an integer selected from 1, 2, 3, 4 and 5; n is 0; $R^1$, $R^2$ and $R^5$ are hydrogen; $R^4$ is cyano; $R^{10}$ is hydrogen or halogen, wherein a group represented by —$(CR^1R^2)_m$—$(CHR^3)_n$—OH and $R^4$ are substituted on the same carbon atom of the cyclic amine. More preferable are compounds represented by the formula [V] in which Y is $CR^{10}$; the cyclic amino group is a 4- to 7-membered saturated cyclic amine; m is an integer selected from 1, 2 and 3; n is 0; $R^1$, $R^2$ and $R^5$ are hydrogen; $R^4$ is cyano; $R^6$ is methyl; $R^7$ and $R^8$ are the same or different, and independently are hydrogen or $C_{1-5}$alkyl; $R^{10}$ is hydrogen or halogen; Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl), wherein a group represented by —$(CR^1R^2)_m$—$(CHR^3)_n$—OH and $R^4$ are substituted on the same carbon atom of the cyclic amine. More preferable are compounds represented by the formula [V] in which Y is $CR^{10}$; the cyclic amino group is a 6-membered saturated cyclic amine; m is an integer selected from 1, 2 and 3; n is 0; $R^1$, $R^2$ and $R^5$ are hydrogen; $R^4$ is cyano; $R^6$ is methyl; $R^7$ and $R^8$ are the same or different, and independently are hydrogen or methyl; $R^{10}$ is hydrogen; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino, wherein a group represented by —$(CR^1R^2)_m$—$(CHR^3)_n$—OH and $R^4$ are substituted on the same carbon atom of the cyclic amine.

Other preferable are compounds represented by the following formula [VII]:

[VII]

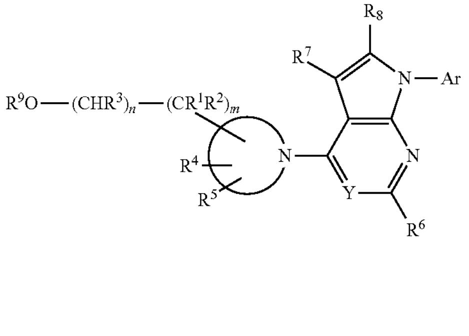

(wherein the cyclic amino group is represented by the following formula [VIII]:

[VIII]

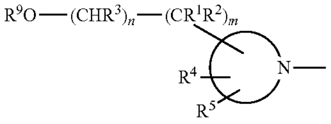

in which the cyclic amino group is a 3- to 8-membered saturated cyclic amine or a 3- to 8-membered saturated cyclic amine bridged with $C_{1-5}$alkylene or $C_{1-4}$alkylene-O—$C_{1-4}$ alkylene between any different two carbon atoms of the cyclic amine, which cyclic amine is substituted with a group represented by —$(CR^1R^2)_m$—$(CHR^3)_n$—$OR^9$, $R^4$ and $R^5$ independently on the same or different carbon atoms of the cyclic amine;

Y is N or $CR^{10}$;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4 and 5;

n is 0 or 1;

with the proviso that when n is 0, m is an integer selected from 1, 2, 3, 4 and 5;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy or —$N(R^{11})R^{12}$;

$R^7$ and $R^8$ are the same or different, and independently are hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —$N(R^{11a})R^{12a}$, —$CO_2R^{13}$, cyano, nitro, $C_{1-5}$alkylthio, trifluoromethyl or trifluoromethoxy; or $R^7$ and $R^8$ are taken together to form —$CH_2$—$CH_2$—$CH_2$—$CH_2$— or —CH═CH—CH═CH—;

$R^9$ is $C_{1-24}$acyl, $C_{1-10}$alkoxycarbonyl, aryl-$C_{1-5}$alkyloxycarbonyl, —CO—O—$CHR^{14}$—O—CO—$R^{15}$, —P(═O)$(OR^{14a})OR^{15a}$, —CO—$(CH_2)_p$—$(CHR^{16})_q$—$NR^{17}R^{18}$, arylcarbonyl or heteroarylcarbonyl, wherein each said acyl, aryl and heteroaryl is unsubstituted or substituted with $C_{1-5}$alkoxy, and $C_{1-24}$acyl optionally includes one to six double bonds;

$R^{10}$ is hydrogen, $C_{1-5}$alkyl, halogen, cyano or —$CO_2R^{19}$;

Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —$CO_2R^{19a}$, —C(═O)$R^{19a}$, —$CONR^{11b}R^{12b}$), —OC(═O)$R^{19a}$, —$NR^{11b}CO_2R^{19a}$, —$S(O)_rNR^{11b}R^{12b}$, hydroxy-$C_{2-5}$alkylamino-$C_{2-5}$alkoxy, trifluoromethyl, trifluoromethoxy, difluoromethoxy, fluoromethoxy, methylenedioxy, ethylenedioxy and —$N(R^{20})R^{21}$;

$R^{11}$ and $R^{12}$ are the same or different, and independently are hydrogen, $C_{1-5}$alkyl, $C_{3-8}$cycloalkyl or $C_{3-8}$cycloalkyl-$C_{1-5}$alkyl;

$R^{11a}$ and $R^{12a}$ are the same or different, and independently are hydrogen, $C_{1-5}$ alkyl, $C_{3-8}$cycloalkyl or $C_{3-8}$cycloalkyl-$C_{1-5}$alkyl;

$R^{11b}$ and $R^{12b}$ are the same or different, and independently are hydrogen, $C_{1-5}$alkyl, $C_{3-8}$cycloalkyl or $C_{3-8}$cycloalkyl-$C_{1-5}$ alkyl;

$R^{13}$ is hydrogen, $C_{1-5}$alkyl, $C_{3-8}$cycloalkyl, $C_{3-8}$cycloalkyl-$C_{1-5}$alkyl, $C_{1-5}$alkoxy-$C_{1-5}$alkyl, $C_{3-8}$cycloalkyloxy-$C_{1-5}$alkyl or phenyl;

$R^{14}$ and $R^{15}$ are the same or different, and independently are hydrogen, $C_{1-5}$alkyl or aryl-$C_{1-5}$alkyl;

$R^{14a}$ and $R^{15a}$ are the same or different, and independently are hydrogen, $C_{1-5}$ alkyl or aryl-$C_{1-5}$alkyl;

$R^{16}$ is hydrogen, $C_{1-5}$alkyl, aryl, heteroaryl, aryl-$C_{1-5}$ alkyl, heteroaryl-$C_{1-5}$alkyl, hydroxy-$C_{1-5}$alkyl, hydroxycarbonyl-$C_{1-5}$alkyl, hydroxyphenyl-$C_{1-5}$ alkyl, $C_{1-5}$alkoxy-$C_{1-5}$alkyl, amino-$C_{1-5}$alkyl, guanidino-$C_{1-5}$alkyl, mercapto-$C_{1-5}$ alkyl, $C_{1-5}$ alkylthio-$C_{1-5}$ alkyl or aminocarbonyl-$C_{1-5}$alkyl;

$R^{17}$ and $R^{18}$ are the same or different, and independently are hydrogen, $C_{1-5}$ alkyl, $C_{3-8}$cycloalkyl, $C_{3-8}$cycloalkyl-$C_{1-5}$ alkyl, $C_{1-10}$acyl, $C_{1-10}$alkoxycarbonyl and aryl-$C_{1-5}$alkyloxycarbonyl, or $R^{16}$ and $R^{17}$ are taken together to form —$CH_2$—, —$CH_2CH_2$—, —$CH_2CH_2CH_2$— or —$CH_2CH_2CH_2CH_2$—;

p is an integer selected from 0, 1, 2, 3, 4 and 5;

q is 0 or 1;

$R^{19}$ is hydrogen or $C_{1-5}$alkyl;

$R^{19a}$ is hydrogen or $C_{1-5}$alkyl;

r is 1 or 2;

$R^{20}$ and $R^{21}$ are the same or different, and independently are hydrogen or $C_{1-5}$alkyl). More preferable are compounds represented by the formula [VII] in which Y is N. More preferable are compounds represented by the formula [VII] in which Y is N; m is an integer selected from 1, 2, 3, 4 and 5; n is 0; $R^1$, $R^2$, $R^4$ and $R^5$ are hydrogen. More preferable are compounds represented by the formula [VII] in which the cyclic amino group is a 4- to 7-membered saturated cyclic amine; m is an integer selected from 1, 2, 3, 4 and 5; n is 0; Y is N; $R^1$, $R^2$, $R^4$ an $R^5$ and are hydrogen; $R^6$ is methyl; $R^7$ and $R^8$ are the same or different, and independently are hydrogen or $C_{1-5}$alkyl; Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl). More preferable are compounds represented by the formula [VII] in which the cyclic amino group is a 6-membered saturated cyclic amine; m is an integer selected from 1, 2 and 3; n is 0; Y is N; $R^2$, $R^4$ and $R^5$ are hydrogen; $R^6$ is methyl; $R^7$ and $R^8$ are the same or different, and independently are hydrogen or methyl; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino.

Other preferable are compounds represented by the formula [VII] in which Y is $CR^{10}$. More preferable are compounds represented by the formula [VII] in which Y is $CR^{10}$; m is an integer selected from 1, 2, 3, 4 and 5; n is 0; $R^1$, $R^2$, $R^4$ and $R^5$ are hydrogen. More preferable are compounds represented by the formula [VII] in which Y is $CR^{10}$; the cyclic amino group is a 4- to 7-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or $C_{1-5}$alkyl; $R^{10}$ is hydrogen or halogen; Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl). More preferable are compounds represented by the formula [VII] in which Y is $CR^{10}$; the cyclic amino group is a 6-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or methyl; $R^{10}$ is hydrogen; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino.

Especially preferable compounds of the present invention are:

2-{1-[7-(2,6-dibromo-4-trifluoromethyl-phenyl)-2,5,6-trimethyl-7H-pyrrolo[2,3-d]pyrimidin-4-yl]-piperidin-2-yl}-ethanol,

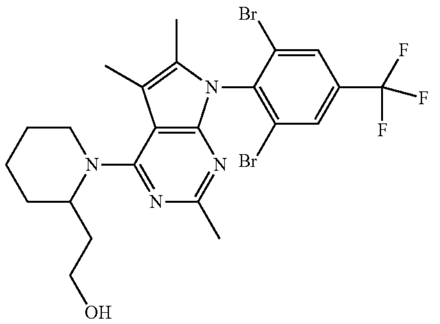 [SMILES: Cc1nc(N2CCCCC2CCO)c2c(C)c(C)n(-c3c(Br)cc(C(F)(F)F)cc3Br)c2n1]

2-{1-[7-(4-bromo-2,6-dimethyl-phenyl)-2,5,6-trimethyl-7H-pyrrolo[2,3-d]pyrimidin-4-yl]-piperidin-2-yl}-ethanol,

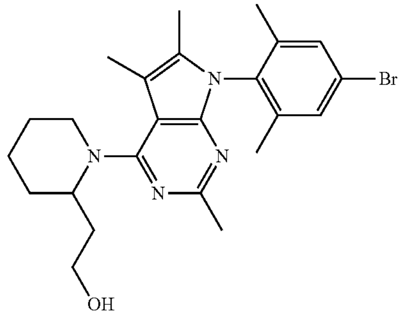 [SMILES: Cc1nc(N2CCCCC2CCO)c2c(C)c(C)n(-c3c(C)cc(Br)cc3C)c2n1]

2-{1-[7-(4-bromo-2,6-dimethyl-phenyl)-2,5-dimethyl-7H-pyrrolo[2,3-d]pyrimidin-4-yl]-piperidin-2-yl}-ethanol,

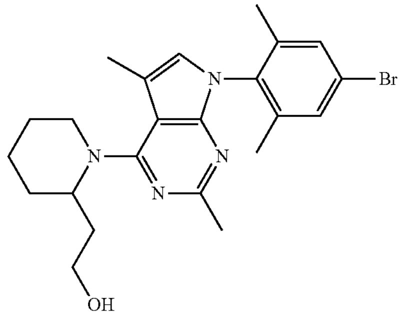 [SMILES: Cc1nc(N2CCCCC2CCO)c2c(C)cn(-c3c(C)cc(Br)cc3C)c2n1]

2-{1-[7-(4-bromo-2,6-diethyl-phenyl)-2,5-dimethyl-7H-pyrrolo[2,3-d]pyrimidin-4-yl]-piperidin-2-yl}-ethanol,

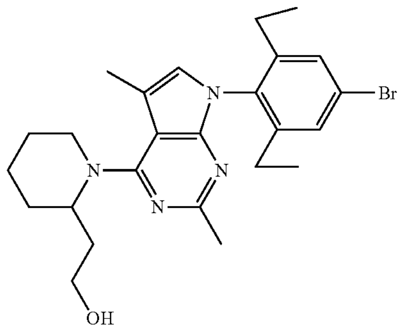 [SMILES: CCc1cc(Br)cc(CC)c1-n1cc(C)c2c(N3CCCCC3CCO)nc(C)nc21]

2-{1-[2,5-dimethyl-7-(2,4,6-tribromo-phenyl)-7H-pyrrolo[2,3-d]pyrimidin-4-yl]-piperidin-2-yl}-ethanol,

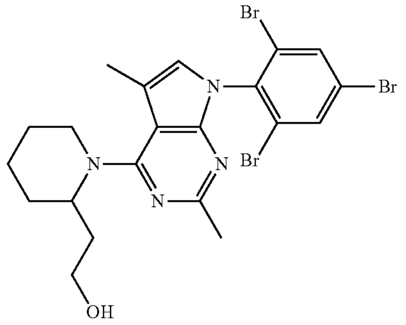 [SMILES: Cc1nc(N2CCCCC2CCO)c2c(C)cn(-c3c(Br)cc(Br)cc3Br)c2n1]

3-{1-[7-(4-bromo-2,6-dimethyl-phenyl)-2,5,6-trimethyl-7H-pyrrolo[2,3-d]pyrimidin-4-yl]-piperidin-2-yl}-propan-1-ol,

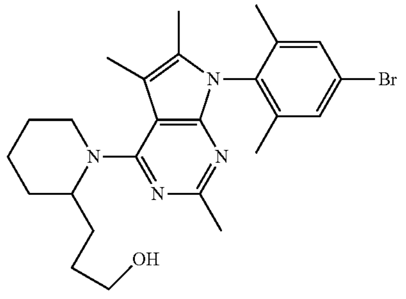 [SMILES: Cc1nc(N2CCCCC2CCCO)c2c(C)c(C)n(-c3c(C)cc(Br)cc3C)c2n1]

3-{1-[7-(4-bromo-2,6-dimethyl-phenyl)-2,5-dimethyl-7H-pyrrolo[2,3-d]pyrimidin-4-yl]-piperidin-2-yl}-propan-1-ol,

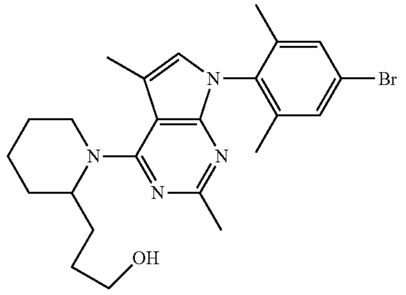 [SMILES: Cc1nc(N2CCCCC2CCCO)c2c(C)cn(-c3c(C)cc(Br)cc3C)c2n1]

{1-[7-(2,4-dibromo-6-methoxy-phenyl)-2,5-dimethyl-7H-pyrrolo[2,3-d]pyrimidin-4-yl]-piperidin-3-yl}-methanol,

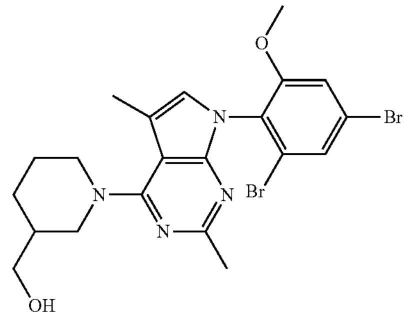 [SMILES: COc1cc(Br)cc(Br)c1-n1cc(C)c2c(N3CCCC(CO)C3)nc(C)nc21]

{1-[7-(2,4-dibromo-6-methylsulfanyl-phenyl)-2,5-dimethyl-7H-pyrrolo[2,3-d]pyrimidin-4-yl]-piperidin-3-yl}-methanol,

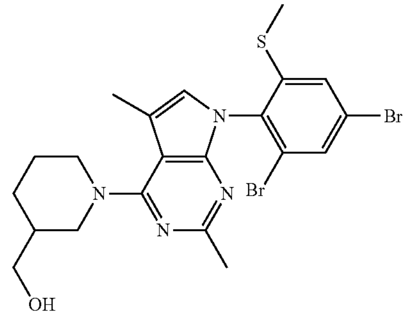 [SMILES: CSc1cc(Br)cc(Br)c1-n1cc(C)c2c(N3CCCC(CO)C3)nc(C)nc21]

{1-[7-(4-bromo-2,6-dimethyl-phenyl)-2,5,6-trimethyl-7H-pyrrolo[2,3-d]pyrimidin-4-yl]-piperidin-3-yl}-methanol,

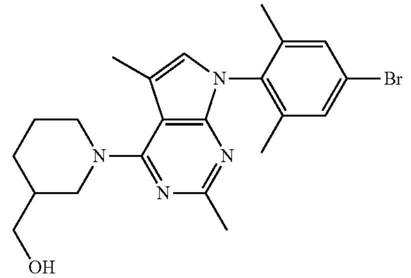

{1-[7-(4-bromo-2,6-dimethyl-phenyl)-2,5-dimethyl-7H-pyrrolo[2,3-d]pyrimidin-4-yl]-piperidin-3-yl}-methanol,

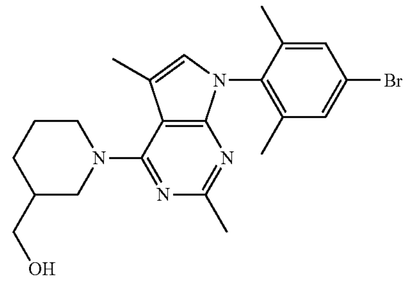 [SMILES: Cc1nc(N2CCCC(CO)C2)c2c(C)cn(-c3c(C)cc(Br)cc3C)c2n1]

{1-[2,5-dimethyl-7-(2,4,6-tribromo-phenyl)-7H-pyrrolo[2,3-d]pyrimidin-4-yl]-piperidin-3-yl}-methanol,

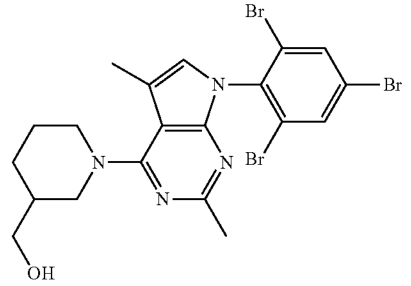 [SMILES: Cc1nc(N2CCCC(CO)C2)c2c(C)cn(-c3c(Br)cc(Br)cc3Br)c2n1]

2-{1-[7-(2,6-dibromo-4-trifluoromethyl-phenyl)-2,5,6-trimethyl-7H-pyrrolo[2,3-d]pyrimidin-4-yl]-piperidin-3-yl}-ethanol,

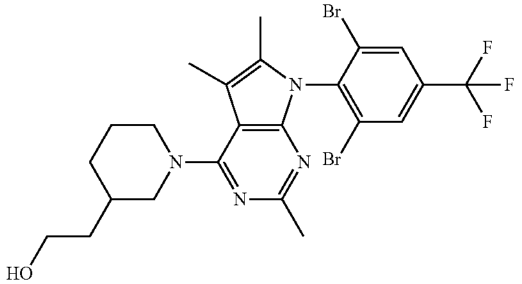 [SMILES: Cc1nc(N2CCCC(CCO)C2)c2c(C)c(C)n(-c3c(Br)cc(C(F)(F)F)cc3Br)c2n1]

2-{1-[7-(4-bromo-2,6-dimethyl-phenyl)-2,5,6-trimethyl-7H-pyrrolo[2,3-d]pyrimidin-4-yl]-piperidin-3-yl}-ethanol,

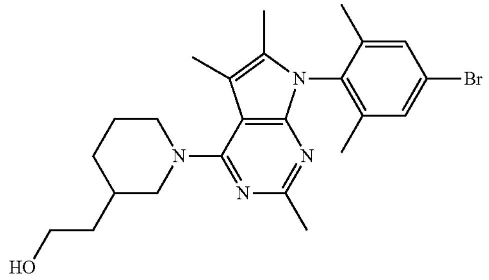

2-{1-[7-(4-bromo-2,6-dimethyl-phenyl)-2,5-dimethyl-7H-pyrrolo[2,3-d]pyrimidin-4-yl]-piperidin-3-yl}-ethanol,

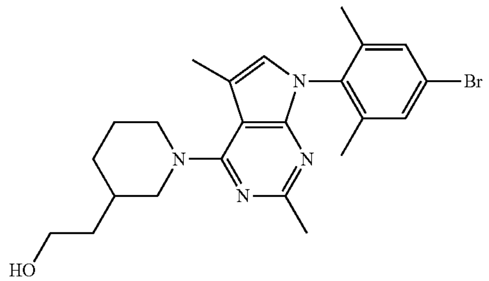

2-{1-[2,5-dimethyl-7-(2,4,6-tribromo-phenyl)-7H-pyrrolo[2,3-d]pyrimidin-4-yl]-piperidin-3-yl}-ethanol,

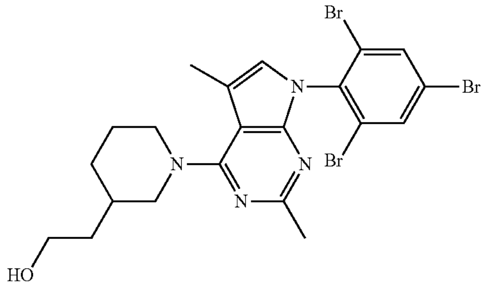 [SMILES: Cc1nc(N2CCCC(CCO)C2)c2c(C)cn(-c3c(Br)cc(Br)cc3Br)c2n1]

{1-[2,5,6-trimethyl-7-(2,4,6-trimethyl-phenyl)-7H-pyrrolo[2,3-d]pyrimidin-4-yl]-piperidin-4-yl}-methanol,

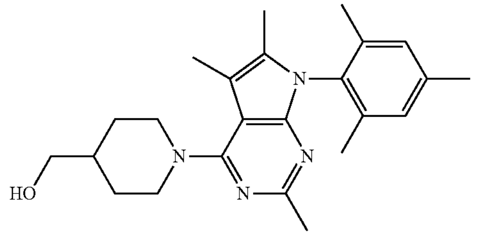 [SMILES: Cc1cc(C)c(-n2c(C)c(C)c3c(N4CCC(CO)CC4)nc(C)nc32)c(C)c1]

{1-[2,5-dimethyl-7-(2,4,6-trimethyl-phenyl)-7H-pyrrolo[2,3-d]pyrimidin-4-yl]-piperidin-4-yl}-methanol,

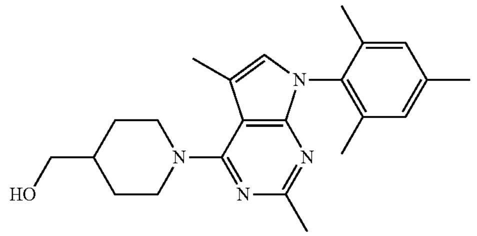 [SMILES: Cc1cc(C)c(-n2cc(C)c3c(N4CCC(CO)CC4)nc(C)nc32)c(C)c1]

{1-[7-(2,6-dibromo-4-trifluoromethyl-phenyl)-2,5,6-trimethyl-7H-pyrrolo[2,3-d]pyrimidin-4-yl]-piperidin-4-yl}-methanol,

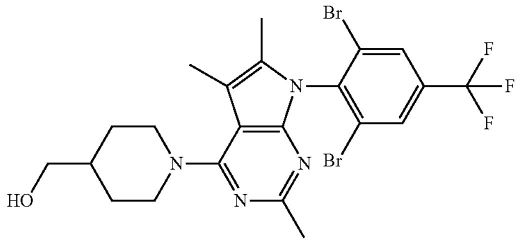 [SMILES: Cc1nc(N2CCC(CO)CC2)c2c(C)c(C)n(-c3c(Br)cc(C(F)(F)F)cc3Br)c2n1]

{1-[7-(4-bromo-2,6-dimethyl-phenyl)-2,5,6-trimethyl-7H-pyrrolo[2,3-d]pyrimidin-4-yl]-piperidin-4-yl}-methanol,

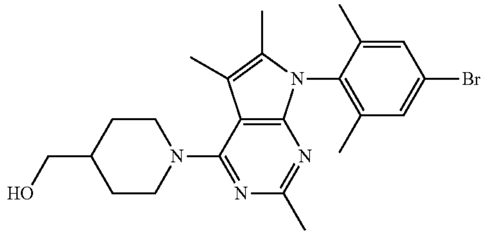

{1-[7-(4-bromo-2,6-dimethyl-phenyl)-2,5-dimethyl-7H-pyrrolo[2,3-d]pyrimidin-4-yl]-piperidin-4-yl}-methanol,

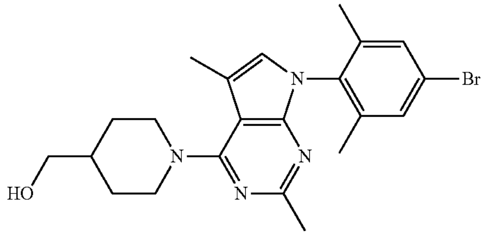

{1-[2-methyl-9-(2,4,6-trimethyl-phenyl)-9H-1,3,9-triaza-fluoren-4-yl]-piperidin-4-yl}-methanol,

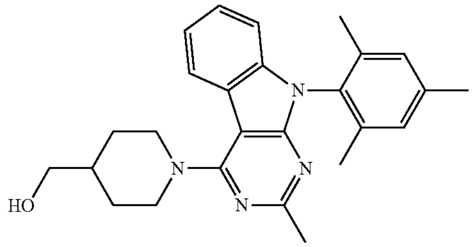 [SMILES: Cc1cc(C)c(-n2c3ccccc3c3c(N4CCC(CO)CC4)nc(C)nc32)c(C)c1]

{1-[7-(4-bromo-2,6-diethyl-phenyl)-2,5,6-trimethyl-7H-pyrrolo[2,3-d]pyrimidin-4-yl]-piperidin-4-yl}-methanol,

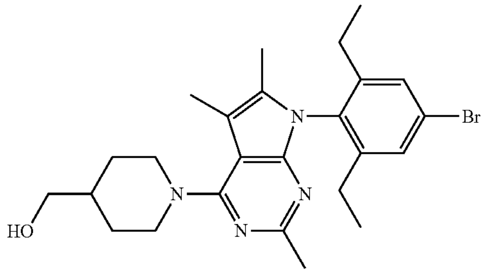 [SMILES: CCc1cc(Br)cc(CC)c1-n1c(C)c(C)c2c(N3CCC(CO)CC3)nc(C)nc21]

{1-[7-(4-bromo-2,6-diethyl-phenyl)-2,5-dimethyl-7H-pyrrolo[2,3-d]pyrimidin-4-yl]-piperidin-4-yl}-methanol,

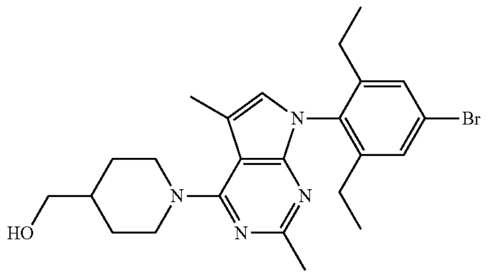 [SMILES: CCc1cc(Br)cc(CC)c1-n1cc(C)c2c(N3CCC(CO)CC3)nc(C)nc21]

{1-[2,5,6-trimethyl-7-(2,4,6-tribromo-phenyl)-7H-pyrrolo[2,3-d]pyrimidin-4-yl]-piperidin-4-yl}-methanol,

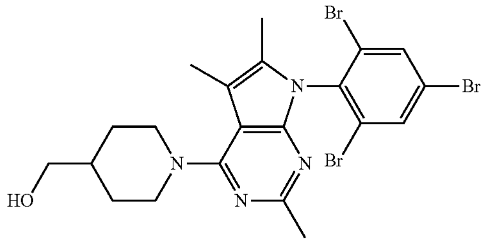 [SMILES: Cc1nc(N2CCC(CO)CC2)c2c(C)c(C)n(-c3c(Cl)cc(Br)cc3Cl)c2n1]

{1-[2,5-dimethyl-7-(2,4,6-tribromo-phenyl)-7H-pyrrolo[2,3-d]pyrimidin-4-yl]-piperidin-4-yl}-methanol,

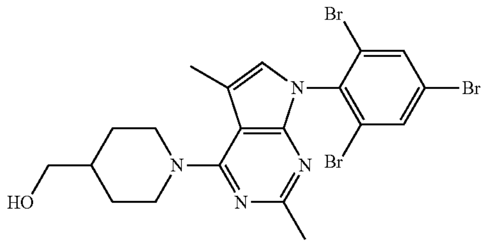

{1-[7-(4-bromo-2,6-dichloro-phenyl)-2,5,6-trimethyl-7H-pyrrolo[2,3-d]pyrimidin-4-yl]-piperidin-4-yl}-methanol,

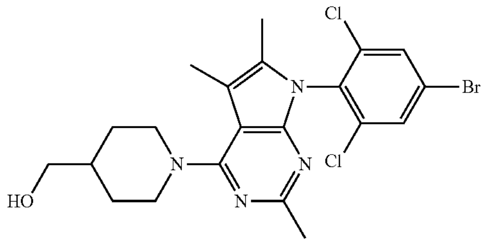

{1-[7-(4-bromo-2,6-dichloro-phenyl)-2,5-dimethyl-7H-pyrrolo[2,3-d]pyrimidin-4-yl]-piperidin-4-yl}-methanol,

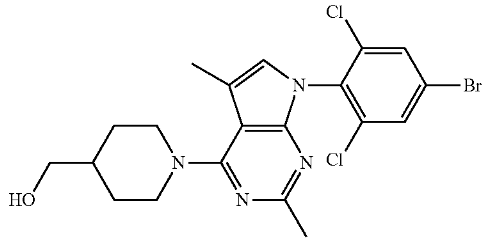

{1-[7-(2,6-dibromo-4-isopropyl-phenyl)-2,5,6-trimethyl-7H-pyrrolo[2,3-d]pyrimidin-4-yl]-piperidin-4-yl}-methanol,

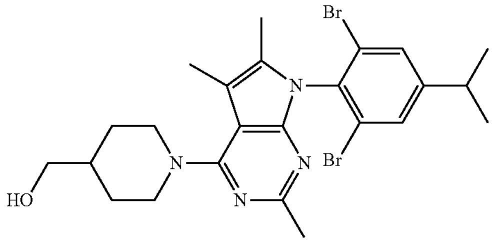 [SMILES: Cc1nc(N2CCC(CO)CC2)c2c(C)c(C)n(-c3c(Br)cc(C(C)C)cc3Br)c2n1]

{1-[7-(2,6-dibromo-4-isopropyl-phenyl)-2,5-dimethyl-7H-pyrrolo[2,3-d]pyrimidin-4-yl]-piperidin-4-yl}-methanol,

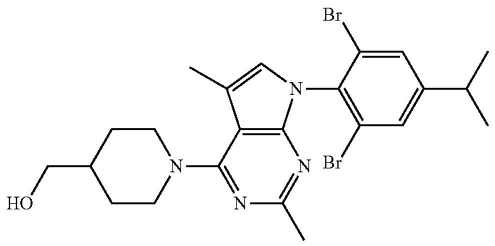 [SMILES: Cc1nc(N2CCC(CO)CC2)c2c(C)cn(-c3c(Br)cc(C(C)C)cc3Br)c2n1]

{1-[7-(4-chloro-2,6-dimethyl-phenyl)-2,5,6-trimethyl-7H-pyrrolo[2,3-d]pyrimidin-4-yl]-piperidin-4-yl}-methanol,

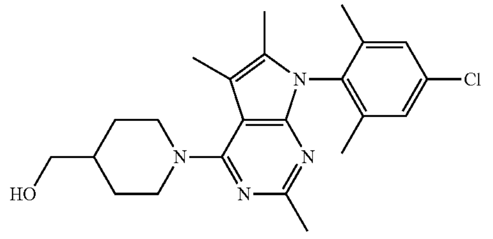

{1-[7-(4-chloro-2,6-dimethyl-phenyl)-2,5-dimethyl-7H-pyrrolo[2,3-d]pyrimidin-4-yl]-piperidin-4-yl}-methanol,

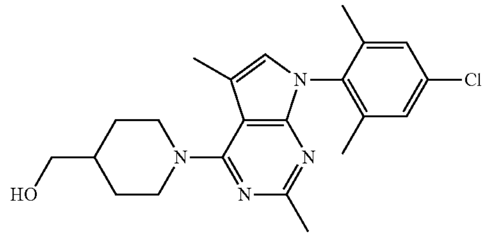

2-{1-[7-(2,6-dibromo-4-trifluoromethyl-phenyl)-2,5,6-trimethyl-7H-pyrrolo[2,3-d]pyrimidin-4-yl]-piperidin-4-yl}-ethanol,

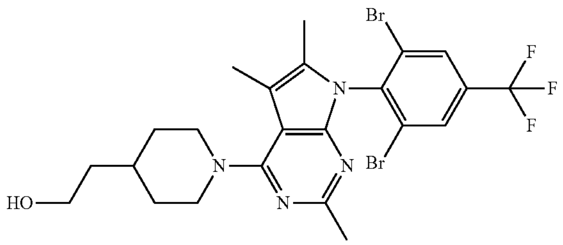 [SMILES: Cc1nc(N2CCC(CCO)CC2)c2c(C)c(C)n(-c3c(Br)cc(C(F)(F)F)cc3Br)c2n1]

2-{1-[7-(4-bromo-2,6-dimethyl-phenyl)-2,5,6-trimethyl-7H-pyrrolo[2,3-d]pyrimidin-4-yl]-piperidin-4-yl}-ethanol,

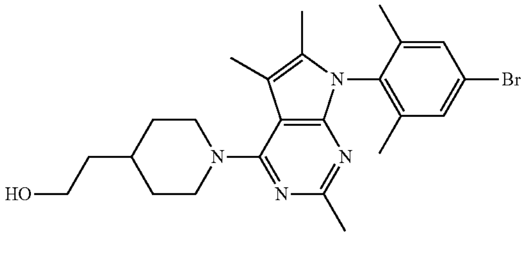

2-{1-[7-(4-bromo-2,6-dimethyl-phenyl)-2,5-dimethyl-7H-pyrrolo[2,3-d]pyrimidin-4-yl]-piperidin-4-yl}-ethanol,

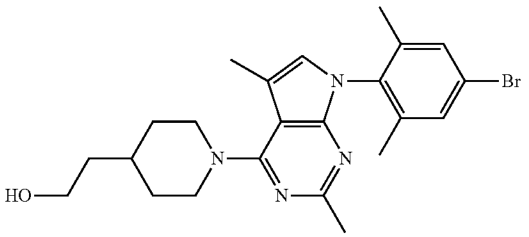

2-{1-[2,5,6-trimethyl-7-(2,4,6-tribromo-phenyl)-7H-pyrrolo[2,3-d]pyrimidin-4-yl]-piperidin-4-yl}-ethanol,

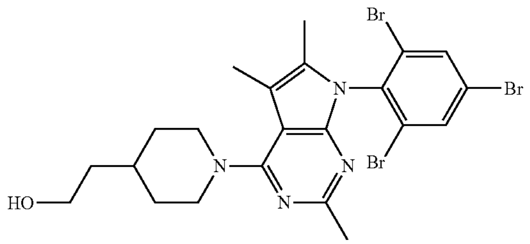

2-{1-[2,5-dimethyl-7-(2,4,6-tribromo-phenyl)-7H-pyrrolo[2,3-d]pyrimidin-4-yl]-piperidin-4-yl}-ethanol,

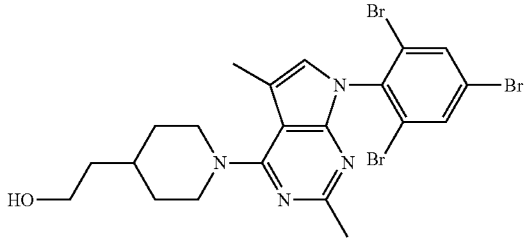

3-{1-[2,5,6-trimethyl-7-(2,4,6-trimethyl-phenyl)-7H-pyrrolo[2,3-d]pyrimidin-4-yl]-piperidin-4-yl}-propan-1-ol,

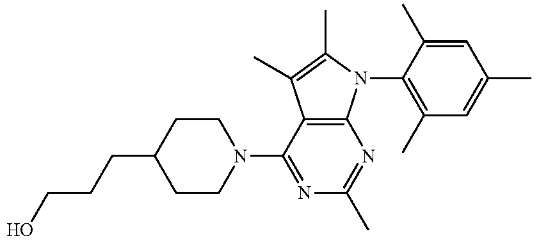 [SMILES: Cc1cc(C)c(-n2c(C)c(C)c3c(N4CCC(CCCO)CC4)nc(C)nc32)c(C)c1]

3-{1-[2,5-dimethyl-7-(2,4,6-trimethyl-phenyl)-7H-pyrrolo[2,3-d]pyrimidin-4-yl]-piperidin-4-yl}-propan-1-ol,

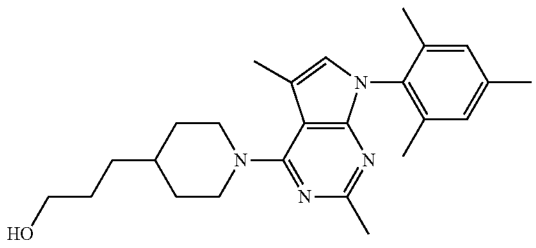 [SMILES: Cc1cc(C)c(-n2cc(C)c3c(N4CCC(CCCO)CC4)nc(C)nc32)c(C)c1]

3-{1-[7-(2,6-dibromo-4-trifluoromethyl-phenyl)-2,5,6-trimethyl-7H-pyrrolo[2,3-d]pyrimidin-4-yl]-piperidin-4-yl}-propan-1-ol,

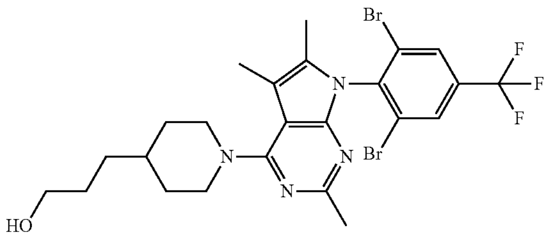 [SMILES: Cc1nc(N2CCC(CCCO)CC2)c2c(C)c(C)n(-c3c(Br)cc(C(F)(F)F)cc3Br)c2n1]

3-{1-[7-(4-bromo-2,6-dimethyl-phenyl)-2,5,6-trimethyl-7H-pyrrolo[2,3-d]pyrimidin-4-yl]-piperidin-4-yl}-propan-1-ol,

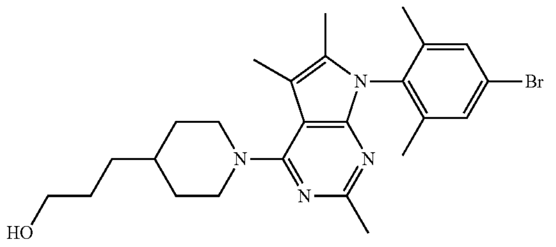

3-{1-[7-(4-bromo-2,6-dimethyl-phenyl)-2,5-dimethyl-7H-pyrrolo[2,3-d]pyrimidin-4-yl]-piperidin-4-yl}-propan-1-ol,

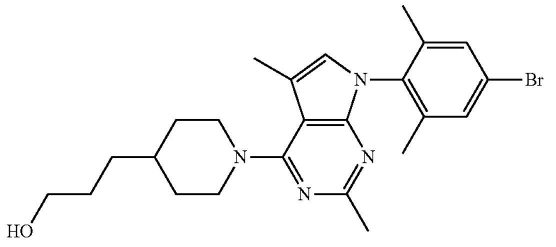 [SMILES: Cc1nc(N2CCC(CCCO)CC2)c2c(C)cn(-c3c(C)cc(Br)cc3C)c2n1]

3-{1-[2,5-dimethyl-7-(2,4,6-tribromo-phenyl)-7H-pyrrolo[2,3-d]pyrimidin-4-yl]-piperidin-4-yl}-propan-1-ol,

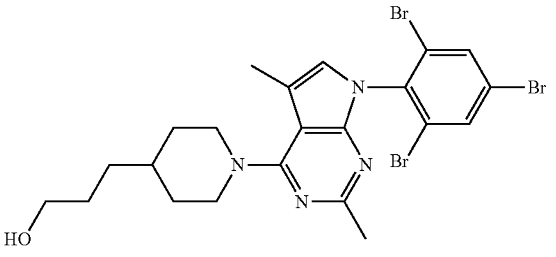 [SMILES: Cc1nc(N2CCC(CCCO)CC2)c2c(C)cn(-c3c(Br)cc(Br)cc3Br)c2n1]

3-{1-[7-(4-bromo-2,6-dichloro-phenyl)-2,5,6-trimethyl-7H-pyrrolo[2,3-d]pyrimidin-4-yl]-piperidin-4-yl}-propan-1-ol,

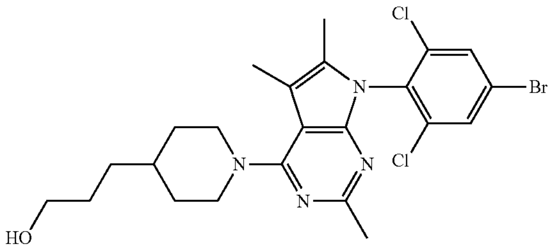 [SMILES: Cc1nc(N2CCC(CCCO)CC2)c2c(C)c(C)n(-c3c(Cl)cc(Br)cc3Cl)c2n1]

3-{1-[7-(4-bromo-2,6-dichloro-phenyl)-2,5-dimethyl-7H-pyrrolo[2,3-d]pyrimidin-4-yl]-piperidin-4-yl}-propan-1-ol,

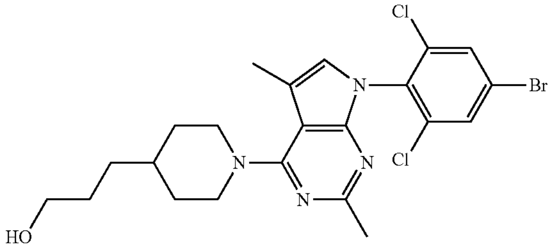 [SMILES: Cc1nc(N2CCC(CCCO)CC2)c2c(C)cn(-c3c(Cl)cc(Br)cc3Cl)c2n1]

{1-[7-(2,6-dibromo-4-trifluoromethyl-phenyl)-2,5,6-trimethyl-7H-pyrrolo[2,3-d]pyrimidin-4-yl]-3-methyl-piperidin-3-yl}-methanol,

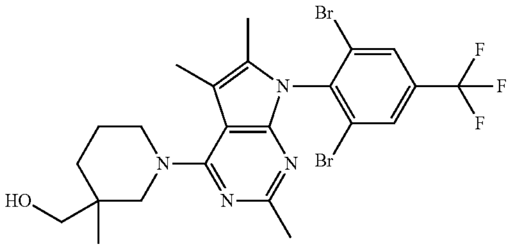 [SMILES: Cc1nc(N2CCCC(C)(CO)C2)c2c(C)c(C)n(-c3c(Br)cc(C(F)(F)F)cc3Br)c2n1]

{1-[7-(4-bromo-2,6-dimethyl-phenyl)-2,5,6-trimethyl-7H-pyrrolo[2,3-d]pyrimidin-4-yl]-3-methyl-piperidin-3-yl}-methanol,

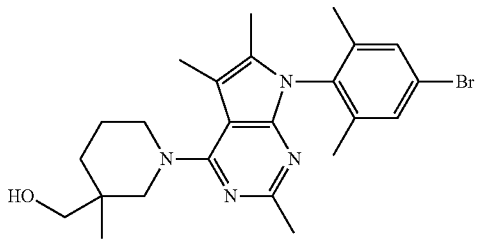 [SMILES: Cc1nc(N2CCCC(C)(CO)C2)c2c(C)c(C)n(-c3c(C)cc(Br)cc3C)c2n1]

{1-[7-(4-bromo-2,6-dimethyl-phenyl)-2,5-dimethyl-7H-pyrrolo[2,3-d]pyrimidin-4-yl]-3-methyl-piperidin-3-yl}-methanol,

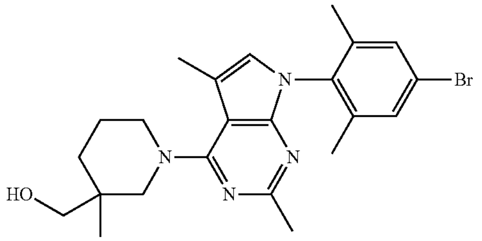 [SMILES: Cc1nc(N2CCCC(C)(CO)C2)c2c(C)cn(-c3c(C)cc(Br)cc3C)c2n1]

1-{1-[7-(4-bromo-2,6-dimethyl-phenyl)-2,5,6-trimethyl-7H-pyrrolo[2,3-d]pyrimidin-4-yl]-piperidin-4-yl}-ethane-1,2-diol,

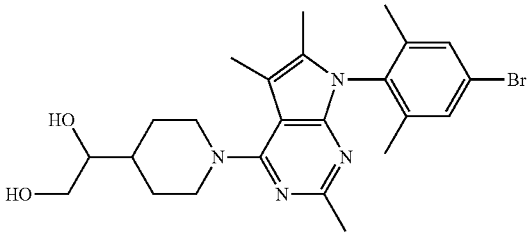 [SMILES: Cc1nc(N2CCC(C(O)CO)CC2)c2c(C)c(C)n(-c3c(C)cc(Br)cc3C)c2n1]

{1-[7-(4-bromo-2,6-dimethyl-phenyl)-2,5,6-trimethyl-7H-pyrrolo[2,3-d]pyrimidin-4-yl]-pyrrolidin-2-yl}-methanol,

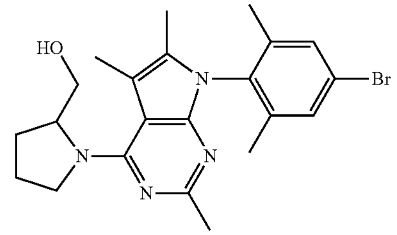 [SMILES: Cc1nc(N2CCCC2CO)c2c(C)c(C)n(-c3c(C)cc(Br)cc3C)c2n1]

{1-[7-(4-bromo-2,6-dimethyl-phenyl)-2,5-dimethyl-7H-pyrrolo[2,3-d]pyrimidin-4-yl]-pyrrolidin-2-yl}-methanol,

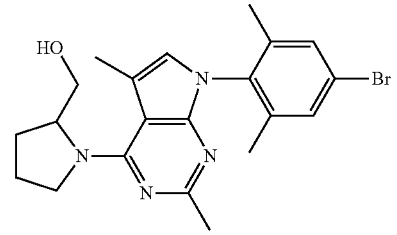 [SMILES: Cc1nc(N2CCCC2CO)c2c(C)cn(-c3c(C)cc(Br)cc3C)c2n1]

2-{1-[7-(4-bromo-2,6-dimethyl-phenyl)-2,5-dimethyl-7H-pyrrolo[2,3-d]pyrimidin-4-yl]-pyrrolidin-3-yl}-ethanol,

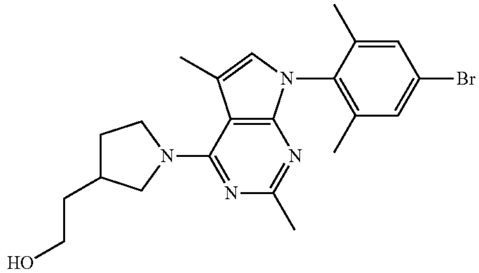 [SMILES: Cc1nc(N2CCC(CCO)C2)c2c(C)cn(-c3c(C)cc(Br)cc3C)c2n1]

{1-[7-(4-bromo-2,6-dimethyl-phenyl)-2,5,6-trimethyl-7H-pyrrolo[2,3-d]pyrimidin-4-yl]azepan-4-yl}-methanol,

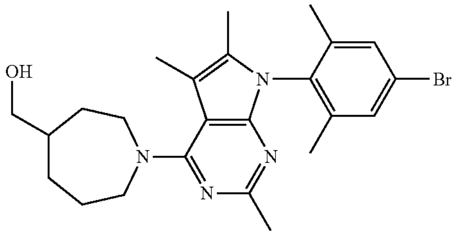 [SMILES: Cc1nc(N2CCCC(CO)CC2)c2c(C)c(C)n(-c3c(C)cc(Br)cc3C)c2n1]

{1-[7-(4-bromo-2,6-dimethyl-phenyl)-2,5-dimethyl-7H-pyrrolo[2,3-d]pyrimidin-4-yl]-azepan-4-yl}-methanol,

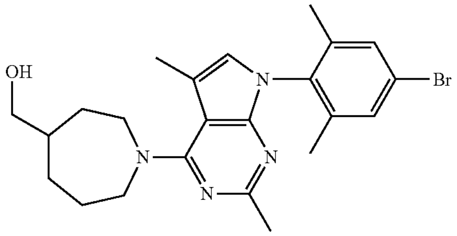 [SMILES: Cc1nc(N2CCCC(CO)CC2)c2c(C)cn(-c3c(C)cc(Br)cc3C)c2n1]

{1-[7-(4-bromo-2,6-dimethyl-phenyl)-2,5,6-trimethyl-7H-pyrrolo[2,3-d]pyrimidin-4-yl]-piperidin-2-yl}-acetonitrile,

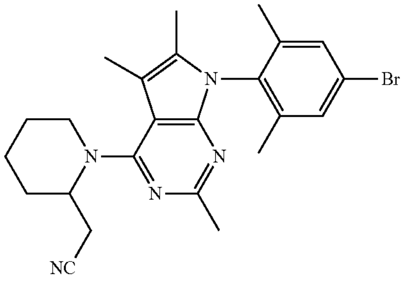 [SMILES: Cc1nc(N2CCCCC2CC#N)c2c(C)c(C)n(-c3c(C)cc(Br)cc3C)c2n1]

1-[2,5,6-trimethyl-7-(2,4,6-trimethyl-phenyl)-7H-pyrrolo[2,3-d]pyrimidin-4-yl]-piperidine-3-carbonitrile,

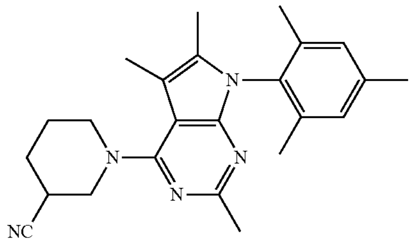 [SMILES: Cc1cc(C)c(-n2c(C)c(C)c3c(N4CCCC(C#N)C4)nc(C)nc32)c(C)c1]

1-[2,5-dimethyl-7-(2,4,6-trimethyl-phenyl)-7H-pyrrolo[2,3-d]pyrimidin-4-yl]-piperidine-3-carbonitrile,

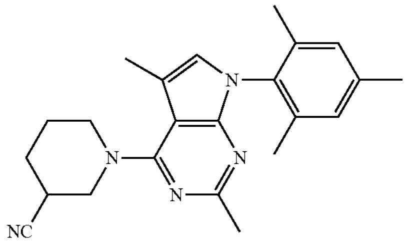 [SMILES: Cc1cc(C)c(-n2cc(C)c3c(N4CCCC(C#N)C4)nc(C)nc32)c(C)c1]

1-[7-(2,4-dibromo-6-methylsulfanyl-phenyl)-2,5-dimethyl-7H-pyrrolo[2,3d]pyrimidin-4-yl]-piperidine-3-carbonitrile,

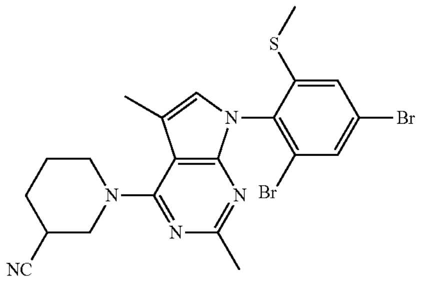 [SMILES: CSc1cc(Br)cc(Br)c1-n1cc(C)c2c(N3CCCC(C#N)C3)nc(C)nc21]

1-[7-(2,6-dibromo-4-trifluoromethyl-phenyl)-2,5,6-trimethyl-7H-pyrrolo[2,3-d]pyrimidin-4-yl]-piperidine-3-carbonitrile,

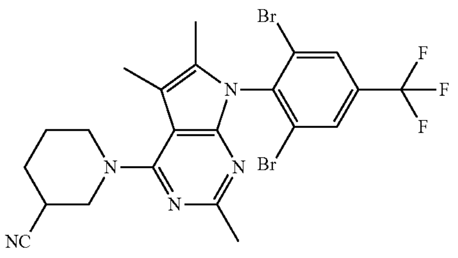 [SMILES: Cc1nc(N2CCCC(C#N)C2)c2c(C)c(C)n(-c3c(Br)cc(C(F)(F)F)cc3Br)c2n1]

1-[7-(4-bromo-2,6-dimethyl-phenyl)-2,5,6-trimethyl-7H-pyrrolo[2,3-d]pyrimidin-4-yl]-piperidine-3-carbonitrile,

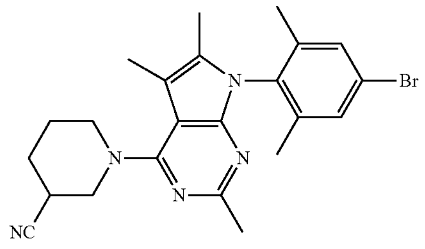 [SMILES: Cc1nc(N2CCCC(C#N)C2)c2c(C)c(C)n(-c3c(C)cc(Br)cc3C)c2n1]

1-[7-(4-bromo-2,6-dimethyl-phenyl)-2,5-dimethyl-7H-pyrrolo[2,3d]pyrimidin-4-yl]-piperidine-3-carbonitrile,

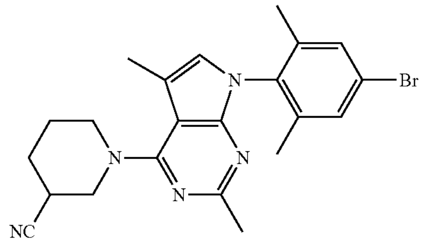 [SMILES: Cc1nc(N2CCCC(C#N)C2)c2c(C)cn(-c3c(C)cc(Br)cc3C)c2n1]

1-[7-(4-isopropyl-2-methylsulfanyl-phenyl)-2,5,6-trimethyl-7H-pyrrolo[2,3-d]pyrimidin-4-yl]-piperidine-3-carbonitrile,

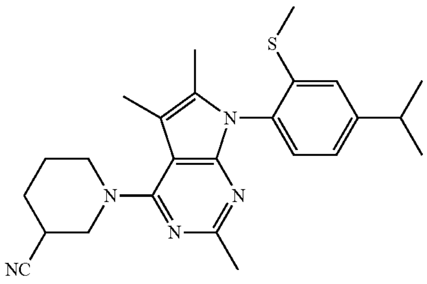 [SMILES: CSc1cc(C(C)C)ccc1-n1c(C)c(C)c2c(N3CCCC(C#N)C3)nc(C)nc21]

1-[7-(4-isopropyl-2-methylsulfanyl-phenyl)-2,5-dimethyl-7H-pyrrolo[2,3-d]pyrimidin-4-yl]-piperidine-3-carbonitrile,

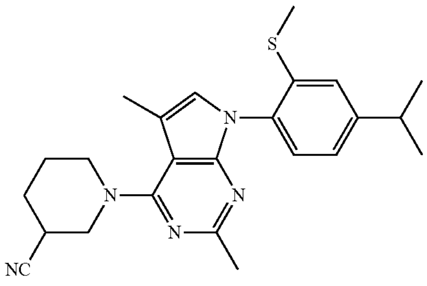 [SMILES: CSc1cc(C(C)C)ccc1-n1cc(C)c2c(N3CCCC(C#N)C3)nc(C)nc21]

1-[7-(2-bromo-4-trifluoromethyl-phenyl)-2,5,6-trimethyl-7H-pyrrolo[2,3-d]pyrimidin-4-yl]-piperidine-3-carbonitrile,

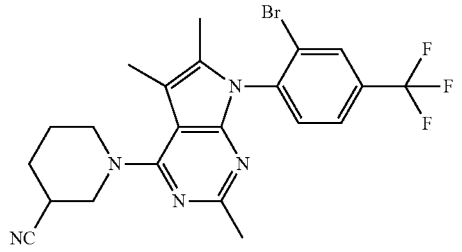 [SMILES: Cc1nc(N2CCCC(C#N)C2)c2c(C)c(C)n(-c3ccc(C(F)(F)F)cc3Br)c2n1]

1-[7-(4-bromo-2,6-diethyl-phenyl)-2,5,6-trimethyl-7H-pyrrolo[2,3-d]pyrimidin-4-yl]-piperidine-3-carbonitrile,

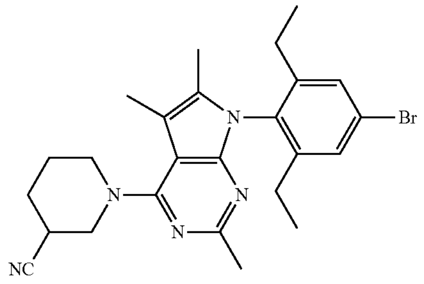 [SMILES: CCc1cc(Br)cc(CC)c1-n1c(C)c(C)c2c(N3CCCC(C#N)C3)nc(C)nc21]

1-[7-(4-bromo-2,6-diethyl-phenyl)-2,5-dimethyl-7H-pyrrolo[2,3-d]pyrimidin-4-yl]-piperidine-3-carbonitrile,

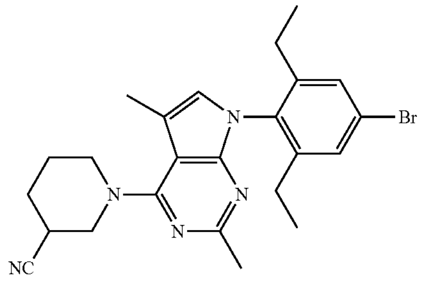 [SMILES: CCc1cc(Br)cc(CC)c1-n1cc(C)c2c(N3CCCC(C#N)C3)nc(C)nc21]

{1-[7-(2,6-dibromo-4-trifluoromethyl-phenyl)-2,5,6-trimethyl-7H-pyrrolo[2,3-d]pyrimidin-4-yl]-piperidin-3-yl}-acetonitrile,

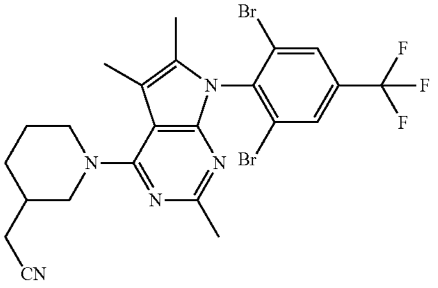 [SMILES: Cc1nc(N2CCCC(CC#N)C2)c2c(C)c(C)n(-c3c(Br)cc(C(F)(F)F)cc3Br)c2n1]

{1-[7-(4-bromo-2,6-dimethyl-phenyl)-2,5,6-trimethyl-7H-pyrrolo[2,3-d]pyrimidin-4-yl]-piperidin-3-yl}-acetonitrile,

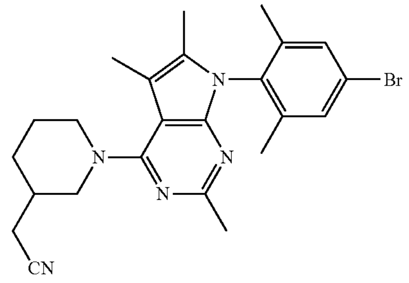 [SMILES: Cc1nc(N2CCCC(CC#N)C2)c2c(C)c(C)n(-c3c(C)cc(Br)cc3C)c2n1]

{1-[7-(4-bromo-2,6-dimethyl-phenyl)-2,5-dimethyl-7H-pyrrolo[2,3-d]pyrimidin-4-yl]-piperidin-3-yl}-acetonitrile,

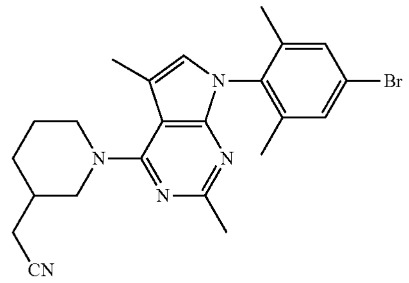 [SMILES: Cc1nc(N2CCCC(CC#N)C2)c2c(C)cn(-c3c(C)cc(Br)cc3C)c2n1]

3-{1-[7-(4-bromo-2,6-dimethyl-phenyl)-2,5,6-trimethyl-7H-pyrrolo[2,3-d]pyrimidin-4-yl]-piperidin-3-yl}-propionitrile,

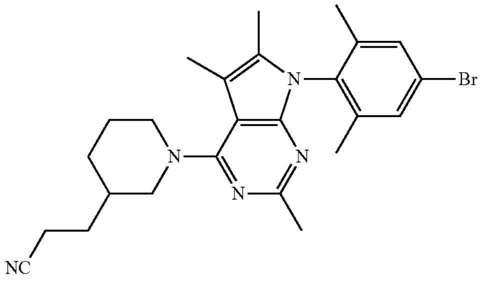 [SMILES: Cc1nc(N2CCCC(CCC#N)C2)c2c(C)c(C)n(-c3c(C)cc(Br)cc3C)c2n1]

3-{1-[7-(4-bromo-2,6-dimethyl-phenyl)-2,5-dimethyl-7H-pyrrolo[2,3-d]pyrimidin-4-yl]-piperidin-3-yl}-propionitrile,

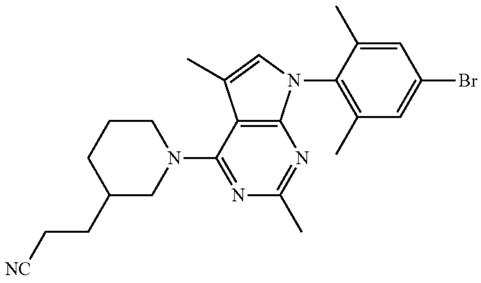 [SMILES: Cc1nc(N2CCCC(CCC#N)C2)c2c(C)cn(-c3c(C)cc(Br)cc3C)c2n1]

1-[7-(4-bromo-2,6-dimethyl-phenyl)-2,5,6-trimethyl-7H-pyrrolo[2,3-d]pyrimidin-4-yl]-piperidine-4-carbonitrile,

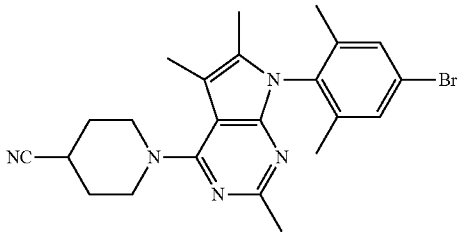

1-[7-(4-bromo-2,6-dimethyl-phenyl)-2,5-dimethyl-7H-pyrrolo[2,3-d]pyrimidin-4-yl]-piperidine-4-carbonitrile,

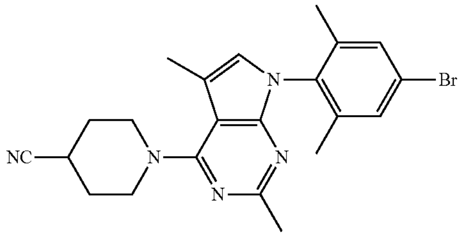

{1-[2,5,6-trimethyl-7-(2,4,6-trimethyl-phenyl)-7H-pyrrolo[2,3-d]pyrimidin-4-yl]-piperidin-4-yl}-acetonitrile,

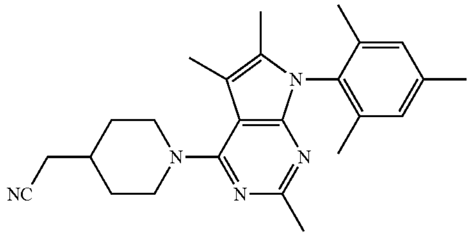

{1-[7-(2,6-dibromo-4-trifluoromethyl-phenyl)-2,5,6-trimethyl-7H-pyrrolo[2,3-d]pyrimidin-4-yl]-piperidin-4-yl}-acetonitrile,

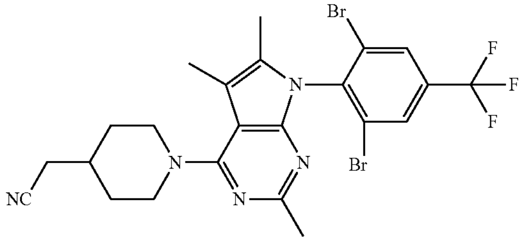 [SMILES: Cc1nc(N2CCC(CC#N)CC2)c2c(C)c(C)n(-c3c(Br)cc(C(F)(F)F)cc3Br)c2n1]

{1-[7-(4-bromo-2,6-dimethyl-phenyl)-2,5,6-trimethyl-7H-pyrrolo[2,3-d]pyrimidin-4-yl]-piperidin-4-yl}-acetonitrile,

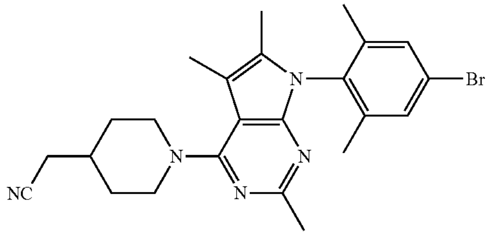 [SMILES: Cc1nc(N2CCC(CC#N)CC2)c2c(C)c(C)n(-c3c(C)cc(Br)cc3C)c2n1]

{1-[7-(4-bromo-2,6-dimethyl-phenyl)-2,5-dimethyl-7H-pyrrolo[2,3-d]pyrimidin-4-yl]-piperidin-4-yl}-acetonitrile,

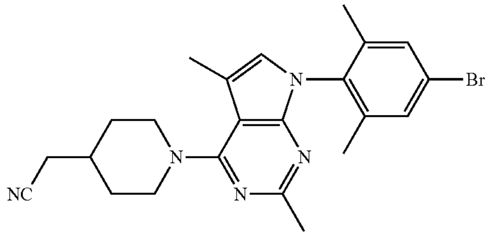 [SMILES: Cc1nc(N2CCC(CC#N)CC2)c2c(C)cn(-c3c(C)cc(Br)cc3C)c2n1]

{1-[7-(4-bromo-2,6-diethyl-phenyl)-2,5,6-trimethyl-7H-pyrrolo[2,3-d]pyrimidin-4-yl]-piperidin-4-yl}-acetonitrile,

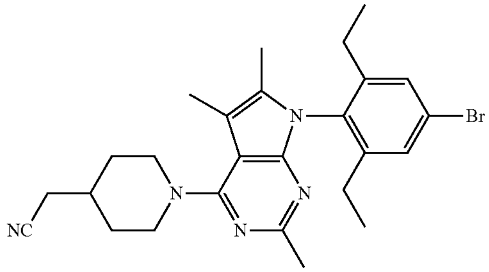 [SMILES: CCc1cc(Br)cc(CC)c1-n1c(C)c(C)c2c(N3CCC(CC#N)CC3)nc(C)nc21]

{1-[7-(4-bromo-2,6-diethyl-phenyl)-2,5-dimethyl-7H-pyrrolo[2,3-d]pyrimidin-4-yl]-piperidin-4-yl}-acetonitrile,

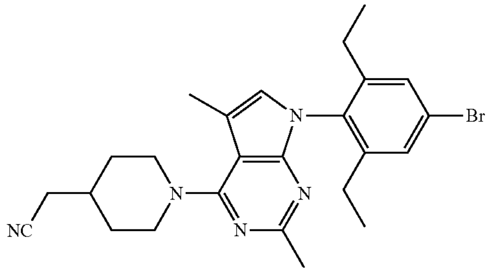 [SMILES: CCc1cc(Br)cc(CC)c1-n1cc(C)c2c(N3CCC(CC#N)CC3)nc(C)nc21]

{1-[2,5,6-trimethyl-7-(2,4,6-tribromo-phenyl)-7H-pyrrolo[2,3-d]pyrimidin-4-yl]-piperidin-4-yl}-acetonitrile,

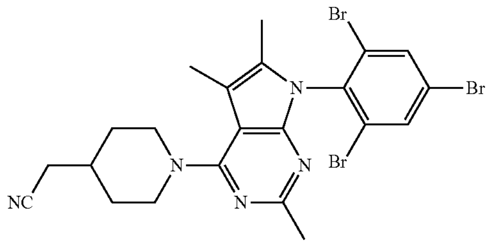 [SMILES: Cc1nc(N2CCC(CC#N)CC2)c2c(C)c(C)n(-c3c(Br)cc(Br)cc3Br)c2n1]

{1-[2,5-dimethyl-7-(2,4,6-tribromo-phenyl)-7H-pyrrolo[2,3-d]pyrimidin-4-yl]-piperidin-4-yl}-acetonitrile,

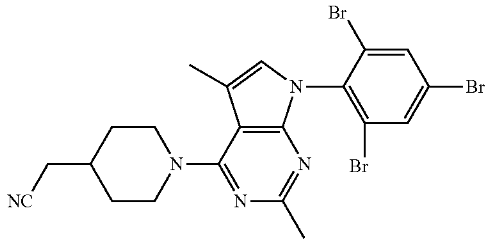 [SMILES: Cc1nc(N2CCC(CC#N)CC2)c2c(C)cn(-c3c(Br)cc(Br)cc3Br)c2n1]

{1-[7-(4-bromo-2,6-dichloro-phenyl)-2,5,6-trimethyl-7H-pyrrolo[2,3-d]pyrimidin-4-yl]-piperidin-4-yl}-acetonitrile,

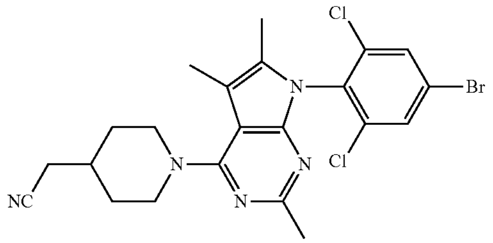 [SMILES: Cc1nc(N2CCC(CC#N)CC2)c2c(C)c(C)n(-c3c(Cl)cc(Br)cc3Cl)c2n1]

{1-[7-(4-bromo-2,6-dichloro-phenyl)-2,5-dimethyl-7H-pyrrolo[2,3-d]pyrimidin-4-yl]-piperidin-4-yl}-acetonitrile,

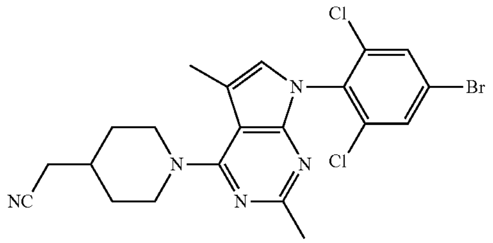 [SMILES: Cc1nc(N2CCC(CC#N)CC2)c2c(C)cn(-c3c(Cl)cc(Br)cc3Cl)c2n1]

{1-[7-(2,6-dibromo-4-isopropyl-phenyl)-2,5,6-trimethyl-7H-pyrrolo[2,3-d]pyrimidin-4-yl]-piperidin-4-yl}-acetonitrile,

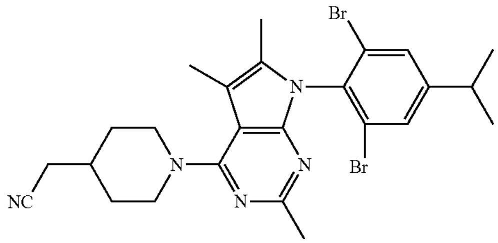 [SMILES: Cc1nc(N2CCC(CC#N)CC2)c2c(C)c(C)n(-c3c(Br)cc(C(C)C)cc3Br)c2n1]

{1-[7-(2,6-dibromo-4-isopropyl-phenyl)-2,5-dimethyl-7H-pyrrolo[2,3-d]pyrimidin-4-yl]-piperidin-4-yl}-acetonitrile,

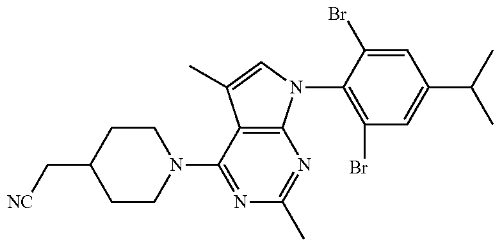 [SMILES: Cc1nc(N2CCC(CC#N)CC2)c2c(C)cn(-c3c(Br)cc(C(C)C)cc3Br)c2n1]

{1-[7-(4-methoxy-2,6-dimethyl-phenyl)-2,5,6-trimethyl-7H-pyrrolo[2,3-d]pyrimidin-4-yl]-piperidin-4-yl}-acetonitrile,

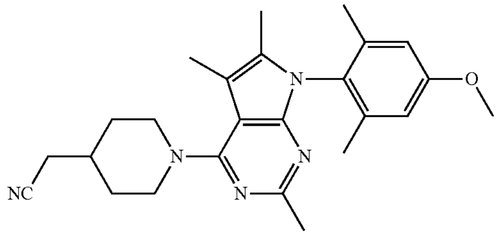 [SMILES: COc1cc(C)c(-n2c(C)c(C)c3c(N4CCC(CC#N)CC4)nc(C)nc32)c(C)c1]

{1-[7-(4-methoxy-2,6-dimethyl-phenyl)-2,5-dimethyl-7H-pyrrolo[2,3-d]pyrimidin-4-yl]-piperidin-4-yl}-acetonitrile,

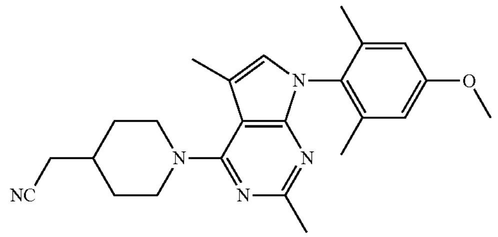 [SMILES: COc1cc(C)c(-n2cc(C)c3c(N4CCC(CC#N)CC4)nc(C)nc32)c(C)c1]

{1-[7-(4-chloro-2,6-dimethyl-phenyl)-2,5,6-trimethyl-7H-pyrrolo[2,3-d]pyrimidin-4-yl]-piperidin-4-yl}-acetonitrile,

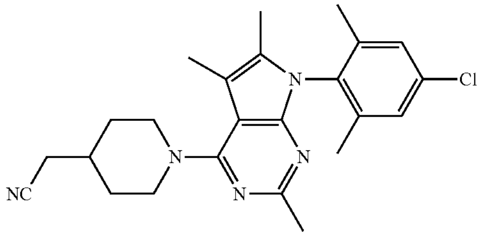 [SMILES: Cc1nc(N2CCC(CC#N)CC2)c2c(C)c(C)n(-c3c(C)cc(Cl)cc3C)c2n1]

{1-[7-(4-chloro-2,6-dimethyl-phenyl)-2,5-dimethyl-7H-pyrrolo[2,3-d]pyrimidin-4-yl]-piperidin-4-yl}-acetonitrile,

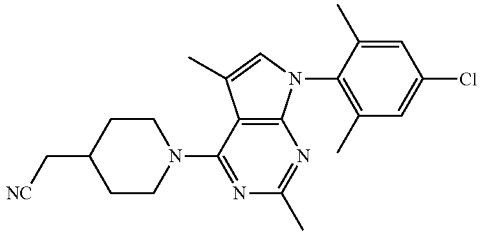 [SMILES: Cc1nc(N2CCC(CC#N)CC2)c2c(C)cn(-c3c(C)cc(Cl)cc3C)c2n1]

8-[7-(4-bromo-2,6-dimethyl-phenyl)-2,5,6-trimethyl-7H-pyrrolo[2,3-d]pyrimidin-4-yl]-8-aza-bicyclo[3.2.1]octane-3-carbonitrile,

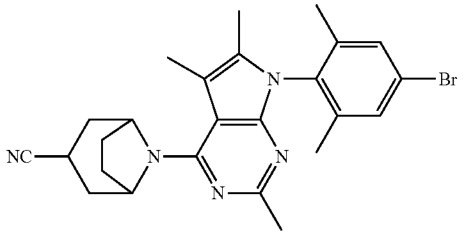 [SMILES: Cc1nc(N2C3CCC2CC(C#N)C3)c2c(C)c(C)n(-c3c(C)cc(Br)cc3C)c2n1]

8-[7-(4-bromo-2,6-dimethyl-phenyl)-2,5-dimethyl-7H-pyrrolo[2,3-d]pyrimidin-4-yl]-8-aza-bicyclo[3.2.1]octane-3-carbonitrile,

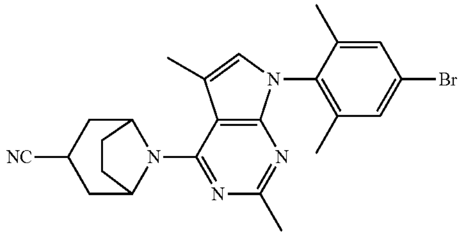 [SMILES: Cc1nc(N2C3CCC2CC(C#N)C3)c2c(C)cn(-c3c(C)cc(Br)cc3C)c2n1]

1-[7-(4-bromo-2,6-dimethyl-phenyl)-2,5,6-trimethyl-7H-pyrrolo[2,3-d]pyrimidin-4-yl]-pyrrolidine-3-carbonitrile,

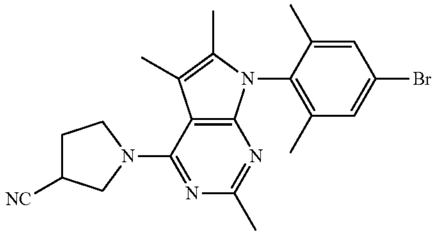 [SMILES: Cc1nc(N2CCC(C#N)C2)c2c(C)c(C)n(-c3c(C)cc(Br)cc3C)c2n1]

1-[7-(4-bromo-2,6-dimethyl-phenyl)-2,5-dimethyl-7H-pyrrolo[2,3-d]pyrimidin-4-yl]-pyrrolidine-3-carbonitrile,

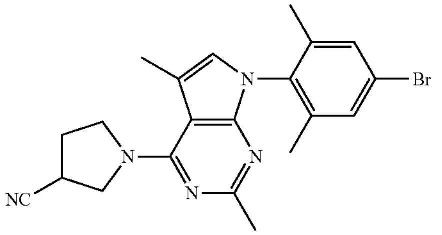 [SMILES: Cc1nc(N2CCC(C#N)C2)c2c(C)cn(-c3c(C)cc(Br)cc3C)c2n1]

1-[7-(4-bromo-2,6-dimethyl-phenyl)-2,5,6-trimethyl-7H-pyrrolo[2,3-d]pyrimidin-4-yl]-azepane-4-carbonitrile,

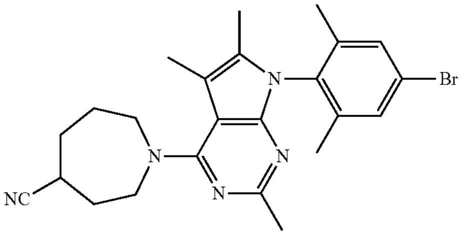 [SMILES: Cc1nc(N2CCCC(C#N)CC2)c2c(C)c(C)n(-c3c(C)cc(Br)cc3C)c2n1]

1-[7-(4-bromo-2,6-dimethyl-phenyl)-2,5-dimethyl-7H-pyrrolo[2,3-d]pyrimidin-4-yl]-azepane-4-carbonitrile,

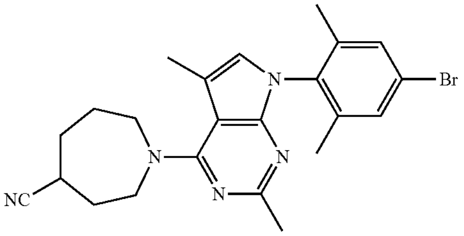 [SMILES: Cc1nc(N2CCCC(C#N)CC2)c2c(C)cn(-c3c(C)cc(Br)cc3C)c2n1]

1-[7-(4-bromo-2,6-dimethyl-phenyl)-2,5,6-trimethyl-7H-pyrrolo[2,3-d]pyrimidin-4-yl]-3-hydroxymethyl-piperidine-3-carbonitrile,

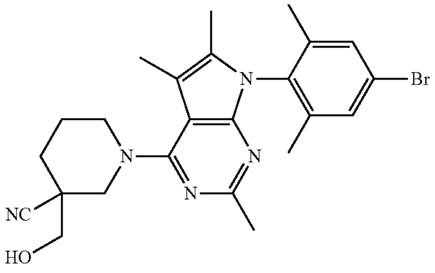 [SMILES: Cc1nc(N2CCCC(C#N)(CO)C2)c2c(C)c(C)n(-c3c(C)cc(Br)cc3C)c2n1]

{1-[7-(4-isopropyl-2-methylsulfanyl-phenyl)-2,5-dimethyl-7H-pyrrolo[2,3-d]pyrimidin-4-yl]-piperidin-4-yl}-methanol,

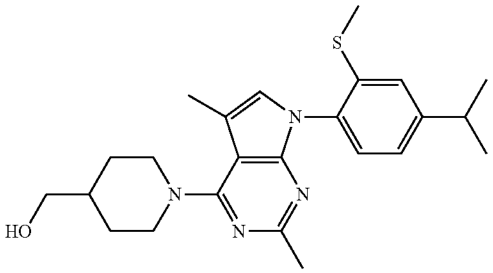

{1-[7-(2-bromo-4-isopropyl-phenyl)-2,5-dimethyl-7H-pyrrolo[2,3-d]pyrimidin-4-yl]-piperidin-4-yl}-methanol,

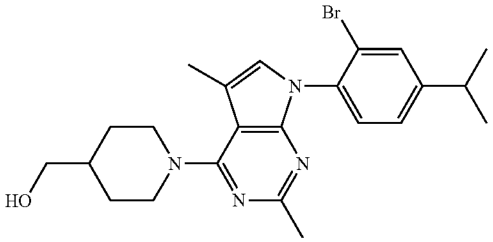

{1-[7-(2,4-dibromo-phenyl)-2,5-dimethyl-7H-pyrrolo[2,3-d]pyrimidin-4-yl]-piperidin-4-yl}-methanol,

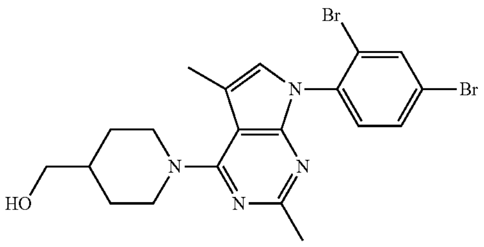

{1-[7-(2,6-dibromo-4-chloro-phenyl)-2,5-dimethyl-7H-pyrrolo[2,3-d]pyrimidin-4-yl]-piperidin-4-yl}-methanol,

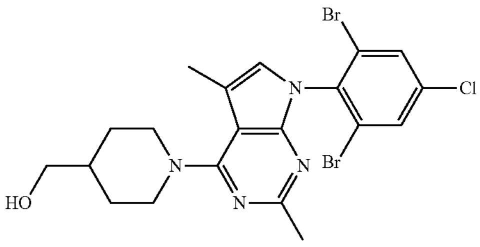 [SMILES: Cc1nc(N2CCC(CC#N)CC2)c2c(C)cn(-c3c(Br)cc(Cl)cc3Br)c2n1]

2-{1-[7-(2,6-dibromo-4-chloro-phenyl)-2,5-dimethyl-7H-pyrrolo[2,3-d]pyrimidin-4-yl]-piperidin-4-yl}-ethanol,

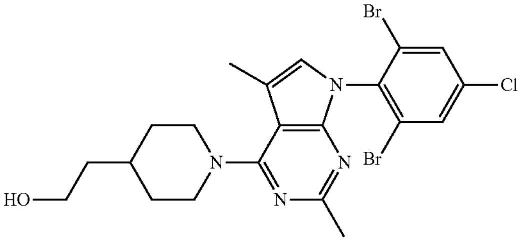

1-{1-[7-(4-bromo-2,6-dimethyl-phenyl)-2,5,6-trimethyl-7H-pyrrolo[2,3-d]pyrimidin-4-yl]-piperidin-4-yl}-propane-1,3-diol,

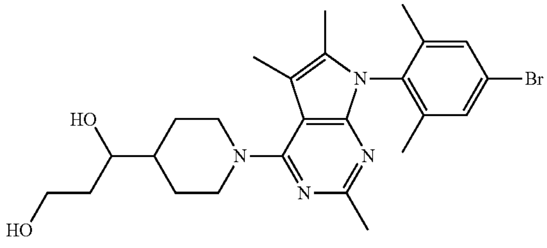

{1-[7-(2,6-dibromo-4-chloro-phenyl)-2,5-dimethyl-7H-pyrrolo[2,3-d]pyrimidin-4-yl]-piperidin-4-yl}-acetonitrile,

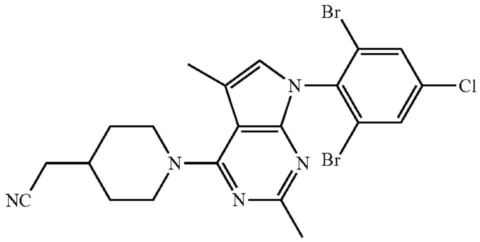

{1-[7-(4-bromo-2,6-dimethyl-phenyl)-2,5,6-trimethyl-7H-pyrrolo[2,3-d]pyrimidin-4-yl]-pyrrolidin-3-yl}-acetonitrile,

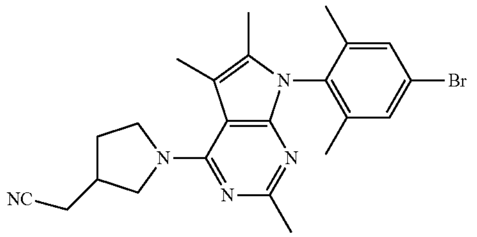 [SMILES: Cc1nc(N2CCC(CC#N)C2)c2c(C)c(C)n(-c3c(C)cc(Br)cc3C)c2n1]

{1-[7-(4-bromo-2,6-dimethyl-phenyl)-2,5-dimethyl-7H-pyrrolo[2,3-d]pyrimidin-4-yl]-pyrrolidin-3-yl}-acetonitrile,

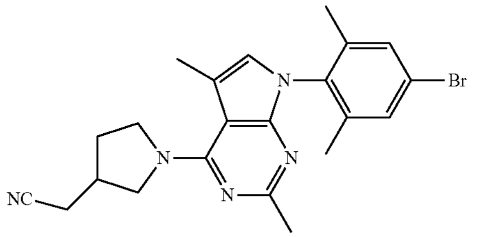 [SMILES: Cc1nc(N2CCC(CC#N)C2)c2c(C)cn(-c3c(C)cc(Br)cc3C)c2n1]

{1-[2,5-dimethyl-7-(2,4,6-trichloro-phenyl)-7H-pyrrolo[2,3-d]pyrimidin-4-yl]-piperidin-4-yl}-methanol,

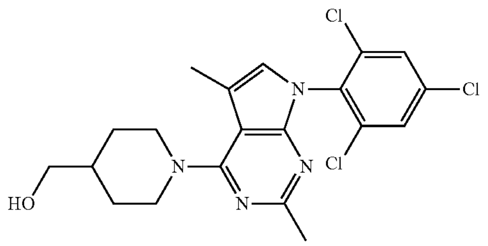

{1-[7-(2,6-dichloro-4-trifluoromethyl-phenyl)-2,5-dimethyl-7H-pyrrolo[2,3-d]pyrimidin-4-yl]-piperidin-4-yl}-methanol,

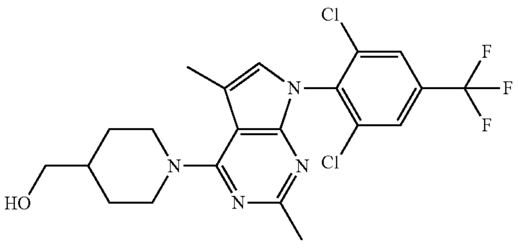 [SMILES: Cc1nc(N2CCC(CO)CC2)c2c(C)cn(-c3c(Cl)cc(C(F)(F)F)cc3Cl)c2n1]

3-{1-[7-(4-chloro-2,6-dimethyl-phenyl)-2,5,6-trimethyl-7H-pyrrolo[2,3-d]pyrimidin-4-yl]-piperidin-4-yl}-propan-1-ol,

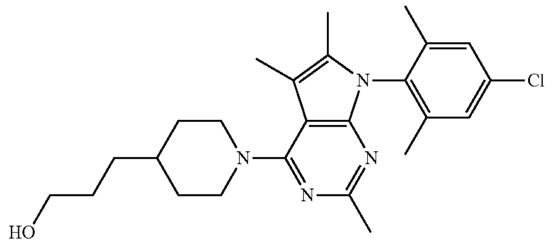

1-[7-(4-chloro-2,6-dimethyl-phenyl)-2,5,6-trimethyl-7H-pyrrolo[2,3-d]pyrimidin-4-yl]-piperidine-4-carbonitrile,

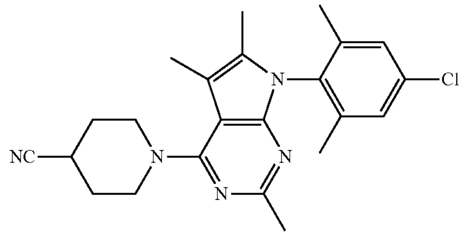 [SMILES: Cc1nc(N2CCC(C#N)CC2)c2c(C)c(C)n(-c3c(C)cc(Cl)cc3C)c2n1]

{1-[7-(2,6-Dichloro-4-trifluoromethyl-phenyl)-2,5-dimethyl-7H-pyrrolo[2,3-d]pyrimidin-4-yl]-piperidin-4-yl}-acetonitrile,

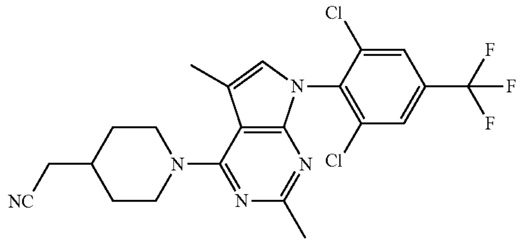

1-[7-(4-bromo-2,6-dimethyl-phenyl)-2,5,6-trimethyl-7H-pyrrolo[2,3-d]pyrimidin-4-yl]-azetidine-3-carbonitrile,

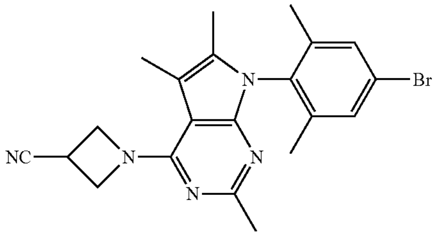 [SMILES: Cc1nc(N2CC(C#N)C2)c2c(C)c(C)n(-c3c(C)cc(Br)cc3C)c2n1]

1-{1-[7-(4-bromo-2,6-dimethyl-phenyl)-2,5,6-trimethyl-7H-pyrrolo[2,3-d]pyrimidin-4-yl]-piperidin-4-yl}-ethanol,

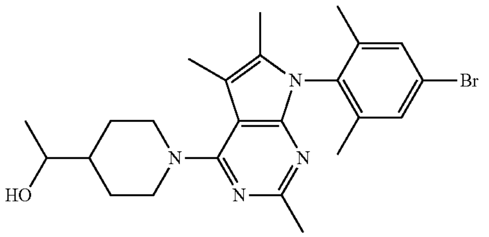 [SMILES: Cc1nc(N2CCC(C(C)O)CC2)c2c(C)c(C)n(-c3c(C)cc(Br)cc3C)c2n1]

1-{1-[7-(4-isopropyl-2-methylsulfanyl-phenyl)-2,5-dimethyl-7H-pyrrolo[2,3-d]pyrimidin-4-yl]-piperidin-4-yl}-ethanol,

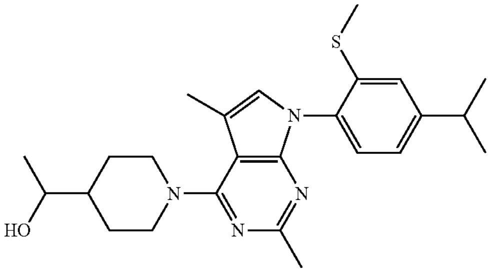

1-{1-[7-(4-chloro-2,6-dimethyl-phenyl)-2,5,6-trimethyl-7H-pyrrolo[2,3-d]pyrimidin-4-yl]-piperidin-4-yl}-ethanol,

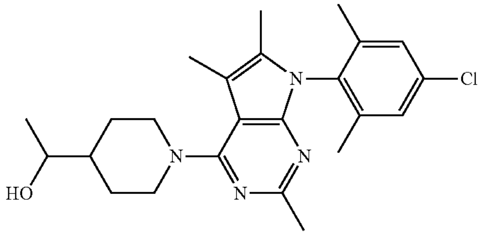

1-{1-[7-(4-chloro-2,6-dimethyl-phenyl)-2,5-dimethyl-7H-pyrrolo[2,3-d]pyrimidin-4-yl]-piperidin-4-yl}-ethanol,

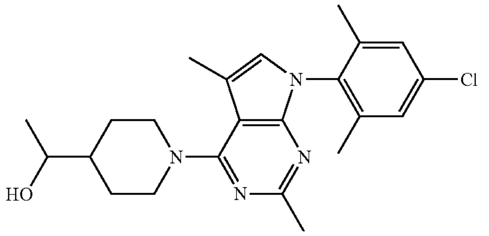

{1-[7-(4-bromo-2,6-dimethyl-phenyl)-2,5,6-trimethyl-7H-pyrrolo[2,3-d]pyrimidin-4-yl]-3-methyl-piperidin-4-yl}-methanol,

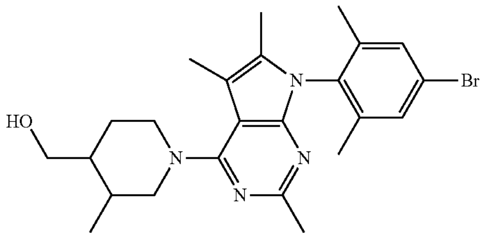 [SMILES: Cc1nc(N2CCC(CO)C(C)C2)c2c(C)c(C)n(-c3c(C)cc(Br)cc3C)c2n1]

{1-[7-(4-bromo-2,6-dimethyl-phenyl)-2,5-dimethyl-7H-pyrrolo[2,3-d]pyrimidin-4-yl]-3-methyl-piperidin-4-yl}-methanol,

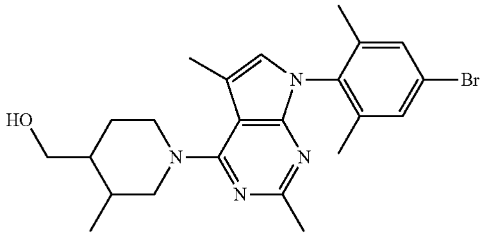 [SMILES: Cc1nc(N2CCC(CO)C(C)C2)c2c(C)cn(-c3c(C)cc(Br)cc3C)c2n1]

{8-[7-(4-bromo-2,6-dimethyl-phenyl)-2,5,6-trimethyl-7H-pyrrolo[2,3-d]pyrimidin-4-yl]-8-aza-bicyclo[3.2.1]oct-3-yl}-methanol,

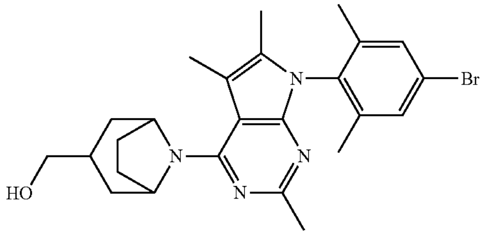 [SMILES: Cc1nc(N2C3CCC2CC(CC#N)C3)c2c(C)c(C)n(-c3c(C)cc(Br)cc3C)c2n1]

{8-[7-(4-bromo-2,6-dimethyl-phenyl)-2,5-dimethyl-7H-pyrrolo[2,3-d]pyrimidin-4-yl]-8-aza-bicyclo[3.2.1]oct-3-yl}-methanol,

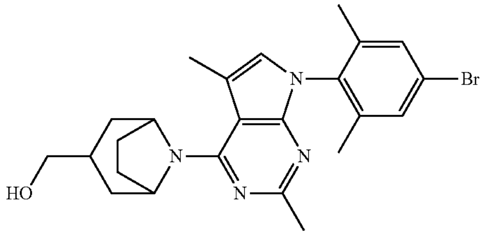 [SMILES: Cc1nc(N2C3CCC2CC(CC#N)C3)c2c(C)cn(-c3c(C)cc(Br)cc3C)c2n1]

{8-[7-(4-bromo-2,6-dimethyl-phenyl)-2,5,6-trimethyl-7H-pyrrolo[2,3-d]pyrimidin-4-yl]-8-aza-bicyclo[3.2.1]oct-3-yl}-acetonitrile,

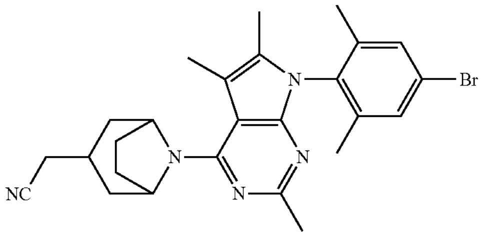

{8-[7-(4-bromo-2,6-dimethyl-phenyl)-2,5-dimethyl-7H-pyrrolo[2,3-d]pyrimidin-4-yl]-8-aza-bicyclo[3.2.1]oct-3-yl}-acetonitrile,

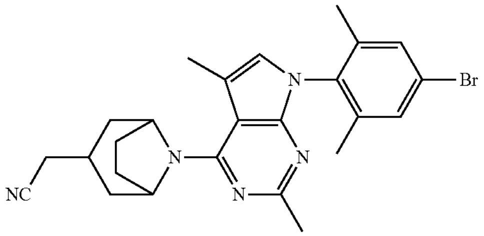

2-{1-[7-(4-bromo-2,6-dimethyl-phenyl)-2,5,6-trimethyl-7H-pyrrolo[2,3-d]pyrimidin-4-yl]-piperidin-4-yl}-malononitrile,

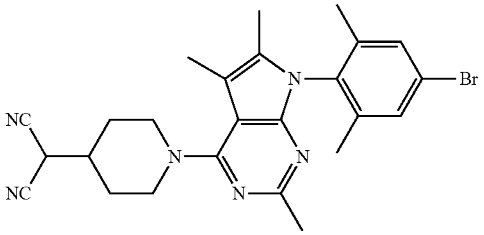 [SMILES: Cc1nc(N2CCC(C(C#N)C#N)CC2)c2c(C)c(C)n(-c3c(C)cc(Br)cc3C)c2n1]

2-{1-[7-(4-bromo-2,6-dimethyl-phenyl)-2,5-dimethyl-7H-pyrrolo[2,3-d]pyrimidin-4-yl]-piperidin-4-yl}-malononitrile,

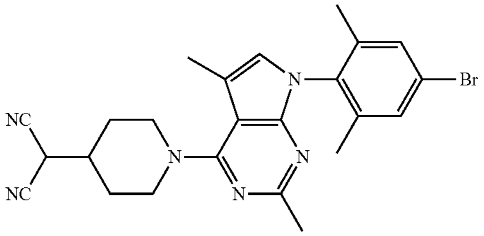 [SMILES: Cc1nc(N2CCC(C(C#N)C#N)CC2)c2c(C)cn(-c3c(C)cc(Br)cc3C)c2n1]

2-{1-[1-(2,4-dichloro-phenyl)-2,3,6-trimethyl-1H-pyrrolo[2,3-b]pyridin-4-yl]-piperidin-3-yl}-ethanol,

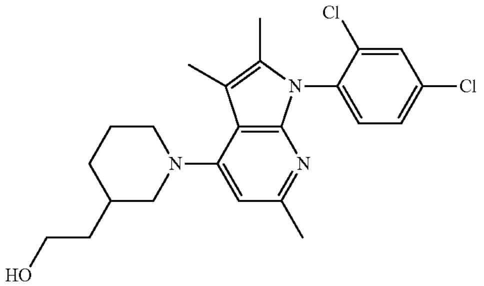 [SMILES: Cc1cc(N2CCCC(CCO)C2)c2c(C)c(C)n(-c3ccc(Cl)cc3Cl)c2n1]

2-{1-[1-(4-bromo-2,6-dimethyl-phenyl)-3,6-dimethyl-1H-pyrrolo[2,3-b]pyridin-4-yl]-piperidin-3-yl}-ethanol,

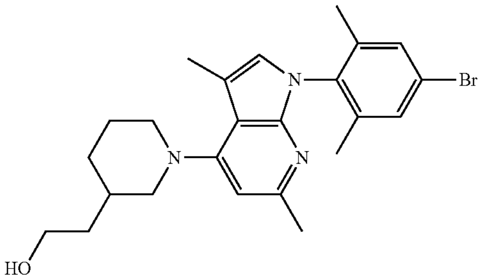

{1-[1-(2,4-dichloro-phenyl)-2,3,6-trimethyl-1H-pyrrolo[2,3-b]pyridin-4-yl]-piperidin-4-yl}-methanol,

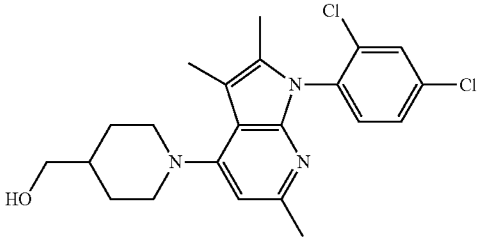

{1-[1-(4-bromo-2,6-dimethyl-phenyl)-3,6-dimethyl-1H-pyrrolo[2,3-b]pyridin-4-yl]-piperidin-4-yl}-methanol,

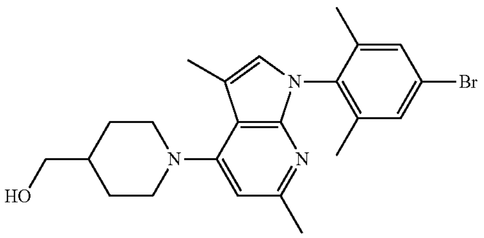

2-{1-[1-(2,4-dichloro-phenyl)-2,3,6-trimethyl-1H-pyrrolo[2,3-b]pyridin-4-yl]-piperidin-4-yl}-ethanol,

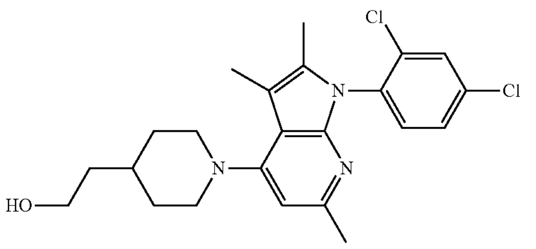

2-{1-[1-(4-bromo-2,6-dimethyl-phenyl)-3,6-dimethyl-1H-pyrrolo[2,3-b]pyridin-4-yl]-piperidin-4-yl}-ethanol,

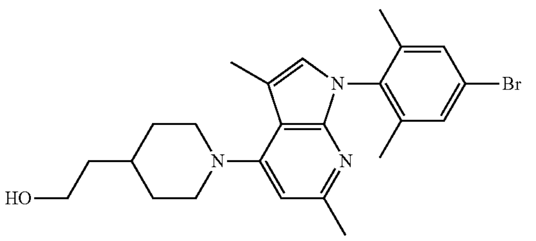 [SMILES: Cc1cc(N2CCC(CCO)CC2)c2c(C)cn(-c3c(C)cc(Br)cc3C)c2n1]

3-{1-[1-(2,4-dichloro-phenyl)-2,3,6-trimethyl-1H-pyrrolo[2,3-b]pyridin-4-yl]-piperidin-4-yl}-propan-1-ol,

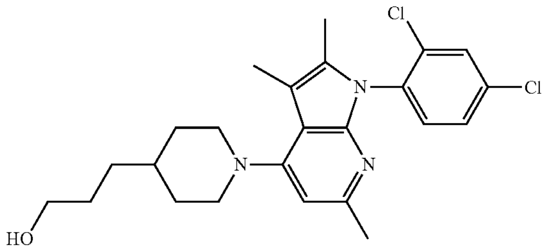 [SMILES: Cc1cc(N2CCC(CCCO)CC2)c2c(C)c(C)n(-c3ccc(Cl)cc3Cl)c2n1]

3-{1-[1-(4-bromo-2,6-dimethyl-phenyl)-3,6-dimethyl-1H-pyrrolo[2,3-b]pyridin-4-yl]-piperidin-4-yl}-propan-1-ol,

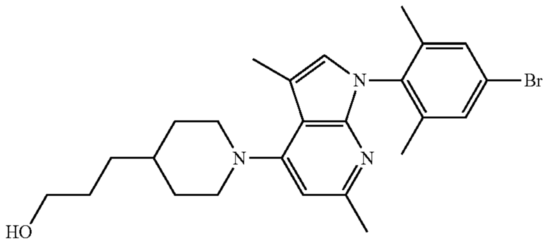

1-[1-(2,4-dichloro-phenyl)-2,3,6-trimethyl-1H-pyrrolo[2,3-b]pyridin-4-yl]-piperidine-3-carbonitrile,

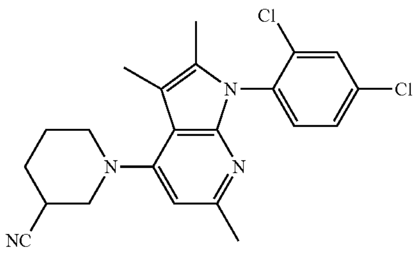 [SMILES: Cc1cc(N2CCCC(C#N)C2)c2c(C)c(C)n(-c3ccc(Cl)cc3Cl)c2n1]

1-[1-(4-bromo-2,6-dimethyl-phenyl)-3,6-dimethyl-1H-pyrrolo[2,3-b]pyridin-4-yl]-piperidine-3-carbonitrile,

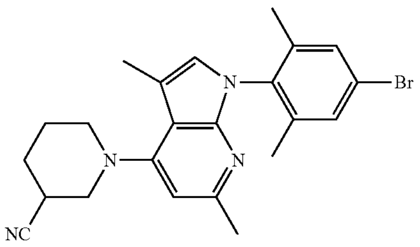 [SMILES: Cc1cc(N2CCCC(C#N)C2)c2c(C)cn(-c3c(C)cc(Br)cc3C)c2n1]

{1-[1-(2,4-dichloro-phenyl)-2,3,6-trimethyl-1H-pyrrolo[2,3-b]pyridin-4-yl]-piperidin-3-yl}-acetonitrile,

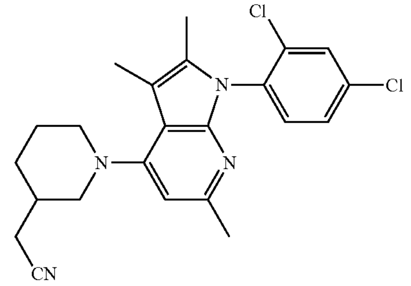 [SMILES: Cc1cc(N2CCCC(CC#N)C2)c2c(C)c(C)n(-c3ccc(Cl)cc3Cl)c2n1]

1-[1-(2,4-dichloro-phenyl)-2,3,6-trimethyl-1H-pyrrolo[2,3-b]pyridin-4-yl]-piperidine-4-carbonitrile,

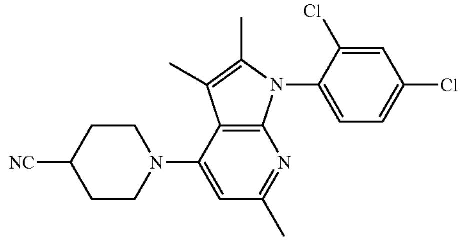 [SMILES: Cc1cc(N2CCC(C#N)CC2)c2c(C)c(C)n(-c3ccc(Cl)cc3Cl)c2n1]

1-[1-(4-bromo-2,6-dimethyl-phenyl)-3,6-dimethyl-1H-pyrrolo[2,3-b]pyridin-4-yl]-piperidine-4-carbonitrile,

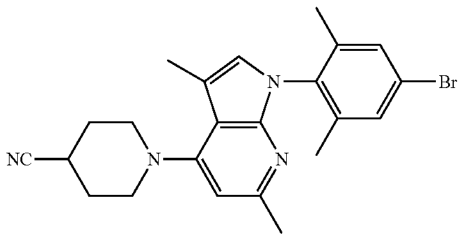 [SMILES: Cc1cc(N2CCC(C#N)CC2)c2c(C)cn(-c3c(C)cc(Br)cc3C)c2n1]

{1-[1-(2,4-dichloro-phenyl)-2,3,6-trimethyl-1H-pyrrolo[2,3-b]pyridin-4-yl]-piperidin-4-yl}-acetonitrile,

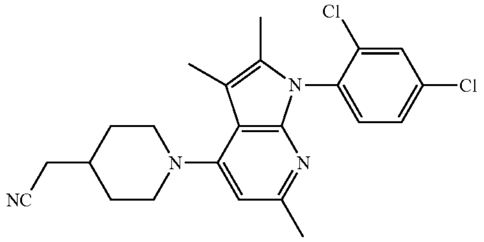 [SMILES: Cc1cc(N2CCC(CC#N)CC2)c2c(C)c(C)n(-c3ccc(Cl)cc3Cl)c2n1]

2-{1-[1-(4-bromo-2,6-dimethyl-phenyl)-2,3,6-trimethyl-1H-pyrrolo[2,3-b]pyridin-4-yl]-piperidin-3-yl}-ethanol,

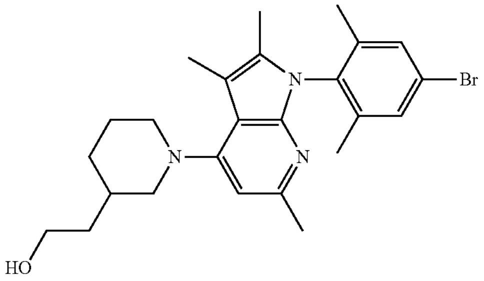 [SMILES: Cc1cc(N2CCCC(CCO)C2)c2c(C)c(C)n(-c3c(C)cc(Br)cc3C)c2n1]

{1-[1-(4-bromo-2,6-dimethyl-phenyl)-2,3,6-trimethyl-1H-pyrrolo[2,3-b]pyridin-4-yl]-piperidin-4-yl}-methanol,

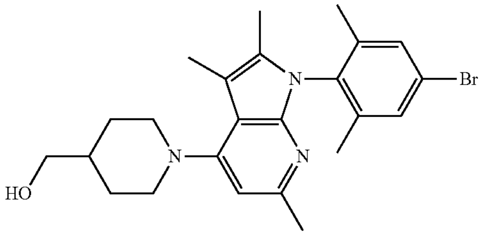 [SMILES: Cc1cc(N2CCC(CO)CC2)c2c(C)c(C)n(-c3c(C)cc(Br)cc3C)c2n1]

{1-[1-(4-chloro-2,6-dimethyl-phenyl)-2,3,6-trimethyl-1H-pyrrolo[2,3-b]pyridin-4-yl]-piperidin-4-yl}-methanol,

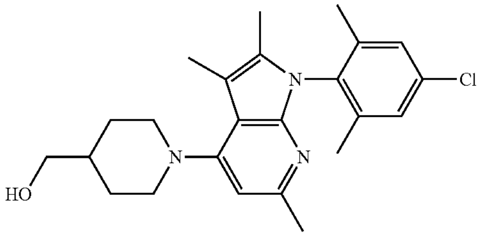

{1-[1-(4-chloro-2,6-dimethyl-phenyl)-3,6-dimethyl-1H-pyrrolo[2,3-b]pyridin-4-yl]-piperidin-4-yl}-methanol,

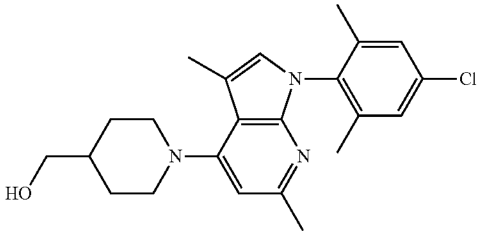

2-{1-[1-(4-bromo-2,6-dimethyl-phenyl)-2,3,6-trimethyl-1H-pyrrolo[2,3-b]pyridin-4-yl]-piperidin-4-yl}-ethanol,

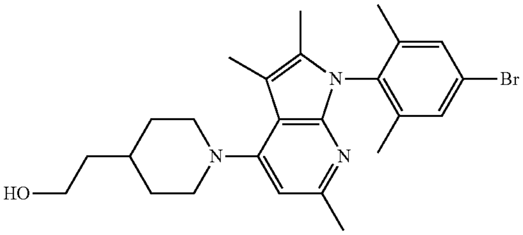 [SMILES: Cc1cc(N2CCC(CCO)CC2)c2c(C)c(C)n(-c3c(C)cc(Br)cc3C)c2n1]

2-{1-[1-(4-chloro-2,6-dimethyl-phenyl)-2,3,6-trimethyl-1H-pyrrolo[2,3-b]pyridin-4-yl]-piperidin-4-yl}-ethanol,

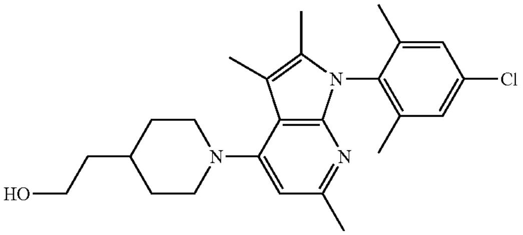 [SMILES: Cc1cc(N2CCC(CCO)CC2)c2c(C)c(C)n(-c3c(C)cc(Cl)cc3C)c2n1]

2-{1-[1-(4-chloro-2,6-dimethyl-phenyl)-3,6-dimethyl-1H-pyrrolo[2,3-b]pyridin-4-yl]-piperidin-4-yl}-ethanol,

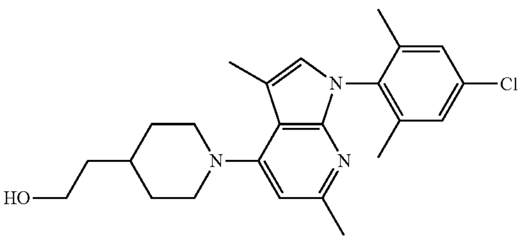

3-{1-[1-(4-bromo-2,6-dimethyl-phenyl)-2,3,6-trimethyl-1H-pyrrolo[2,3-b]pyridin-4-yl]-piperidin-4-yl}-propan-1-ol,

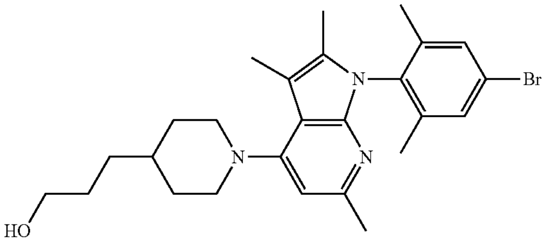 [SMILES: Cc1cc(N2CCC(CCCO)CC2)c2c(C)c(C)n(-c3c(C)cc(Br)cc3C)c2n1]

3-{1-[1-(4-chloro-2,6-dimethyl-phenyl)-2,3,6-trimethyl-1H-pyrrolo[2,3-b]pyridin-4-yl]-piperidin-4-yl}-propan-1-ol,

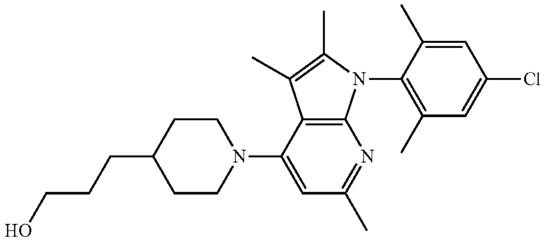

3-{1-[1-(4-chloro-2,6-dimethyl-phenyl)-3,6-dimethyl-1H-pyrrolo[2,3-b]pyridin-4-yl]-piperidin-4-yl}-propan-1-ol,

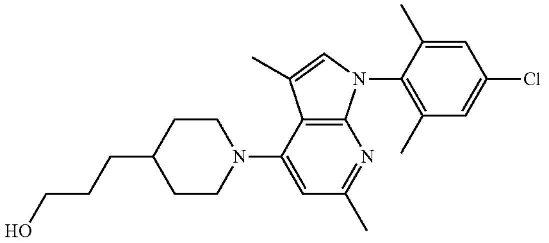 [SMILES: Cc1cc(N2CCC(CCCO)CC2)c2c(C)cn(-c3c(C)cc(Cl)cc3C)c2n1]

1-[1-(4-bromo-2,6-dimethyl-phenyl)-2,3,6-trimethyl-1H-pyrrolo[2,3-b]pyridin-4-yl]-piperidine-3-carbonitrile,

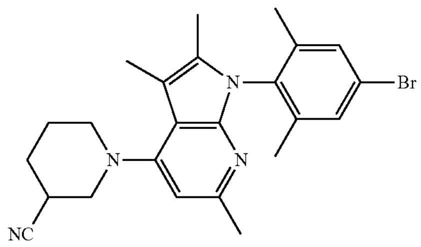

1-[1-(4-bromo-2,6-dimethyl-phenyl)-2,3,6-trimethyl-1H-pyrrolo[2,3-b]pyridin-4-yl]-piperidine-4-carbonitrile,

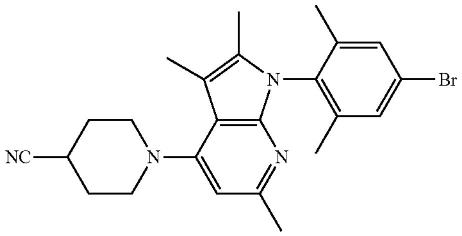 [SMILES: Cc1cc(N2CCC(C#N)CC2)c2c(C)c(C)n(-c3c(C)cc(Br)cc3C)c2n1]

1-[1-(4-chloro-2,6-dimethyl-phenyl)-2,3,6-trimethyl-1H-pyrrolo[2,3-b]pyridin-4-yl]-piperidine-4-carbonitrile,

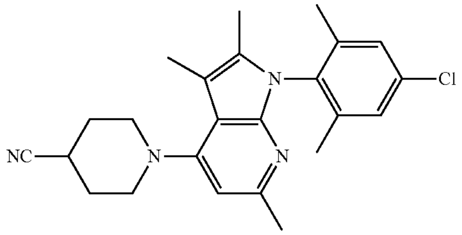

1-[1-(4-chloro-2,6-dimethyl-phenyl)-3,6-dimethyl-1H-pyrrolo[2,3-b]pyridin-4-yl]-piperidine-4-carbonitrile,

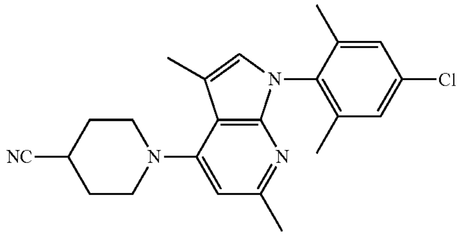 [SMILES: Cc1cc(N2CCC(C#N)CC2)c2c(C)cn(-c3c(C)cc(Cl)cc3C)c2n1]

{1-[1-(4-bromo-2,6-dimethyl-phenyl)-2,3,6-trimethyl-1H-pyrrolo[2,3-b]pyridin-4-yl]-piperidin-4-yl}-acetonitrile,

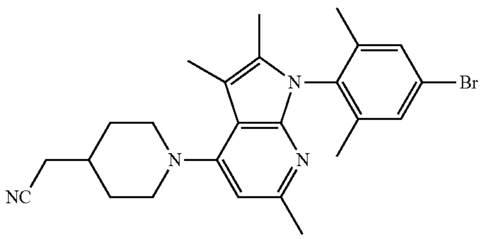

{1-[1-(4-bromo-2,6-dimethyl-phenyl)-3,6-dimethyl-1H-pyrrolo[2,3-b]pyridin-4-yl]-piperidin-4-yl}-acetonitrile,

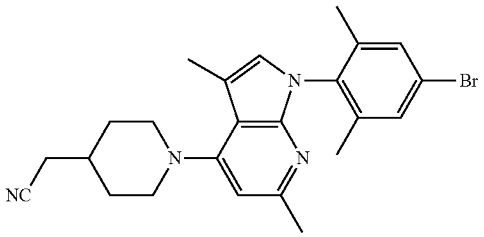 [SMILES: Cc1cc(N2CCC(CC#N)CC2)c2c(C)cn(-c3c(C)cc(Br)cc3C)c2n1]

{1-[1-(4-chloro-2,6-dimethyl-phenyl)-3,6-dimethyl-1H-pyrrolo[2,3-b]pyridin-4-yl]-piperidin-4-yl}-acetonitrile,

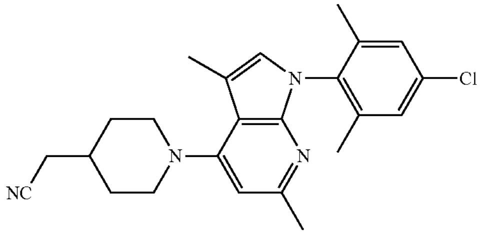

{1-[1-(2,6-dibromo-4-isopropyl-phenyl)-2,3,6-trimethyl-1H-pyrrolo[2,3-b]pyridin-4-yl]-piperidin-4-yl}-methanol,

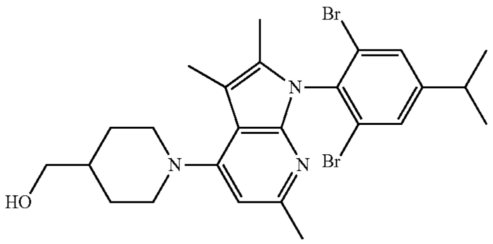

{1-[1-(2,6-dibromo-4-isopropyl-phenyl)-3,6-dimethyl-1H-pyrrolo[2,3-b]pyridin-4-yl]-piperidin-4-yl}-methanol,

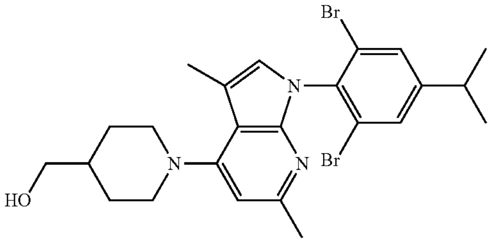

{1-[2,3,6-trimethyl-1-(2,4,6-tribromo-phenyl)-1H-pyrrolo[2,3-b]pyridin-4-yl]-piperidin-4-yl}-methanol,

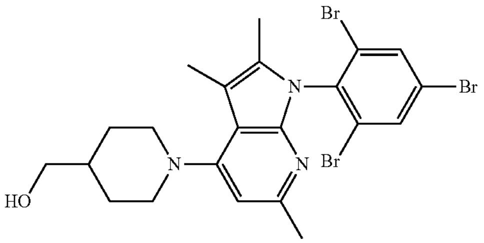

{1-[3,6-dimethyl-1-(2,4,6-tribromo-phenyl)-1H-pyrrolo[2,3-b]pyridin-4-yl]-piperidin-4-yl}-methanol,

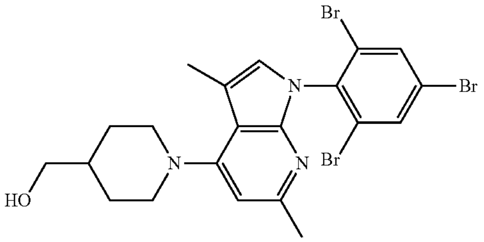

{1-[1-(4-bromo-2,6-dichloro-phenyl)-2,3,6-trimethyl-1H-pyrrolo[2,3-b]pyridin-4-yl]-piperidin-4-yl}-methanol,

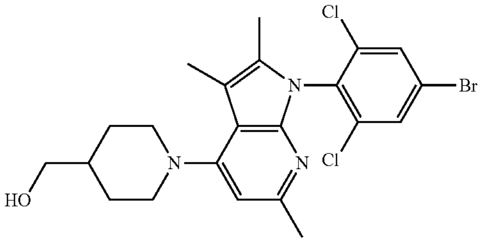

{1-[1-(4-bromo-2,6-dichloro-phenyl)-3,6-dimethyl-1H-pyrrolo[2,3-b]pyridin-4-yl]-piperidin-4-yl}-methanol,

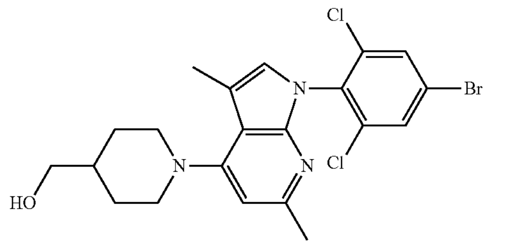

{1-[2,3,6-trimethyl-1-(2,4,6-trichloro-phenyl)-1H-pyrrolo[2,3-b]pyridin-4-yl]-piperidin-4-yl}-methanol,

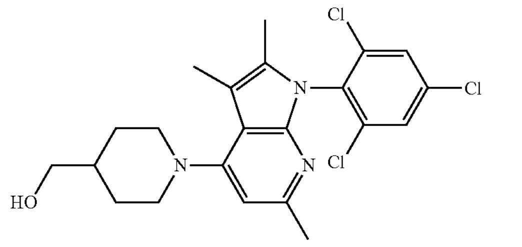

{1-[3,6-dimethyl-1-(2,4,6-trichloro-phenyl)-1H-pyrrolo[2,3-b]pyridin-4-yl]-piperidin-4-yl}-methanol,

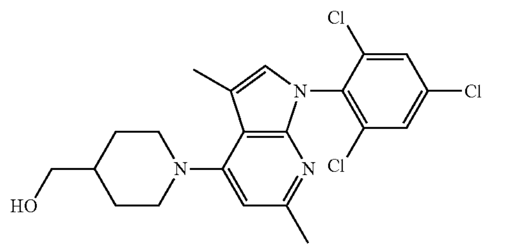

{1-[1-(2,6-dibromo-4-chloro-phenyl)-2,3,6-trimethyl-1H-pyrrolo[2,3-b]pyridin-4-yl]-piperidin-4-yl}-methanol,

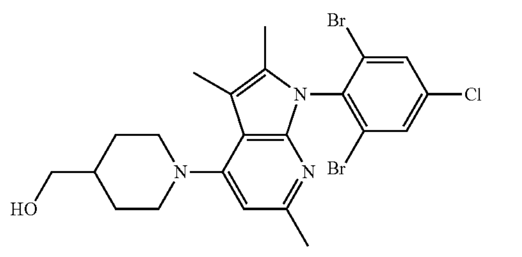

{1-[1-(2,6-dibromo-4-chloro-phenyl)-3,6-dimethyl-1H-pyrrolo[2,3-b]pyridin-4-yl]-piperidin-4-yl}-methanol,

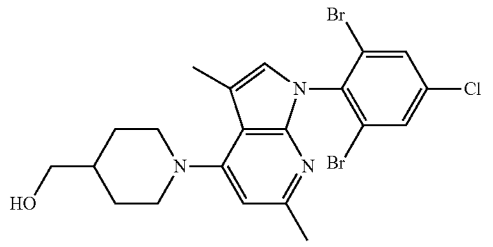

{1-[1-(4-methoxy-2,6-dimethyl-phenyl)-2,3,6-trimethyl-1H-pyrrolo[2,3-b]pyridin-4-yl]-piperidin-4-yl}-methanol,

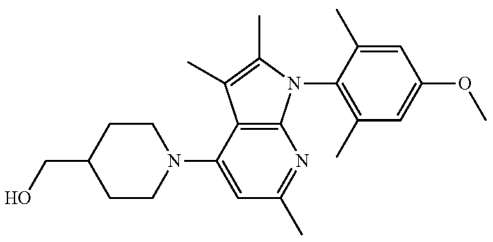

{1-[1-(4-methoxy-2,6-dimethyl-phenyl)-3,6-dimethyl-1H-pyrrolo[2,3-b]pyridin-4-yl]-piperidin-4-yl}-methanol,

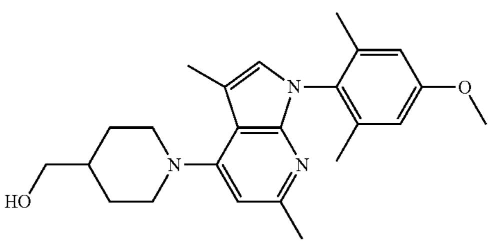

{1-[1-(2-bromo-4-isopropyl-phenyl)-3,6-dimethyl-1H-pyrrolo[2,3-b]pyridin-4-yl]-piperidin-4-yl}-methanol,

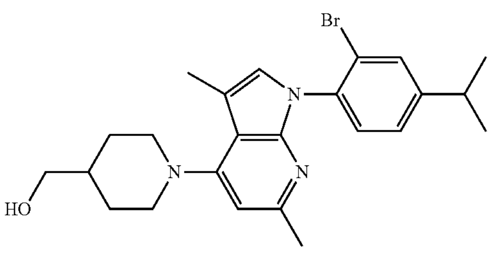

{1-[1-(4-isopropyl-2-methylsulfanyl-phenyl)-3,6-dimethyl-1H-pyrrolo[2,3-b]pyridin-4-yl]-piperidin-4-yl}-methanol,

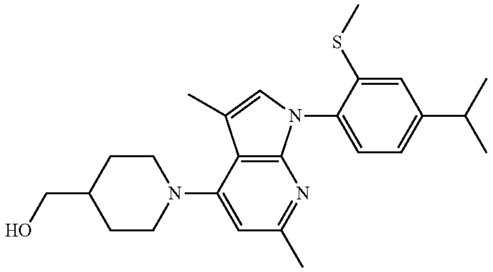

{1-[1-(2,4-dibromo-phenyl)-3,6-dimethyl-1H-pyrrolo[2,3-b]pyridin-4-yl]-piperidin-4-yl}-methanol,

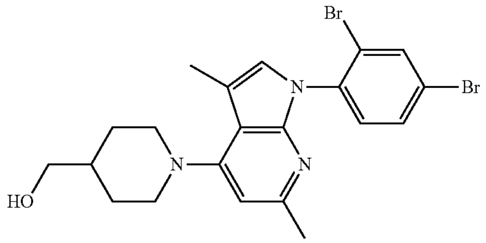 [SMILES: Cc1cc(N2CCC(CO)CC2)c2c(C)cn(-c3ccc(Br)cc3Br)c2n1]

{1-[1-(2-bromo-4-trifluoromethyl-phenyl)-3,6-dimethyl-1H-pyrrolo[2,3-b]pyridin-4-yl]-piperidin-4-yl}-methanol,

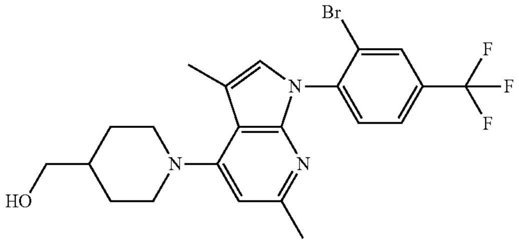

{1-[2,3,6-trimethyl-1-(2,4,5-tribromo-phenyl)-1H-pyrrolo[2,3-b]pyridin-4-yl]-piperidin-4-yl}-methanol,

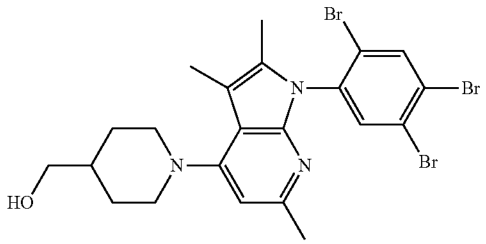 [SMILES: Cc1cc(N2CCC(CO)CC2)c2c(C)c(C)n(-c3cc(Br)c(Br)cc3Br)c2n1]

{1-[3,6-dimethyl-1-(2,4,5-tribromo-phenyl)-1H-pyrrolo[2,3-b]pyridin-4-yl]-piperidin-4-yl}-methanol,

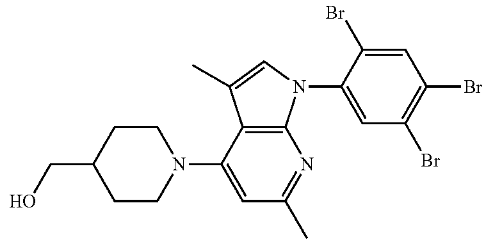 [SMILES: Cc1cc(N2CCC(CO)CC2)c2c(C)cn(-c3cc(Br)c(Br)cc3Br)c2n1]

2-{1-[1-(2,6-dibromo-4-isopropyl-phenyl)-2,3,6-trimethyl-1H-pyrrolo[2,3-b]pyridin-4-yl]-piperidin-4-yl}-ethanol,

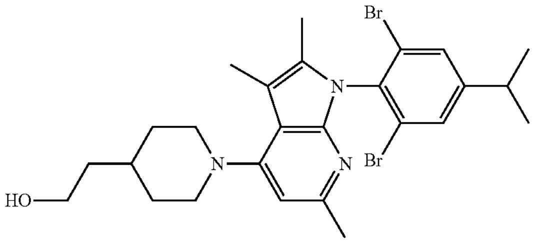 [SMILES: Cc1cc(N2CCC(CCO)CC2)c2c(C)c(C)n(-c3c(Br)cc(C(C)C)cc3Br)c2n1]

2-{1-[1-(2,6-dibromo-4-isopropyl-phenyl)-3,6-dimethyl-1H-pyrrolo[2,3-b]pyridin-4-yl]-piperidin-4-yl}-ethanol,

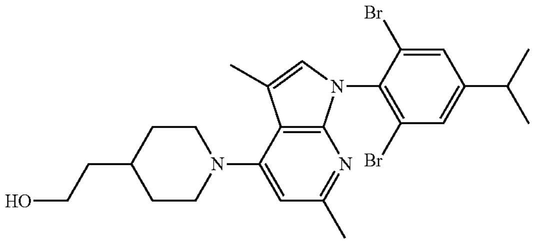 [SMILES: Cc1cc(N2CCC(CCO)CC2)c2c(C)cn(-c3c(Br)cc(C(C)C)cc3Br)c2n1]

2-{1-[2,3,6-trimethyl-1-(2,4,6-tribromo-phenyl)-1H-pyrrolo[2,3-b]pyridin-4-yl]-piperidin-4-yl}-ethanol,

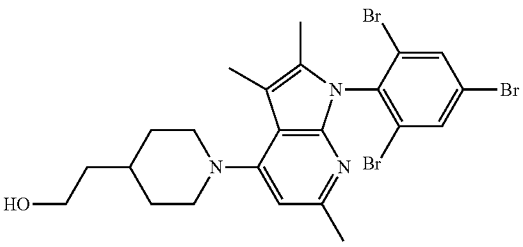 [SMILES: Cc1cc(N2CCC(CCO)CC2)c2c(C)c(C)n(-c3c(Cl)cc(Br)cc3Cl)c2n1]

2-{1-[3,6-dimethyl-1-(2,4,6-tribromo-phenyl)-1H-pyrrolo[2,3-b]pyridin-4-yl]-piperidin-4-yl}-ethanol,

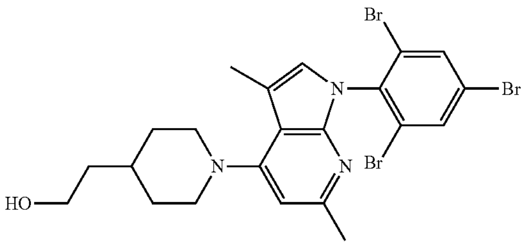 [SMILES: Cc1cc(N2CCC(CCO)CC2)c2c(C)cn(-c3c(Cl)cc(Br)cc3Cl)c2n1]

2-{1-[1-(4-bromo-2,6-dichloro-phenyl)-2,3,6-trimethyl-1H-pyrrolo[2,3-b]pyridin-4-yl]-piperidin-4-yl}-ethanol,

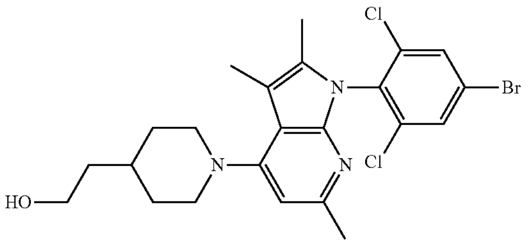

2-{1-[1-(4-bromo-2,6-dichloro-phenyl)-3,6-dimethyl-1H-pyrrolo[2,3-b]pyridin-4-yl]-piperidin-4-yl}-ethanol,

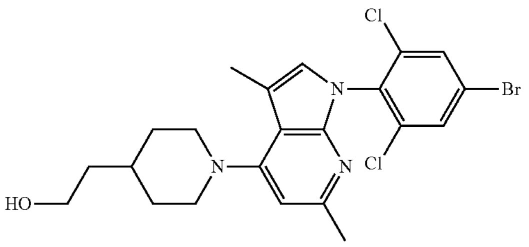

2-{1-[2,3,6-trimethyl-1-(2,4,6-trichloro-phenyl)-1H-pyrrolo[2,3-b]pyridin-4-yl]-piperidin-4-yl}-ethanol,

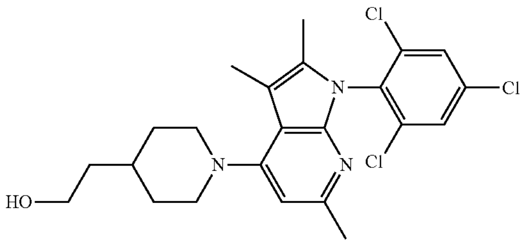

2-{1-[3,6-dimethyl-1-(2,4,6-trichloro-phenyl)-1H-pyrrolo[2,3-b]pyridin-4-yl]-piperidin-4-yl}-ethanol,

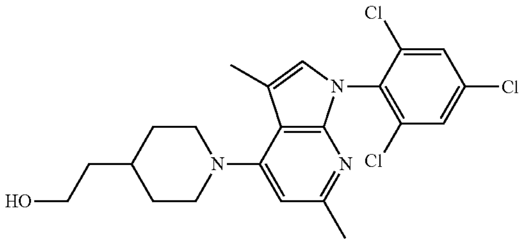

2-{1-[1-(2,6-dibromo-4-chloro-phenyl)-2,3,6-trimethyl-1H-pyrrolo[2,3-b]pyridin-4-yl]-piperidin-4-yl}-ethanol,

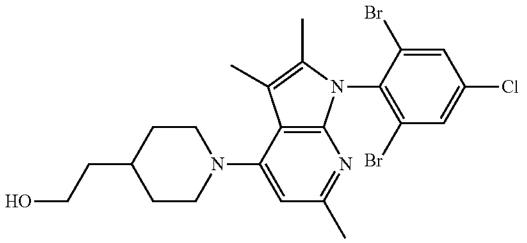 [SMILES: Cc1cc(N2CCC(CCO)CC2)c2c(C)c(C)n(-c3c(Cl)cc(Cl)cc3Cl)c2n1]

2-{1-[1-(2,6-dibromo-4-chloro-phenyl)-3,6-dimethyl-1H-pyrrolo[2,3-b]pyridin-4-yl]-piperidin-4-yl}-ethanol,

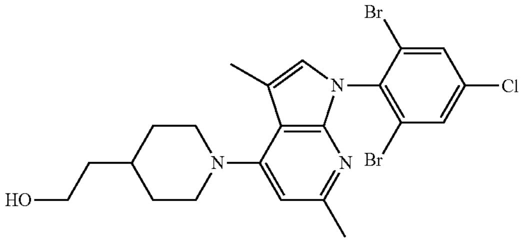 [SMILES: Cc1cc(N2CCC(CCO)CC2)c2c(C)cn(-c3c(Cl)cc(Cl)cc3Cl)c2n1]

2-{1-[1-(4-methoxy-2,6-dimethyl-phenyl)-2,3,6-trimethyl-1H-pyrrolo[2,3-b]pyridin-4-yl]-piperidin-4-yl}-ethanol,

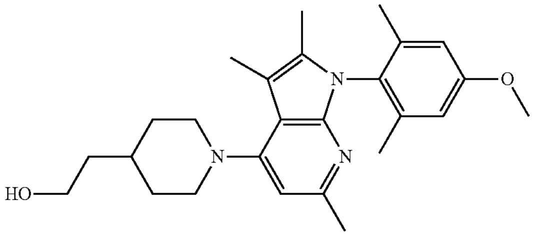 [SMILES: COc1cc(C)c(-n2c(C)c(C)c3c(N4CCC(CCO)CC4)cc(C)nc32)c(C)c1]

2-{1-[1-(4-methoxy-2,6-dimethyl-phenyl)-3,6-dimethyl-1H-pyrrolo[2,3-b]pyridin-4-yl]-piperidin-4-yl}-ethanol,

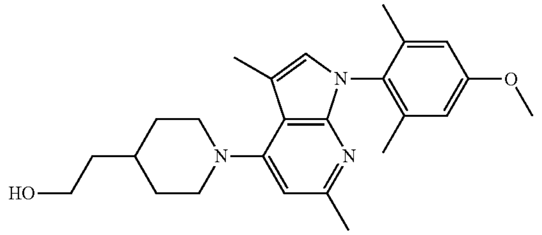 [SMILES: COc1cc(C)c(-n2cc(C)c3c(N4CCC(CCO)CC4)cc(C)nc32)c(C)c1]

2-{1-[1-(2-bromo-4-isopropyl-phenyl)-3,6-dimethyl-1H-pyrrolo[2,3-b]pyridin-4-yl]-piperidin-4-yl}-ethanol,

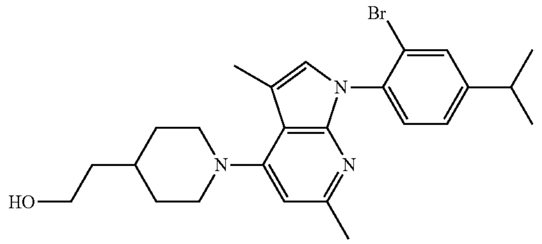 [SMILES: Cc1cc(N2CCC(CCO)CC2)c2c(C)cn(-c3ccc(C(C)C)cc3Br)c2n1]

2-{1-[1-(4-isopropyl-2-methylsulfanyl-phenyl)-3,6-dimethyl-1H-pyrrolo[2,3-b]pyridin-4-yl]piperidin-4-yl}-ethanol,

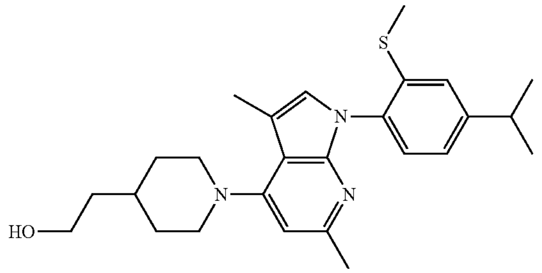 [SMILES: CSc1cc(C(C)C)ccc1-n1cc(C)c2c(N3CCC(CCO)CC3)cc(C)nc21]

2-{1-[1-(2,4-dibromo-phenyl)-3,6-dimethyl-1H-pyrrolo[2,3-b]pyridin-4-yl]-piperidin-4-yl}-ethanol,

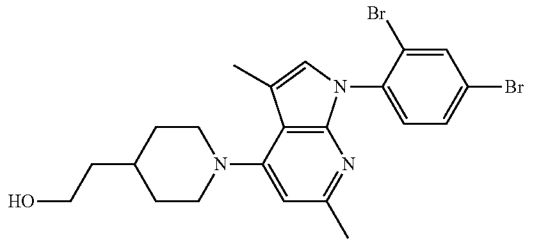 [SMILES: Cc1cc(N2CCC(CCO)CC2)c2c(C)cn(-c3ccc(Br)cc3Br)c2n1]

2-{1-[2,3,6-trimethyl-1-(2,4,5-tribromo-phenyl)-1H-pyrrolo[2,3-b]pyridin-4-yl]-piperidin-4-yl}-ethanol,

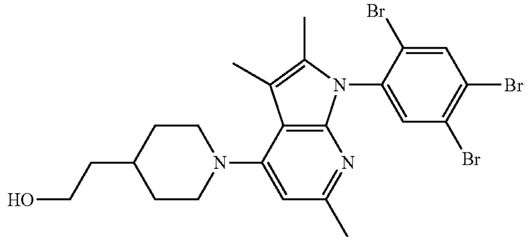 [SMILES: Cc1cc(N2CCC(CCO)CC2)c2c(C)c(C)n(-c3cc(Br)c(Br)cc3Br)c2n1]

2-{1-[3,6-dimethyl-1-(2,4,5-tribromo-phenyl)-1H-pyrrolo[2,3-b]pyridin-4-yl]-piperidin-4-yl}-ethanol,

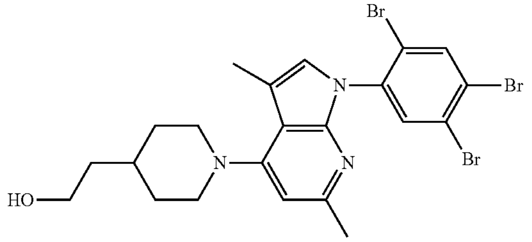 [SMILES: Cc1cc(N2CCC(CCO)CC2)c2c(C)cn(-c3cc(Br)c(Br)cc3Br)c2n1]

2-{1-[5-bromo-1-(4-chloro-2,6-dimethyl-phenyl)-3,6-dimethyl-1H-pyrrolo[2,3-b]pyridin-4-yl]-piperidin-4-yl}-ethanol,

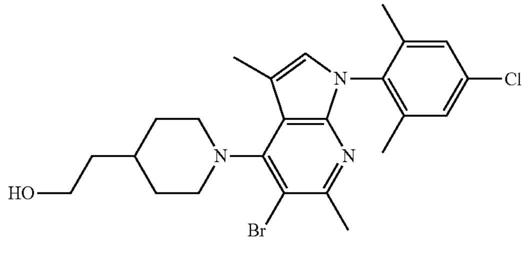 [SMILES: Cc1cc(Cl)cc(C)c1-n1cc(C)c2c(N3CCC(CCO)CC3)c(Br)c(C)nc21]

3-{1-[1-(2,6-dibromo-4-isopropyl-phenyl)-2,3,6-trimethyl-1H-pyrrolo[2,3-b]pyridin-4-yl]-piperidin-4-yl}-propan-1-ol,

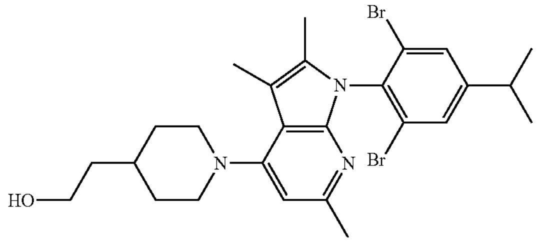 [SMILES: Cc1cc(N2CCC(CCO)CC2)c2c(C)c(C)n(-c3c(Br)cc(C(C)C)cc3Br)c2n1]

3-{1-[1-(2,6-dibromo-4-isopropyl-phenyl)-3,6-dimethyl-1H-pyrrolo[2,3-b]pyridin-4-yl]-piperidin-4-yl}-propan-1-ol,

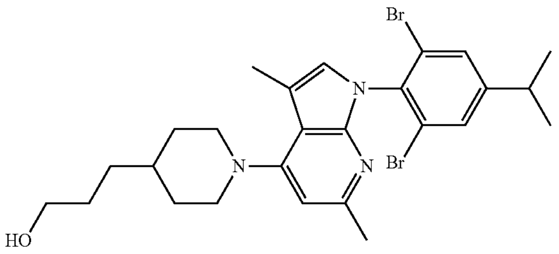 [SMILES: Cc1cc(N2CCC(CCCO)CC2)c2c(C)cn(-c3c(Br)cc(C(C)C)cc3Br)c2n1]

3-{1-[2,3,6-trimethyl-1-(2,4,6-tribromo-phenyl)-1H-pyrrolo[2,3-b]pyridin-4-yl]-piperidin-4-yl}-propan-1-ol,

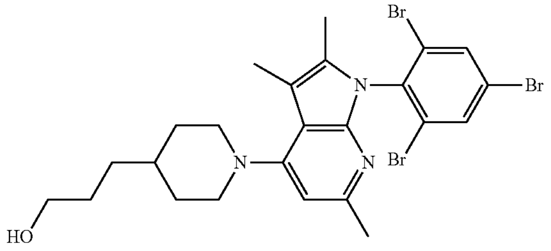 [SMILES: Cc1cc(N2CCC(CCCO)CC2)c2c(C)c(C)n(-c3c(Cl)cc(Br)cc3Cl)c2n1]

3-{1-[3,6-dimethyl-1-(2,4,6-tribromo-phenyl)-1H-pyrrolo[2,3-b]pyridin-4-yl]-piperidin-4-yl}-propan-1-ol,

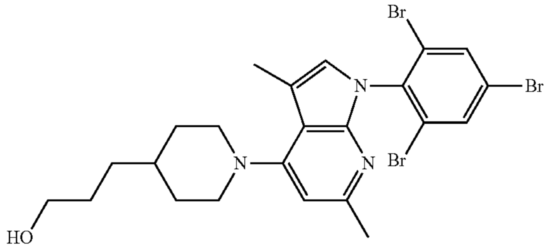

3-{1-[1-(4-bromo-2,6-dichloro-phenyl)-2,3,6-trimethyl-1H-pyrrolo[2,3-b]pyridin-4-yl]-piperidin-4-yl}-propan-1-ol,

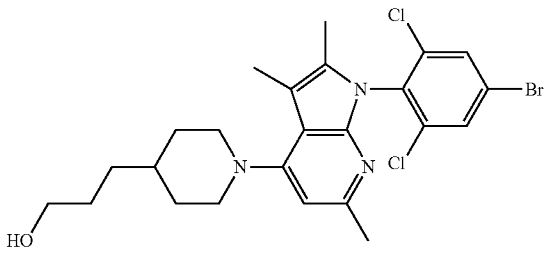

3-{1-[1-(4-bromo-2,6-dichloro-phenyl)-3,6-dimethyl-1H-pyrrolo[2,3-b]pyridin-4-yl]-piperidin-4-yl}-propan-1-ol,

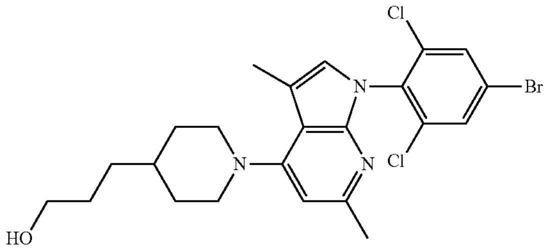 [SMILES: Cc1cc(N2CCC(CCCO)CC2)c2c(C)cn(-c3c(Cl)cc(Br)cc3Cl)c2n1]

3-{1-[2,3,6-trimethyl-1-(2,4,6-trichloro-phenyl)-1H-pyrrolo[2,3-b]pyridin-4-yl]-piperidin-4-yl}-propan-1-ol,

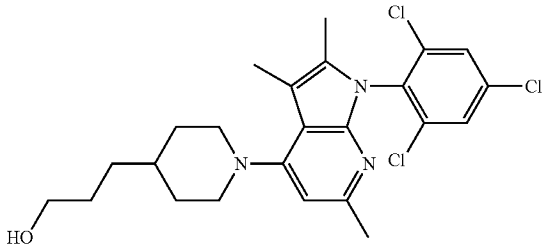

3-{1-[3,6-dimethyl-1-(2,4,6-trichloro-phenyl)-1H-pyrrolo[2,3-b]pyridin-4-yl]-piperidin-4-yl}-propan-1-ol,

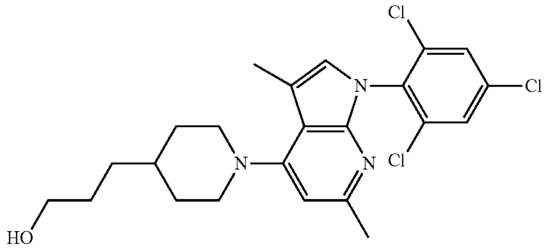

3-{1-[1-(2,6-dibromo-4-chloro-phenyl)-2,3,6-trimethyl-1H-pyrrolo[2,3-b]pyridin-4-yl]-piperidin-4-yl}-propan-1-ol,

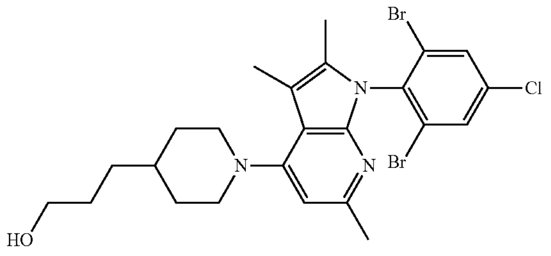 [SMILES: Cc1cc(N2CCC(CCCO)CC2)c2c(C)c(C)n(-c3c(Cl)cc(Cl)cc3Cl)c2n1]

3-{1-[1-(2,6-dibromo-4-chloro-phenyl)-3,6-dimethyl-1H-pyrrolo[2,3-b]pyridin-4-yl]-piperidin-4-yl}-propan-1-ol,

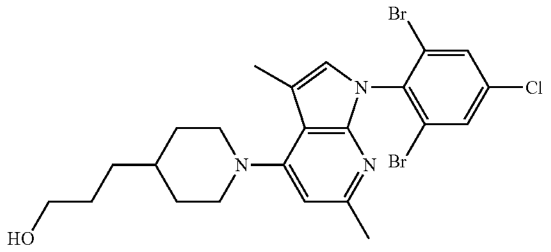 [SMILES: Cc1cc(N2CCC(CCCO)CC2)c2c(C)cn(-c3c(Cl)cc(Cl)cc3Cl)c2n1]

3-{1-[1-(4-methoxy-2,6-dimethyl-phenyl)-2,3,6-trimethyl-1H-pyrrolo[2,3-b]pyridin-4-yl]-piperidin-4-yl}-propan-1-ol,

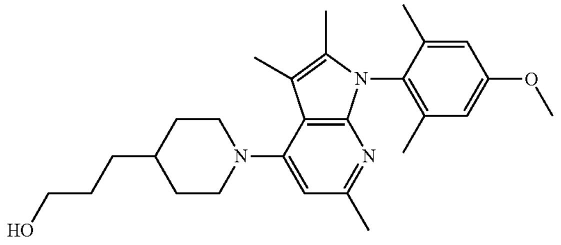 [SMILES: COc1cc(C)c(-n2c(C)c(C)c3c(N4CCC(CCCO)CC4)cc(C)nc32)c(C)c1]

3-{1-[1-(4-methoxy-2,6-dimethyl-phenyl)-3,6-dimethyl-1H-pyrrolo[2,3-b]pyridin-4-yl]-piperidin-4-yl}-propan-1-ol,

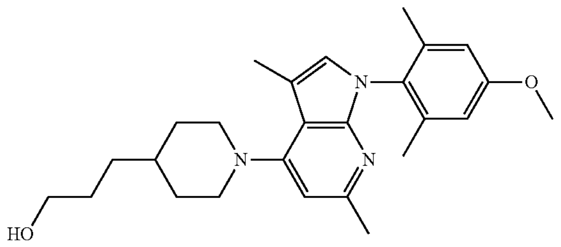 [SMILES: COc1cc(C)c(-n2cc(C)c3c(N4CCC(CCCO)CC4)cc(C)nc32)c(C)c1]

3-{1-[1-(4-isopropyl-2-methylsulfanyl-phenyl)-3,6-dimethyl-1H-pyrrolo[2,3-b]pyridin-4-yl]-piperidin-4-yl}-propan-1-ol,

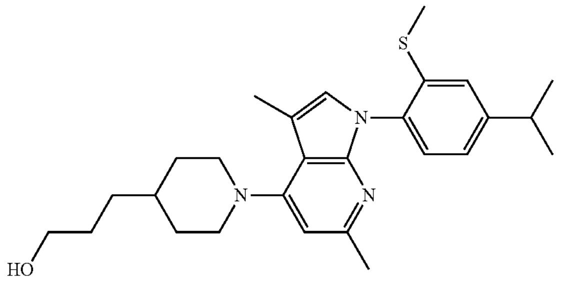 [SMILES: CSc1cc(C(C)C)ccc1-n1cc(C)c2c(N3CCC(CCCO)CC3)cc(C)nc21]

3-{1-[2,3,6-trimethyl-1-(2,4,5-tribromo-phenyl)-1H-pyrrolo[2,3-b]pyridin-4-yl]-piperidin-4-yl}-propan-1-ol,

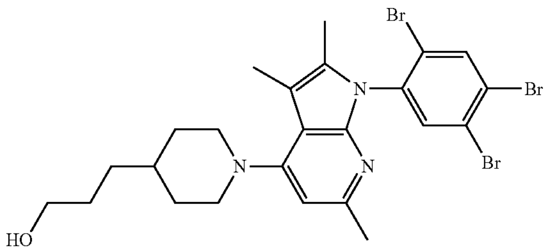 [SMILES: Cc1cc(N2CCC(CCCO)CC2)c2c(C)c(C)n(-c3cc(Br)c(Br)cc3Br)c2n1]

3-{1-[3,6-dimethyl-1-(2,4,5-tribromo-phenyl)-1H-pyrrolo[2,3-b]pyridin-4-yl]-piperidin-4-yl}-propan-1-ol,

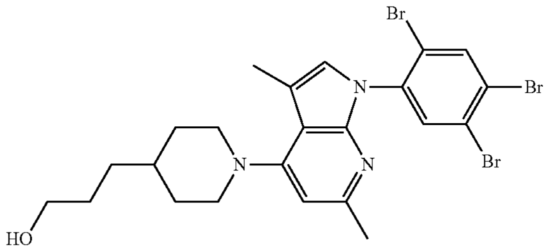 [SMILES: Cc1cc(N2CCC(CCCO)CC2)c2c(C)cn(-c3cc(Br)c(Br)cc3Br)c2n1]

1-{1-[1-(4-bromo-2,6-dimethyl-phenyl)-2,3,6-trimethyl-1H-pyrrolo[2,3-b]pyridin-4-yl]-piperidin-4-yl}-ethane-1,2-diol,

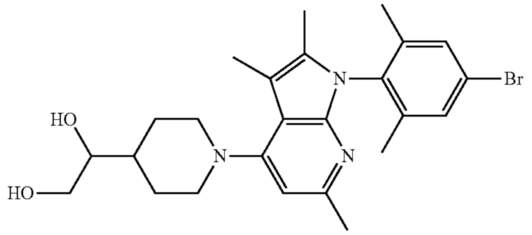 [SMILES: Cc1cc(N2CCC(C(O)CO)CC2)c2c(C)c(C)n(-c3c(C)cc(Br)cc3C)c2n1]

1-{1-[1-(4-bromo-2,6-dimethyl-phenyl)-3,6-dimethyl-1H-pyrrolo[2,3-b]pyridin-4-yl]-piperidin-4-yl}-ethane-1,2-diol,

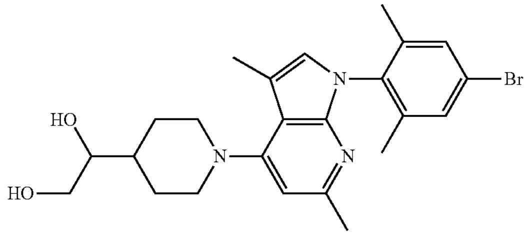 [SMILES: Cc1cc(N2CCC(C(O)CO)CC2)c2c(C)cn(-c3c(C)cc(Br)cc3C)c2n1]

1-{1-[1-(4-bromo-2,6-dimethyl-phenyl)-2,3,6-trimethyl-1H-pyrrolo[2,3-b]pyridin-4-yl]-piperidin-4-yl}-propane-1,3-diol,

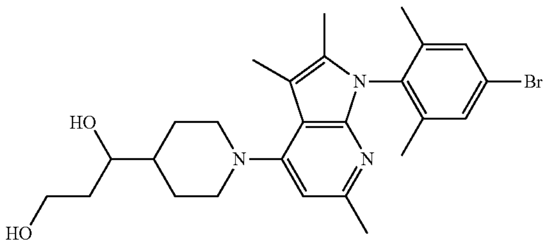

1-{1-[1-(4-bromo-2,6-dimethyl-phenyl)-3,6-dimethyl-1H-pyrrolo[2,3-b]pyridin-4-yl]-piperidin-4-yl}-propane-1,3-diol,

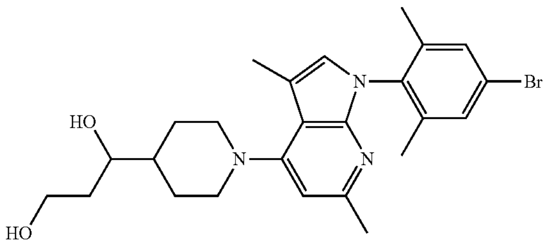 [SMILES: Cc1cc(N2CCC(C(O)CCO)CC2)c2c(C)cn(-c3c(C)cc(Br)cc3C)c2n1]

1-[1-(2,6-dibromo-4-isopropyl-phenyl)-2,3,6-trimethyl-1H-pyrrolo[2,3-b]pyridin-4-yl]-piperidine-4-carbonitrile,

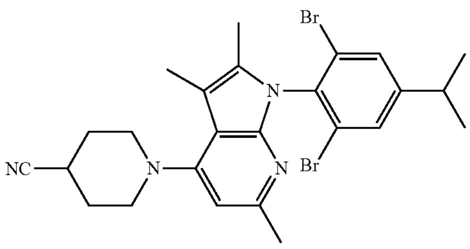 [SMILES: Cc1cc(N2CCC(C#N)CC2)c2c(C)c(C)n(-c3c(Br)cc(C(C)C)cc3Br)c2n1]

1-[1-(2,6-dibromo-4-isopropyl-phenyl)-3,6-dimethyl-1H-pyrrolo[2,3-b]pyridin-4-yl]-piperidine-4-carbonitrile,

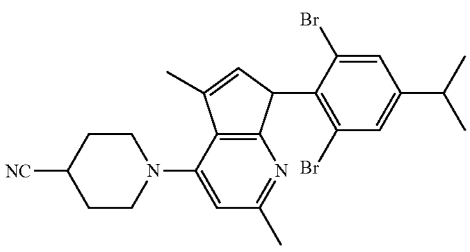 [SMILES: CC1=CC(c2c(Br)cc(C(C)C)cc2Br)c2nc(C)cc(N3CCC(C#N)CC3)c21]

1-[2,3,6-trimethyl-1-(2,4,6-tribromo-phenyl)-1H-pyrrolo[2,3-b]pyridin-4-yl]-piperidine-4-carbonitrile,

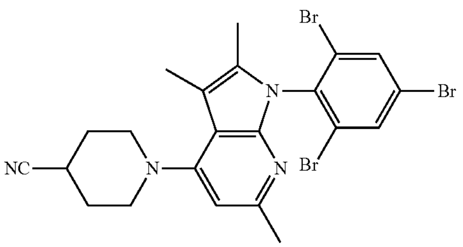 [SMILES: Cc1cc(N2CCC(C#N)CC2)c2c(C)c(C)n(-c3c(Br)cc(Br)cc3Br)c2n1]

1-[3,6-dimethyl-1-(2,4,6-tribromo-phenyl)-1H-pyrrolo[2,3-b]pyridin-4-yl]-piperidine-4-carbonitrile,

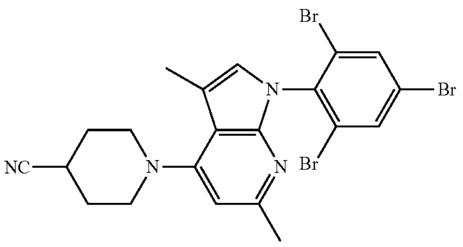 [SMILES: Cc1cc(N2CCC(C#N)CC2)c2c(C)cn(-c3c(Br)cc(Br)cc3Br)c2n1]

1-[1-(4-bromo-2,6-dichloro-phenyl)-2,3,6-trimethyl-1H-pyrrolo[2,3-b]pyridin-4-yl]-piperidine-4-carbonitrile,

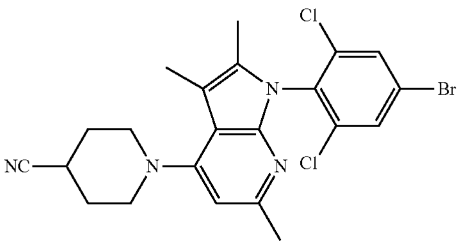

1-[1-(4-bromo-2,6-dichloro-phenyl)-3,6-dimethyl-1H-pyrrolo[2,3-b]pyridin-4-yl]-piperidine-4-carbonitrile,

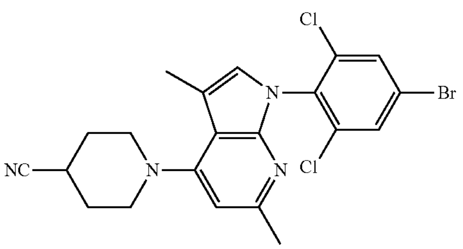

1-[2,3,6-trimethyl-1-(2,4,6-trichloro-phenyl)-1H-pyrrolo[2,3-b]pyridin-4-yl]-piperidine-4-carbonitrile,

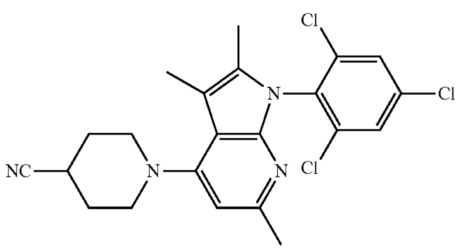 [SMILES: Cc1cc(N2CCC(C#N)CC2)c2c(C)c(C)n(-c3c(Cl)cc(Br)cc3Cl)c2n1]

1-[3,6-dimethyl-1-(2,4,6-trichloro-phenyl)-1H-pyrrolo[2,3-b]pyridin-4-yl]-piperidine-4-carbonitrile,

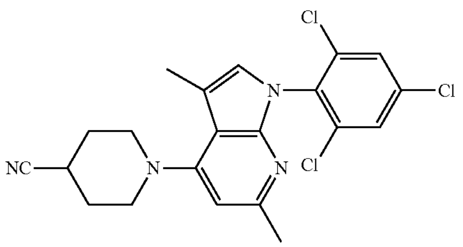 [SMILES: Cc1cc(N2CCC(C#N)CC2)c2c(C)cn(-c3c(Cl)cc(Cl)cc3Cl)c2n1]

1-[1-(2,6-dibromo-4-chloro-phenyl)-2,3,6-trimethyl-1H-pyrrolo[2,3-b]pyridin-4-yl]-piperidine-4-carbonitrile,

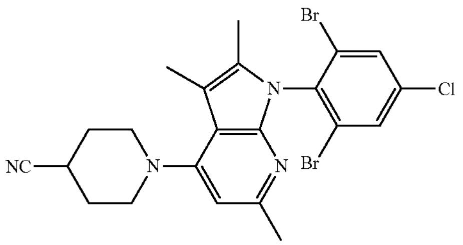

1-[1-(2,6-dibromo-4-chloro-phenyl)-3,6-dimethyl-1H-pyrrolo[2,3-b]pyridin-4-yl]-piperidine-4-carbonitrile,

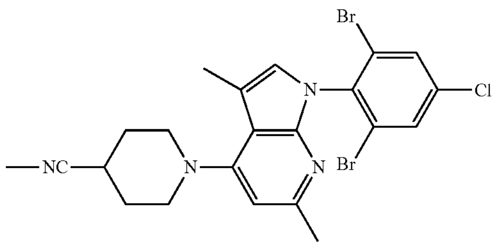

1-[1-(4-methoxy-2,6-dimethyl-phenyl)-2,3,6-trimethyl-1H-pyrrolo[2,3-b]pyridin-4-yl]-piperidine-4-carbonitrile,

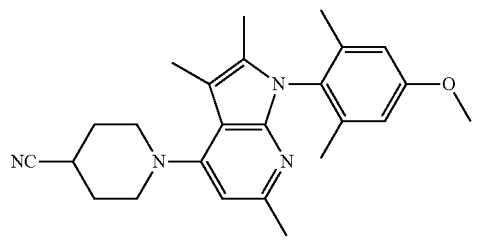 [SMILES: COc1cc(C)c(-n2c(C)c(C)c3c(N4CCC(C#N)CC4)cc(C)nc32)c(C)c1]

1-[1-(4-methoxy-2,6-dimethyl-phenyl)-3,6-dimethyl-1H-pyrrolo[2,3-b]pyridin-4-yl]-piperidine-4-carbonitrile,

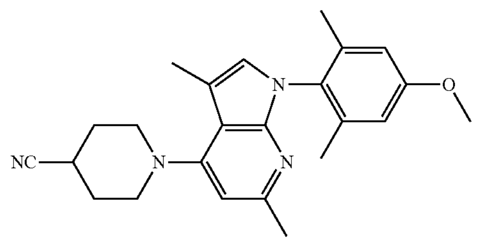

1-[1-(2-bromo-4-isopropyl-phenyl)-3,6-dimethyl-1H-pyrrolo[2,3-b]pyridin-4-yl]-piperidine-4-carbonitrile,

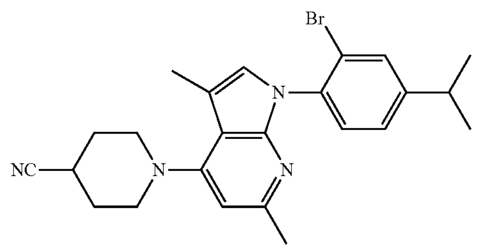 [SMILES: Cc1cc(N2CCC(C#N)CC2)c2c(C)cn(-c3ccc(C(C)C)cc3Br)c2n1]

1-[1-(4-isopropyl-2-methyl sulfanyl-phenyl)-3,6-dimethyl-1H-pyrrolo[2,3-b]pyridin-4-yl]-piperidine-4-carbonitrile,

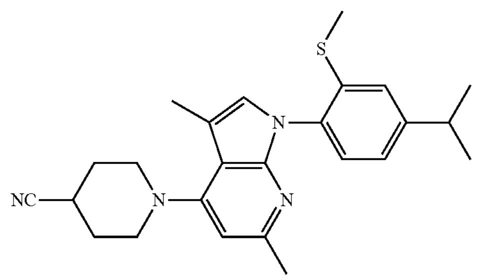 [SMILES: CSc1cc(C(C)C)ccc1-n1cc(C)c2c(N3CCC(C#N)CC3)cc(C)nc21]

1-[1-(2,4-dibromo-phenyl)-3,6-dimethyl-1H-pyrrolo[2,3-b]pyridin-4-yl]-piperidine-4-carbonitrile,

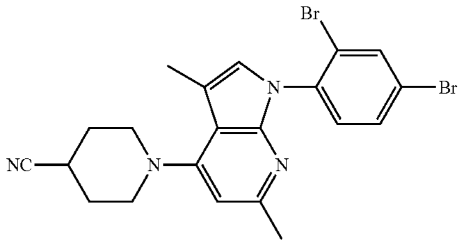 [SMILES: Cc1cc(N2CCC(C#N)CC2)c2c(C)cn(-c3ccc(Br)cc3Br)c2n1]

1-[1-(2-bromo-4-trifluoromethyl-phenyl)-3,6-dimethyl-1H-pyrrolo[2,3-b]pyridin-4-yl]-piperidine-4-carbonitrile,

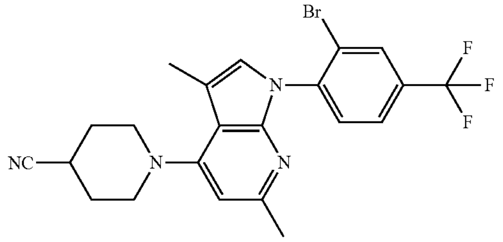 [SMILES: Cc1cc(N2CCC(C#N)CC2)c2c(C)cn(-c3ccc(C(F)(F)F)cc3Br)c2n1]

1-[2,3,6-trimethyl-1-(2,4,5-tribromo-phenyl)-1H-pyrrolo[2,3-b]pyridin-4-yl]-piperidine-4-carbonitrile,

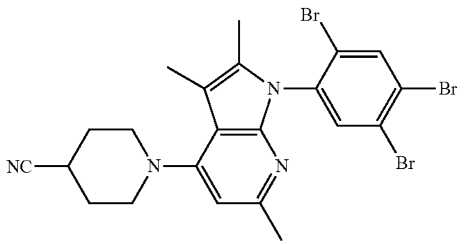 [SMILES: Cc1cc(N2CCC(C#N)CC2)c2c(C)c(C)n(-c3cc(Br)c(Br)cc3Br)c2n1]

1-[3,6-dimethyl-1-(2,4,5-tribromo-phenyl)-1H-pyrrolo[2,3-b]pyridin-4-yl]-piperidine-4-carbonitrile,

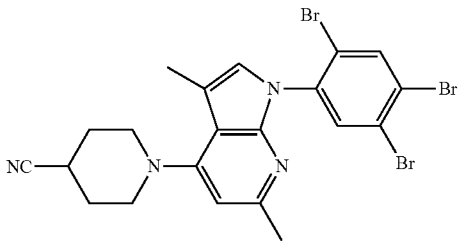 [SMILES: Cc1cc(N2CCC(C#N)CC2)c2c(C)cn(-c3cc(Br)c(Br)cc3Br)c2n1]

{1-[1-(4-chloro-2,6-dimethyl-phenyl)-2,3,6-trimethyl-1H-pyrrolo[2,3-b]pyridin-4-yl]-piperidin-4-yl}-acetonitrile,

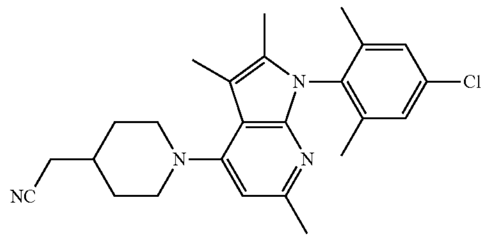

{1-[1-(2,6-dibromo-4-isopropyl-phenyl)-2,3,6-trimethyl-1H-pyrrolo[2,3-b]pyridin-4-yl]-piperidin-4-yl}-acetonitrile,

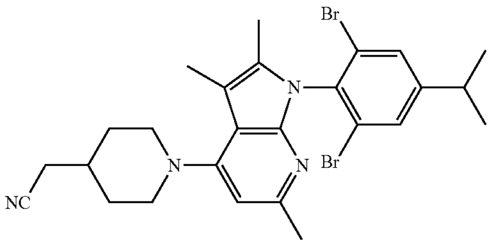

{1-[1-(2,6-dibromo-4-isopropyl-phenyl)-3,6-dimethyl-1H-pyrrolo[2,3-b]pyridin-4-yl]-piperidin-4-yl}-acetonitrile,

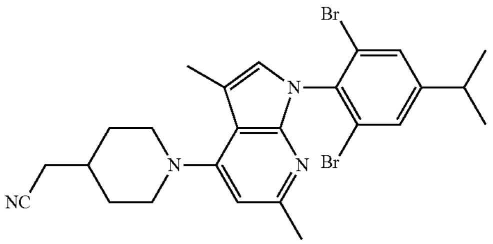 [SMILES: Cc1cc(N2CCC(CC#N)CC2)c2c(C)cn(-c3c(Br)cc(C(C)C)cc3Br)c2n1]

{1-[2,3,6-trimethyl-1-(2,4,6-tribromo-phenyl)-1H-pyrrolo[2,3-b]pyridin-4-yl]-piperidin-4-yl}-acetonitrile,

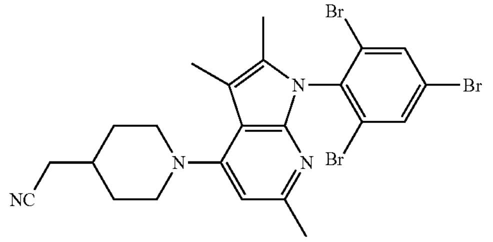 [SMILES: Cc1cc(N2CCC(CC#N)CC2)c2c(C)c(C)n(-c3c(Br)cc(Br)cc3Br)c2n1]

{1-[3,6-dimethyl-1-(2,4,6-tribromo-phenyl)-1H-pyrrolo[2,3-b]pyridin-4-yl]-piperidin-4-yl}-acetonitrile,

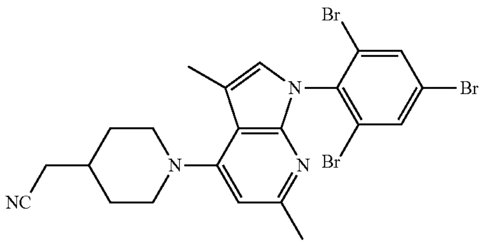

{1-[1-(4-bromo-2,6-dichloro-phenyl)-2,3,6-trimethyl-1H-pyrrolo[2,3-b]pyridin-4-yl]-piperidin-4-yl}-acetonitrile,

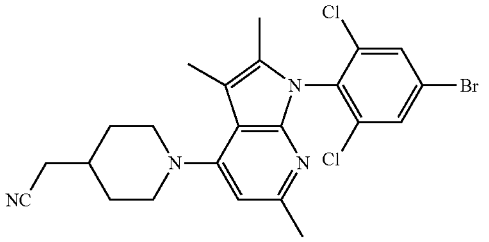

{1-[1-(4-bromo-2,6-dichloro-phenyl)-3,6-dimethyl-1H-pyrrolo[2,3-b]pyridin-4-yl]-piperidin-4-yl}-acetonitrile,

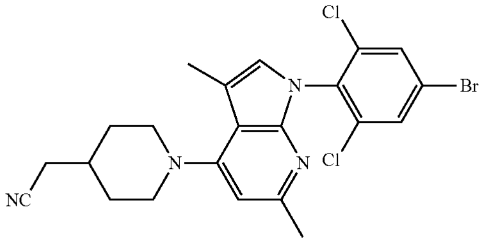 [SMILES: Cc1cc(N2CCC(CC#N)CC2)c2c(C)cn(-c3c(Cl)cc(Br)cc3Cl)c2n1]

{1-[2,3,6-trimethyl-1-(2,4,6-trichloro-phenyl)-1H-pyrrolo[2,3-b]pyridin-4-yl]-piperidin-4-yl}-acetonitrile,

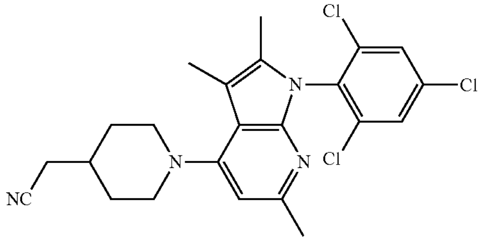

{1-[3,6-dimethyl-1-(2,4,6-trichloro-phenyl)-1H-pyrrolo[2,3-b]pyridin-4-yl]-piperidin-4-yl}-acetonitrile,

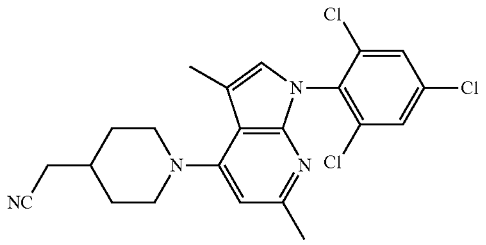 [SMILES: Cc1cc(N2CCC(CC#N)CC2)c2c(C)cn(-c3c(Cl)cc(Cl)cc3Cl)c2n1]

{1-[1-(2,6-dibromo-4-chloro-phenyl)-2,3,6-trimethyl-1H-pyrrolo[2,3-b]pyridin-4-yl]-piperidin-4-yl}-acetonitrile,

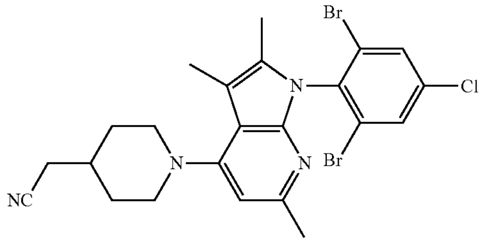 [SMILES: Cc1cc(N2CCC(CC#N)CC2)c2c(C)c(C)n(-c3c(Br)cc(Cl)cc3Br)c2n1]

{1-[1-(2,6-dibromo-4-chloro-phenyl)-3,6-dimethyl-1H-pyrrolo[2,3-b]pyridin-4-yl]-piperidin-4-yl}-acetonitrile,

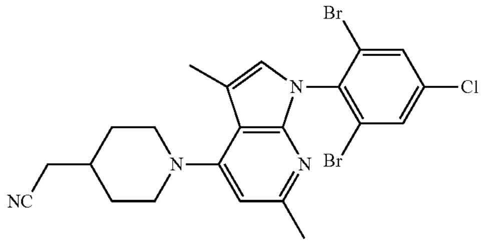

{1-[1-(4-methoxy-2,6-dimethyl-phenyl)-2,3,6-trimethyl-1H-pyrrolo[2,3-b]pyridin-4-yl]-piperidin-4-yl}-acetonitrile,

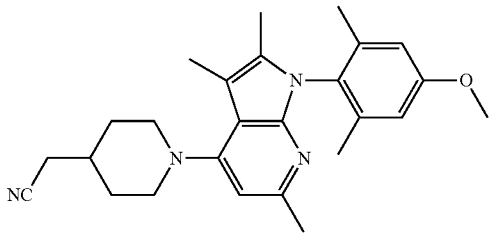 [SMILES: COc1cc(C)c(-n2c(C)c(C)c3c(N4CCC(CC#N)CC4)cc(C)nc32)c(C)c1]

{1-[1-(4-methoxy-2,6-dimethyl-phenyl)-3,6-dimethyl-1H-pyrrolo[2,3-b]pyridin-4-yl]-piperidin-4-yl}-acetonitrile,

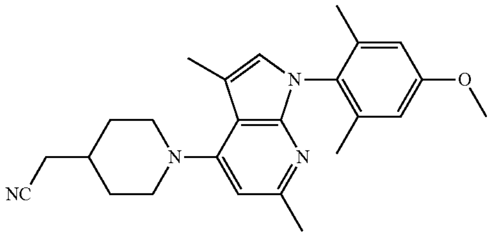 [SMILES: COc1cc(C)c(-n2cc(C)c3c(N4CCC(CC#N)CC4)cc(C)nc32)c(C)c1]

{1-[1-(2-bromo-4-isopropyl-phenyl)-3,6-dimethyl-1H-pyrrolo[2,3-b]pyridin-4-yl]-piperidin-4-yl}-acetonitrile,

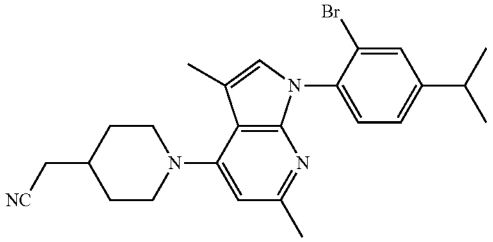 [SMILES: Cc1cc(N2CCC(CC#N)CC2)c2c(C)cn(-c3ccc(C(C)C)cc3Br)c2n1]

{1-[1-(4-isopropyl-2-methylsulfanyl-phenyl)-3,6-dimethyl-1H-pyrrolo[2,3-b]pyridin-4-yl]-piperidin-4-yl}-acetonitrile,

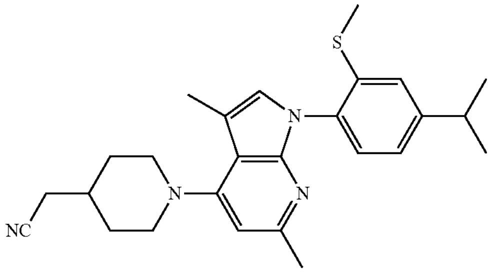 [SMILES: CSc1cc(C(C)C)ccc1-n1cc(C)c2c(N3CCC(CC#N)CC3)cc(C)nc21]

{1-[1-(2,4-dibromo-phenyl)-3,6-dimethyl-1H-pyrrolo[2,3-b]pyridin-4-yl]-piperidin-4-yl}-acetonitrile,

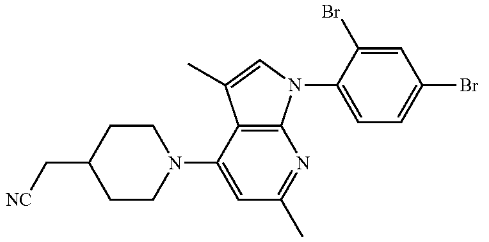 [SMILES: Cc1cc(N2CCC(CC#N)CC2)c2c(C)cn(-c3ccc(Br)cc3Br)c2n1]

{1-[1-(2-bromo-4-trifluoromethyl-phenyl)-3,6-dimethyl-1H-pyrrolo[2,3-b]pyridin-4-yl]-piperidin-4-yl}-acetonitrile,

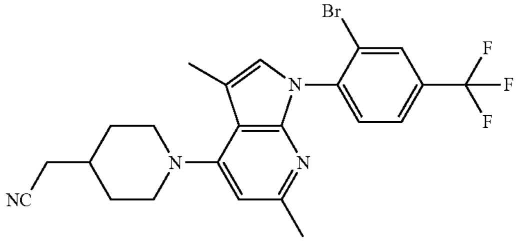

{1-[3,6-dimethyl-1-(2,4,5-tribromo-phenyl)-1H-pyrrolo[2,3-b]pyridin-4-yl]-piperidin-4-yl}-acetonitrile,

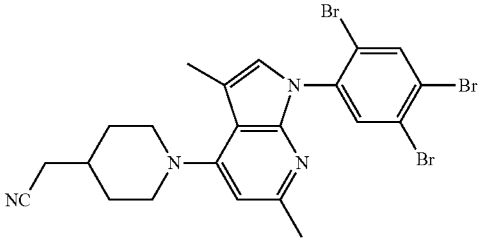

carbonic acid 1-[7-(4-bromo-2,6-dimethyl-phenyl)-2,5-dimethyl-7H-pyrrolo[2,3-d]pyrimidin-4-yl]-piperidin-4-ylmethyl ester ethyl ester,

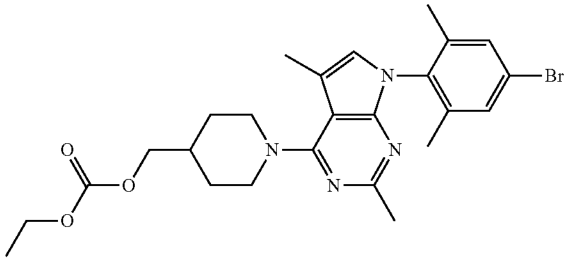 [SMILES: CCOC(=O)OCC1CCN(c2nc(C)nc3c2c(C)cn3-c2c(C)cc(Br)cc2C)CC1]

pyridine-2-carboxylic acid 1-[7-(4-bromo-2,6-dimethyl-phenyl)-2,5-dimethyl-7H-pyrrolo[2,3-d]pyrimidin-4-yl]-piperidin-4-ylmethyl ester,

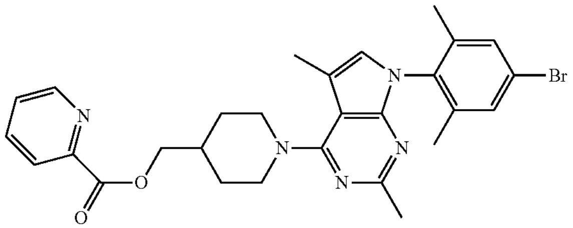 [SMILES: Cc1nc(N2CCC(COC(=O)c3ccccn3)CC2)c2c(C)cn(-c3c(C)cc(Br)cc3C)c2n1]

methoxy-acetic acid 1-[7-(4-bromo-2,6-dimethyl-phenyl)-2,5-dimethyl-7H-pyrrolo[2,3-d]pyrimidin-4-yl]-piperidin-4-ylmethyl ester,

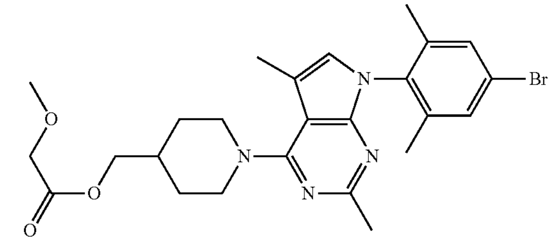 [SMILES: COCC(=O)OCC1CCN(c2nc(C)nc3c2c(C)cn3-c2c(C)cc(Br)cc2C)CC1]

methoxy-acetic acid 1-[1-(4-bromo-2,6-dimethyl-phenyl)-3,6-dimethyl-1H-pyrrolo[2,3-b]pyridin-4-yl]-piperidin-4-ylmethyl ester,

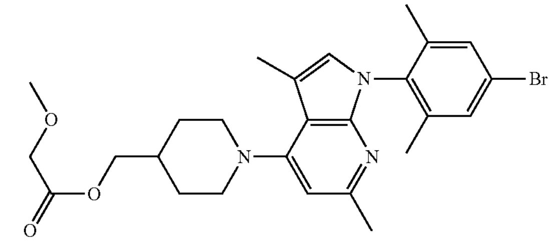 [SMILES: COCC(=O)OCC1CCN(c2cc(C)nc3c2c(C)cn3-c2c(C)cc(Br)cc2C)CC1]

carbonic acid benzyl ester 1-[7-(4-bromo-2,6-dimethyl-phenyl)-2,5-dimethyl-7H-pyrrolo[2,3-d]pyrimidin-4-yl]-piperidin-4-ylmethyl ester,

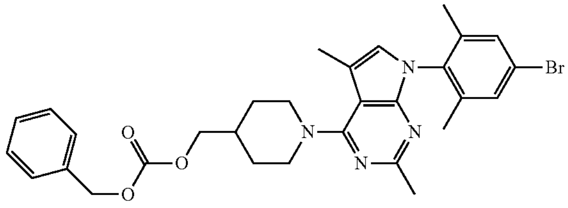 [SMILES: Cc1nc(N2CCC(COC(=O)OCc3ccccc3)CC2)c2c(C)cn(-c3c(C)cc(Br)cc3C)c2n1]

decanoic acid 1-[7-(4-bromo-2,6-dimethyl-phenyl)-2,5-dimethyl-7H-pyrrolo[2,3-d]pyrimidin-4-yl]-piperidin-4-ylmethyl ester,

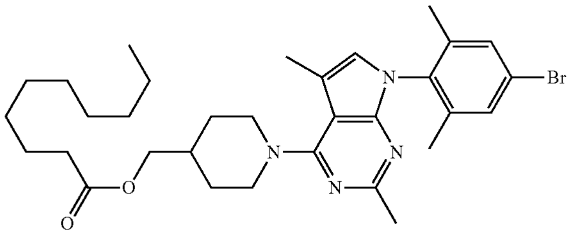 [SMILES: CCCCCCCCCC(=O)OCC1CCN(c2nc(C)nc3c2c(C)cn3-c2c(C)cc(Br)cc2C)CC1]

3-diethylamino-propionic acid 1-[7-(4-bromo-2,6-dimethyl-phenyl)-2,5-dimethyl-7H-pyrrolo[2,3-d]pyrimidin-4-yl]-piperidin-4-ylmethyl ester,

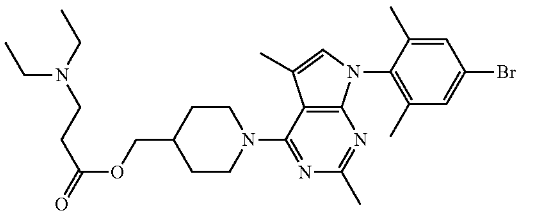 [SMILES: CCN(CC)CCC(=O)OCC1CCN(c2nc(C)nc3c2c(C)cn3-c2c(C)cc(Br)cc2C)CC1]

and phosphoric acid mono-{1-[7-(4-bromo-2,6-dimethyl-phenyl)-2,5-dimethyl-7H-pyrrolo[2,3-d]pyrimidin-4-yl]-piperidin-4-ylmethyl}ester.

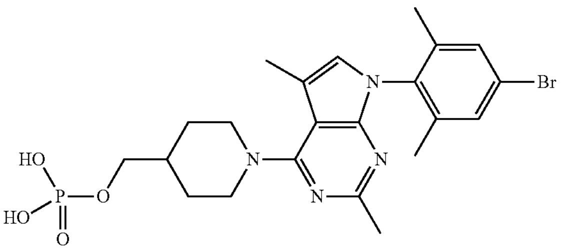 [SMILES: Cc1nc(N2CCC(COP(=O)(O)O)CC2)c2c(C)cn(-c3c(C)cc(Br)cc3C)c2n1]

The compound represented by the formula [I] can be produced, for example, by the process shown in the following reaction scheme 1-4 [in the following reaction scheme, $R^1$, $R^2$, $R^3$, $R^4$, $R^5$, $R^6$, $R^7$, $R^8$, m, n, X, Y and Ar are as defined above; LG is chloro, bromo, iodo, methanesulfonyloxy, benzenesulfonyloxy, 4-toluenesulfonyloxy or trifluoromethanesulfonyloxy group; $Z^1$ and $Z^2$ are the same or different, and independently are chloride or bromide; $R^a$ and $R^b$ are the same or different, and independently are hydrogen, $C_{1-5}$alkyl, $C_{3-8}$cycloalkyl or $C_{3-8}$cycloalkyl-$C_{1-5}$alkyl; and $X^a$ is $-(CHR^3)_n-OH$, $-(CHR^3)_n-CN$ or $-CO_2-(C_{1-5}$ alkyl)].

Reaction Scheme 1

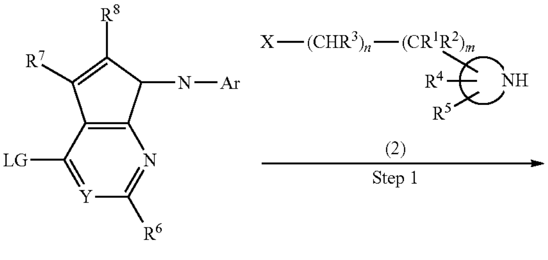

(1)

-continued

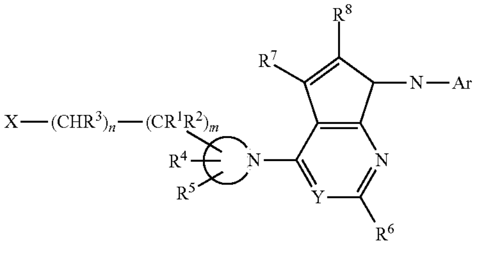

(3)

Step 1:

Compound (3), a compound of the present invention, can be obtained by reacting Compound (1) with Compound (2) in an inert solvent in the presence or absence of a base. Herein, the base includes, for example, amines such as triethylamine, N,N-diisopropylethylamine, pyridine and the like; inorganic bases such as sodium carbonate, potassium carbonate, sodium hydrogencarbonate, potassium hydrogencarbonate, sodium hydroxide, potassium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methylmagnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; amides such as N,N-dimethylformamide, N-methylpyrrolidone, N,N-dimethylacetamide and the like; acetonitrile; dimethyl sulfoxide; pyridine; water; and mixtures of solvents selected from these inert solvents.

The compound of the present invention can be converted to a salt in an inert solvent with an inorganic acid such as sulfuric acid, hydrochloric acid, hydrobromic acid, phosphoric acid, nitric acid or the like, with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, naphthalene-2-sulfonic acid or the like, with an inorganic base such as lithium hydroxide, sodium hydroxide, potassium hydroxide, calcium hydroxide, magnesium hydroxide, zinc hydroxide, aluminum hydroxide or the like or with an organic base such as ammonia, arginine, lysine, piperazine, choline, diethylamine, 4-phenylcyclohexylamine, 2-aminoethanol, benzathine or the like. The inert solvent includes, for example, alcohols such as methanol, ethanol, isopropyl alcohol, ethylene glycol and the like; ethers such as diethyl ether, diisopropyl ether, tetrahydrofuran, 1,4-dioxane, 1,2-dimethoxyethane and the like; hydrocarbons such as benzene, toluene and the like; esters such as ethyl acetate, ethyl formate and the like; ketones such as acetone, methylethylketone and the like; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

Reaction Scheme 2

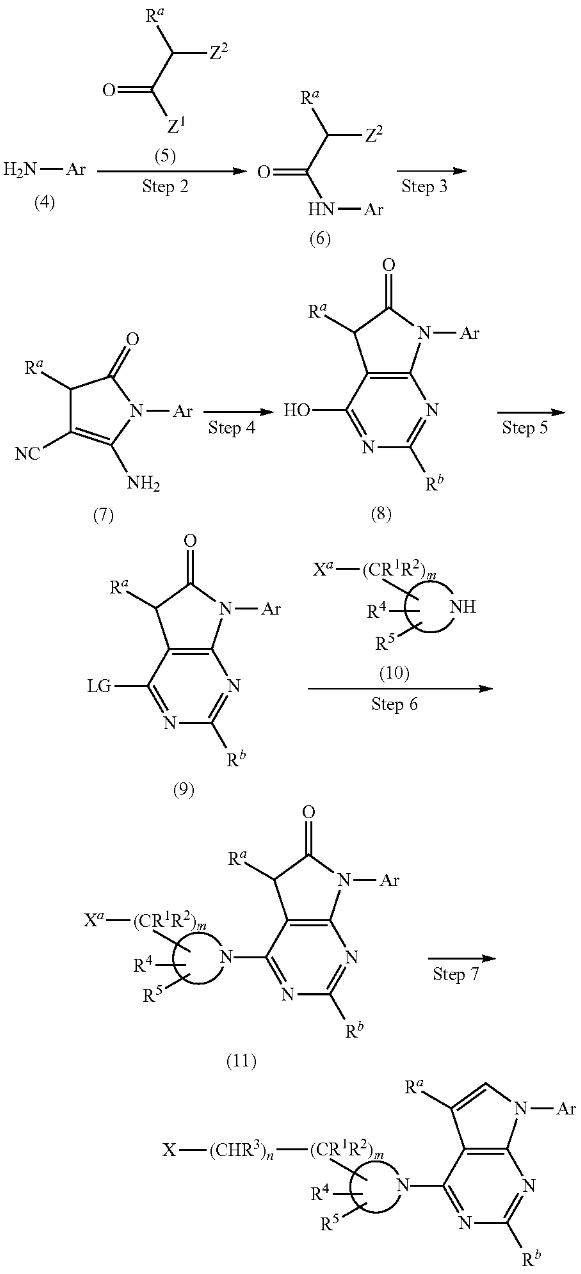

(4) (5) (6) (7) (8) (9) (10) (11) (12)

Step 2:

Compound (4) can be converted to Compound (6) by reacting Compound (4) with Compound (5) in an inert solvent in the presence or absence of a base. Herein, the base includes, for example, amines such as triethylamine, N,N-diisopropylethylamine, pyridine and the like; inorganic bases such as sodium carbonate, potassium carbonate, sodium hydrogencarbonate, potassium hydrogencarbonate, sodium hydroxide, potassium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methyl magnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; amides such as N,N-dimethylformamide, N-methylpyrrolidone, N,N-dimethylacetamide and the like; acetonitrile; dimethyl sulfoxide; pyridine; water; and mixtures of solvents selected from these inert solvents.

Step 3:

Compound (6) can be converted to Compound (7) by reacting Compound (6) with malononitrile in an inert solvent in the presence or absence of a base. Herein, the base includes, for example, amines such as triethylamine, N,N-diisopropylethylamine, pyridine and the like; inorganic bases such as sodium carbonate, potassium carbonate, sodium hydrogencarbonate, potassium hydrogencarbonate, sodium hydroxide, potassium hydroxide, barium hydroxide, sodium hydride, potassium hydride and the like; metal alcoholates such as sodium methoxide, sodium ethoxide, potassium tert-butoxide and the like; metal amides such as sodium amide, lithium diisopropylamide, lithium hexamethyldisilazanide, sodium hexamethyldisilazanide, potassium hexamethyldisilazanide and the like; alkyl lithiums such as methyl lithium, n-butyl lithium, sec-butyl lithium, tert-butyl lithium and phenyl lithium; and Grignard reagents such as methyl magnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dimethyl sulfoxide; pyridine; water; and mixtures of solvents selected from these inert solvents.

Step 4:

Compound (7) can be converted to Compound (8) by acylation of amino group in Compound (7) and followed by formation of pyrimidine ring. The acylation and the formation of pyrimidine ring may occur continuously in one pot. The acylation can be achieved by reacting Compound (7) with an acylating reagent in an inert solvent in the presence or absence of a base or an acid. The following formation of pyrimidine ring can be carried out by heating the acylated compound in an inert solvent in the presence or absence of an acid. Herein, the acylating reagent includes, for example, halogenated acyls such as acetyl chloride, acetyl bromide, propionyl chloride, propionyl bromide, butyryl chloride, cyclopropanecarbonyl chloride, benzoyl chloride and the like; acid anhydride such as acetic anhydride, propionic anhydride, butyric anhydride, benzoic anhydride and the like. The base includes, for example, amines such as triethylamine, N,N-diisopropylethylamine, pyridine and the like; inorganic bases such as sodium carbonate, potassium carbonate, sodium hydrogencarbonate, potassium hydrogencarbonate, sodium hydroxide, potassium hydroxide, barium hydroxide, sodium hydride, potassium hydride and the like; metal alcoholates such as sodium methoxide, sodium ethoxide, potassium tert-butoxide and the like; metal amides such as sodium amide, lithium diisopropylamide, lithium hexamethyldisilazanide, sodium hexamethyldisilazanide, potassium hexamethyldisilazanide and the like; and Grignard reagents such as methyl magnesium bromide and the like. The acid includes, for example, organic acids such as formic acid, acetic acid, trifluoroacetic acid, benzenesulfonic acid, methanesulfonic acid, p-toluenesulfonic acid, benzoic acid, trifluoromethanesulfonic acid and the like; inorganic acids such as sulfuric acid, hydrochloric acid, hydrobromic acid, phosphoric acid, polyphosphoric acid, nitric acid or the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; amides such as N,N-dimethylformamide, N-methylpyrrolidone, N,N-dimethylacetamide and the like; acetonitrile; dimethyl sulfoxide; pyridine; acetic acid; water; and mixtures of solvents selected from these inert solvents.

Step 5

Compound (8) can be converted to Compound (9) by reacting (8) with a halogenating reagent or a sulfonating reagent in the presence or absence of a base in an inert solvent or without any solvent. Herein, the halogenating reagent includes, for example, phosphoryl chloride, phosphoryl bromide, phosphorous pentachloride, phosphorous trichloride, phosphorous pentabromide, phosphorous tribromide, thionyl chloride, thionyl bromide, oxalyl chloride, oxalyl bromide and the like. The sulfonating reagent includes, for example, p-toluenesulfonyl chloride, methanesulfonyl chloride, p-toluenesulfonic anhydride, methansulfonic anhydride, trifluoromethanesulfonic anhydride, N-phenylbis (trifluoromethanesulfonimide) and the like. The base includes, for example, amines such as triethylamine, N,N-diisopropylethylamine, pyridine, N,N-dimethylaniline, N,N-diethylaniline and the like; inorganic bases such as sodium carbonate, potassium carbonate, sodium hydrogencarbonate, potassium hydrogencarbonate, sodium hydroxide, potassium hydroxide, barium hydroxide, sodium hydride and the like; metal alcoholates such as sodium methoxide, sodium ethoxide, potassium tert-butoxide and the like; metal amides such as sodium amid; lithium diisopropylamide and the like; and Grignard reagents such as methyl magnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; dichloromethane; chloroform; acetonitrile; dimethyl sulfoxide; pyridine; water; and mixtures of solvents selected from these inert solvents.

Step 6

Compound (9) can be converted to Compound (11) by reacting Compound (9) with Compound (10) in the same method as step 1.

Step 7

Compound (11) can be converted to Compound (12) by reduction of Compound (11) with a conventional reducing agent in an inert solvent. Or if necessary, treatment with an acid in the presence or absence of inert solvent after the reduction can provide Compound (12). When $X^a$ is —$CO_2$—($C_{1-5}$alkyl), the ester group can be converted to a hydroxymethyl group at the same time. Herein, the reducing agent includes, for example, lithium borohydride, sodium borohydride, calcium borohydride, lithium triethylborohydride, lithium tri-sec-butylborohydride, potassium tri-sec-butylborohydride, zinc borohydride, borane, lithium trimethoxyborohydride, lithium triacetoxyborohydride, tetramethylammonium borohydride, lithium aluminum hydride, sodium aluminum hydride, sodium bis(2-methoxyethoxy)aluminum hydride, diisobutylaluminum hydride, trichlorosilane and the like. The reduction can be also carried out by hydrogenation using a catalyst including palladium, platinum dioxide, Raney nickel or the like. The acid includes, for example, organic acids such as acetic acid, trifluoroacetic acid, benzenesulfonic acid, methanesulfonic acid, p-toluenesulfonic acid, benzoic acid and the like; inorganic acids such as sulfuric acid, hydrochloric acid, hydrobromic acid, phosphoric acid, polyphosphoric acid, nitric acid or the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dimethyl sulfoxide; pyridine; water; and mixtures of solvents selected from these inert solvents.

Reaction Scheme 3

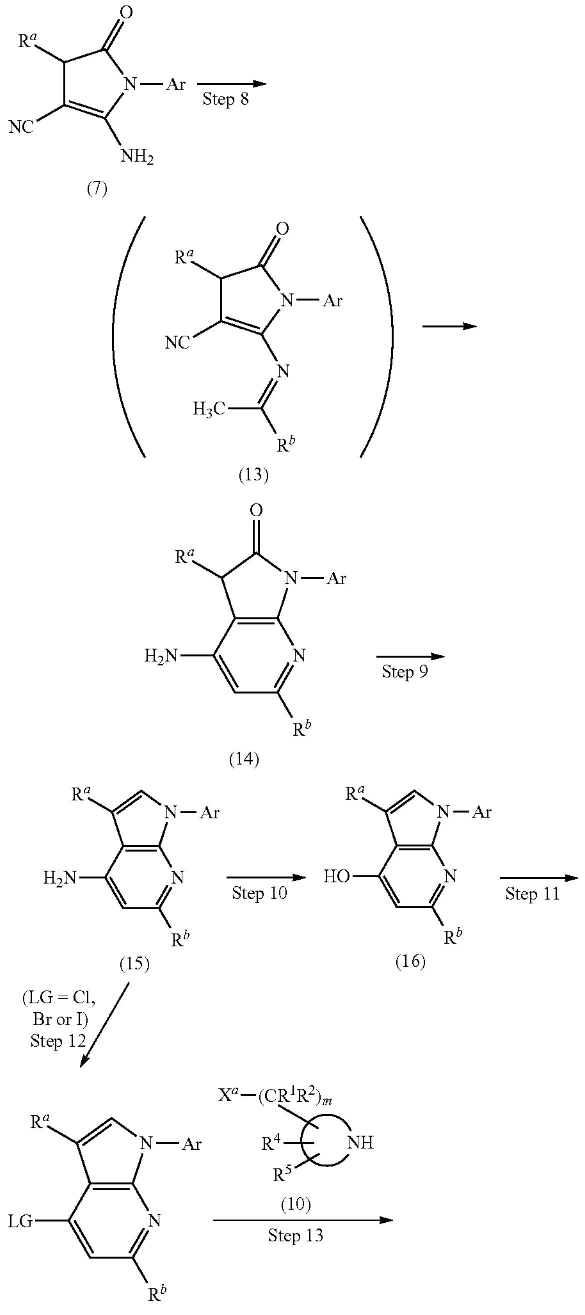

(7)

(13)

(14)

(15)

(16)

(17)

(10)

-continued

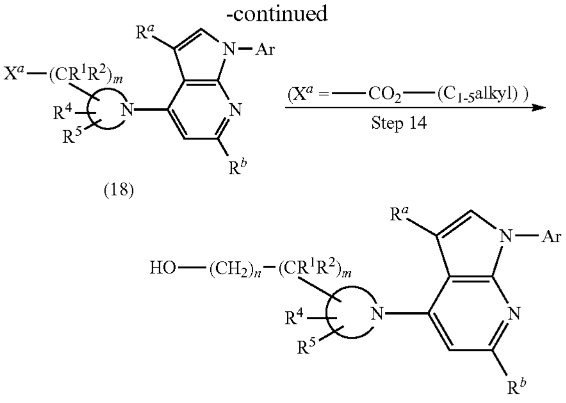

(18)

(19)

Step 8

Compound (7) can be converted to Compound (13) by reacting Compound (7) with ketones such as acetone and the like; vinyl ethers such as isopropenyl methyl ether and the like in an inert solvent in the presence or absence of an acid, and the following conversion from Compound (13) to Compound (14) can be carried out in the presence of base in an inert solvent. Herein, the acid includes, for example, organic acids such as acetic acid, trifluoroacetic acid, benzenesulfonic acid, methanesulfonic acid, p-toluenesulfonic acid, benzoic acid and the like. The base includes, for example, amines such as triethylamine, N,N-diisopropylethylamine, pyridine, 1,8-diazabicyclo[5.4.0]undec-7-ene and the like; inorganic bases such as sodium carbonate, potassium carbonate, sodium hydrogencarbonate, potassium hydrogencarbonate, sodium hydroxide, potassium hydroxide, barium hydroxide, sodium hydride and the like; metal alcoholates such as sodium methoxide, sodium ethoxide, potassium tert-butoxide and the like; metal amides such as sodium amide, lithium diisopropylamide, lithium hexamethyldisilazanide, sodium hexamethyldisilazanide, potassium hexamethyldisilazanide and the like; alkyl lithiums such as n-butyl lithium, sec-butyl lithium, tert-butyl lithium, methyl lithium and the like; and Grignard reagents such as methyl magnesium bromide and the like. The inert solvent includes, for example, ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dimethyl sulfoxide; pyridine; and mixtures of solvents selected from these inert solvents.

Step 9

Compound (14) can be converted to Compound (15) in the same manner as step 7.

Step 10

Compound (15) can be converted into Compound (16) via the corresponding diazonium compound. The conversion to the diazonium compound can be carried out using, for example, sodium nitrite, potassium nitrite, butylnitrite, tert-butylnitrite, iso-butylnitrite or the like in the presence or absence of an acid in an inert solvent. The acid includes, for example, inorganic acids such as sulfuric acid, hydrochloric acid, hydrobromic acid, nitric acid or the like. The inert solvent includes, for example, ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dimethyl sulfoxide; pyridine; water; and mixtures of solvents selected from these inert solvents.

Step 11

Compound (16) can be converted to Compound (17) in the same manner as step 5.

Step 12

When LG is chloride, bromide or iodide, Compound (17) can be obtained from Compound (15) directly by formation of the diazonium compound in the presence of one or more metal salts in an inert solvent. The formation of the diazonium compound can be carried out in the same manner as step 10. The metal salts include, for example, potassium iodide, potassium bromide, sodium iodide, sodium bromide, sodium chloride, copper (I) chloride, copper (II) chloride, copper (I) bromide, copper (II) bromide, copper (I) iodide and the like. The inert solvent includes, for example, ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dimethyl sulfoxide; pyridine; water; and mixtures of solvents selected from these inert solvents.

Step 13

Compound (17) can be converted to Compound (18) in the same manner as step 1.

Step 14

When $X^a$ is $-CO_2-(C_{1-5}alkyl)$, the ester group can be converted to hydroxymethyl group in the same manner as step 7.

Reaction Scheme 4

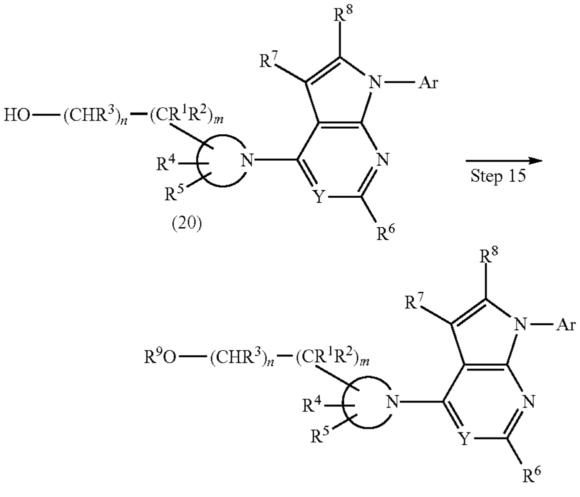

(20)

(21)

Step 15

Compound (20) can be converted to Compound (21) by a coupling of Compound (20) with the corresponding carboxylic acid using a conventional coupling reagent in the presence or absence of an additive or a base in an inert solvent or a coupling of Compound (20) with the corresponding acyl halide in the presence or absence of a base in an inert solvent. When $R^9$ has protective groups of an amino group, a hydroxy group, a mercapto group, a carboxy group, a guanidine group or a phosphoric acid group, those protective groups can be removed by conventional methods for deprotection (ref. Theodora W. Greene and Peter G. M. Wuts "Protective Groups in Organic Synthesis"; Wiley-Interscience) after the above coupling. Herein, the coupling reagent includes, for example, N,N'-dicyclohexylcarbodiimide (DCC), 1-(3-dimethylaminopropyl)-3-ethylcarbodiimide (EDC), 1,1'-carbonyldiimidazole (CDI), diphenylphosphorylazide (DPPA), diethyl cyanophosphate and the like. The additive includes, for example, 1-hydroxybenzotriazole (HOBt), N-hydroxysuccinimide, 4-dimethylaminopyridine and the like. The base includes amines such as triethylamine, N,N-diisopropylethylamine, pyridine, 1,8-diazabicyclo[5.4.0]undec-7-ene and the like; inorganic bases such as sodium carbonate, potassium carbonate, sodium hydrogencarbonate, potassium hydrogencarbonate, sodium hydroxide, potassium hydroxide, barium hydroxide, sodium hydride and the like; metal alcoholates such as sodium methoxide, sodium ethoxide, potassium tert-butoxide and the like; metal amides such as sodium amide, lithium diisopropylamide, lithium hexamethyldisilazanide, sodium hexamethyldisilazanide, potassium hexamethyldisilazanide and the like; alkyl lithiums such as n-butyl lithium, sec-butyl lithium, tert-butyl lithium, methyl lithium and the like; and Grignard reagents such as methyl magnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dimethyl sulfoxide; pyridine; chloroform; dichloromethane; water; and mixtures of solvents selected from these inert solvents.

The compound of the present invention is useful as a therapeutic or prophylactic agent for diseases in which CRF is considered to be involved. For this purpose, the compound of the present invention can be formulated into tablets, pills, capsules, granules, powders, solutions, emulsions, suspensions, injections and the like by a conventional preparation technique by adding conventional fillers, binders, disintegrators, pH-adjusting agents, solvents, etc.

The compound of the present invention can be administered to an adult patient in a dose of 0.1 to 500 mg per day in one portion or several portions orally or parenterally. The dose can be properly increased or decreased depending on the kind of a disease and the age, body weight and symptom of a patient.

EMBODIMENTS OF THE INVENTION

The present invention is concretely explained with reference to the following examples and test example, but is not limited thereto.

Example 1

Synthesis of 2-{1-[7-(4-bromo-2,6-dimethylphenyl)-2,5-dimethyl-7H-pyrrolo[2,3-d]pyrimidin-4-yl]piperidin-4-yl}ethanol hydrochloride (compound 1-074)

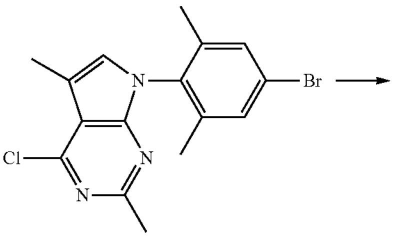

-continued

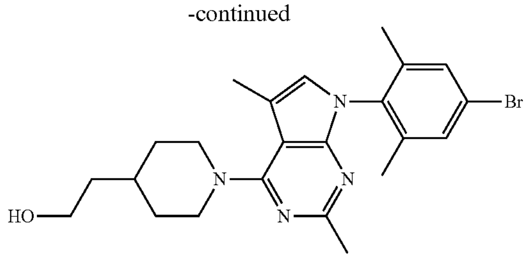

(1) A mixture of 7-(4-bromo-2,6-dimethylphenyl)-4-chloro-2,5-dimethyl-7H-pyrrolo[2,3-d]pyrimidine (6.0 g), 4-(2-hydroxyethyl)piperidine (3.2 g), N,N-diisopropylethylamine (3.2 g) in ethanol (15 mL) was heated at reflux for 5.5 hours. The reaction mixture was cooled to room temperature, poured into a saturated aqueous sodium hydrogencarbonate, and then extracted with ethyl acetate three times. The organic layer was washed with brine, dried over anhydrous sodium sulfate and filtered. The filtrate was concentrated under reduced pressure and purified by a silica gel column chromatography (silica gel: Wako Gel (C200), eluent: hexane/ethyl acetate=2:1) to obtain 2-{1-[7-(4-bromo-2,6-dimethyl-phenyl)-2,5-dimethyl-7H-pyrrolo[2,3-d]pyrimidin-4-yl]-piperidin-4-yl}-ethanol as a white solid (6.41 g).

(2) To a suspension of 2-{1-[7-(4-bromo-2,6-dimethyl-phenyl)-2,5-dimethyl-7H-pyrrolo[2,3-d]pyrimidin-4-yl]-piperidin-4-yl}-ethanol (6.41 g) in ethanol (51 mL) was added 4 M HCl in ethyl acetate (4.2 mL) under ice-cooling. After removing the solvent, ethyl acetate (26 mL) was added to the residue. The mixture was stirred overnight to afford a white crystal. The crystal was collected by filtration to give the title compound (6.1 g).

m.p. 187-189° C.

Table 1 and Table 2 list the compound obtained in Example 1 and compounds obtained by the similar procedure as in Example 1.

Example 2

Synthesis of optically active 1-[7-(2-bromo-4-trifluoromethylphenyl)-2,5,6-trimethyl-7H-pyrrolo[2,3-d]pyrimidine-4-yl]piperidine-3-carbonitrile (compound 1-134, 1-135, 1-136 and 1-137)

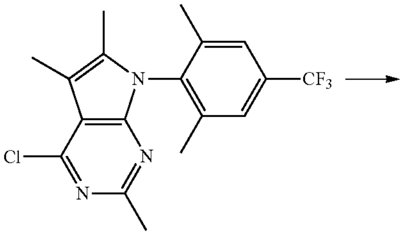

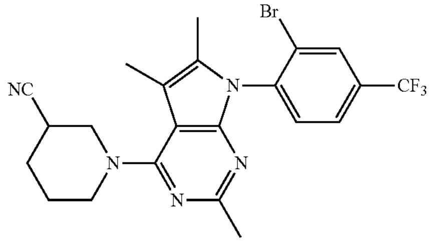

A mixture of 7-(2-bromo-4-trifluoromethylphenyl)-4-chloro-2,5,6-trimethyl-7H-pyrrolo[2,3-d]pyrimidine (400 mg), piperidine-3-carbonitrile (290 mg), N,N-diisopropylethylamine (309 mg) in ethanol (2 mL) was heated at reflux for 6 days. The reaction mixture was cooled to room temperature, and concentrated under reduced pressure. The residue was purified by a silica gel column chromatography (silica gel: Wako Gel (C200), eluent: hexane/ethyl acetate=5:1) to obtain two diastereoisomers (low polar diastereoisomer: 62 mg and high polar diastereoisomer: 36 mg) of 1-[7-(2-bromo-4-trifluoromethylphenyl)-2,5,6-trimethyl-7H-pyrrolo[2,3-d]pyrimidine-4-yl]piperidine-3-carbonitrile.

Low Polar Diastereoisomer:

Rf value 0.64 (developing solvent: hexane/ethyl acetate=1:1, TLC plate Silica gel 60 $F_{254}$ (Merck))

$^1$H NMR (300 MHz) δ 1.68-1.83 (1H, m), 1.85-2.07 (3H, m), 2.08 (3H, s), 2.40 (3H, s), 2.51 (3H, s), 3.04-3.16 (1H, m), 3.26-3.62 (3H, m), 3.81-3.95 (1H, m), 7.43 (1H, d, J=8.2 Hz), 7.74 (1H, d, J=8.2 Hz), 8.02 (1H, s)

High Polar Diastereoisomer:

Rf value 0.56 (developing solvent: hexane/ethyl acetate=1:1, TLC plate Silica gel 60 $F_{254}$ (Merck))

$^1$H NMR (300 MHz) δ 1.65-1.83 (1H, m), 1.82-2.16 (6H, m), 2.40 (3H, s), 2.51 (3H, s), 3.04-3.17 (1H, m), 3.28-3.63 (3H, m), 3.85-3.98 (1H, m), 7.47 (1H, d, J=8.6 Hz), 7.74 (1H, d, J=8.6 Hz), 8.02 (1H, s)

The low polar diastereoisomer was optically resolved by high performance liquid chromatography to give each enantiomer.

Compound 1-134:

$^1$H NMR (300 MHz) δ 1.68-1.83 (1H, m), 1.85-2.07 (3H, m), 2.08 (3H, s), 2.40 (3H, s), 2.51 (3H, s), 3.04-3.16 (1H, m), 3.26-3.62 (3H, m), 3.81-3.95 (1H, m), 7.43 (1H, d, J=8.2 Hz), 7.74 (1H, d, J=8.2 Hz), 8.02 (1H, s)

HPLC retention time: 20.0 min. (CHIRAL PAK AD (DAICEL CHEMICAL INDUSTRIES, LTD), 2.0 cm I.D.×25 cm, mobile phase: hexane–IPA=4:1, flow rate: 5.0 mL/min.)

Compound 1-135:

$^1$H NMR (300 MHz) δ 1.68-1.83 (1H, m), 1.85-2.07 (3H, m), 2.08 (3H, s), 2.40 (3H, s), 2.51 (3H, s), 3.04-3.16 (1H, m), 3.26-3.62 (3H, m), 3.81-3.95 (1H, m), 7.43 (1H, d, J=8.2 Hz), 7.74 (1H, d, J=8.2 Hz), 8.02 (1H, s)

HPLC retention time: 23.0 min. (CHIRAL PAK AD (DAICEL CHEMICAL INDUSTRIES, LTD), 2.0 cm I.D.×25 cm, mobile phase: hexane–IPA=4:1, flow rate: 5.0 mL/min.)

The high polar diastereoisomer was also optically resolved by high performance liquid chromatography to give each enantiomer.

Compound 1-136:

$^1$H NMR (300 MHz) δ 1.65-1.83 (1H, m), 1.82-2.16 (6H, m), 2.40 (3H, s), 2.51 (3H, s), 3.04-3.17 (1H, m), 3.28-3.63 (3H, m), 3.85-3.98 (1H, m), 7.47 (1H, d, J=8.6 Hz), 7.74 (1H, d, J=8.6 Hz), 8.02 (1H, s)

HPLC retention time: 21.4 min. (CHIRAL PAK AD (DAICEL CHEMICAL INDUSTRIES, LTD), 2.0 cm I.D.×25 cm, mobile phase: hexane–IPA=4:1, flow rate: 5.0 mL/min.)

Compound 1-137:

$^1$H NMR (300 MHz) δ 1.65-1.83 (1H, m), 1.82-2.16 (6H, m), 2.40 (3H, s), 2.51 (3H, s), 3.04-3.17 (1H, m), 3.28-3.63 (3H, m), 3.85-3.98 (1H, m), 7.47 (1H, d, J=8.6 Hz), 7.74 (1H, d, J=8.6 Hz), 8.02 (1H, s)

HPLC retention time: 32.8 min. (CHIRAL PAK AD (DAICEL CHEMICAL INDUSTRIES, LTD), 2.0 cm I.D.×25 cm, mobile phase: hexane–IPA=4:1, flow rate: 5.0 mL/min.)

Table 1 lists the compounds obtained in Example 2.

Example 3

Synthesis of {1-[7-(4-bromo-2,6-dimethylphenyl)-2,5-dimethyl-7H-pyrrolo[2,3-d]pyrimidin-4-yl]piperidin-4-yl}methanol hydrochloride (1-054)

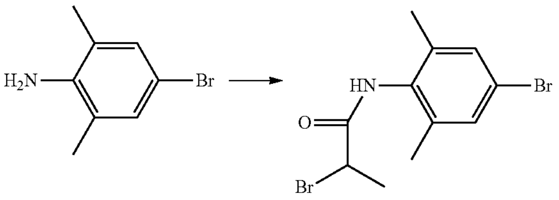

(1) To a solution of 4-bromo-2,6-dimethylaniline (100.0 g) in tetrahydrofuran (400 mL) was added triethylamine (60.7 g) and 2-bromopropionyl bromide (129.5 g) under ice-cooling. The mixture was stirred at room temperature for 1 hour and cooled in an ice-cooling bath. To the reaction mixture was added a sodium hydrogencarbonate aqueous solution and the mixture was stirred at room temperature for 30 minutes. The precipitate was collected by filtration, washed with water and diethyl ether, and dried to give 2-bromo-N-(4-bromo-2,6-dimethylphenyl)propionamide (151.2 g).

m.p. 187-189° C.

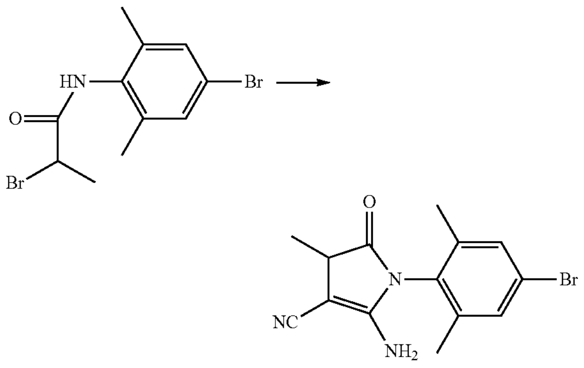

(2) To a suspension of NaH (17.2 g) in tetrahydrofuran (500 mL) was added a solution of malononitrile (28.4 g) in tetrahydrofuran (100 mL) under ice-cooling and the mixture was stirred at room temperature for 1 hour. 2-Bromo-N-(4-bromo-2,6-dimethylphenyl)propionamide (120 g) was added and the mixture was heated at reflux for 1 hour. With ice-cooling, an ammonium chloride aqueous solution was added and extracted with ethyl acetate. The organic layer was washed with brine, dried over anhydrous sodium sulfate and filtered. The filtrate was concentrated under reduced pressure to give a solid. The solid was washed with a mixture of diisopropylether and ethyl acetate and filtered, dried to give 2-amino-1-(4-bromo-2,6-dimethylphenyl)-4-methyl-5-oxo-4,5-dihydro-1H-pyrrole-3-carbonitrile (110.1 g).

m.p. 175-177° C.

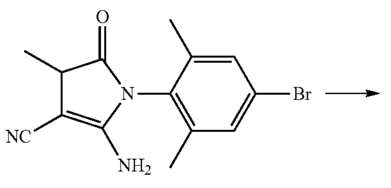

-continued

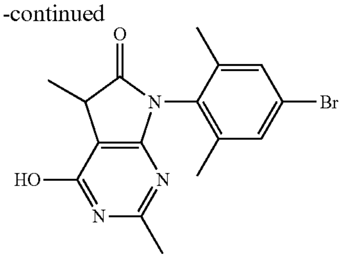

(3) To a suspension of 2-amino-1-(4-bromo-2,6-dimethylphenyl)-4-methyl-5-oxo-4,5-dihydro-1H-pyrrole-3-carbonitrile (100 g) in acetic acid (100 mL) was added acetic anhydride (38.3 g) and the mixture was heated at reflux for 8 hours. After cooling to room temperature, the solvent was concentrated under reduced pressure, and water was added and extracted with ethyl acetate. The organic layer was washed with brine, dried over anhydrous sodium sulfate and filtered. The filtrate was concentrated under reduced pressure and the residue was crystallized from a mixture of ethyl acetate and diisopropylether to give 7-(4-bromo-2,6-dimethylphenyl)-4-hydroxy-2,5-dimethyl-5,7-dihydropyrrolo[2,3-d]pyrimidin-6-one (56.6 g).

m.p. 271-273° C.

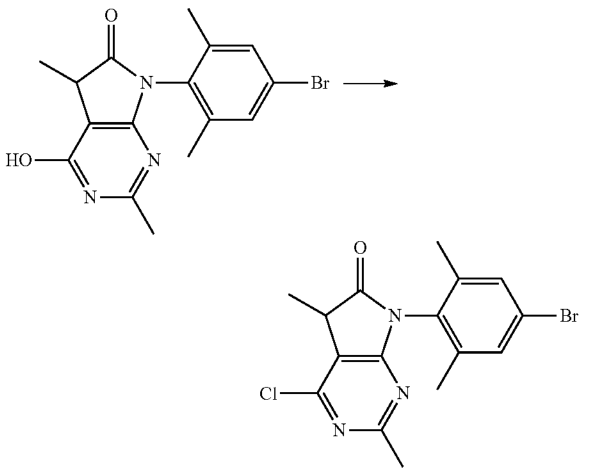

(4) To a suspension of 7-(4-bromo-2,6-dimethylphenyl)-4-hydroxy-2,5-dimethyl-5,7-dihydropyrrolo[2,3-d]pyrimidin-6-one (10.0 g) in phosphoryl chloride (25.7 mL) was added N,N-dimethylaniline (2.6 mL) and the mixture was heated at 120° C. for 6 hours. After cooling to room temperature the mixture was poured into ice-cold water and extracted with ethyl acetate. The organic layer was washed with a sodium hydrogencarbonate aqueous solution and brine, dried over anhydrous sodium sulfate and filtered. The filtrate was concentrated under reduced pressure to give a solid. The solid was washed with diisopropylether to afford 7-(4-bromo-2,6-dimethylphenyl)-4-chloro-2,5-dimethyl-5,7-dihydropyrrolo[2,3-d]pyrimidin-6-one (8.0 g)

m.p. 148-150° C.

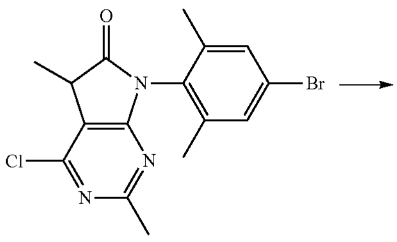

-continued

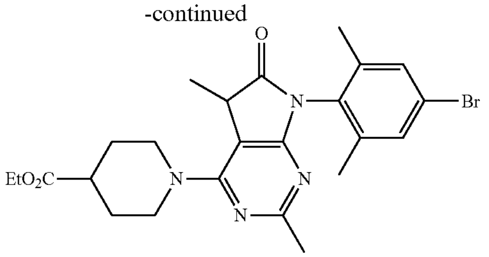

(5) A suspension of 7-(4-bromo-2,6-dimethylphenyl)-4-chloro-2,5-dimethyl-5,7-dihydropyrrolo[2,3-d]pyrimidin-6-one (7.5 g), ethyl isonipecotate (4.7 g), N,N-diisopropylethylamine (3.8 g) in ethanol (35 mL) was heated at reflux for 12 hours. The reaction mixture was stirred at room temperature to afford a solid. The solid was collected by filtration and washed with cold ethanol to give 1-[7-(4-bromo-2,6-dimethylphenyl)-2,5-dimethyl-6-oxo-6,7-dihydro-5H-pyrrolo[2,3-d]pyrimidin-4-yl]piperidine-4-carboxylic acid ethyl ester (7.7 g).

m.p. 159-161° C.

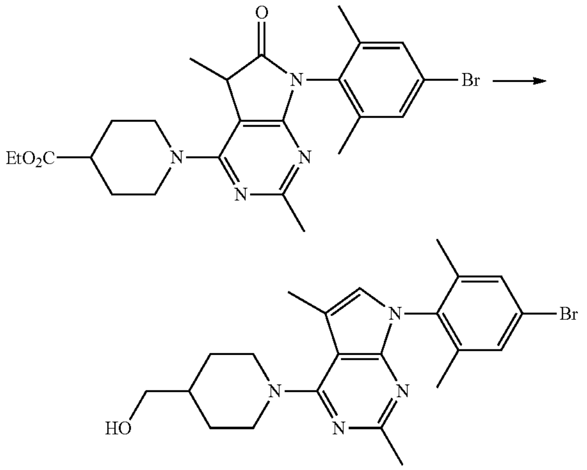

(6) To a solution of lithium borohydride (2.61 g) in tetrahydrofuran (60 mL) was added a solution of 1-[7-(4-bromo-2,6-dimethylphenyl)-2,5-dimethyl-6-oxo-6,7-dihydro-5H-pyrrolo[2,3-d]pyrimidin-4-yl]piperidine-4-carboxylic acid ethyl ester (6.0 g) in a mixture of tetrahydrofuran (60 mL) and methanol (3 mL) dropwise over 10 minutes under ice-cooling. The reaction mixture was warmed up to room temperature and stirred for 3 hours. After cooling with an ice-bath, 6 M HCl aqueous solution (30 mL) was added and stirred at room temperature for 1 hour. The solution was made to alkaline (pH=9) with 6 M NaOH aqueous solution, and extracted with ethyl acetate. The organic layer was washed with brine, dried over anhydrous sodium sulfate and filtered. The filtrate was concentrated under reduced pressure and the residue was purified by a silica gel column chromatography (silica gel: Wako Gel (C200), eluent: hexane/ethyl acetate=1:1) to give {1-[7-(4-bromo-2,6-dimethylphenyl)-2,5-dimethyl-7H-pyrrolo[2,3-d]pyrimidin-4-yl]piperidin-4-yl}methanol (4.6 g).

(7) To a suspension of {1-[7-(4-bromo-2,6-dimethylphenyl)-2,5-dimethyl-7H-pyrrolo[2,3-d]pyrimidin-4-yl]piperidin-4-yl}methanol (0.71 g) in water (7 mL) was added concentrated HCl aqueous solution (0.15 mL) under ice-cooling. The mixture was stirred at room temperature for 5 minutes, cooled with an ice-bath again, and stirred for 15 minutes in an ice-cooling bath. The precipitate was collected by filtration, washed with water and dried to give the title compound (0.73 g).

Example 4

Synthesis of {1-[1-(4-chloro-2,6-dimethylphenyl)-3,6-dimethyl-1H-pyrrolo[2,3-b]pyridin-4-yl]piperidin-4-yl}methanol hydrochloride (2-019)

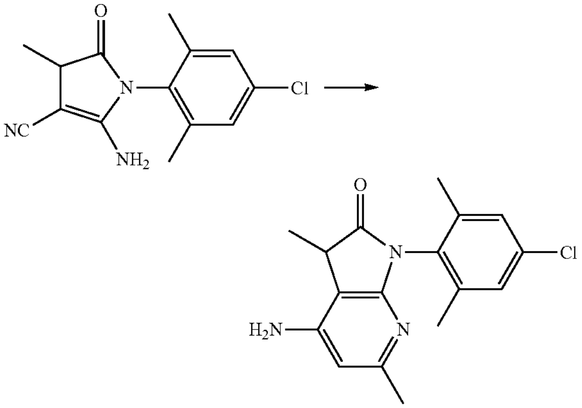

(1) To a solution of 2-amino-1-(4-chloro-2,6-dimethylphenyl)-4-methyl-5-oxo-4,5-dihydro-1H-pyrrole-3-carbonitrile (44.1 g), which was obtained in the same method as example 3, in tetrahydrofuran (220 mL) was added isopropenyl methyl ether (46.2 g) and p-toluenesulfonic acid (608 mg). The mixture was heated at reflux for 1 hour. After removing the solvent under reduced pressure, the residue was dissolved in tetrahydrofuran (500 mL) and cooled in an ice-NaCl bath. Lithium diisopropylamide in tetrahydrofuran solution (generated from 2.64M n-butyl lithium in hexane (127 mL), diisopropylamine (40.5 g) and tetrahydrofuran (300 mL)) was added dropwise over 30 minutes, and stirred at room temperature for 1 hour. To the reaction mixture a saturated $NH_4Cl$ aqueous solution was added and separated. The aqueous layer was extracted with $CHCl_3$. The organic layer was washed with water, dried over anhydrous sodium sulfate and filtered. The filtrate was concentrated under reduced pressure and the residue was purified by a silica gel column chromatography (silica gel: Wako Gel (C200), eluent: hexane/ethyl acetate=1:1) to give 4-amino-1-(4-chloro-2,6-dimethylphenyl)-3,6-dimethyl-1,3-dihydropyrrolo[2,3-b]pyridin-2-one (35.8 g) as an amorphous.

MS (ES, Pos.): 316 $(M+1)^+$, 318 $(M+3)^+$, 338 $(M+Na)^+$, 340 $(M+Na+2)^+$

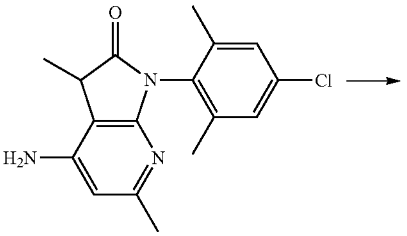

-continued

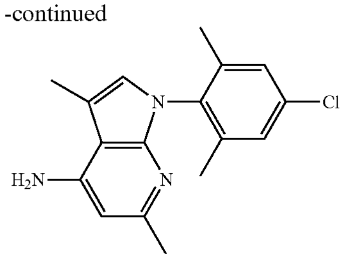

(2) To a suspension of lithium borohydride (11.6 g) in tetrahydrofuran (50 mL) was added a solution of 4-amino-1-(4-chloro-2,6-dimethylphenyl)-3,6-dimethyl-1,3-dihydro-pyrrolo[2,3-b]pyridin-2-one (33.7 g) in tetrahydrofuran (100 mL) was added. The mixture was stirred at reflux for 1 hour. After cooling with ice-cooling bath, a 6M HCl aqueous solution was added slowly. The solution was made to alkaline (pH=9) with 4 M NaOH aqueous solution, and extracted with ethyl acetate. The organic layer was washed with brine, dried over anhydrous sodium sulfate and filtered. The filtrate was concentrated under reduced pressure and the residue was purified by a silica gel column chromatography (silica gel: Wako Gel (C200), eluent: hexane/ethyl acetate=3:1) to give 1-(4-chloro-2,6-dimethylphenyl)-3,6-dimethyl-1H-pyrrolo [2,3-b]pyridin-4-ylamine (17.9 g) as a solid.

m.p. 190-192° C.

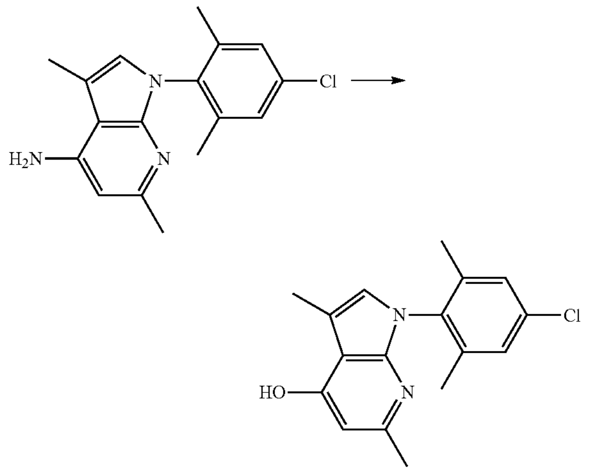

(3) With ice-cooling, to a suspension of 1-(4-chloro-2,6-dimethylphenyl)-3,6-dimethyl-1H-pyrrolo[2,3-b]pyridin-4-ylamine (17.9 g) in a mixture of 1,4-dioxane (45 mL) and water (45 mL) was added dropwise a mixture of concentrated $H_2SO_4$ (17.8 mL) and water (90 mL) and then a solution of $NaNO_2$ (6.2 g) in water (62 mL). The mixture was stirred at room temperature for 20 minutes, and heated at 100° C. for 1.5 hours. After cooling in an ice-cooling bath, the reaction mixture was poured into a cold saturated $NaHCO_3$ aqueous solution and extracted with $CHCl_3$. The organic layer was dried over anhydrous sodium sulfate, and filtered. The filtrate was concentrated under reduced pressure to give a solid. The solid was washed with a mixture of ethyl acetate and diisopropylether (1:5) to give 1-(4-chloro-2,6-dimethylphenyl)-3,6-dimethyl-1H-pyrrolo[2,3-b]pyridin-4-ol (14.4 g).

m.p. 260° C. (decomp.)

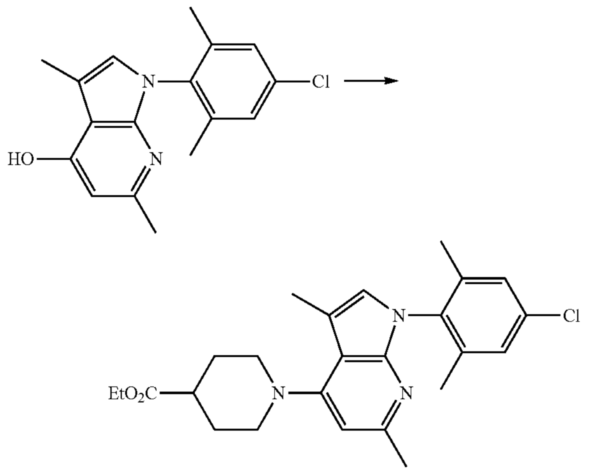

(4) To a mixture of 1-(4-chloro-2,6-dimethylphenyl)-3,6-dimethyl-1H-pyrrolo[2,3-b]pyridin-4-ol (14.4 g) and triethylamine (9.7 g) in $CHCl_3$ (100 mL) was added trifluoromethansulfonic anhydride (9.7 mL) in an ice-cooling bath. After stirring for 10 minutes, water was added and extracted with $CHCl_3$. The organic layer was washed with water and brine successively, dried over anhydrous sodium sulfate and filtered. The filtrate was concentrated under reduced pressure to give crude trifluoromethanesulfonic acid 1-(4-chloro-2,6-dimethylphenyl)-3,6-dimethyl-1H-pyrrolo[2,3-b]pyridin-4-yl ester (20.7 g).

A mixture of the crude trifluoromethanesulfonic acid 1-(4-chloro-2,6-dimethylphenyl)-3,6-dimethyl-1H-pyrrolo[2,3-b]pyridin-4-yl ester (20.5 g), ethyl isonipecotate (74.4 g) and N,N-diisopropylethylamine (12.2 g) was heated at 150-170° C. for 1 hour. To the reaction mixture, water was added and extracted with ethyl acetate. The organic layer was washed with water, and brine, dried over anhydrous sodium sulfate and filtered. The filtrate was concentrated under reduced pressure and the residue was purified by a silica gel column chromatography (silica gel: Wako Gel (C200), eluent: hexane/ethyl acetate=5:1) to give 1-[1-(4-chloro-2,6-dimethylphenyl)-3,6-dimethyl-1H-pyrrolo[2,3-b]pyridin-4-yl]piperidine-4-carboxylic acid ethyl ester (16.6 g) as a pale yellow solid.

m.p. 140-142° C.

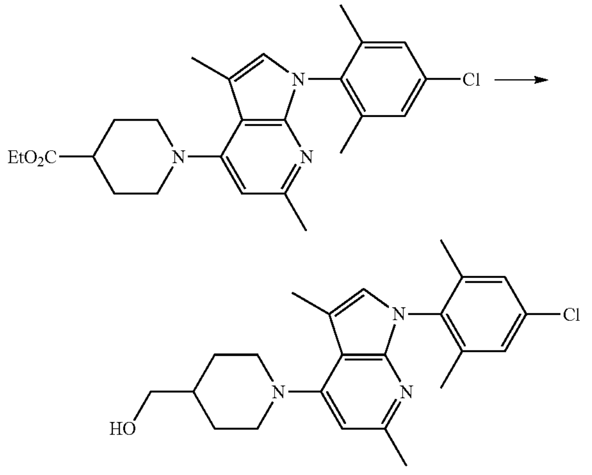

(5) To a suspension of lithium borohydride (4.11 g) in tetrahydrofuran (50 mL) was added a solution of 1-[1-(4- chloro-2,6-dimethylphenyl)-3,6-dimethyl-1H-pyrrolo[2,3-b]pyridin-4-yl]piperidine-4-carboxylic acid ethyl ester (16.6 g) in a mixture of tertrahydrofuran (80 mL) and methanol (7.7 mL) in an ice-cooling bath. The mixture was stirred at room temperature for 2 hours. After cooling with an ice-cooling bath, water was added and the mixture was poured slowly into a 3M HCl aqueous solution. The solution was made to alkaline (pH=8) with 4 M NaOH aqueous solution to give a solid. The solid was collected by filtration and washed with water and diethylether. The solid was recrystallized from a mixture of ethanol and ethyl acetate to give {1-[1-(4-chloro-2,6-dimethylphenyl)-3,6-dimethyl-1H-pyrrolo[2,3-b]pyridin-4-yl]piperidin-4-yl}methanol (9.1 g).

(6) In the same method as example 1-(2), the title compound (8.0 g) was obtained from {1-[1-(4-chloro-2,6-dimethylphenyl)-3,6-dimethyl-1H-pyrrolo[2,3-b]pyridin-4-yl]piperidin-4-yl}methanol (9.1 g).

Example 5

Synthesis of carbonic acid 1-[7-(4-bromo-2,6-dimethyl-phenyl)-2,5-dimethyl-7H-pyrrolo[2,3-d]pyrimidin-4-yl]-piperidin-4-ylmethyl ester ethyl ester (3-001)

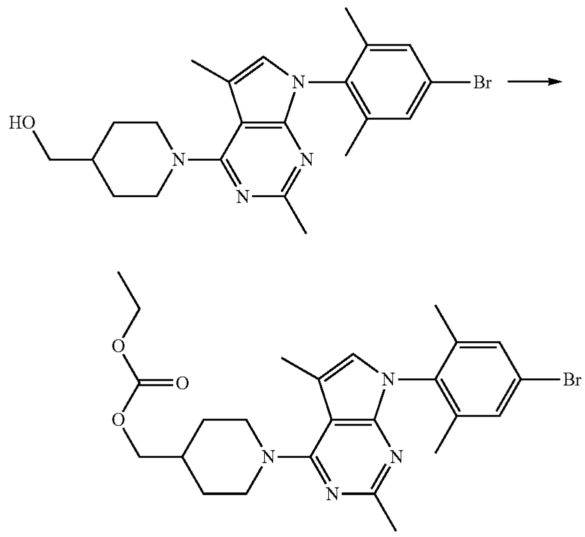

{1-[7-(4-Bromo-2,6-dimethylphenyl)-2,5-dimethyl-7H-pyrrolo[2,3-d]pyrimidin-4-yl]piperidin-4-yl}methanol (1.15 g) synthesized in the similar manner as example 1 in tetrahydrofuran (25 mL) was stirred, then NaH (60% in paraffin, 0.10 g) was added and the mixture was healed at reflux for 3 hours. After cooling to 0° C., ethyl chloroformate (0.28 g) in a small amount of tetrahydrofuran was added and the reaction mixture was allowed to reach room temperature and evaporated. The residue was purified over a silica gel on a glass filter (eluent: $CH_2Cl_2/CH_3CN$=95:5 then 90:10) to give the title product (366 mg).

Table 3 lists the compound obtained in Example 5 and compounds obtained by the similar procedure as in Example 5.

Example 6

Synthesis of decanoic acid 1-[7-(4-bromo-2,6-dimethyl-phenyl)-2,5-dimethyl-7H-pyrrolo[2,3-d]pyrimidin-4-yl]-piperidin-4-ylmethyl ester (3-009)

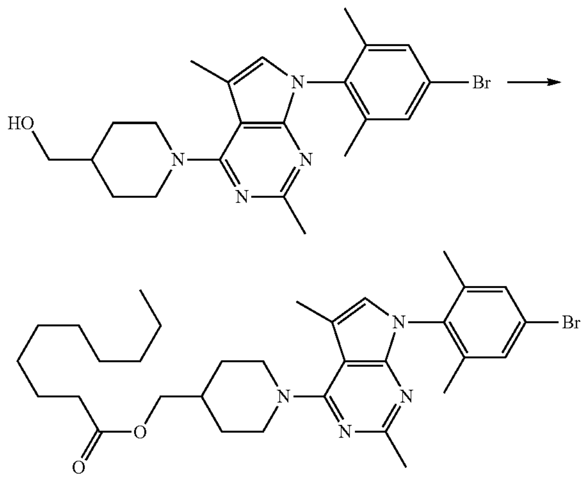

Under nitrogen atmosphere, {1-[7-(4-bromo-2,6-dimethylphenyl)-2,5-dimethyl-7H-pyrrolo[2,3-d]pyrimidin-4-yl]piperidin-4-yl}methanol (1.15 g) synthesized in the similar manner as example 1 in tetrahydrofuran (25 mL) was stirred, then NaH (60% in paraffin, 0.10 g) was added and the mixture was heated at reflux overnight, giving mixture (I). Decanoic acid (0.45 g) in tetrahydrofuran (25 mL) was stirred, then 1,1'-carbonyldiimidazole (0.42 g) was added and the mixture was stirred overnight at room temperature, giving mixture (II). The mixture (II) was added dropwise to the mixture (I) at 0-5° C. and the resulting reaction mixture was allowed to reach room temperature. The solvent was evaporated and the residue was purified over a silica gel on a glass filter (eluent: $CH_2Cl_2/CH_3CN$=100:0, 95:5 then 90:10) to give the title product (888 mg).

Table 3 lists the compound obtained in Example 6 and compounds obtained by the similar procedure as in Example 6.

Example 7

Synthesis of eicosa-5,8,11,14-tetraenoic acid 1-[7-(4-bromo-2,6-dimethyl-phenyl)-2,5-dimethyl-7H-pyrrolo[2,3-d]pyrimidin-4-yl]-piperidin-4-ylmethyl ester (3-020)

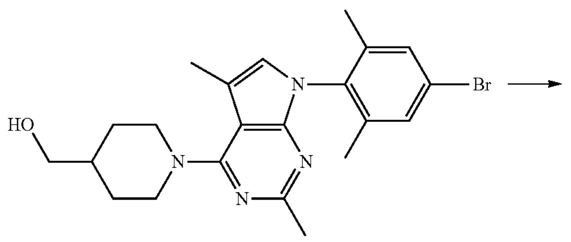

-continued

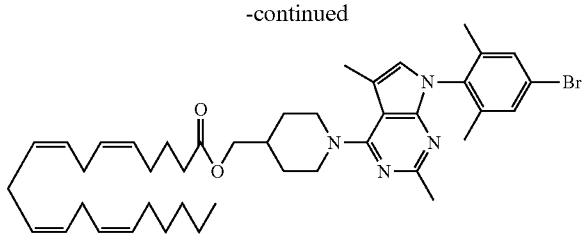

Under nitrogen atmosphere, to a solution of 1-[7-(4-bromo-2,6-dimethylphenyl)-2,5-dimethyl-7H-pyrrolo[2,3-d]pyrimidin-4-yl]piperidin-4-yl}methanol (606 mg) in $CH_2Cl_2$ (20 ml) was added arachidonic acid (500 mg), 4-dimethylaminopyridine (33 mg) and N,N'-dicyclohexylcarbodiimide (565 mg). The mixture was stirred at room temperature for 2 hours and concentrated under reduced pressure. The residue was purified by a silica gel column chromatography (silica gel: Wako Gel (C200), eluent: hexane/ethyl acetate=7:1) to give the title compound (990 mg) as an oil.

Table 3 lists the compound obtained in Example 7 and compounds obtained by the similar procedure as in Example 7.

Example 8

Synthesis of (S)-2-tert-butoxycarbonylamino-3-(1H-indol-3-yl)-propionic acid 1-[7-(4-bromo-2,6-dimethyl-phenyl)-2,5-dimethyl-7H-pyrrolo[2,3-d]pyrimidin-4-yl]-piperidin-4-ylmethyl ester (3-014) and (S)-2-amino-3-(1H-indol-3-yl)-propionic acid 1-[7-(4-bromo-2,6-dimethyl-phenyl)-2,5-dimethyl-7H-pyrrolo[2,3-d]pyrimidin-4-yl]-piperidin-4-ylmethyl ester (3-016)

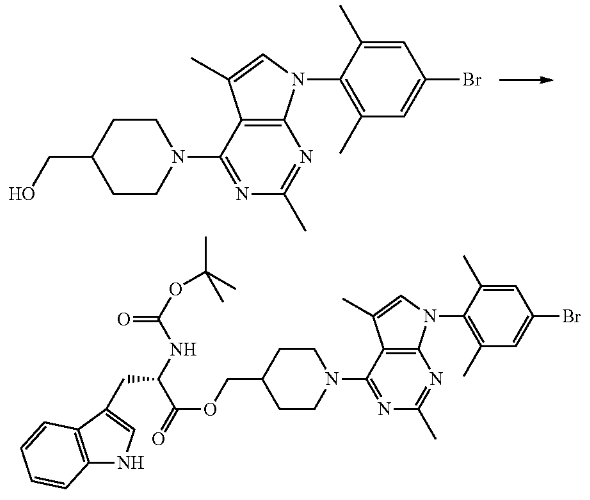

(1) A solution of N-(tert-butoxycarbonyl)-L-tryptophan (510 mg) and 1,1'-carbonyldiimidazole (330 mg) in acetonitrile (10 mL) was stirred at room temperature overnight. The solvent is evaporated and the residue is redissolved in toluene (5 mL). Sequentially {1-[7-(4-bromo-2,6-dimethylphenyl)-2,5-dimethyl-7H-pyrrolo[2,3-d]pyrimidin-4-yl]piperidin-4-yl}methanol (594 mg) and 1,8-diazabicyclo[5.4.0]undec-7-ene (40 μL) were added and stirred at room temperature for 2 days. After evaporation of the solvent the residue was extracted with ethylacetate and dilute $NaHCO_3$ solution. After the usual work-up the residue of the extract was purified over silica gel (eluent: $CH_2Cl_2$/MeOH=95:5) to give the title product 3-014 (578 mg).

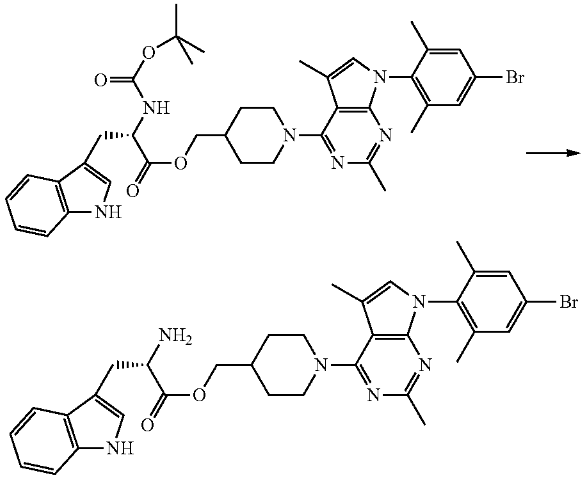

(2) To a solution of 3-014 (1.16 g) in $CH_2Cl_2$ (200 mL) a 6M solution of HCl in isopropanol (2.7 mL) was added and stirred at room temperature for 2 days. After evaporation, the residue is purified by reversed-phase chromatography (BDS RP18, 8 μm particle size, 200 g, ID 5 cm column, eluent: (0.5% $NH_4Ac/CH_3CN$: 9:1 (v/v)) $CH_3CN$ 85/15 to 1/9 gradient). After partial evaporation of the aqueous fractions a fine precipitate of pure compound is formed and recuperated, yielding the tittle compound 3-016 (139 mg). The aqueous filtrate was extracted with $CH_2Cl_2$ and the organic extract was washed with dilute ammonia. After the usual work-up of the organic extract some more product 3-016 was recuperated (304 mg).

Example 9

Synthesis of phosphoric acid 1-[7-(4-bromo-2,6-dimethyl-phenyl)-2,5-dimethyl-7H-pyrrolo[2,3-d]pyrimidin-4-yl]-piperidin-4-ylmethyl ester diethyl ester (3-017)

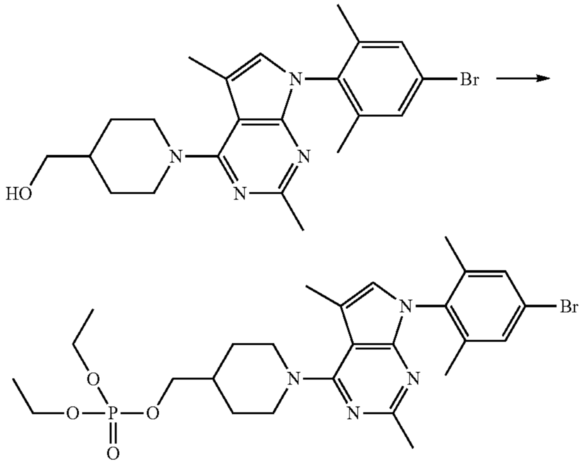

Under nitrogen atmosphere, to a solution of {1-[7-(4-bromo-2,6-dimethylphenyl)-2,5-dimethyl-7H-pyrrolo[2,3-d]pyrimidin-4-yl]piperidin-4-yl}methanol (0.50 g) and 4-dimethylaminopyridine (0.55 g) in $CH_2Cl_2$ (50 mL) at 0° C. diethyl chlorophosphate (0.38 g) was added dropwise and the reaction is slowly heated up to room temperature. The reaction mixture is poured on ice-water and extracted with $CH_2Cl_2$. After the usual work-up the residue is purified over silica gel on a glass filter (eluent: $CH_2Cl_2$/MeOH=98:2) yielding product 3-017 (0.31 g).

Example 10

Synthesis of phosphoric acid mono-{1-[7-(4-bromo-2,6-dimethyl-phenyl)-2,5-dimethyl-7H-pyrrolo[2,3-d]pyrimidin-4-yl]-piperidin-4-ylmethyl}ester (3-018)

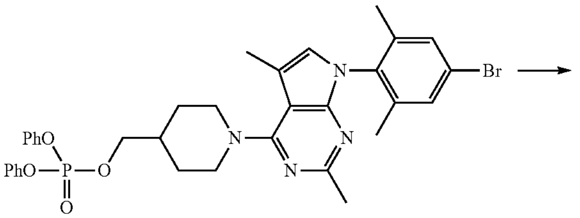

-continued

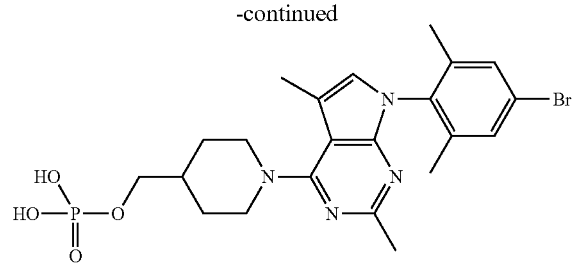

{1-[7-(4-bromo-2,6-dimethylphenyl)-2,5-dimethyl-7H-pyrrolo[2,3-d]pyrimidin-4-yl]piperidin-4-yl}methyl diphenoxyphosphate ester (1.8 g), which was produced in a similar way as in example 9, was dissolved in 50% NaOH (1 mL) and dioxane (50 mL) and stirred at 60° C. for several hours until completion of the hydrolysis. The solution was treated with water (25 mL), acidified with HCl until pH=2 and extracted five times with portions $CH_2Cl_2$, using NaCl to improve the phase separation. After the usual work-up the residue is purified over silica gel on a glass filter (eluent: $CH_2Cl_2$/MeOH=9:1 to pure MeOH) yielding the title product 3-018 (0.38 g).

TABLE 1*[1]

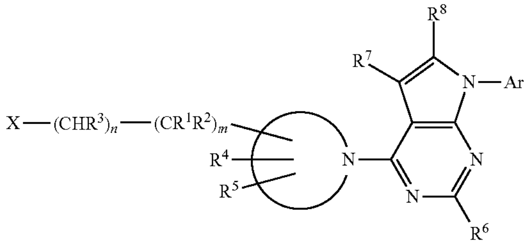

| Com. No. | Ex. No. | 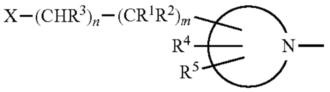 | $R^6$ | $R^7$ | $R^8$ | —Ar | melting point (° C.) (solvent for crystallization) |
|---|---|---|---|---|---|---|---|
| 1-001 | 1 | 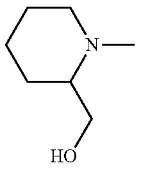 | $CH_3$ | $CH_3$ | $CH_3$ | 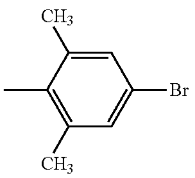 | 142-144 (hexane) |
| 1-002 | 1 | 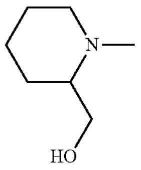 | $CH_3$ | $CH_3$ | H | 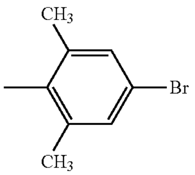 | 124-126 (hexane) |
| 1-003 | 1 | 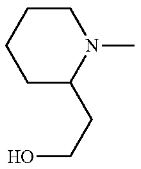 | $CH_3$ | $CH_3$ | $CH_3$ | 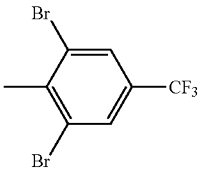 | amorphous |

TABLE 1*[1]-continued
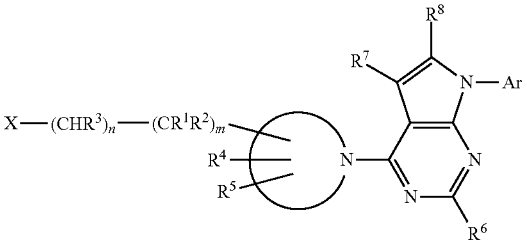
| Com. No. | Ex. No. | 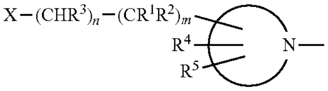 | $R^6$ | $R^7$ | $R^8$ | —Ar | melting point (° C.) (solvent for crystallization) |
|---|---|---|---|---|---|---|---|
| 1-004 | 1 | 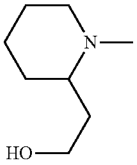 | $CH_3$ | $CH_3$ | $CH_3$ | 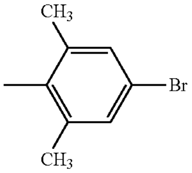 | 146-148*[2] (EtOAc/EtOH) |
| 1-005 | 1 | 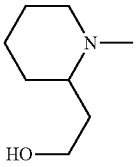 | $CH_3$ | $CH_3$ | H | 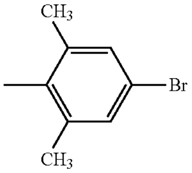 | amorphous |
| 1-006 | 1 | 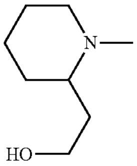 | $CH_3$ | $CH_3$ | $CH_3$ | 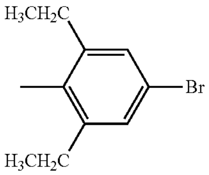 | 144-146 (hexane) |
| 1-007 | 1 | 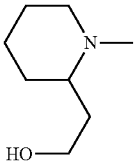 | $CH_3$ | $CH_3$ | H | 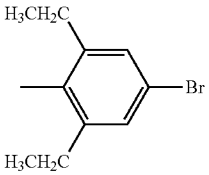 | 121-122 (hexane) |
| 1-008 | 1 | 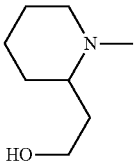 | $CH_3$ | $CH_3$ | H | 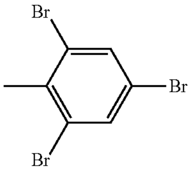 | 141-143*[2] (EtOAc/EtOH) |
| 1-009 | 1 | 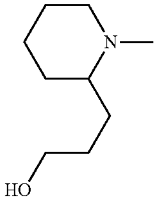 | $CH_3$ | $CH_3$ | $CH_3$ | 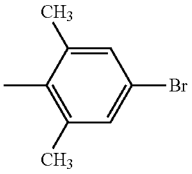 | 134-136*[2] (EtOAc/EtOH) |

TABLE 1*[1]-continued
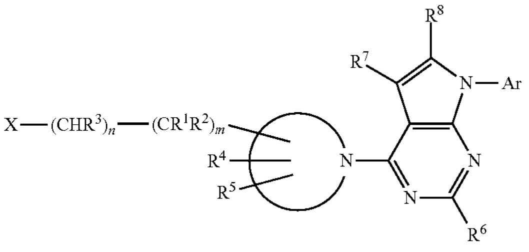
| Com. No. | Ex. No. | 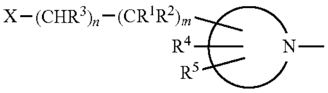 | $R^6$ | $R^7$ | $R^8$ | —Ar | melting point (° C.) (solvent for crystallization) |
|---|---|---|---|---|---|---|---|
| 1-010 | 1 | 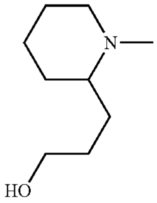 | $CH_3$ | $CH_3$ | H | 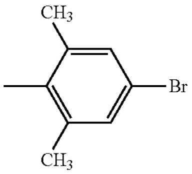 | 157-159*[2] (EtOAc/EtOH) |
| 1-011 | 1 | 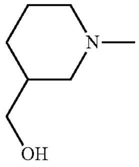 | $CH_3$ | $CH_3$ | $CH_3$ | 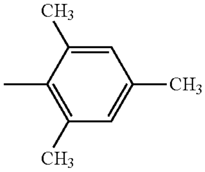 | amorphous |
| 1-012 | 1 | 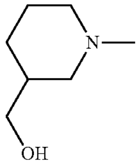 | $CH_3$ | $CH_3$ | H | 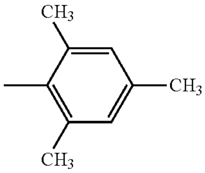 | amorphous |
| 1-013 | 1 | 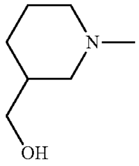 | $CH_3$ | $CH_3$ | H | 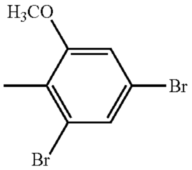 | amorphous*[3] |
| 1-014 | 1 | 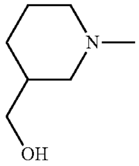 | $CH_3$ | $CH_3$ | H | 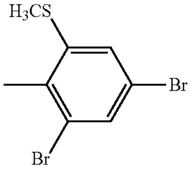 | amorphous*[3] |
| 1-015 | 1 | 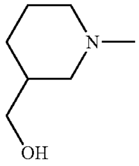 | $CH_3$ | $CH_3$ | $CH_3$ | 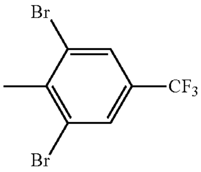 | amorphous |

TABLE 1*1-continued
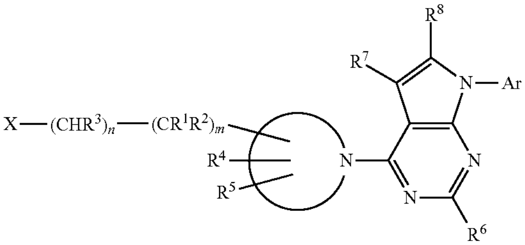
| Com. No. | Ex. No. | 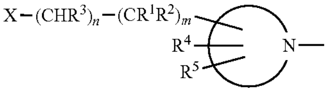 | $R^6$ | $R^7$ | $R^8$ | —Ar | melting point (° C.) (solvent for crystallization) |
|---|---|---|---|---|---|---|---|
| 1-016 | 1 | 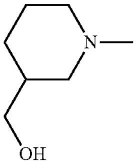 | $CH_3$ | $CH_3$ | $CH_3$ | 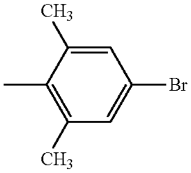 | amorphous |
| 1-017 | 1 | 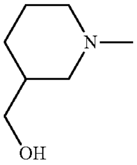 | $CH_3$ | $CH_3$ | $CH_3$ | 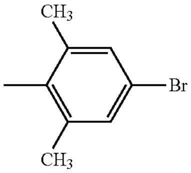 | 144-146*2*4 (EtAc/EtOH) |
| 1-018 | 1 | 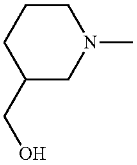 | $CH_3$ | $CH_3$ | $CH_3$ | 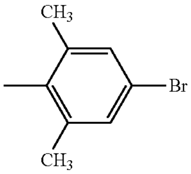 | 131-133*2*4 (EtOAc/EtOH) |
| 1-019 | 1 | 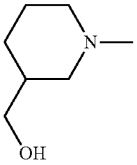 | $CH_3$ | $CH_3$ | H | 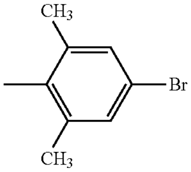 | amorphous |
| 1-020 | 1 | 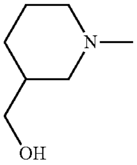 | $CH_3$ | $CH_3$ | H | 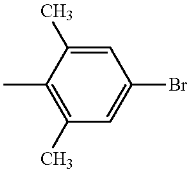 | 152-154*2*4 (EtOAc/EtOH) |
| 1-021 | 1 | 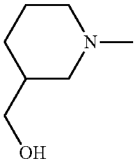 | $CH_3$ | $CH_3$ | H | 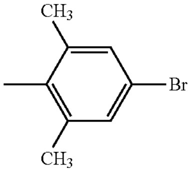 | 145-147*2*4 (EtOAc) |
| 1-022 | 1 | 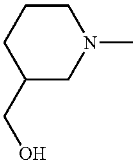 | $CH_3$ | $CH_3$ | $CH_3$ | 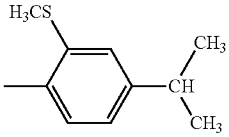 | amorphous*3 |

TABLE 1*[1]-continued
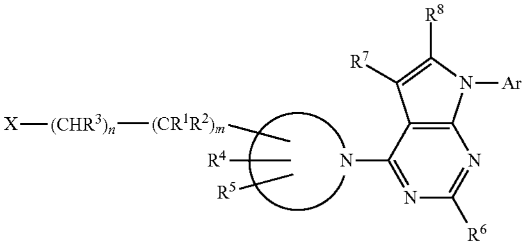
| Com. No. | Ex. No. | 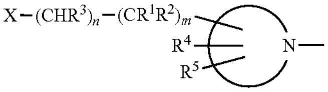 | $R^6$ | $R^7$ | $R^8$ | —Ar | melting point (° C.) (solvent for crystallization) |
|---|---|---|---|---|---|---|---|
| 1-023 | 1 | 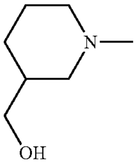 | $CH_3$ | $CH_3$ | H | 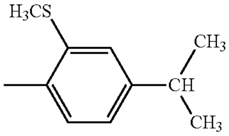 | amorphous |
| 1-024 | 1 | 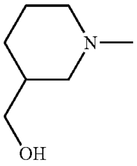 | $CH_3$ | $CH_3$ | $CH_3$ | 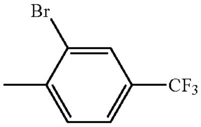 | amorphous |
| 1-025 | 1 | 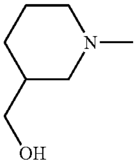 | $CH_3$ | $CH_3$ | H | 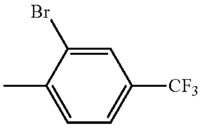 | amorphous |
| 1-026 | 1 | 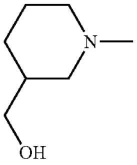 | $CH_3$ | $CH_2CH_3$ | $CH_2CH_3$ | 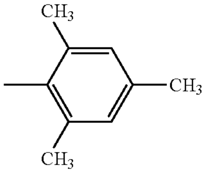 | amorphous |
| 1-027 | 1 | 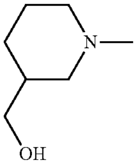 | $CH_3$ | $CH_3$ | $CH_3$ | 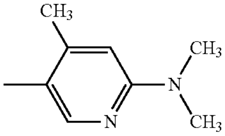 | amorphous*[3] |
| 1-028 | 1 | 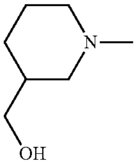 | $CH_3$ | $—(CH_2)_4—$ | | 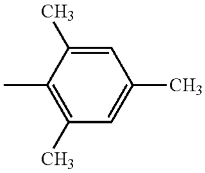 | amorphous |
| 1-029 | 1 | 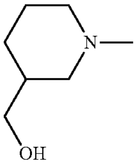 | $CH_3$ | —CH=CH—CH=CH— | | 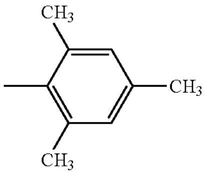 | amorphous |

TABLE 1*[1]-continued
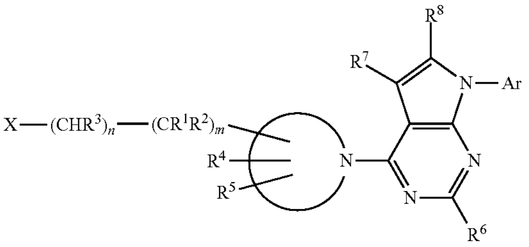
| Com. No. | Ex. No. | 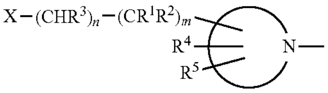 | $R^6$ | $R^7$ | $R^8$ | —Ar | melting point (° C.) (solvent for crystallization) |
|---|---|---|---|---|---|---|---|
| 1-030 | 1 | 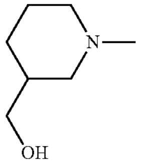 | $CH_3$ | $CH_3$ | $CH_3$ | 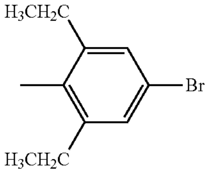 | amorphous |
| 1-031 | 1 | 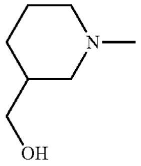 | $CH_3$ | $CH_3$ | H | 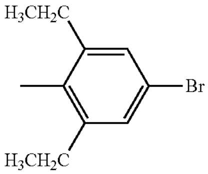 | amorphous |
| 1-032 | 1 | 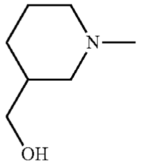 | $CH_3$ | $CH_3$ | H | 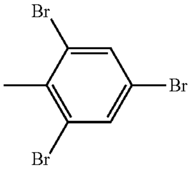 | 159-161*[2] (EtOAc/EtOH) |
| 1-033 | 1 | 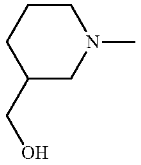 | $CH_3$ | $CH_3$ | $CH_3$ | 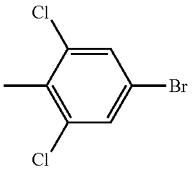 | 163-164*[2] (EtOAc/EtOH) |
| 1-034 | 1 | 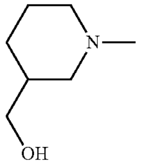 | $CH_3$ | $CH_3$ | H | 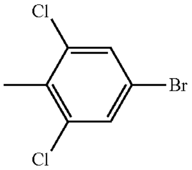 | 160-162*[2] (EtOAc/EtOH) |
| 1-035 | 1 | 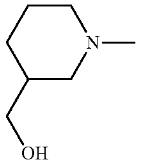 | $CH_3$ | $CH_3$ | H | 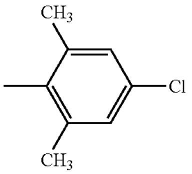 | 157-159*[2] (EtOAc/EtOH) |

TABLE 1*1-continued
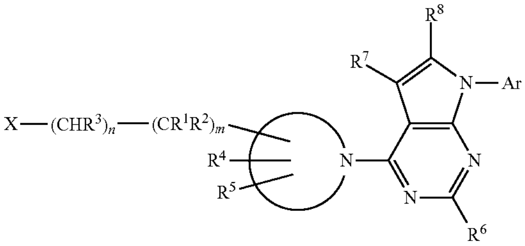
| Com. No. | Ex. No. | 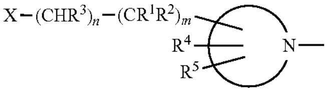 | $R^6$ | $R^7$ | $R^8$ | —Ar | melting point (° C.) (solvent for crystallization) |
|---|---|---|---|---|---|---|---|
| 1-036 | 1 | 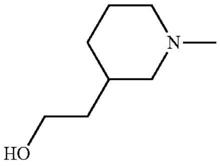 | $CH_3$ | $CH_3$ | $CH_3$ | 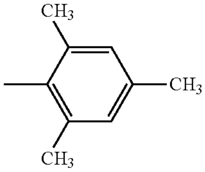 | amorphous |
| 1-037 | 1 | 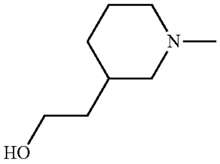 | $CH_3$ | $CH_3$ | H | 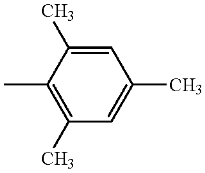 | amorphous |
| 1-038 | 1 | 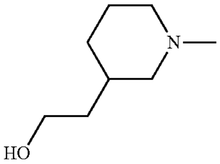 | $CH_3$ | $CH_3$ | $CH_3$ | 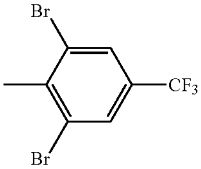 | 159-161 (IPE) |
| 1-039 | 1 | 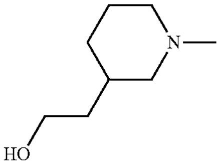 | $CH_3$ | $CH_3$ | $CH_3$ | 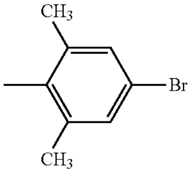 | amorphous |
| 1-040 | 1 | 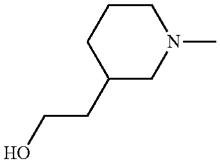 | $CH_3$ | $CH_3$ | H | 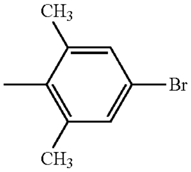 | amorphous |
| 1-041 | 1 | 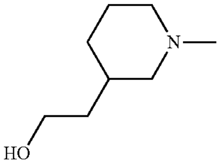 | $CH_3$ | $CH_2CH_3$ | $CH_2CH_3$ | 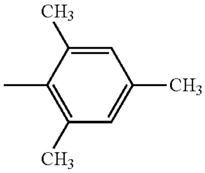 | amorphous |
| 1-042 | 1 | 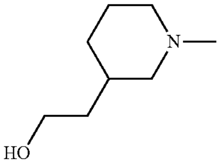 | $CH_3$ | $—(CH_2)_4—$ | | 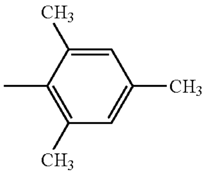 | 134-136*5 |

TABLE 1*[1]-continued
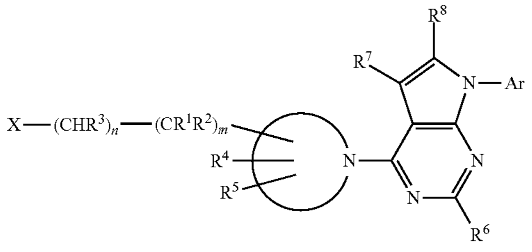
| Com. No. | Ex. No. | 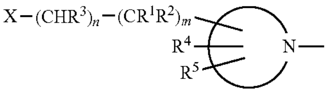 | $R^6$ | $R^7$ | $R^8$ | —Ar | melting point (° C.) (solvent for crystallization) |
|---|---|---|---|---|---|---|---|
| 1-043 | 1 | 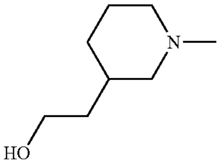 | $CH_3$ | —CH═CH—CH═CH— | | 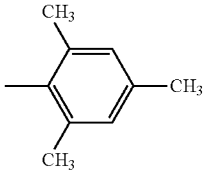 | amorphous |
| 1-044 | 1 | 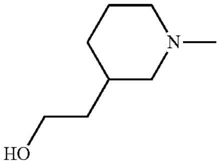 | $CH_3$ | $CH_3$ | $CH_3$ | 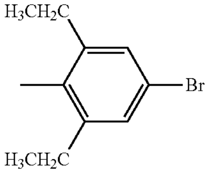 | amorphous |
| 1-045 | 1 | 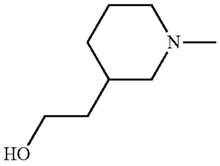 | $CH_3$ | $CH_3$ | H | 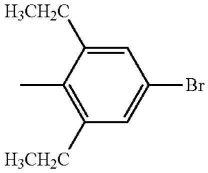 | amorphous |
| 1-046 | 1 | 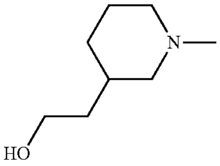 | $CH_3$ | $CH_3$ | H | 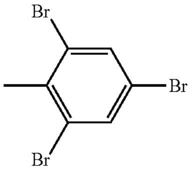 | 172-174*[2] (EtOAc/EtOH) |
| 1-047 | 1 | 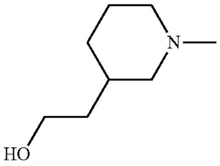 | $CH_3$ | $CH_3$ | $CH_3$ | 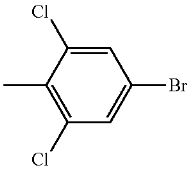 | 150-152*[2] (EtOAc/EtOH) |
| 1-048 | 1 | 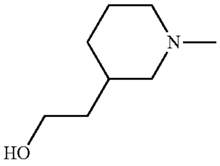 | $CH_3$ | $CH_3$ | H | 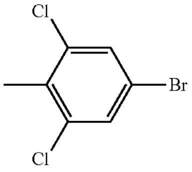 | 177-179*[2] (EtOAc/EtOH) |

TABLE 1*1-continued
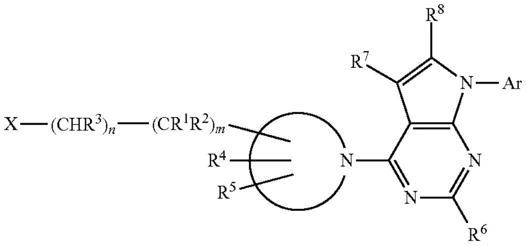
| Com. No. | Ex. No. | 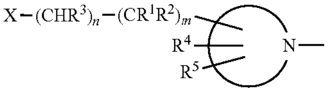 | $R^6$ | $R^7$ | $R^8$ | —Ar | melting point (° C.) (solvent for crystallization) |
|---|---|---|---|---|---|---|---|
| 1-049 | 1 | 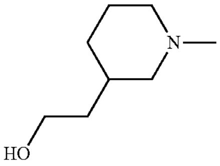 | $CH_3$ | $CH_3$ | H | 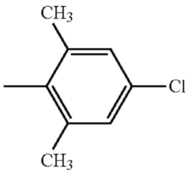 | 156-158*2 (EtOAc/EtOH) |
| 1-050 | 1 | 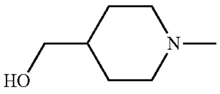 | $CH_3$ | $CH_3$ | $CH_3$ | 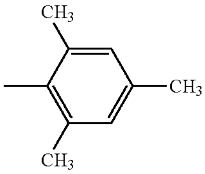 | 170-172 (hexane) |
| 1-051 | 1 | 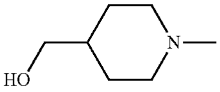 | $CH_3$ | $CH_3$ | H | 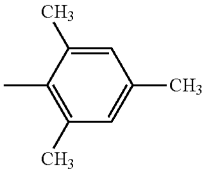 | 178-180 (hexane) |
| 1-052 | 1 | 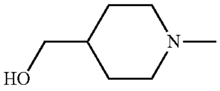 | $CH_3$ | $CH_3$ | $CH_3$ | 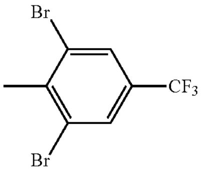 | 157-159 (IPE/hexane) |
| 1-053 | 1 | 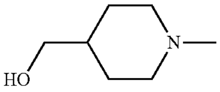 | $CH_3$ | $CH_3$ | $CH_3$ | 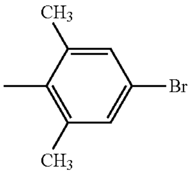 | 167-169*2 (EtOAc) |
| 1-054 | 1 | 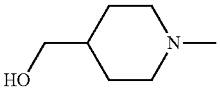 | $CH_3$ | $CH_3$ | H | 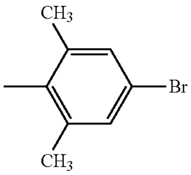 | 173-175*2 (EtOH) |
| 1-055 | 1 | 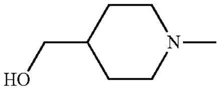 | $CH_3$ | $—(CH_2)_4—$ | | 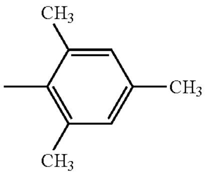 | 177-179 (IPE) |

TABLE 1*[1]-continued
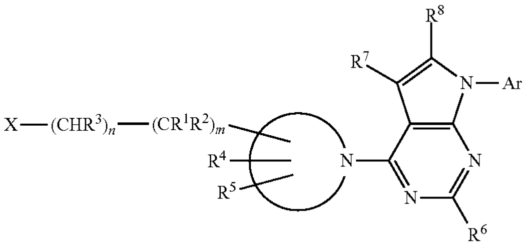
| Com. No. | Ex. No. | 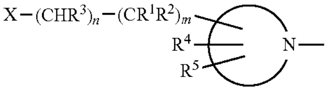 | $R^6$ | $R^7$ | $R^8$ | —Ar | melting point (° C.) (solvent for crystallization) |
|---|---|---|---|---|---|---|---|
| 1-056 | 1 | 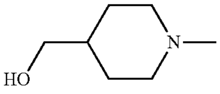 | $CH_3$ | —CH═CH—CH═CH— | | 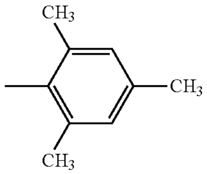 | amorphous |
| 1-057 | 1 | 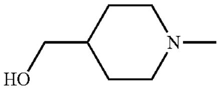 | $CH_3$ | $CH_3$ | $CH_3$ | 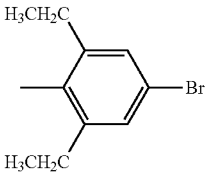 | amorphous |
| 1-058 | 1 | 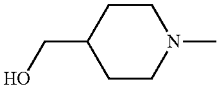 | $CH_3$ | $CH_3$ | H | 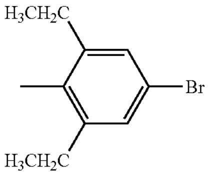 | 166-168*[2] (EtOAc) |
| 1-059 | 1 | 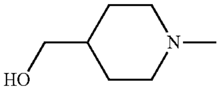 | $CH_3$ | $CH_3$ | $CH_3$ | 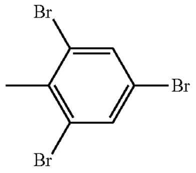 | 155-157*[2] (EtOAc) |
| 1-060 | 1 | 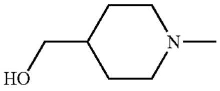 | $CH_3$ | $CH_3$ | H | 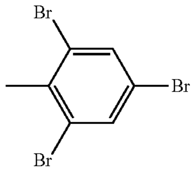 | 176-178*[2] (EtOAc) |
| 1-061 | 1 | 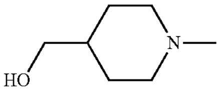 | $CH_3$ | $CH_3$ | $CH_3$ | 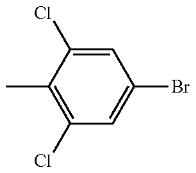 | 164-166*[2] (EtOAc) |

TABLE 1*[1]-continued
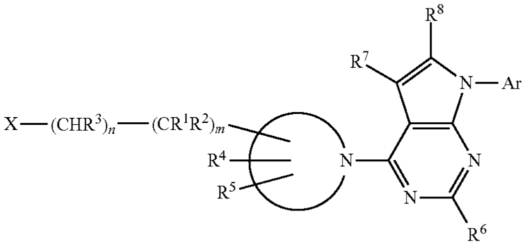
| Com. No. | Ex. No. | 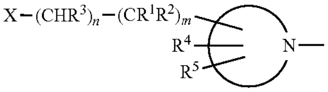 | $R^6$ | $R^7$ | $R^8$ | —Ar | melting point (° C.) (solvent for crystallization) |
|---|---|---|---|---|---|---|---|
| 1-062 | 1 | 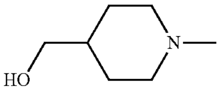 | $CH_3$ | $CH_3$ | H | 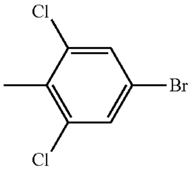 | 170-172*[2] (EtOAc) |
| 1-063 | 1 | 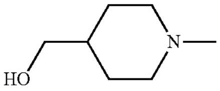 | $CH_3$ | $CH_3$ | $CH_3$ | 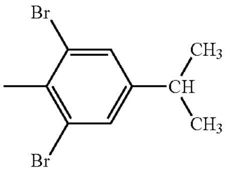 | amorphous*[2] |
| 1-064 | 1 | 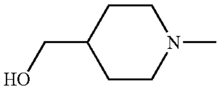 | $CH_3$ | $CH_3$ | H | 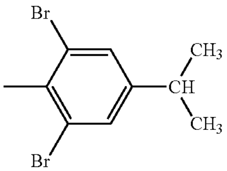 | 164-166*[2] (EtOAc) |
| 1-065 | 1 | 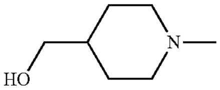 | $CH_3$ | $CH_3$ | $CH_3$ | 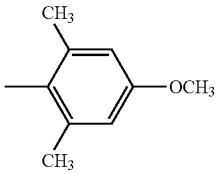 | 188-190*[2] (EtOAc) |
| 1-066 | 1 | 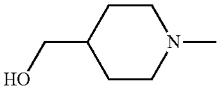 | $CH_3$ | $CH_3$ | H | 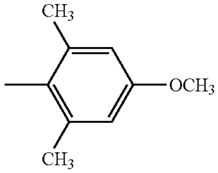 | 184-186*[2] (EtOAc) |
| 1-067 | 1 | 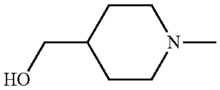 | $CH_3$ | $CH_3$ | $CH_3$ | 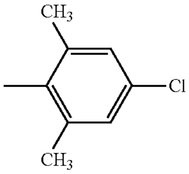 | 179-181*[2] (EtOAc) |
| 1-068 | 1 | 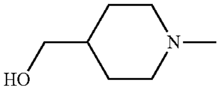 | $CH_3$ | $CH_3$ | H | 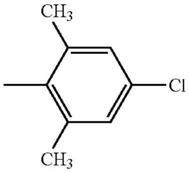 | 178-180*[2] (EtOAc) |

TABLE 1*1-continued
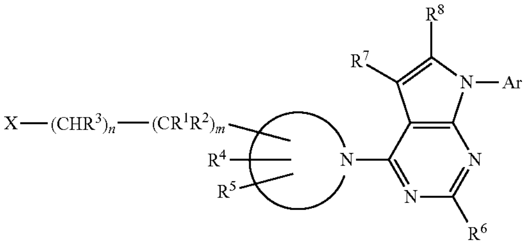
| Com. No. | Ex. No. | 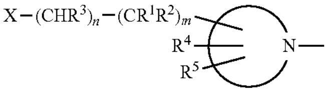 | $R^6$ | $R^7$ | $R^8$ | —Ar | melting point (° C.) (solvent for crystallization) |
|---|---|---|---|---|---|---|---|
| 1-069 | 1 | 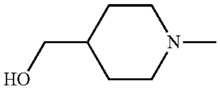 | $CH_3$ | $CH_3$ | H | 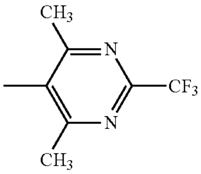 | 197-199*2 (EtOAc/EtOH) |
| 1-070 | 1 | 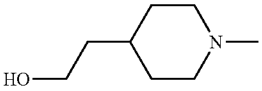 | $CH_3$ | $CH_3$ | $CH_3$ | 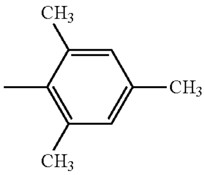 | 155-157*2 (EtOAc) |
| 1-071 | 1 | 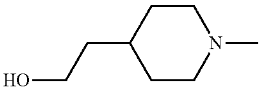 | $CH_3$ | $CH_3$ | H | 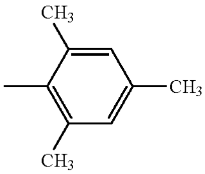 | 167-169*2 (EtOAc/EtOH) |
| 1-072 | 1 | 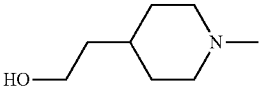 | $CH_3$ | $CH_3$ | $CH_3$ | 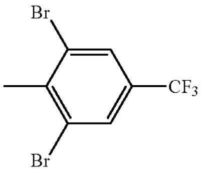 | 220-222 (hexane) |
| 1-073 | 1 | 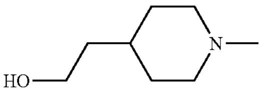 | $CH_3$ | $CH_3$ | $CH_3$ | 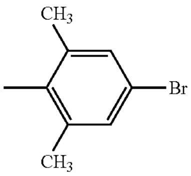 | 212-214*2 (EtOAc) |
| 1-074 | 1 | 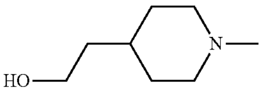 | $CH_3$ | $CH_3$ | H | 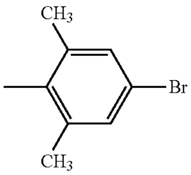 | 187-189*2 (EtOAc) |

TABLE 1*[1]-continued
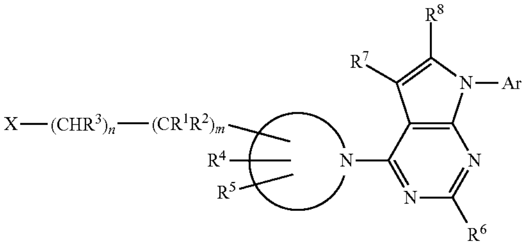
| Com. No. | Ex. No. | 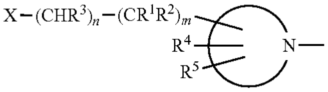 | $R^6$ | $R^7$ | $R^8$ | —Ar | melting point (° C.) (solvent for crystallization) |
|---|---|---|---|---|---|---|---|
| 1-075 | 1 | 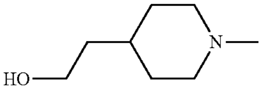 | $CH_3$ | $CH_3$ | $CH_3$ | 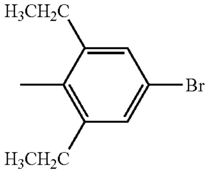 | 180-182*[2] (hexane) |
| 1-076 | 1 | 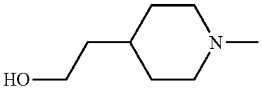 | $CH_3$ | $CH_3$ | H | 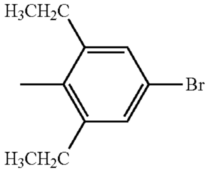 | 188-190*[2] (IPE) |
| 1-077 | 1 | 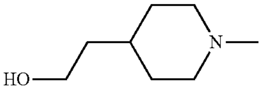 | $CH_3$ | $CH_3$ | $CH_3$ | 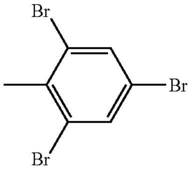 | 179-181*[2] (EtOAc/EtOH) |
| 1-078 | 1 | 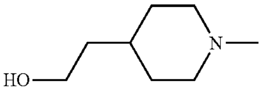 | $CH_3$ | $CH_3$ | H | 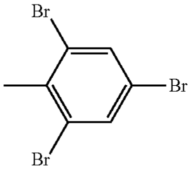 | 194-196*[2] (EtOAc/EtOH) |
| 1-079 | 1 | 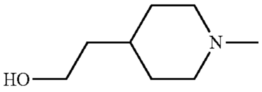 | $CH_3$ | $CH_3$ | $CH_3$ | 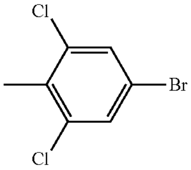 | 199-201*[2] (EtOAc/EtOH) |
| 1-080 | 1 | 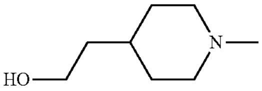 | $CH_3$ | $CH_3$ | H | 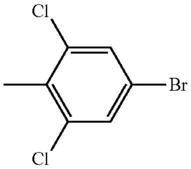 | 193-195*[2] (EtOAc/EtOH) |
| 1-081 | 1 | 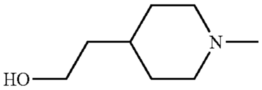 | $CH_3$ | $CH_3$ | $CH_3$ | 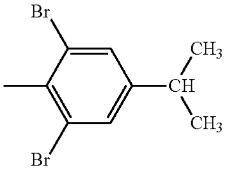 | 164-166*[2] (EtOAc/EtOH) |

TABLE 1*[1]-continued
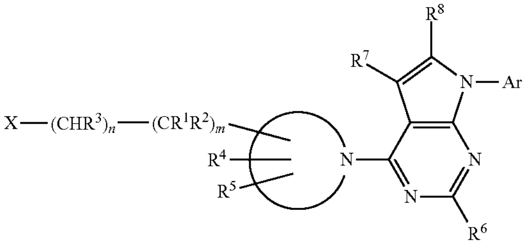
| Com. No. | Ex. No. | 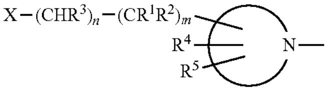 | $R^6$ | $R^7$ | $R^8$ | —Ar | melting point (° C.) (solvent for crystallization) |
|---|---|---|---|---|---|---|---|
| 1-082 | 1 | 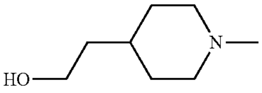 | $CH_3$ | $CH_3$ | H | 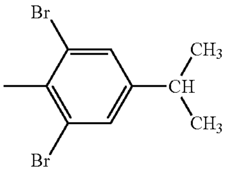 | 177-179*[2] (EtOAc/EtOH) |
| 1-083 | 1 | 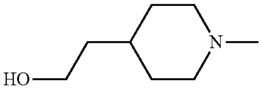 | $CH_3$ | $CH_3$ | $CH_3$ | 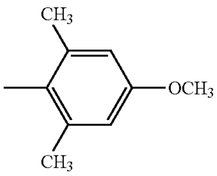 | 170-172*[2] (EtOAc/EtOH) |
| 1-084 | 1 | 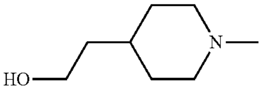 | $CH_3$ | $CH_3$ | H | 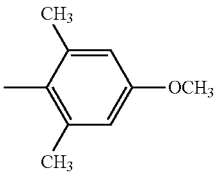 | 162-164*[2] (EtOAc) |
| 1-085 | 1 | 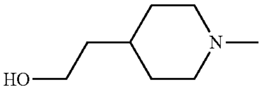 | $CH_3$ | $CH_3$ | $CH_3$ | 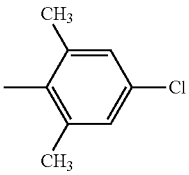 | 168-170*[2] (EtOAc) |
| 1-086 | 1 | 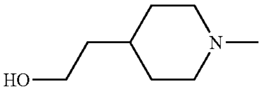 | $CH_3$ | $CH_3$ | H | 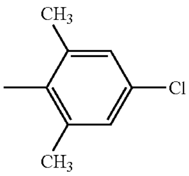 | 187-189*[2] (EtOAc/EtOH) |
| 1-087 | 1 | 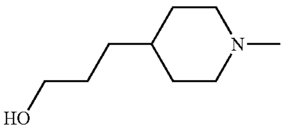 | $CH_3$ | $CH_3$ | $CH_3$ | 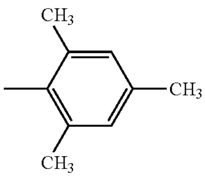 | 183-184 (hexane) |

TABLE 1*1-continued
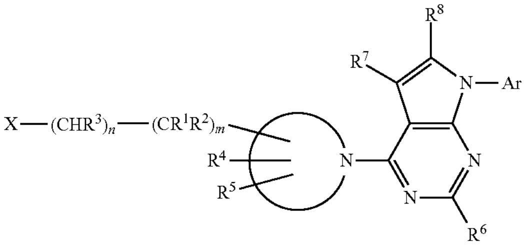
| Com. No. | Ex. No. | 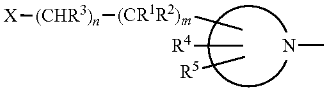 | $R^6$ | $R^7$ | $R^8$ | —Ar | melting point (° C.) (solvent for crystallization) |
|---|---|---|---|---|---|---|---|
| 1-088 | 1 | 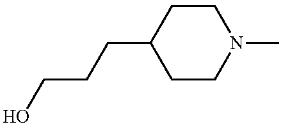 | $CH_3$ | $CH_3$ | H | 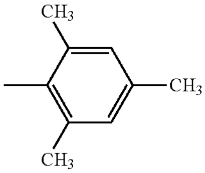 | 165-167 (hexane) |
| 1-089 | 1 | 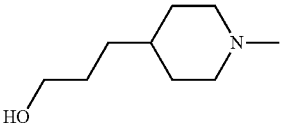 | $CH_3$ | $CH_3$ | $CH_3$ | 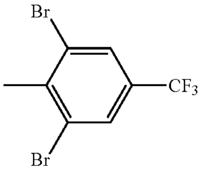 | 191-193 (IPA) |
| 1-090 | 1 | 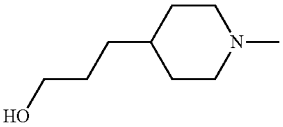 | $CH_3$ | $CH_3$ | $CH_3$ | 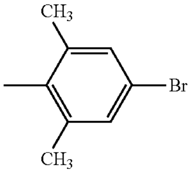 | 189-191*2 (THF/EtOAc) |
| 1-091 | 1 | 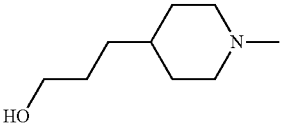 | $CH_3$ | $CH_3$ | H | 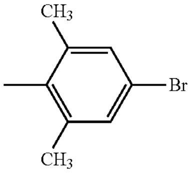 | 202-204*2 (EtOAc/EtOH) |
| 1-092 | 1 | 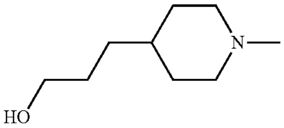 | $CH_3$ | $CH_2CH_3$ | $CH_2CH_3$ | 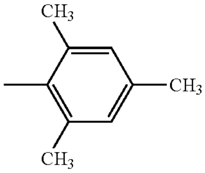 | amorphous |
| 1-093 | 1 | 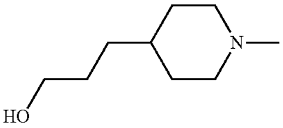 | $CH_3$ | $—(CH_2)_4—$ | | 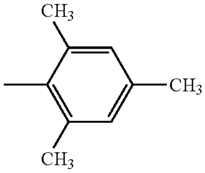 | 177-179 (IPE) |
| 1-094 | 1 | 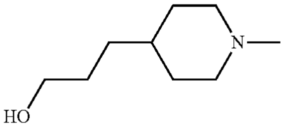 | $CH_3$ | —CH=CH—CH=CH— | | 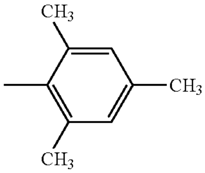 | amorphous |

TABLE 1*1-continued
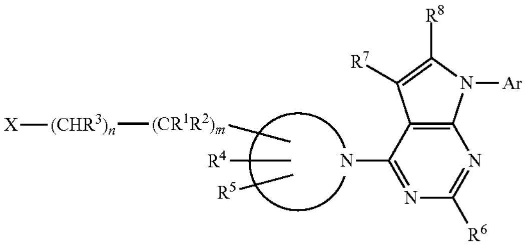
| Com. No. | Ex. No. | 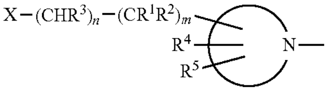 | $R^6$ | $R^7$ | $R^8$ | —Ar | melting point (° C.) (solvent for crystallization) |
|---|---|---|---|---|---|---|---|
| 1-095 | 1 | 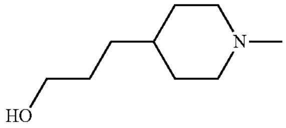 | $CH_3$ | $CH_3$ | $CH_3$ | 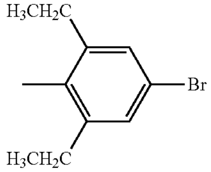 | 175-177*2 (hexane) |
| 1-096 | 1 | 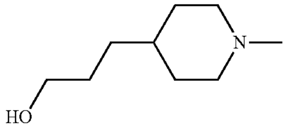 | $CH_3$ | $CH_3$ | H | 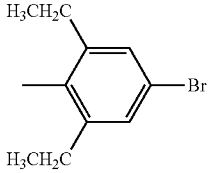 | 174-176*2 (EtOAc) |
| 1-097 | 1 | 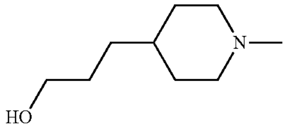 | $CH_3$ | $CH_3$ | H | 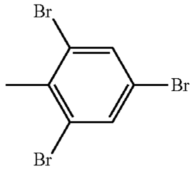 | 207-209*2 (EtOAc/EtOH) |
| 1-098 | 1 | 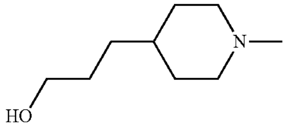 | $CH_3$ | $CH_3$ | $CH_3$ | 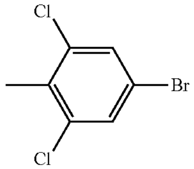 | 205-207*2 (EtOAc/EtOH) |
| 1-099 | 1 | 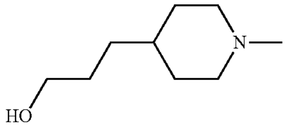 | $CH_3$ | $CH_3$ | H | 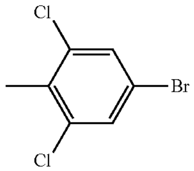 | 195-197*2 (EtOAc/EtOH) |
| 1-100 | 1 | 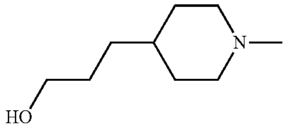 | $CH_3$ | $CH_3$ | H | 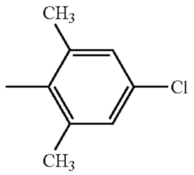 | 192-194*2 (EtOAc/EtOH) |

TABLE 1*[1]-continued
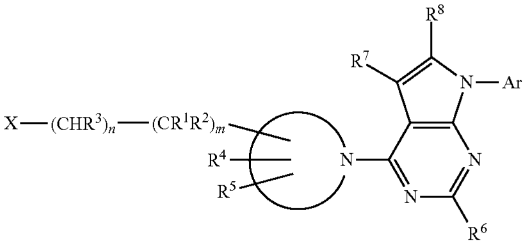
| Com. No. | Ex. No. | 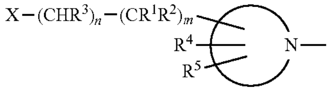 | $R^6$ | $R^7$ | $R^8$ | —Ar | melting point (° C.) (solvent for crystallization) |
|---|---|---|---|---|---|---|---|
| 1-101 | 1 | 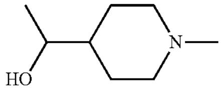 | $CH_3$ | $CH_3$ | $CH_3$ | 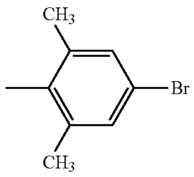 | 175-177*[2] (EtOAc) |
| 1-102 | 1 | 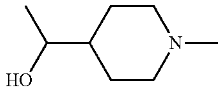 | $CH_3$ | $CH_3$ | H | 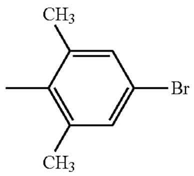 | 158-160*[2] (EtOAc/EtOH) |
| 1-103 | 1 | 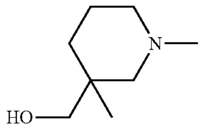 | $CH_3$ | $CH_3$ | $CH_3$ | 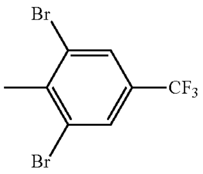 | amorphous |
| 1-104 | 1 | 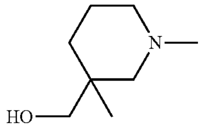 | $CH_3$ | $CH_3$ | $CH_3$ | 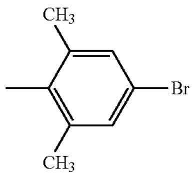 | amorphous |
| 1-105 | 1 | 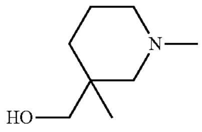 | $CH_3$ | $CH_3$ | H | 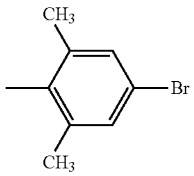 | amorphous |
| 1-106 | 1 | 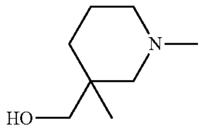 | $CH_3$ | $CH_3$ | $CH_3$ | 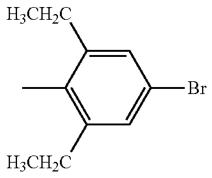 | amorphous |

TABLE 1*[1]-continued
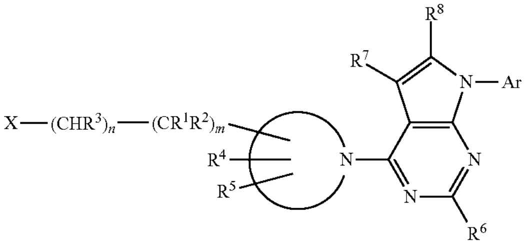
| Com. No. | Ex. No. | 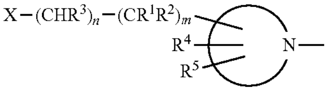 | $R^6$ | $R^7$ | $R^8$ | —Ar | melting point (° C.) (solvent for crystallization) |
|---|---|---|---|---|---|---|---|
| 1-107 | 1 | 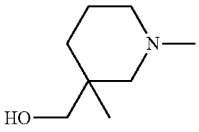 | $CH_3$ | $CH_3$ | H | 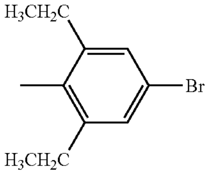 | amorphous |
| 1-108 | 1 | 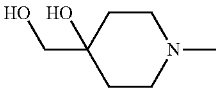 | $CH_3$ | $CH_3$ | $CH_3$ | 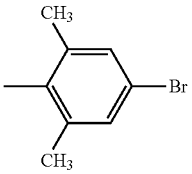 | 206-208 (IPE) |
| 1-109 | 1 | 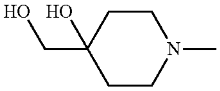 | $CH_3$ | $CH_3$ | H | 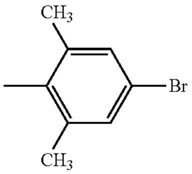 | 161-163 (IPE) |
| 1-110 | 1 | 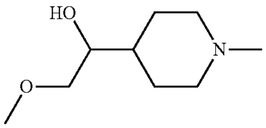 | $CH_3$ | $CH_3$ | $CH_3$ | 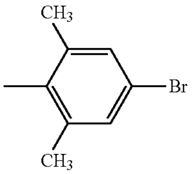 | amorphous |
| 1-111 | 1 | 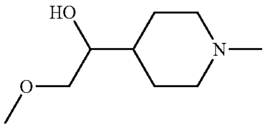 | $CH_3$ | $CH_3$ | H | 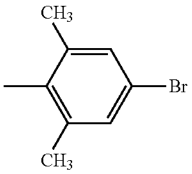 | 141-143 (IPE) |
| 1-112 | 1 | 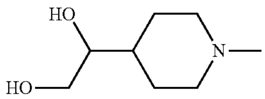 | $CH_3$ | $CH_3$ | $CH_3$ | 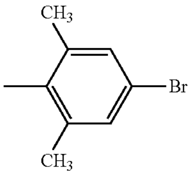 | 184-186*[2] (EtOH) |

TABLE 1*[1]-continued
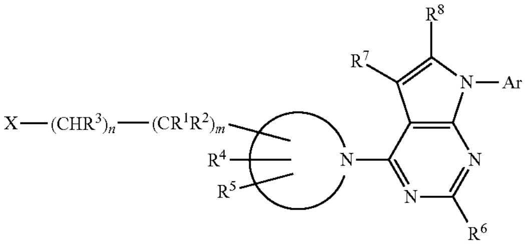
| Com. No. | Ex. No. | 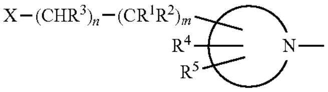 | $R^6$ | $R^7$ | $R^8$ | —Ar | melting point (° C.) (solvent for crystallization) |
|---|---|---|---|---|---|---|---|
| 1-113 | 1 | 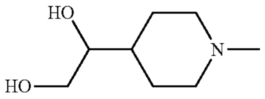 | $CH_3$ | $CH_3$ | H | 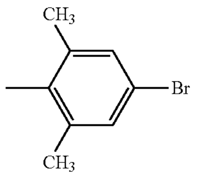 | 181-182 (IPE) |
| 1-114 | 1 | 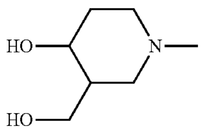 | $CH_3$ | $CH_3$ | $CH_3$ | 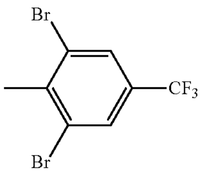 | amorphous |
| 1-115 | 1 | 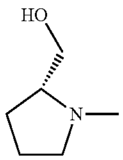 | $CH_3$ | $CH_3$ | $CH_3$ | 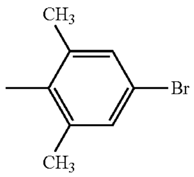 | 167-169*[2]*[4] (EtOAc) |
| 1-116 | 1 | 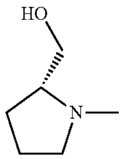 | $CH_3$ | $CH_3$ | H | 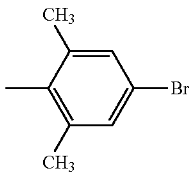 | amorphous*[2]*[4] |
| 1-117 | 1 | 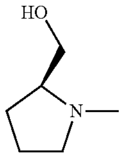 | $CH_3$ | $CH_3$ | $CH_3$ | 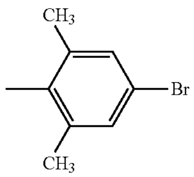 | 148-150*[2]*[4] (EtOAc) |
| 1-118 | 1 | 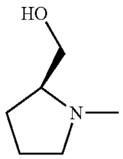 | $CH_3$ | $CH_3$ | H | 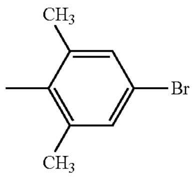 | amorphous*[2]*[4] |

TABLE 1*1-continued
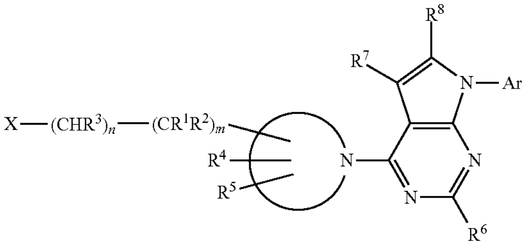
| Com. No. | Ex. No. | 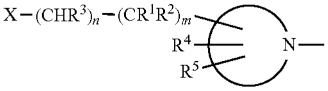 | $R^6$ | $R^7$ | $R^8$ | —Ar | melting point (° C.) (solvent for crystallization) |
|---|---|---|---|---|---|---|---|
| 1-119 | 1 | 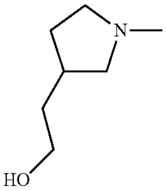 | $CH_3$ | $CH_3$ | $CH_3$ | 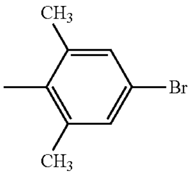 | 214-216*2 (EtOAc) |
| 1-120 | 1 | 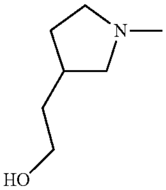 | $CH_3$ | $CH_3$ | H | 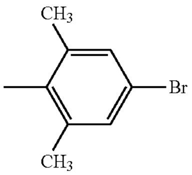 | 153-155*2 (EtOH/EtOAc) |
| 1-121 | 1 | 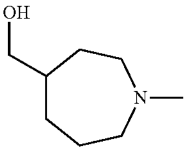 | $CH_3$ | $CH_3$ | $CH_3$ | 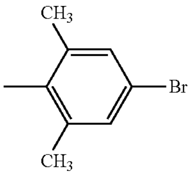 | 214-215*2 (EtOAc) |
| 1-122 | 1 | 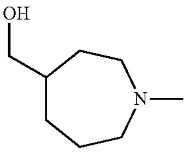 | $CH_3$ | $CH_3$ | H | 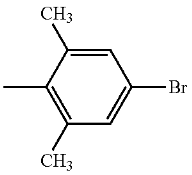 | 148-150*2 (EtOH/EtOAc) |
| 1-123 | 1 | 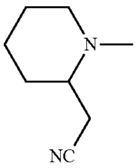 | $CH_3$ | $CH_3$ | $CH_3$ | 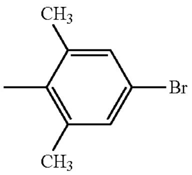 | 170-172*2 (EtOAc) |
| 1-124 | 1 | 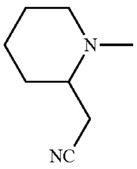 | $CH_3$ | $CH_3$ | H | 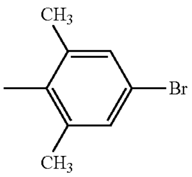 | 91-93*2 (EtOH/EtOAc) |

TABLE 1*1-continued
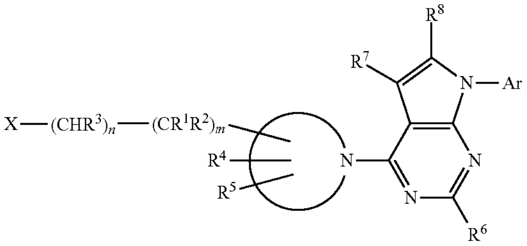
| Com. No. | Ex. No. | 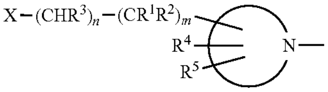 | $R^6$ | $R^7$ | $R^8$ | —Ar | melting point (° C.) (solvent for crystallization) |
|---|---|---|---|---|---|---|---|
| 1-125 | 1 | 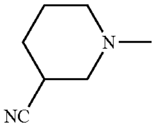 | $CH_3$ | $CH_3$ | $CH_3$ | 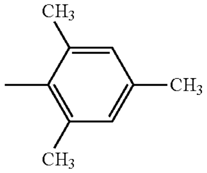 | amorphous |
| 1-126 | 1 | 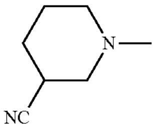 | $CH_3$ | $CH_3$ | H | 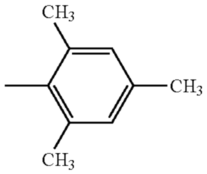 | amorphous |
| 1-127 | 2 | 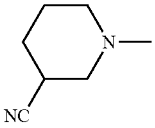 | $CH_3$ | $CH_3$ | H | 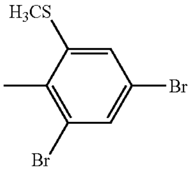 | amorphous |
| 1-128 | 2 | 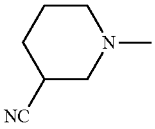 | $CH_3$ | $CH_3$ | H | 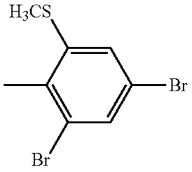 | amorphous |
| 1-129 | 1 | 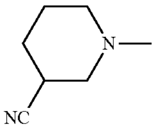 | $CH_3$ | $CH_3$ | $CH_3$ | 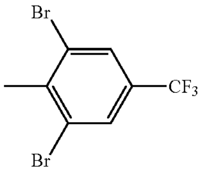 | amorphous |
| 1-130 | 1 | 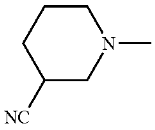 | $CH_3$ | $CH_3$ | $CH_3$ | 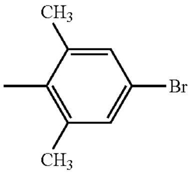 | amorphous |
| 1-131 | 1 | 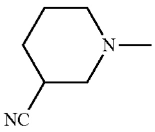 | $CH_3$ | $CH_3$ | H | 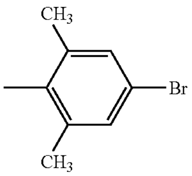 | amorphous |

TABLE 1*[1]-continued
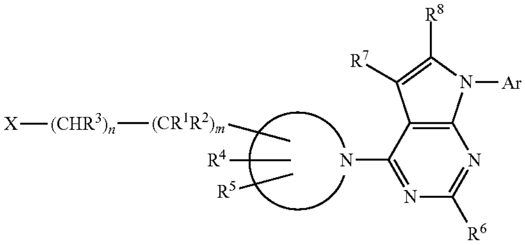
| Com. No. | Ex. No. | 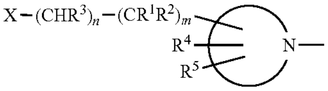 | $R^6$ | $R^7$ | $R^8$ | —Ar | melting point (° C.) (solvent for crystallization) |
|---|---|---|---|---|---|---|---|
| 1-132 | 1 | 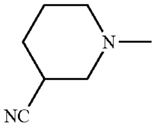 | $CH_3$ | $CH_3$ | $CH_3$ | 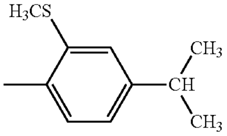 | amorphous*[3] |
| 1-133 | 1 | 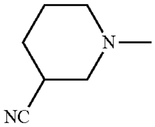 | $CH_3$ | $CH_3$ | H | 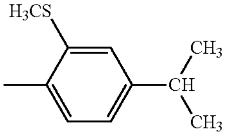 | amorphous |
| 1-134 | 2 | 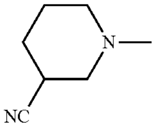 | $CH_3$ | $CH_3$ | $CH_3$ | 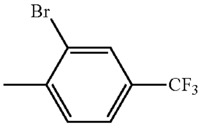 | amorphous*[4] |
| 1-135 | 2 | 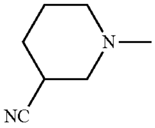 | $CH_3$ | $CH_3$ | $CH_3$ | 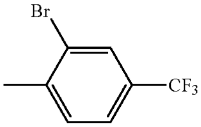 | amorphous*[4] |
| 1-136 | 2 | 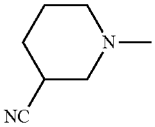 | $CH_3$ | $CH_3$ | $CH_3$ | 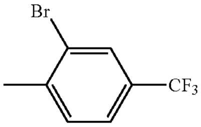 | amorphous*[4] |
| 1-137 | 2 | 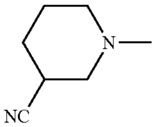 | $CH_3$ | $CH_3$ | $CH_3$ | 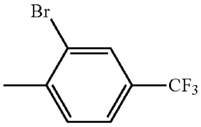 | amorphous*[4] |
| 1-138 | 1 | 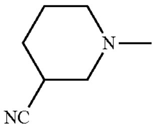 | $CH_3$ | $CH_3$ | H | 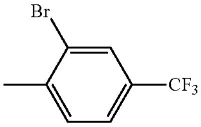 | amorphous |
| 1-139 | 1 | 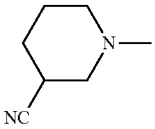 | $CH_3$ | $—(CH_2)_4—$ | | 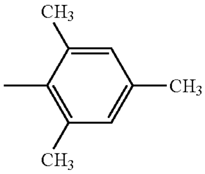 | 173-175*[5] |

TABLE 1*[1]-continued
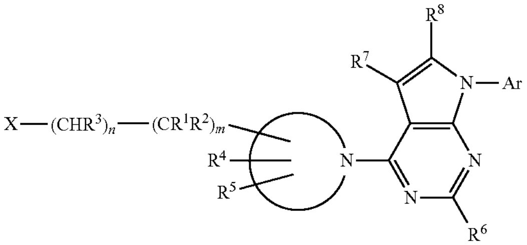
| Com. No. | Ex. No. | 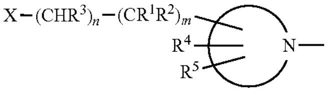 | $R^6$ | $R^7$ | $R^8$ | —Ar | melting point (° C.) (solvent for crystallization) |
|---|---|---|---|---|---|---|---|
| 1-140 | 1 | 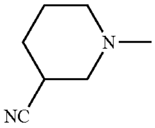 | $CH_3$ | —CH═CH—CH═CH— | | 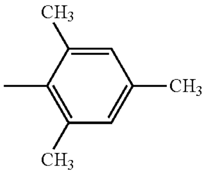 | amorphous |
| 1-141 | 1 | 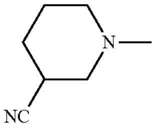 | $CH_3$ | $CH_3$ | $CH_3$ | 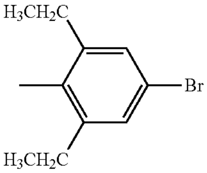 | amorphous |
| 1-142 | 1 | 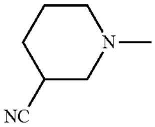 | $CH_3$ | $CH_3$ | H | 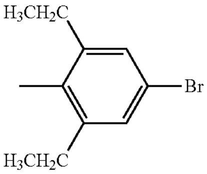 | amorphous |
| 1-143 | 1 | 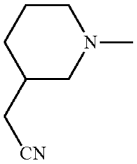 | $CH_3$ | $CH_3$ | $CH_3$ | 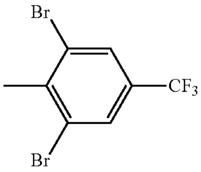 | amorphous |
| 1-144 | 1 | 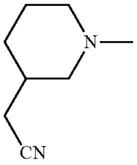 | $CH_3$ | $CH_3$ | $CH_3$ | 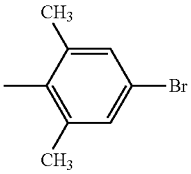 | amorphous |
| 1-145 | 1 | 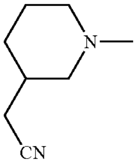 | $CH_3$ | $CH_3$ | H | 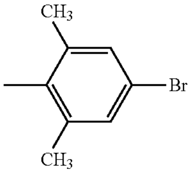 | 147-149 (hexane) |
| 1-146 | 1 | 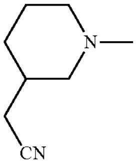 | $CH_3$ | $CH_3$ | $CH_3$ | 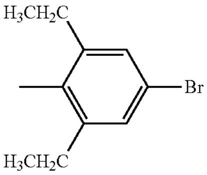 | amorphous |

TABLE 1*1-continued
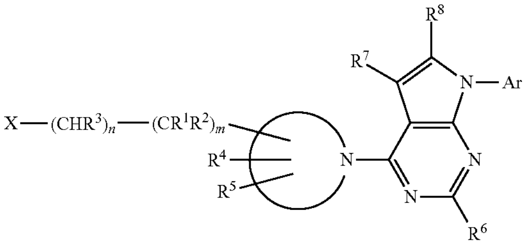
| Com. No. | Ex. No. | 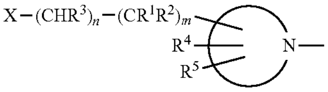 | $R^6$ | $R^7$ | $R^8$ | —Ar | melting point (° C.) (solvent for crystallization) |
|---|---|---|---|---|---|---|---|
| 1-147 | 1 | 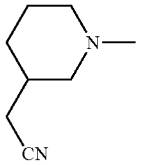 | $CH_3$ | $CH_3$ | H | 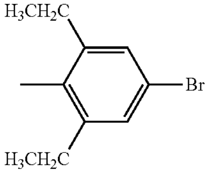 | amorphous |
| 1-148 | 1 | 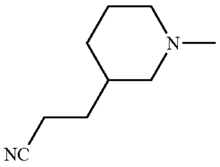 | $CH_3$ | $CH_3$ | $CH_3$ | 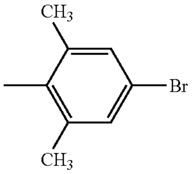 | 195-197*2 (EtOAc) |
| 1-149 | 1 | 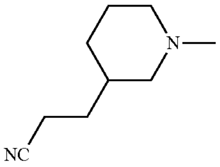 | $CH_3$ | $CH_3$ | H | 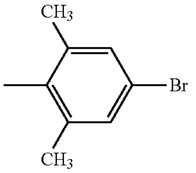 | amorphous*2 |
| 1-150 | 1 | 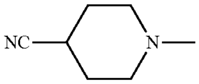 | $CH_3$ | $CH_3$ | $CH_3$ | 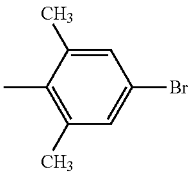 | 164-166*2 (EtOAc) |
| 1-151 | 1 | 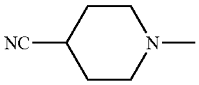 | $CH_3$ | $CH_3$ | H | 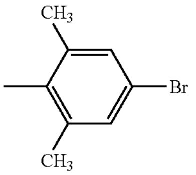 | 168-170*2 (EtOAc) |
| 1-152 | 1 | 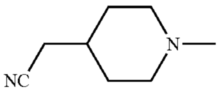 | $CH_3$ | $CH_3$ | $CH_3$ | 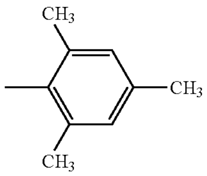 | 145-147*2 (EtOAc/IPE) |

TABLE 1*1-continued
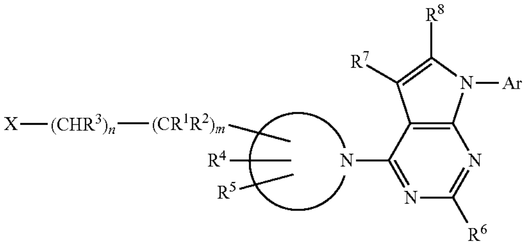
| Com. No. | Ex. No. | 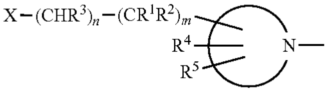 | $R^6$ | $R^7$ | $R^8$ | —Ar | melting point (° C.) (solvent for crystallization) |
|---|---|---|---|---|---|---|---|
| 1-153 | 1 | 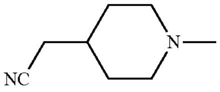 | $CH_3$ | $CH_3$ | $CH_3$ | 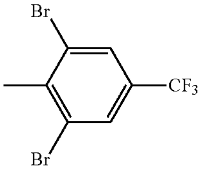 | 182-184 (hexane) |
| 1-154 | 1 | 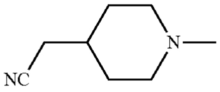 | $CH_3$ | $CH_3$ | $CH_3$ | 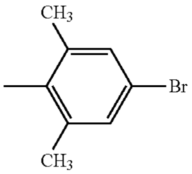 | 166-168*2 (IPE) |
| 1-155 | 1 | 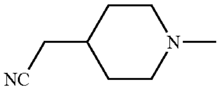 | $CH_3$ | $CH_3$ | H | 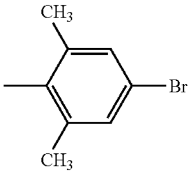 | 145-146*2 (EtOAc) |
| 1-156 | 1 | 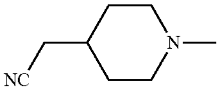 | $CH_3$ | $CH_3$ | $CH_3$ | 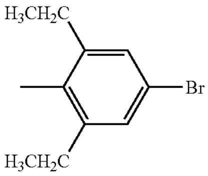 | 164-166*2 (EtOAc/IPE) |
| 1-157 | 1 | 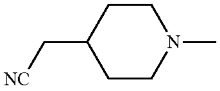 | $CH_3$ | $CH_3$ | H | 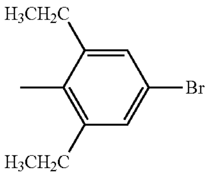 | 174-176*2 (EtOAc/IPE) |
| 1-158 | 1 | 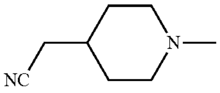 | $CH_3$ | $CH_3$ | $CH_3$ | 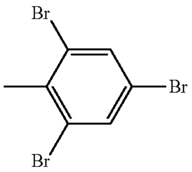 | 194-196*2 (EtOAc) |
| 1-159 | 1 | 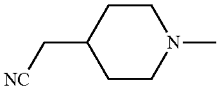 | $CH_3$ | $CH_3$ | H | 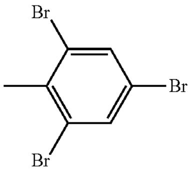 | 199-201*2 (EtOAc) |

TABLE 1*[1]-continued
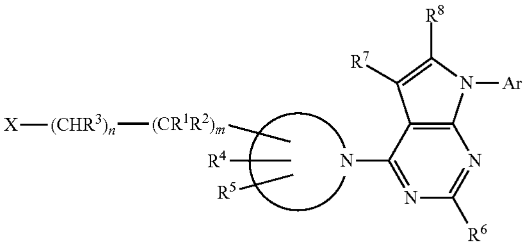
| Com. No. | Ex. No. | 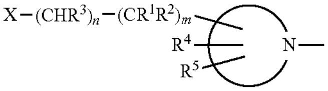 | $R^6$ | $R^7$ | $R^8$ | —Ar | melting point (° C.) (solvent for crystallization) |
|---|---|---|---|---|---|---|---|
| 1-160 | 1 | 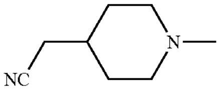 | $CH_3$ | $CH_3$ | $CH_3$ | 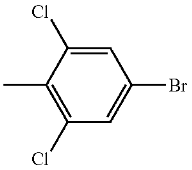 | 162-164*[2] (EtOAc) |
| 1-161 | 1 | 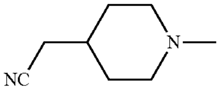 | $CH_3$ | $CH_3$ | H | 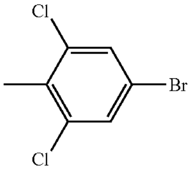 | 170-172*[2] (EtOAc) |
| 1-162 | 1 | 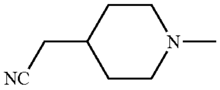 | $CH_3$ | $CH_3$ | $CH_3$ | 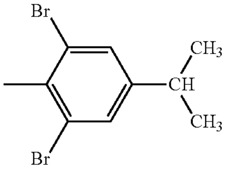 | 164-166*[2] (EtOAc) |
| 1-163 | 1 | 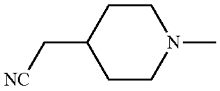 | $CH_3$ | $CH_3$ | H | 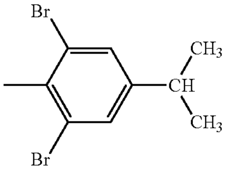 | 152-154*[2] (EtOAc) |
| 1-164 | 1 | 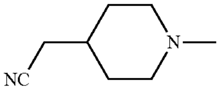 | $CH_3$ | $CH_3$ | $CH_3$ | 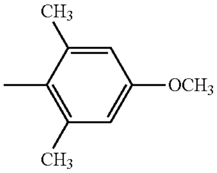 | 158-160*[2] (EtOAc) |
| 1-165 | 1 | 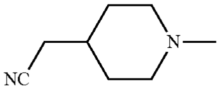 | $CH_3$ | $CH_3$ | H | 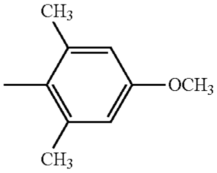 | 139-141*[2] (EtOAc/EtOH) |

TABLE 1*[1]-continued
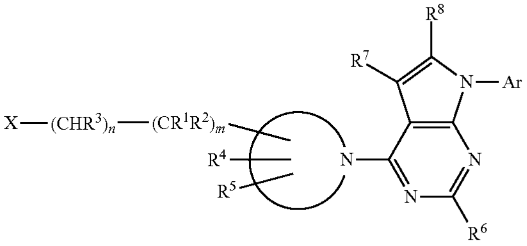
| Com. No. | Ex. No. | 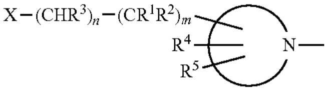 | $R^6$ | $R^7$ | $R^8$ | —Ar | melting point (° C.) (solvent for crystallization) |
|---|---|---|---|---|---|---|---|
| 1-166 | 1 | 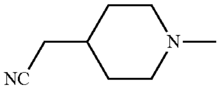 | $CH_3$ | $CH_3$ | $CH_3$ | 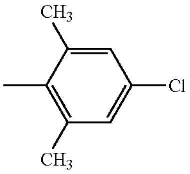 | 140-141*[2] (EtOAc) |
| 1-167 | 1 | 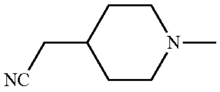 | $CH_3$ | $CH_3$ | H | 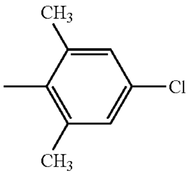 | 137-139*[2] (EtOAc) |
| 1-168 | 1 | 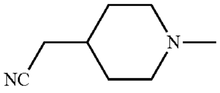 | $CH_3$ | $CH_3$ | H | 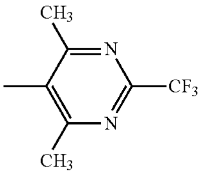 | amorphous*[2] |
| 1-169 | 1 | 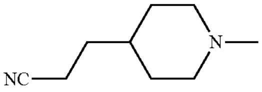 | $CH_3$ | $CH_3$ | $CH_3$ | 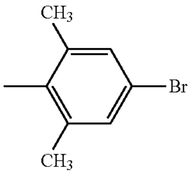 | 219-221 (IPE) |
| 1-170 | 1 | 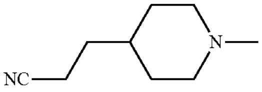 | $CH_3$ | $CH_3$ | H | 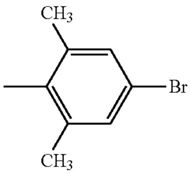 | 179-181 (IPE) |
| 1-171 | 1 | 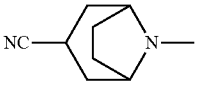 | $CH_3$ | $CH_3$ | $CH_3$ | 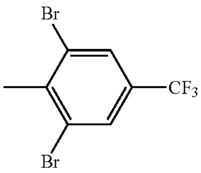 | amorphous |

TABLE 1*[1]-continued
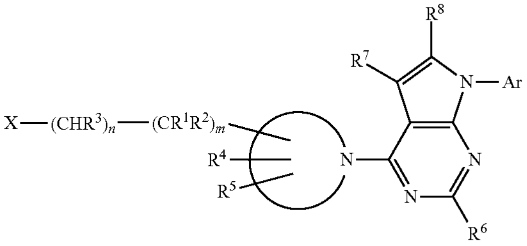
| Com. No. | Ex. No. | 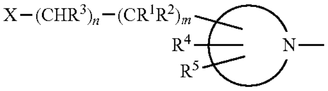 | $R^6$ | $R^7$ | $R^8$ | —Ar | melting point (° C.) (solvent for crystallization) |
|---|---|---|---|---|---|---|---|
| 1-172 | 1 | 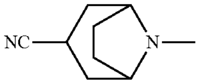 | $CH_3$ | $CH_3$ | $CH_3$ | 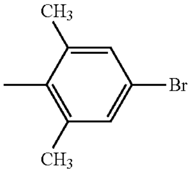 | 269-270 (IPE) |
| 1-173 | 1 | 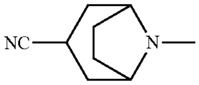 | $CH_3$ | $CH_3$ | H | 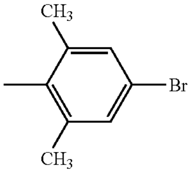 | 236-238 (IPE) |
| 1-174 | 1 | 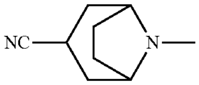 | $CH_3$ | $CH_3$ | $CH_3$ | 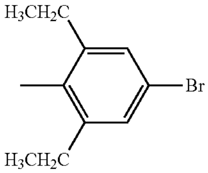 | amorphous |
| 1-175 | 1 | 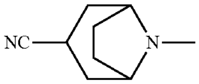 | $CH_3$ | $CH_3$ | H | 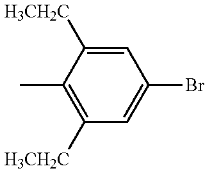 | 196-198 (IPE) |
| 1-176 | 1 | 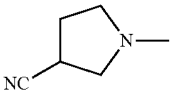 | $CH_3$ | $CH_3$ | $CH_3$ | 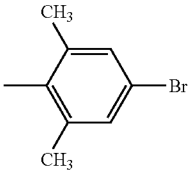 | 153-155*[2] (EtOAc) |
| 1-177 | 1 | 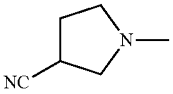 | $CH_3$ | $CH_3$ | H | 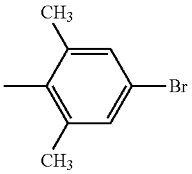 | 205-207*[2] (EtOAc/EtOH) |

TABLE 1*1-continued
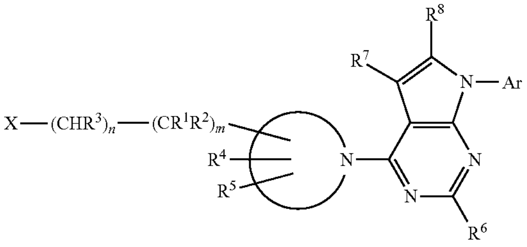
| Com. No. | Ex. No. | 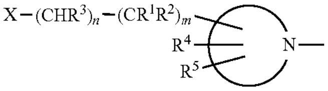 | $R^6$ | $R^7$ | $R^8$ | —Ar | melting point (° C.) (solvent for crystallization) |
|---|---|---|---|---|---|---|---|
| 1-178 | 1 | 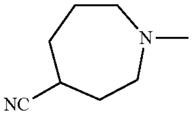 | $CH_3$ | $CH_3$ | $CH_3$ | 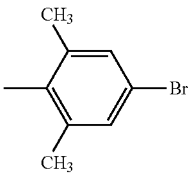 | 182-184*2 (EtOAc) |
| 1-179 | 1 | 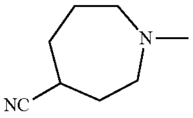 | $CH_3$ | $CH_3$ | H | 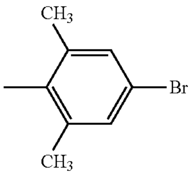 | amorphous*2 |
| 1-180 | 1 | 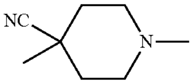 | $CH_3$ | $CH_3$ | $CH_3$ | 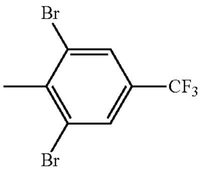 | 215-217 (hexane) |
| 1-181 | 1 | 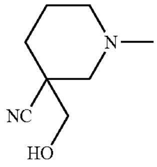 | $CH_3$ | $CH_3$ | $CH_3$ | 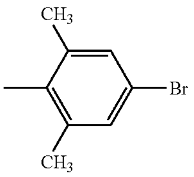 | 150-152*2 (EtOAc/EtOH) |
| 1-182 | 1 | 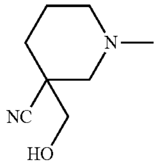 | $CH_3$ | $CH_3$ | H | 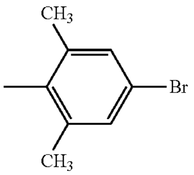 | 121-123*2 (EtOAc/EtOH) |
| 1-183 | 1 | 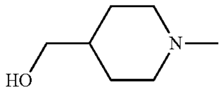 | $CH_3$ | $CH_3$ | H | 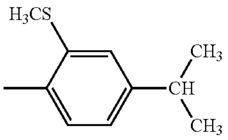 | 125-127*2 (EtOAc) |
| 1-184 | 1 | 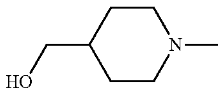 | $CH_3$ | $CH_3$ | H | 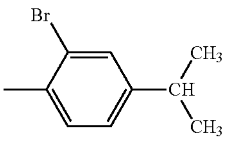 | 161-163*2 (EtOAc/EtOH) |

TABLE 1*[1]-continued
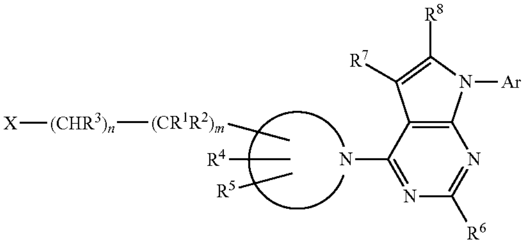
| Com. No. | Ex. No. | 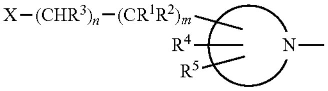 | $R^6$ | $R^7$ | $R^8$ | —Ar | melting point (° C.) (solvent for crystallization) |
|---|---|---|---|---|---|---|---|
| 1-185 | 1 | 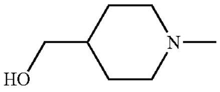 | $CH_3$ | $CH_3$ | H | 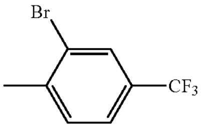 | 149-151*[2] (EtOAc/EtOH) |
| 1-186 | 1 | 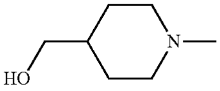 | $CH_3$ | $CH_3$ | H | 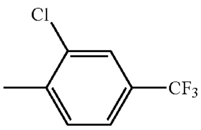 | 152-154*[2] (EtOAc/EtOH) |
| 1-187 | 1 | 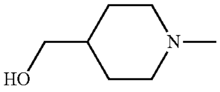 | $CH_3$ | $CH_3$ | H | 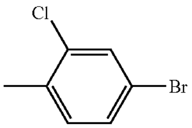 | 170-172*[2] (EtOAc/EtOH) |
| 1-188 | 1 | 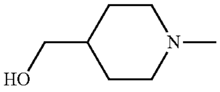 | $CH_3$ | $CH_3$ | H | 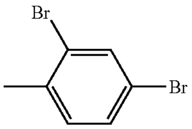 | 158-160*[2] (EtOAc) |
| 1-189 | 1 | 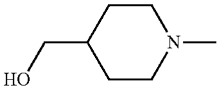 | $CH_3$ | $CH_3$ | H | 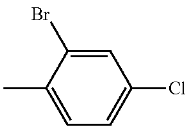 | 173-175*[2] (EtOAc/EtOH) |
| 1-190 | 1 | 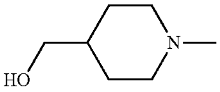 | $CH_3$ | $CH_3$ | H | 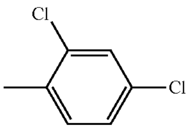 | 155-157*[2] (EtOAc/EtOH) |
| 1-191 | 1 | 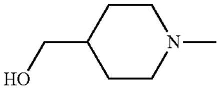 | $CH_3$ | $CH_3$ | H | 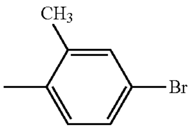 | 146-148*[2] (EtOAc/EtOH) |
| 1-192 | 1 | 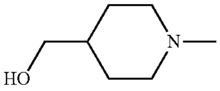 | $CH_3$ | $CH_3$ | H | 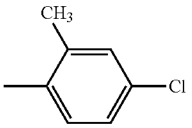 | 150-152*[2] (EtOAc/EtOH) |
| 1-193 | 1 | 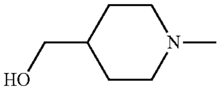 | $CH_3$ | $CH_3$ | H | 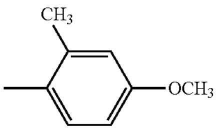 | 158-160*[2] (EtOAc/EtOH) |

TABLE 1*1-continued
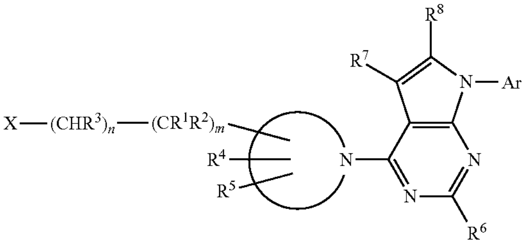
| Com. No. | Ex. No. | 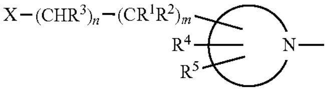 | $R^6$ | $R^7$ | $R^8$ | —Ar | melting point (° C.) (solvent for crystallization) |
|---|---|---|---|---|---|---|---|
| 1-194 | 1 | 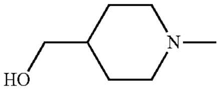 | $CH_3$ | $CH_2CH_3$ | $CH_2CH_3$ | 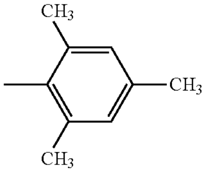 | amorphous |
| 1-195 | 1 | 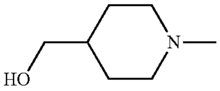 | $CH_3$ | $CH_3$ | H | 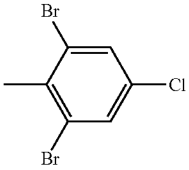 | 177-179*2 (EtOAc/EtOH) |
| 1-196 | 1 | 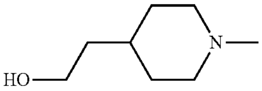 | $CH_3$ | $CH_3$ | H | 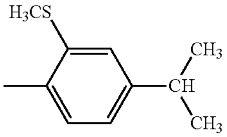 | 154-156*2 (EtOAc/EtOH) |
| 1-197 | 1 | 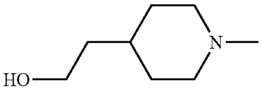 | $CH_3$ | $CH_3$ | H | 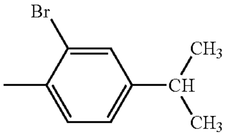 | 153-155*2 (EtOAc) |
| 1-198 | 1 | 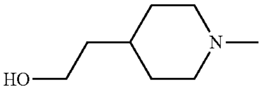 | $CH_3$ | $CH_3$ | H | 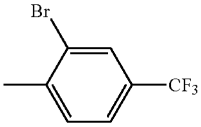 | 128-130*2 (EtOAc/EtOH) |
| 1-199 | 1 | 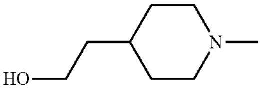 | $CH_3$ | $CH_3$ | H | 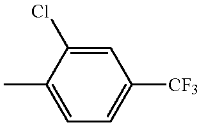 | 140-142*2 (EtOAc) |
| 1-200 | 1 | 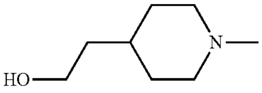 | $CH_3$ | $CH_3$ | H | 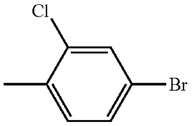 | 149-151*2 (EtOAc/EtOH) |
| 1-201 | 1 | 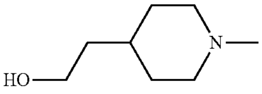 | $CH_3$ | $CH_3$ | H | 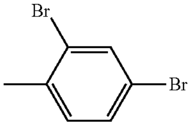 | 168-170*2 (EtOAc/EtOH) |

TABLE 1*[1]-continued
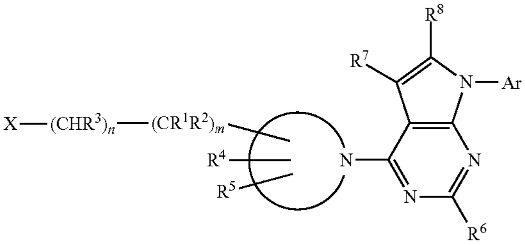
| Com. No. | Ex. No. | 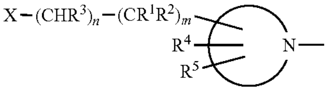 | R^6 | R^7 | R^8 | —Ar | melting point (° C.) (solvent for crystallization) |
|---|---|---|---|---|---|---|---|
| 1-202 | 1 | 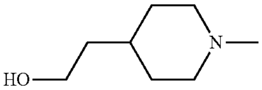 | $CH_3$ | $CH_3$ | H | 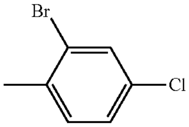 | 152-154*[2] (EtOAc/EtOH) |
| 1-203 | 1 | 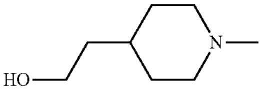 | $CH_3$ | $CH_3$ | H | 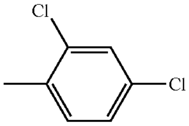 | 153-155*[2] (EtOAc/EtOH) |
| 1-204 | 1 | 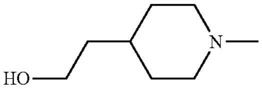 | $CH_3$ | $CH_3$ | H | 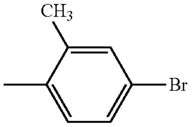 | 157-159*[2] (EtOAc/EtOH) |
| 1-205 | 1 | 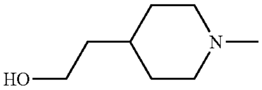 | $CH_3$ | $CH_3$ | H | 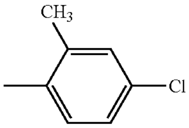 | 179-181*[2] (EtOAc/EtOH) |
| 1-206 | 1 | 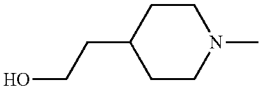 | $CH_3$ | $CH_3$ | H | 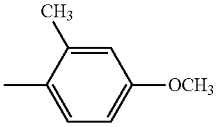 | 170-172*[2] (EtOAc/EtOH) |
| 1-207 | 1 | 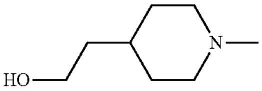 | $CH_3$ | $CH_3$ | H | 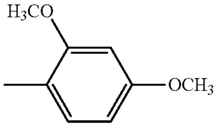 | 184-186*[2] (EtOAc) |
| 1-208 | 1 | 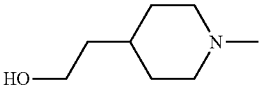 | $CH_3$ | $CH_3$ | H | 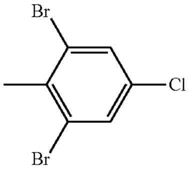 | 172-174*[2] (EtOAc/EtOH) |
| 1-209 | 1 | 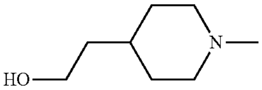 | $CH_3$ | $CH_3$ | $CH_3$ | 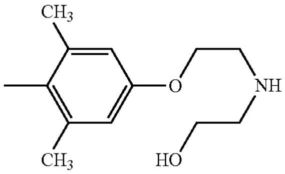 | amorphous |

TABLE 1*1-continued
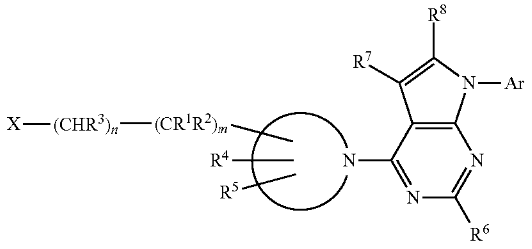
| Com. No. | Ex. No. | 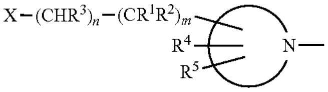 | $R^6$ | $R^7$ | $R^8$ | —Ar | melting point (° C.) (solvent for crystallization) |
|---|---|---|---|---|---|---|---|
| 1-210 | 1 | 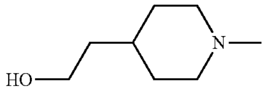 | $CH_3$ | $CH_3$ | H | 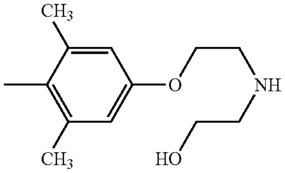 | amorphous |
| 1-211 | 1 | 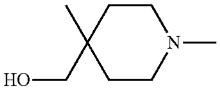 | $CH_3$ | $CH_3$ | $CH_3$ | 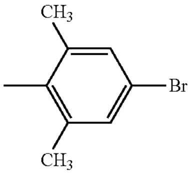 | 193-195*2 (EtOAc) |
| 1-212 | 1 | 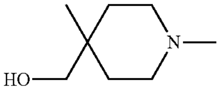 | $CH_3$ | $CH_3$ | H | 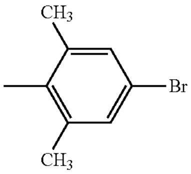 | 164-166*2 (EtOAc/EtOH) |
| 1-213 | 1 | 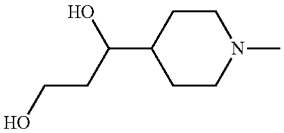 | $CH_3$ | $CH_3$ | $CH_3$ | 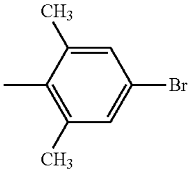 | 163-165 (IPE) |
| 1-214 | 1 | 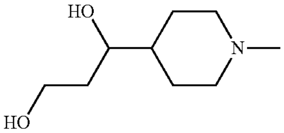 | $CH_3$ | $CH_3$ | H | 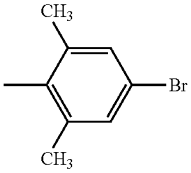 | 182-184 (IPE) |
| 1-215 | 1 | 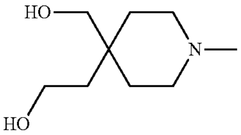 | $CH_3$ | $CH_3$ | $CH_3$ | 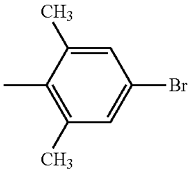 | 180-182 (EtOAc/EtOH) |
| 1-216 | 1 | 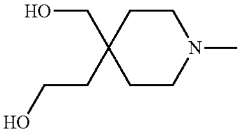 | $CH_3$ | $CH_3$ | H | 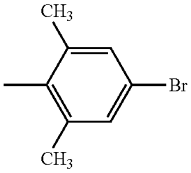 | 153-155 (IPE) |

TABLE 1*1-continued
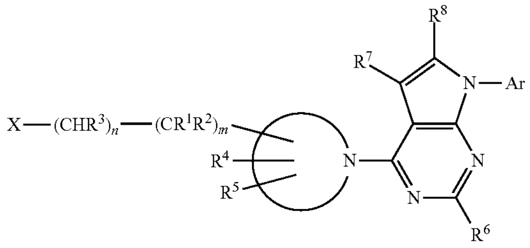
| Com. No. | Ex. No. | 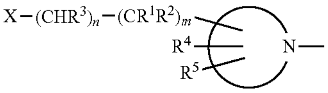 | $R^6$ | $R^7$ | $R^8$ | —Ar | melting point (° C.) (solvent for crystallization) |
|---|---|---|---|---|---|---|---|
| 1-217 | 1 | 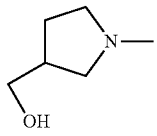 | $CH_3$ | $CH_3$ | $CH_3$ | 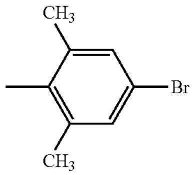 | 177-179*2 (EtOAc) |
| 1-218 | 1 | 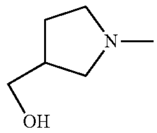 | $CH_3$ | $CH_3$ | H | 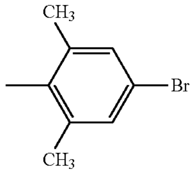 | 162-164*2 (EtOAc/EtOH) |
| 1-219 | 1 | 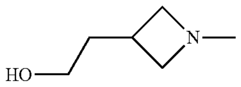 | $CH_3$ | $CH_3$ | H | 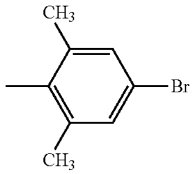 | 151-153*2 (EtOAc/EtOH) |
| 1-220 | 1 | 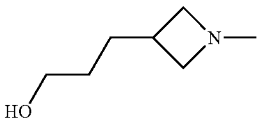 | $CH_3$ | $CH_3$ | $CH_3$ | 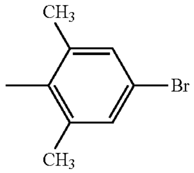 | 138-140*2 (EtOAc/EtOH) |
| 1-221 | 1 | 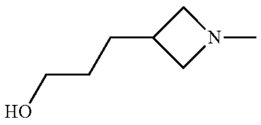 | $CH_3$ | $CH_3$ | H | 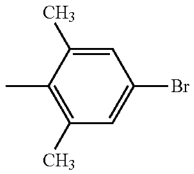 | 164-166*2 (EtOAc/EtOH) |
| 1-222 | 1 | 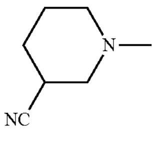 | $CH_3$ | $CH_2CH_3$ | $CH_2CH_3$ | 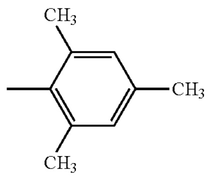 | amorphous |

TABLE 1*1-continued
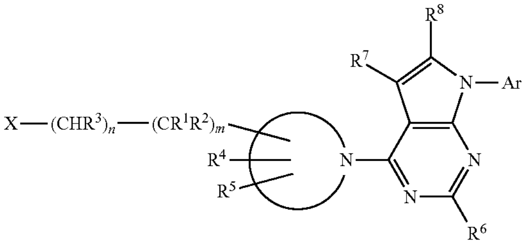
| Com. No. | Ex. No. | 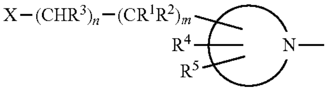 | $R^6$ | $R^7$ | $R^8$ | —Ar | melting point (° C.) (solvent for crystallization) |
|---|---|---|---|---|---|---|---|
| 1-223 | 1 | 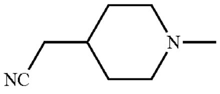 | $CH_3$ | $CH_3$ | H | 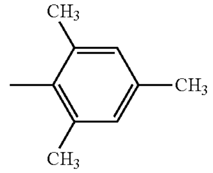 | 129-131*2 (EtOAc/IPE) |
| 1-224 | 1 | 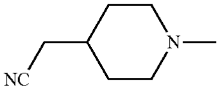 | $CH_3$ | $CH_3$ | H | 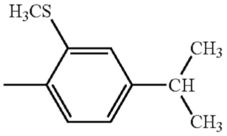 | 138-140*2 (EtOAc/EtOH) |
| 1-225 | 1 | 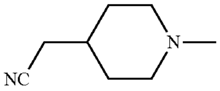 | $CH_3$ | $CH_3$ | H | 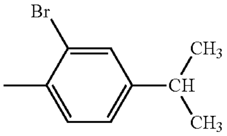 | 131-133*2 (EtOAc) |
| 1-226 | 1 | 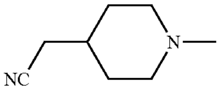 | $CH_3$ | $CH_3$ | H | 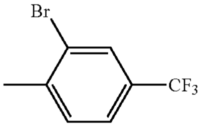 | 205-207*2 (EtOAc) |
| 1-227 | 1 | 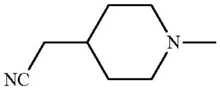 | $CH_3$ | $CH_3$ | H | 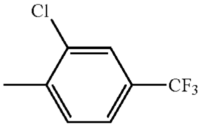 | 180-182*2 (EtOAc) |
| 1-228 | 1 | 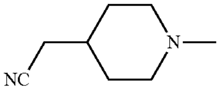 | $CH_3$ | $CH_3$ | H | 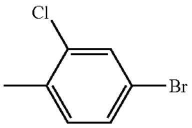 | 165-167*2 (EtOAc/EtOH) |
| 1-229 | 1 | 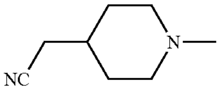 | $CH_3$ | $CH_3$ | H | 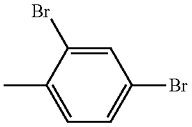 | 185-187*2 (IPE) |
| 1-230 | 1 | 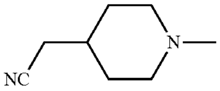 | $CH_3$ | $CH_3$ | H | 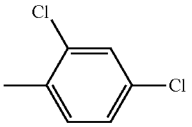 | 130-132*2 (EtOAc/EtOH) |

TABLE 1*[1]-continued
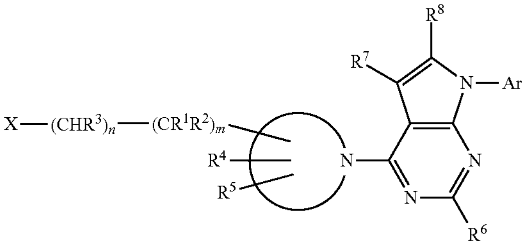
| Com. No. | Ex. No. | 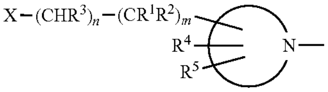 | $R^6$ | $R^7$ | $R^8$ | —Ar | melting point (° C.) (solvent for crystallization) |
|---|---|---|---|---|---|---|---|
| 1-231 | 1 | 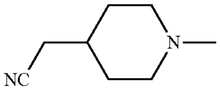 | $CH_3$ | $CH_3$ | H | 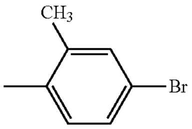 | 131-133*[2] (EtOH) |
| 1-232 | 1 | 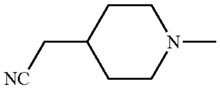 | $CH_3$ | $CH_3$ | H | 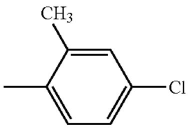 | 146-148*[2] (EtOAc/EtOH) |
| 1-233 | 1 | 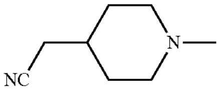 | $CH_3$ | $CH_3$ | H | 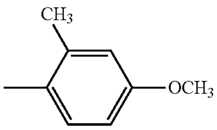 | 160-162*[2] (EtOAc/EtOH) |
| 1-234 | 1 | 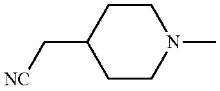 | $CH_3$ | $CH_3$ | H | 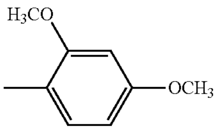 | 193-195*[2] (EtOAc/EtOH) |
| 1-235 | 1 | 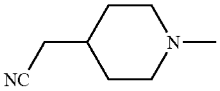 | $CH_3$ | $CH_3$ | H | 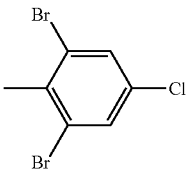 | 190-192*[2] (EtOAc/EtOH) |
| 1-236 | 1 | 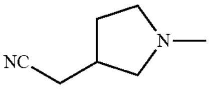 | $CH_3$ | $CH_3$ | $CH_3$ | 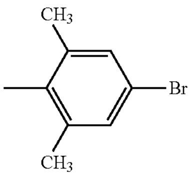 | 180-182*[2] (EtOAc/EtOH) |
| 1-237 | 1 | 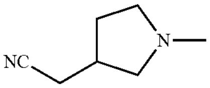 | $CH_3$ | $CH_3$ | H | 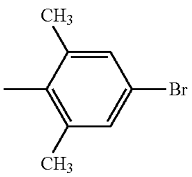 | 159-161*[2] (EtOAc/EtOH) |
| 1-238 | 1 | 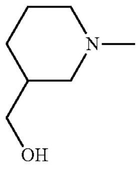 | $CH_3$ | $CH_3$ | $CH_3$ | 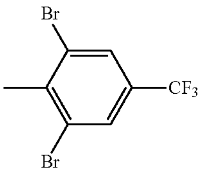 | amorphous*[4] |

TABLE 1*[1]-continued
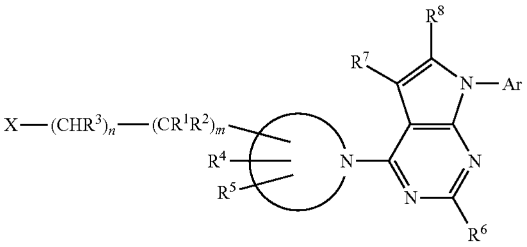
| Com. No. | Ex. No. | 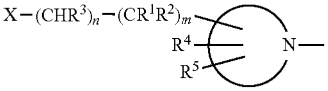 | $R^6$ | $R^7$ | $R^8$ | —Ar | melting point (° C.) (solvent for crystallization) |
|---|---|---|---|---|---|---|---|
| 1-239 | 1 | 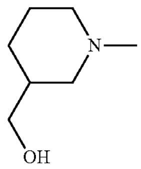 | $CH_3$ | $CH_3$ | $CH_3$ | 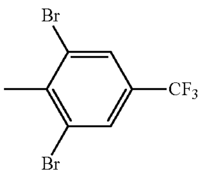 | amorphous*[4] |
| 1-240 | 1 | 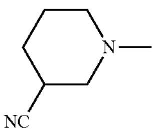 | $CH_3$ | $CH_3$ | $CH_3$ | 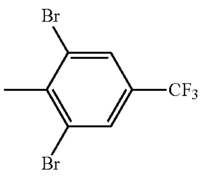 | amorphous*[4] |
| 1-241 | 1 | 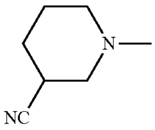 | $CH_3$ | $CH_3$ | $CH_3$ | 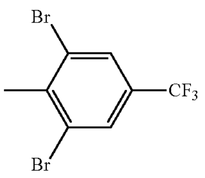 | amorphous*[4] |
| 1-242 | 1 | 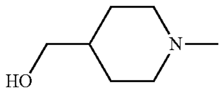 | $CH_3$ | $CH_3$ | H | 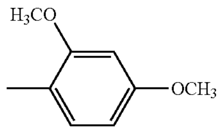 | 185-187*[2] (EtOH) |
| 1-243 | 1 | 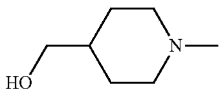 | $CH_3$ | $CH_3$ | H | 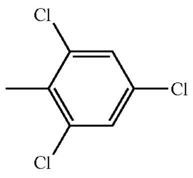 | 186-188*[2] (EtOAc/EtOH) |
| 1-244 | 1 | 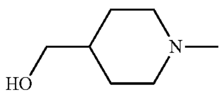 | $CH_3$ | $CH_3$ | H | 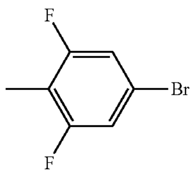 | 174-176*[2] (EtOAc/EtOH) |
| 1-245 | 1 | 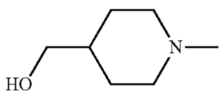 | $CH_3$ | $CH_3$ | H | 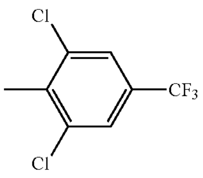 | 165-167*[2] (EtOAc/EtOH) |

TABLE 1*1-continued
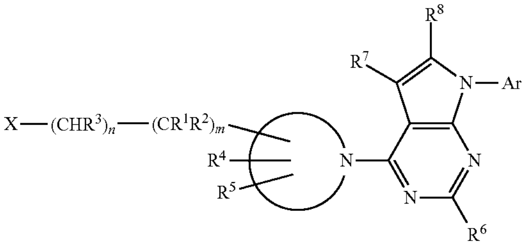
| Com. No. | Ex. No. | 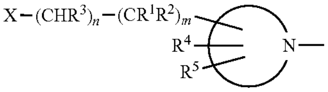 | $R^6$ | $R^7$ | $R^8$ | —Ar | melting point (° C.) (solvent for crystallization) |
|---|---|---|---|---|---|---|---|
| 1-246 | 1 | 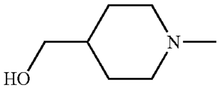 | $CH_3$ | $CH_3$ | H | 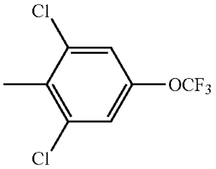 | 172-174*2 (EtOAc/EtOH) |
| 1-247 | 1 | 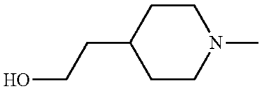 | $CH_3$ | $CH_3$ | H | 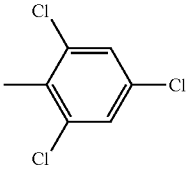 | 155-157*2 (EtOAc/EtOH) |
| 1-248 | 1 | 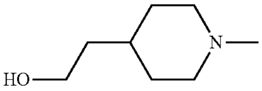 | $CH_3$ | $CH_3$ | H | 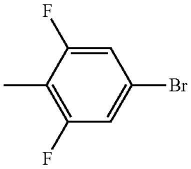 | 139-141*2 (EtOAc/EtOH) |
| 1-249 | 1 | 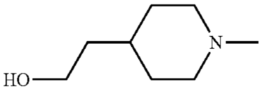 | $CH_3$ | $CH_3$ | H | 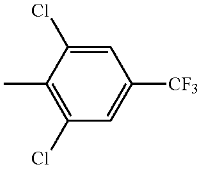 | 176-178*2 (EtOAc/IPE) |
| 1-250 | 1 | 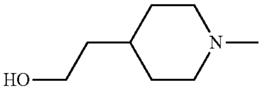 | $CH_3$ | $CH_3$ | H | 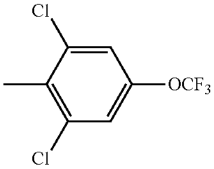 | 147-149*2 (EtOAc) |
| 1-251 | 1 | 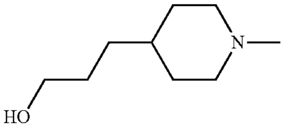 | $CH_3$ | $CH_3$ | $CH_3$ | 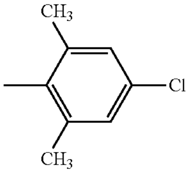 | 170-172*2 (EtOAc) |
| 1-252 | 1 | 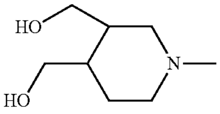 | $CH_3$ | $CH_3$ | $CH_3$ | 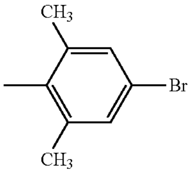 | 193-195 (EtOAc/IPE) |

TABLE 1*[1]-continued
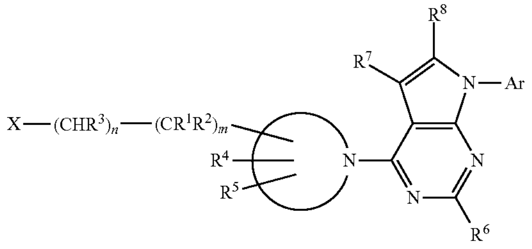
| Com. No. | Ex. No. | 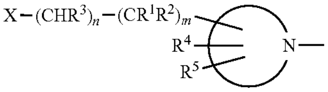 | $R^6$ | $R^7$ | $R^8$ | —Ar | melting point (° C.) (solvent for crystallization) |
|---|---|---|---|---|---|---|---|
| 1-253 | 1 | 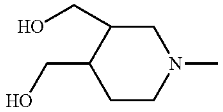 | $CH_3$ | $CH_3$ | H | 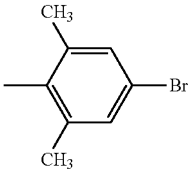 | 200-202 (IPE) |
| 1-254 | 1 | 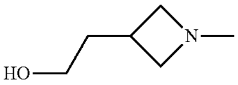 | $CH_3$ | $CH_3$ | $CH_3$ | 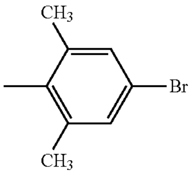 | 155-157*[2] (EtOAc/EtOH) |
| 1-255 | 1 | 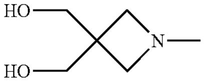 | $CH_3$ | $CH_3$ | $CH_3$ | 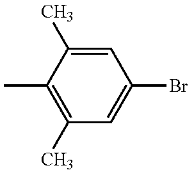 | 222-224 (IPE) |
| 1-256 | 1 | 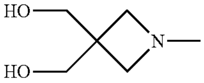 | $CH_3$ | $CH_3$ | H | 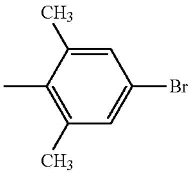 | 193-195 (IPE) |
| 1-257 | 1 | 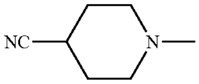 | $CH_3$ | $CH_3$ | $CH_3$ | 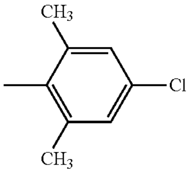 | 199-201*[2] (EtOAc/EtOH) |
| 1-258 | 1 | 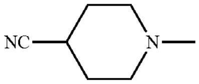 | $CH_3$ | $CH_3$ | H | 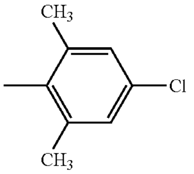 | 166-168*[2] (EtOAc/EtOH) |
| 1-259 | 1 | 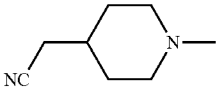 | $CH_3$ | $CH_3$ | H | 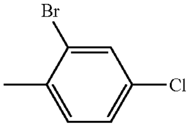 | 165-167*[2] (EtOAc/EtOH) |

TABLE 1*1-continued
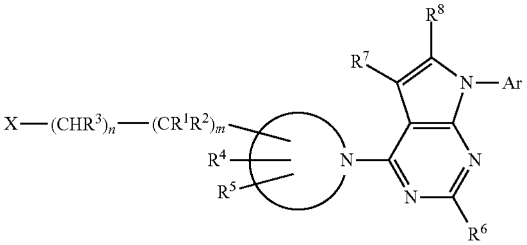
| Com. No. | Ex. No. | 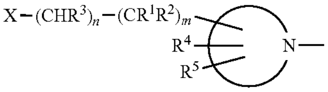 | $R^6$ | $R^7$ | $R^8$ | —Ar | melting point (° C.) (solvent for crystallization) |
|---|---|---|---|---|---|---|---|
| 1-260 | 1 | 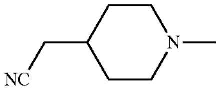 | $CH_3$ | $CH_3$ | H | 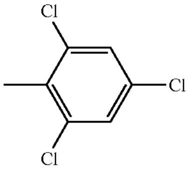 | 167-169*2 (EtOAc) |
| 1-261 | 1 | 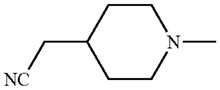 | $CH_3$ | $CH_3$ | H | 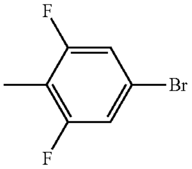 | 187-189*2 (EtOAc/EtOH) |
| 1-262 | 1 | 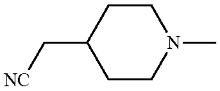 | $CH_3$ | $CH_3$ | H | 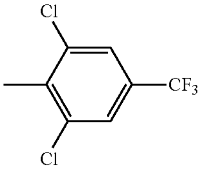 | 185-187*2 (EtOAc/IPE) |
| 1-263 | 1 | 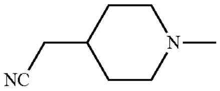 | $CH_3$ | $CH_3$ | H | 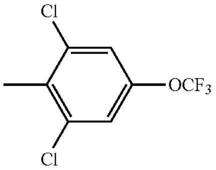 | 141-143*2 (EtOAc) |
| 1-264 | 1 | 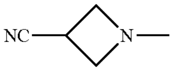 | $CH_3$ | $CH_3$ | $CH_3$ | 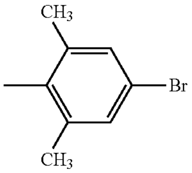 | 179-181 (IPE) |
| 1-265 | 1 | 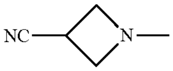 | $CH_3$ | $CH_3$ | H | 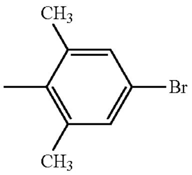 | 218-220 (EtOAc/EtOH) |

TABLE 1*1-continued
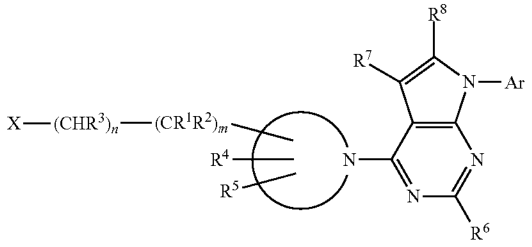
| Com. No. | Ex. No. | 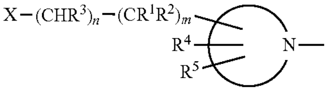 | $R^6$ | $R^7$ | $R^8$ | —Ar | melting point (° C.) (solvent for crystallization) |
| --- | --- | --- | --- | --- | --- | --- | --- |
| 1-266 | 1 | 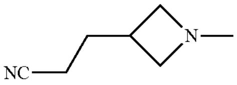 | $CH_3$ | $CH_3$ | $CH_3$ | 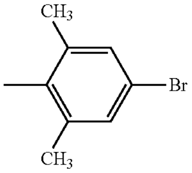 | 166-168*2 (EtOAc/EtOH) |
| 1-267 | 1 | 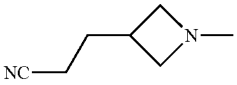 | $CH_3$ | $CH_3$ | H | 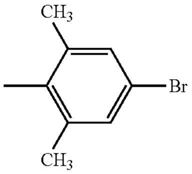 | amorphous*2 |
| 1-268 | 1 | 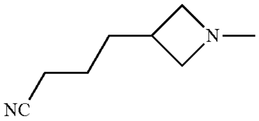 | $CH_3$ | $CH_3$ | $CH_3$ | 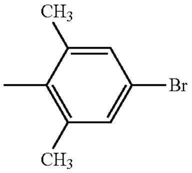 | 158-160*2 (EtOAc/EtOH) |
| 1-269 | 1 | 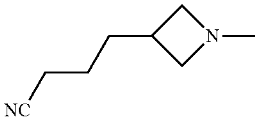 | $CH_3$ | $CH_3$ | H | 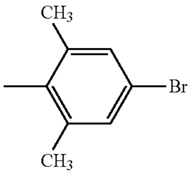 | 160-162*2 (EtOAc/EtOH) |
| 1-270 | 1 | 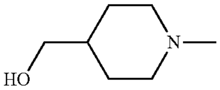 | $CH_3$ | H | H | 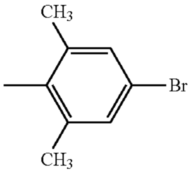 | 162-164 (EtOAc/IPE) |
| 1-271 | 1 | 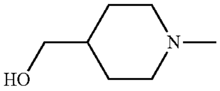 | $CH_3$ | $CH_3$ | H | 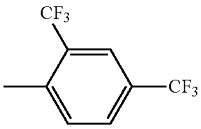 | 133-136*2 (EtOAc/EtOH) |
| 1-272 | 1 | 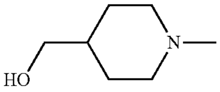 | $CH_3$ | $CH_3$ | $CH_3$ | 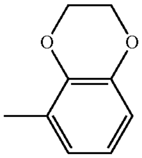 | 229-231 (CH3CN) |

TABLE 1*[1]-continued
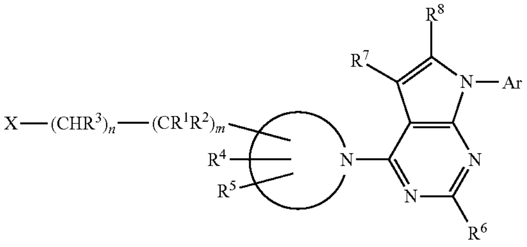
| Com. No. | Ex. No. | 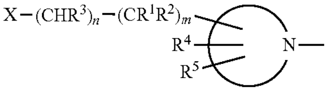 | $R^6$ | $R^7$ | $R^8$ | —Ar | melting point (° C.) (solvent for crystallization) |
|---|---|---|---|---|---|---|---|
| 1-273 | 1 | 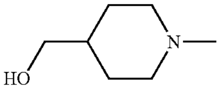 | $CH_3$ | $CH_3$ | H | 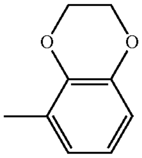 | 208-210 (CH3CN) |
| 1-274 | 1 | 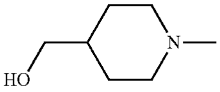 | $CH_3$ | $CH_3$ | OH | 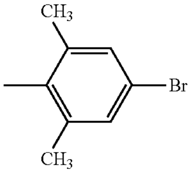 | 196-198 (EtOH) |
| 1-275 | 1 | 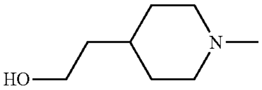 | $CH_3$ | $CH_3$ | H | 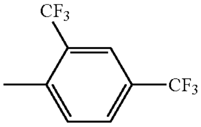 | 129-131*[2] (EtOAc) |
| 1-276 | 1 | 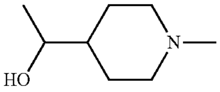 | $CH_3$ | $CH_3$ | $CH_3$ | 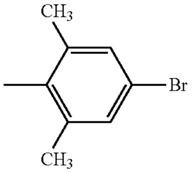 | 166-168*[2]*[4] (EtOAc/EtOH) |
| 1-277 | 1 | 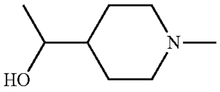 | $CH_3$ | $CH_3$ | H | 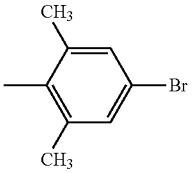 | 131-133*[2]*[4] (EtOAc/EtOH) |
| 1-278 | 1 | 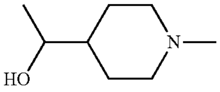 | $CH_3$ | $CH_3$ | $CH_3$ | 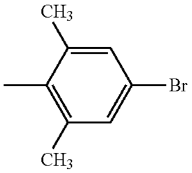 | 158-160*[2]*[4] (EtOAc/EtOH) |
| 1-279 | 1 | 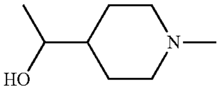 | $CH_3$ | $CH_3$ | H | 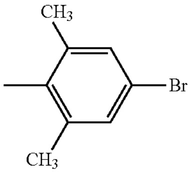 | 129-131*[2]*[4] (EtOAc/EtOH) |

TABLE 1*1-continued
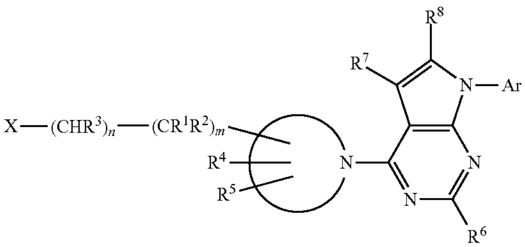
| Com. No. | Ex. No. | 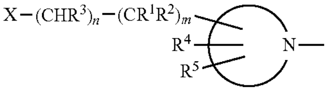 | $R^6$ | $R^7$ | $R^8$ | —Ar | melting point (° C.) (solvent for crystallization) |
|---|---|---|---|---|---|---|---|
| 1-280 | 1 | 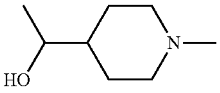 | $CH_3$ | $CH_3$ | H | 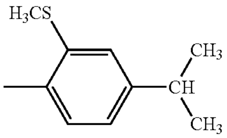 | 144-146*2*4 (EtOAc/EtOH) |
| 1-281 | 1 | 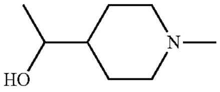 | $CH_3$ | $CH_3$ | H | 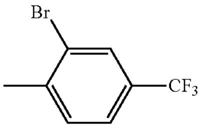 | 170-173*2*4 (EtOAc/EtOH) |
| 1-282 | 1 | 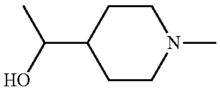 | $CH_3$ | $CH_3$ | H | 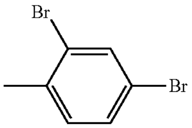 | 152-155*2*4 (EtOAc/EtOH) |
| 1-283 | 1 | 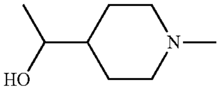 | $CH_3$ | $CH_3$ | $CH_3$ | 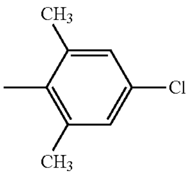 | 184-185*2*4 (EtOAc/EtOH) |
| 1-284 | 1 | 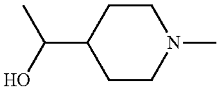 | $CH_3$ | $CH_3$ | H | 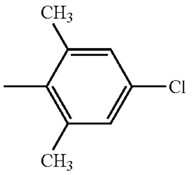 | 122-124*2*4 (EtOAc/EtOH) |
| 1-285 | 1 | 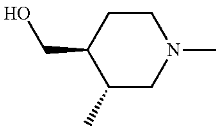 | $CH_3$ | $CH_3$ | $CH_3$ | 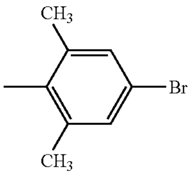 | 150-152*2 (EtOAc/EtOH) |
| 1-286 | 1 | 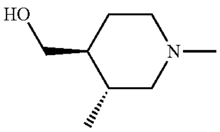 | $CH_3$ | $CH_3$ | H | 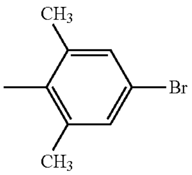 | 165-167*2 (EtOAc/EtOH) |

TABLE 1*[1]-continued
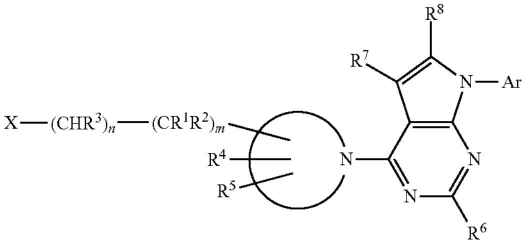
| Com. No. | Ex. No. | 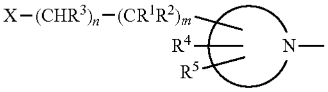 | $R^6$ | $R^7$ | $R^8$ | —Ar | melting point (° C.) (solvent for crystallization) |
|---|---|---|---|---|---|---|---|
| 1-287 | 1 | 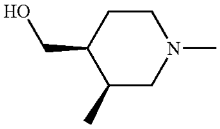 | $CH_3$ | $CH_3$ | $CH_3$ | 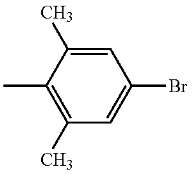 | 182-184*[2] (EtOAc/EtOH) |
| 1-288 | 1 | 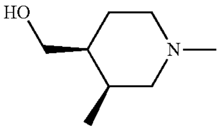 | $CH_3$ | $CH_3$ | H | 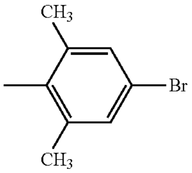 | 172-174*[2] (EtOAc/EtOH) |
| 1-289 | 1 | 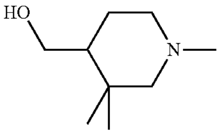 | $CH_3$ | $CH_3$ | $CH_3$ | 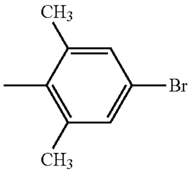 | 162-165*[2] (EtOAc/EtOH) |
| 1-290 | 1 | 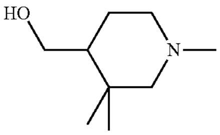 | $CH_3$ | $CH_3$ | H | 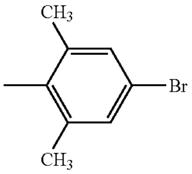 | 149-151*[2] (EtOAc/EtOH) |
| 1-291 | 1 | 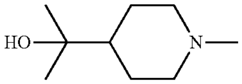 | $CH_3$ | $CH_3$ | $CH_3$ | 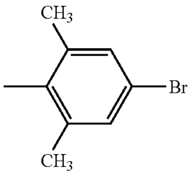 | 232-234*[2] (EtOAc/EtOH) |
| 1-292 | 1 | 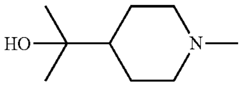 | $CH_3$ | $CH_3$ | H | 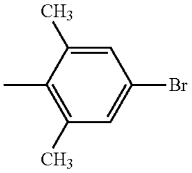 | 164-166*[2] (EtOAc/EtOH) |

TABLE 1*1-continued
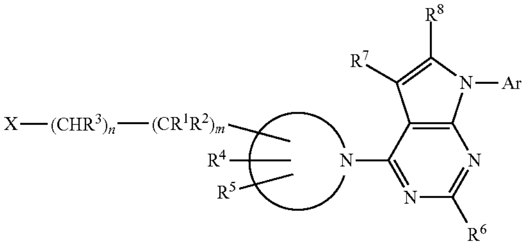
| Com. No. | Ex. No. | 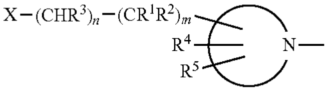 | $R^6$ | $R^7$ | $R^8$ | —Ar | melting point (° C.) (solvent for crystallization) |
|---|---|---|---|---|---|---|---|
| 1-293 | 1 | 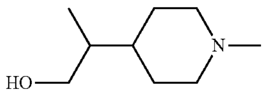 | $CH_3$ | $CH_3$ | $CH_3$ | 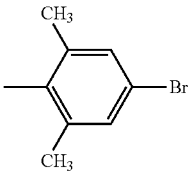 | 192-194*2 (EtOAc/EtOH) |
| 1-294 | 1 | 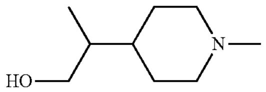 | $CH_3$ | $CH_3$ | H | 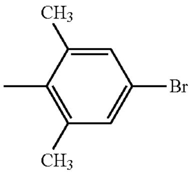 | 153-155*2 (EtOAc/EtOH) |
| 1-295 | 1 | 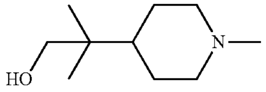 | $CH_3$ | $CH_3$ | $CH_3$ | 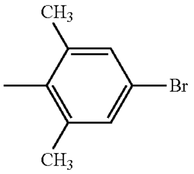 | 162-164*2 (EtOAc) |
| 1-296 | 1 | 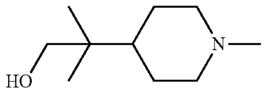 | $CH_3$ | $CH_3$ | H | 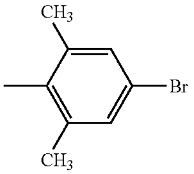 | 204-206*2 (EtOAc/EtOH) |
| 1-297 | 1 | 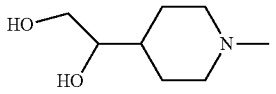 | $CH_3$ | $CH_3$ | H | 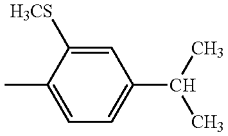 | 145-147 (EtOAc/IPE) |
| 1-298 | 1 | 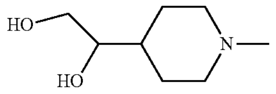 | $CH_3$ | $CH_3$ | H | 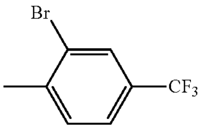 | 195-196 (EtOAc/IPE) |
| 1-299 | 1 | 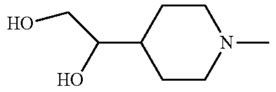 | $CH_3$ | $CH_3$ | H | 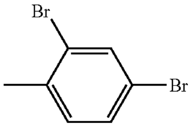 | 202-203 (EtOAc/IPE) |

TABLE 1*[1]-continued
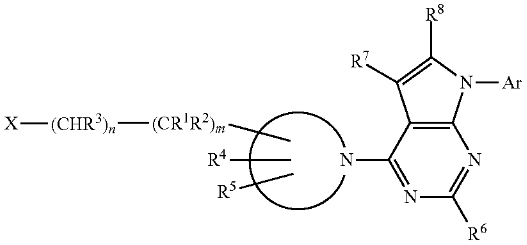
| Com. No. | Ex. No. | 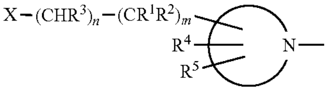 | $R^6$ | $R^7$ | $R^8$ | —Ar | melting point (° C.) (solvent for crystallization) |
|---|---|---|---|---|---|---|---|
| 1-300 | 1 | 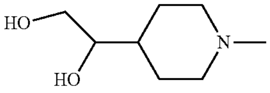 | $CH_3$ | $CH_3$ | $CH_3$ | 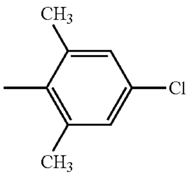 | 202-203 (EtOAc/IPE) |
| 1-301 | 1 | 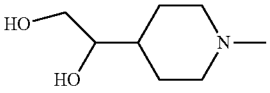 | $CH_3$ | $CH_3$ | H | 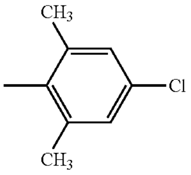 | 181-183 (EtOAc/IPE) |
| 1-302 | 1 | 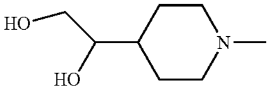 | $CH_3$ | $CH_3$ | $CH_3$ | 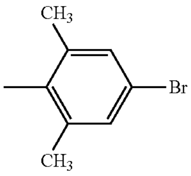 | 203-205*[4] (IPE) |
| 1-303 | 1 | 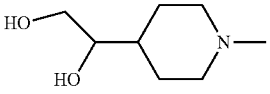 | $CH_3$ | $CH_3$ | H | 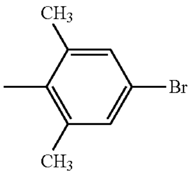 | 156-158*[4] (IPE) |
| 1-304 | 1 | 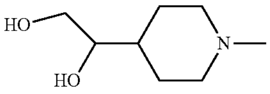 | $CH_3$ | $CH_3$ | $CH_3$ | 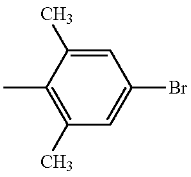 | 212-213*[4] (IPE) |
| 1-305 | 1 | 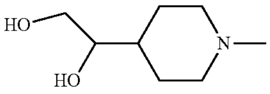 | $CH_3$ | $CH_3$ | H | 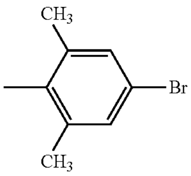 | 164-166*[4] (IPE) |

TABLE 1*1-continued
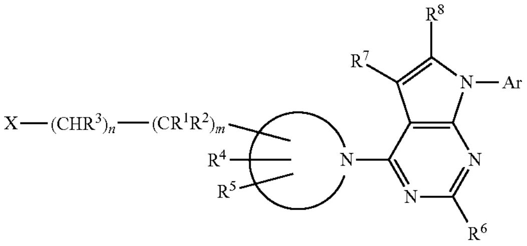
| Com. No. | Ex. No. | 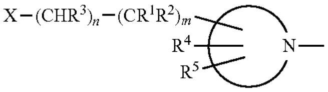 | $R^6$ | $R^7$ | $R^8$ | —Ar | melting point (° C.) (solvent for crystallization) |
|---|---|---|---|---|---|---|---|
| 1-306 | 1 | 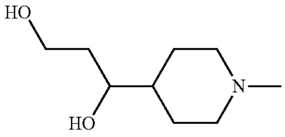 | $CH_3$ | $CH_3$ | $CH_3$ | 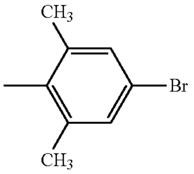 | 188-190 (IPE)*4 |
| 1-307 | 1 | 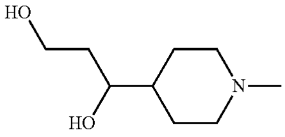 | $CH_3$ | $CH_3$ | H | 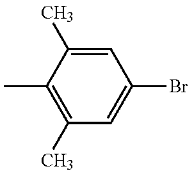 | 191-192 (IPE)*4 |
| 1-308 | 1 | 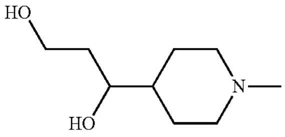 | $CH_3$ | $CH_3$ | $CH_3$ | 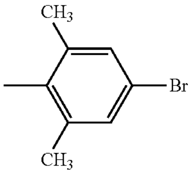 | 188-189 (IPE)*4 |
| 1-309 | 1 | 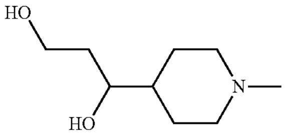 | $CH_3$ | $CH_3$ | H | 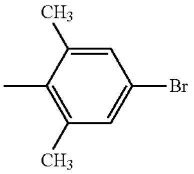 | 190-191 (IPE)*4 |
| 1-310 | 1 | 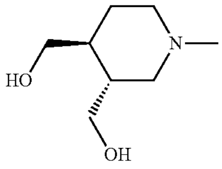 | $CH_3$ | $CH_3$ | $CH_3$ | 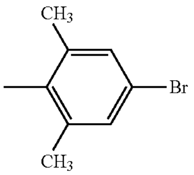 | 200-202 (IPE) |
| 1-311 | 1 | 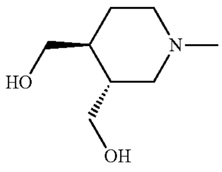 | $CH_3$ | $CH_3$ | H | 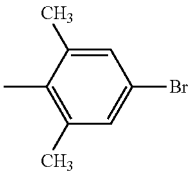 | 131-133 (IPE) |

TABLE 1*1-continued
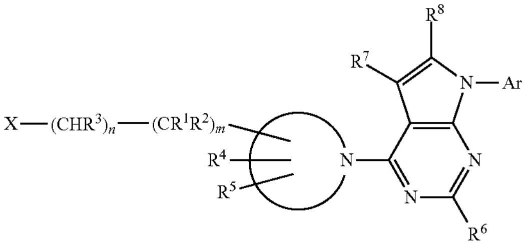
| Com. No. | Ex. No. | 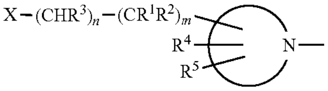 | $R^6$ | $R^7$ | $R^8$ | —Ar | melting point (° C.) (solvent for crystallization) |
|---|---|---|---|---|---|---|---|
| 1-312 | 1 | 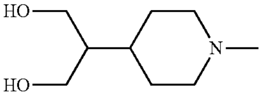 | $CH_3$ | $CH_3$ | $CH_3$ | 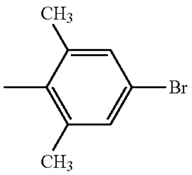 | 223-224 (IPE) |
| 1-313 | 1 | 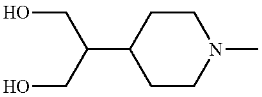 | $CH_3$ | $CH_3$ | H | 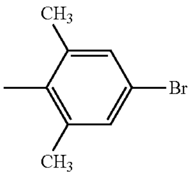 | 184-186 (IPE) |
| 1-314 | 1 | 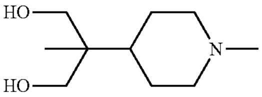 | $CH_3$ | $CH_3$ | $CH_3$ | 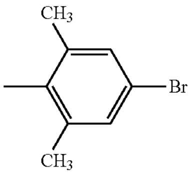 | 215-216 (IPE) |
| 1-315 | 1 | 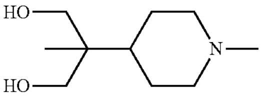 | $CH_3$ | $CH_3$ | H | 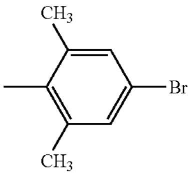 | 214-215 (IPE) |
| 1-316 | 1 | 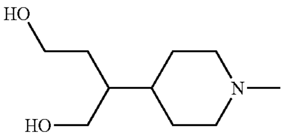 | $CH_3$ | $CH_3$ | $CH_3$ | 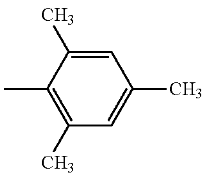 | amorphous |
| 1-317 | 1 | 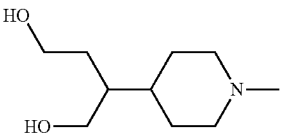 | $CH_3$ | $CH_3$ | $CH_3$ | 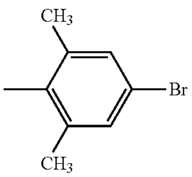 | 151-153 (EtOAc) |

TABLE 1*[1]-continued
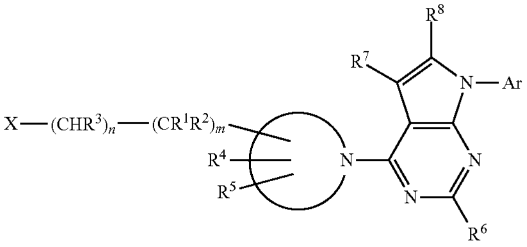
| Com. No. | Ex. No. | 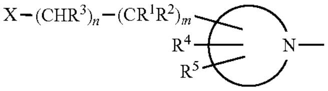 | $R^6$ | $R^7$ | $R^8$ | —Ar | melting point (° C.) (solvent for crystallization) |
|---|---|---|---|---|---|---|---|
| 1-318 | 1 | 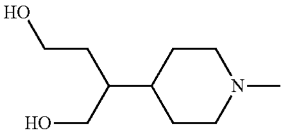 | $CH_3$ | $CH_3$ | H | 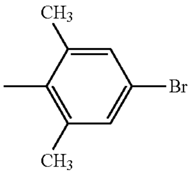 | 149-151 (IPE) |
| 1-319 | 1 | 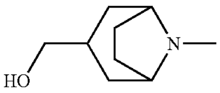 | $CH_3$ | $CH_3$ | $CH_3$ | 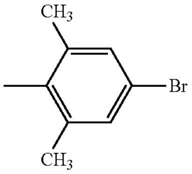 | 240-242*[2] (EtOAc/EtOH) |
| 1-320 | 1 | 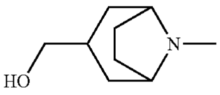 | $CH_3$ | $CH_3$ | H | 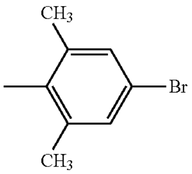 | 216-218*[2] (EtOAc/EtOH) |
| 1-321 | 1 | 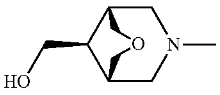 | $CH_3$ | $CH_3$ | $CH_3$ | 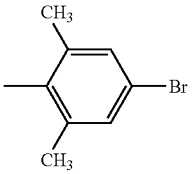 | 180-183*[2] (EtOAc/EtOH) |
| 1-322 | 1 | 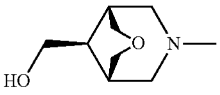 | $CH_3$ | $CH_3$ | H | 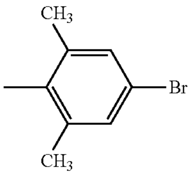 | 214-216*[2] (EtOAc/EtOH) |
| 1-323 | 1 | 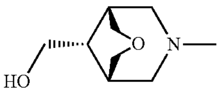 | $CH_3$ | $CH_3$ | $CH_3$ | 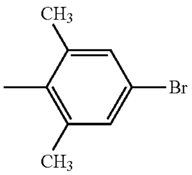 | 198-200*[2] (EtOAc/EtOH) |

TABLE 1*[1]-continued
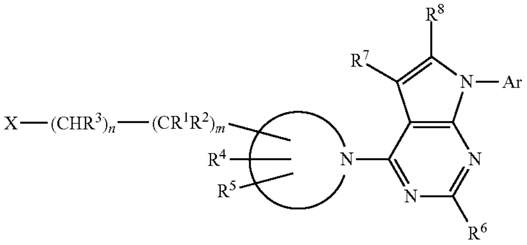
| Com. No. | Ex. No. | 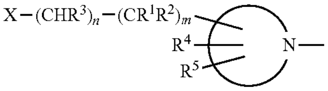 | $R^6$ | $R^7$ | $R^8$ | —Ar | melting point (° C.) (solvent for crystallization) |
|---|---|---|---|---|---|---|---|
| 1-324 | 1 | 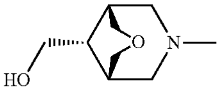 | $CH_3$ | $CH_3$ | H | 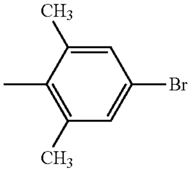 | 291-293*[2] (EtOAc/EtOH) |
| 1-325 | 1 | 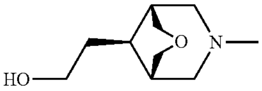 | $CH_3$ | $CH_3$ | $CH_3$ | 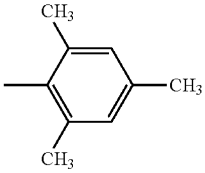 | amorphous |
| 1-326 | 1 | 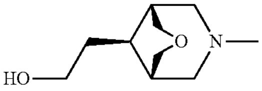 | $CH_3$ | $CH_3$ | $CH_3$ | 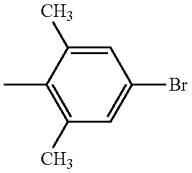 | 183-186*[2] (EtOAc/EtOH) |
| 1-327 | 1 | 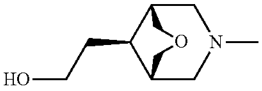 | $CH_3$ | $CH_3$ | H | 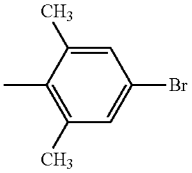 | 154-156*[2] (EtOAc/EtOH) |
| 1-328 | 1 | 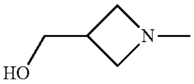 | $CH_3$ | $CH_3$ | $CH_3$ | 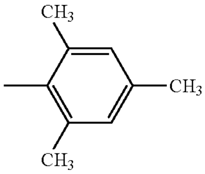 | 192-194 (No solvent) |
| 1-329 | 1 | 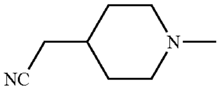 | $CH_3$ | H | H | 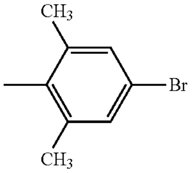 | 156-158*[2]*[5] |
| 1-330 | 1 | 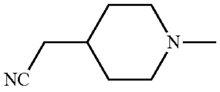 | $CH_3$ | $CH_3$ | H | 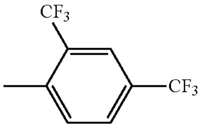 | 159-161*[2] (IPE) |

TABLE 1*1-continued
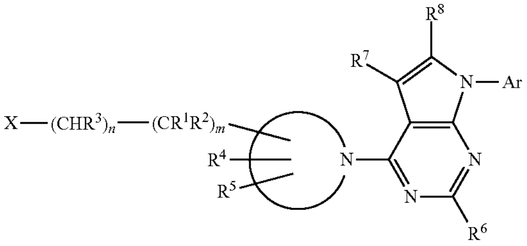
| Com. No. | Ex. No. | 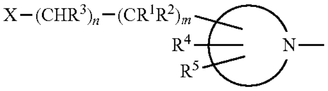 | $R^6$ | $R^7$ | $R^8$ | —Ar | melting point (° C.) (solvent for crystallization) |
|---|---|---|---|---|---|---|---|
| 1-331 | 1 | 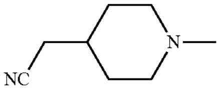 | $CH_3$ | $CH_3$ | OH | 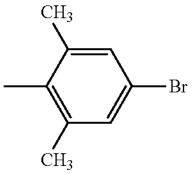 | 242-244*5 |
| 1-332 | 1 | 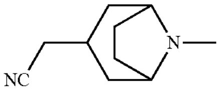 | $CH_3$ | $CH_3$ | $CH_3$ | 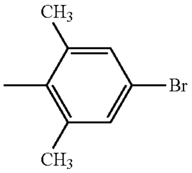 | 217-219*2 (EtOAc/EtOH) |
| 1-333 | 1 | 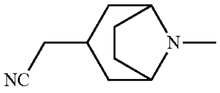 | $CH_3$ | $CH_3$ | H | 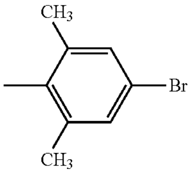 | 204-206*2 (EtOAc/EtOH) |
| 1-334 | 1 | 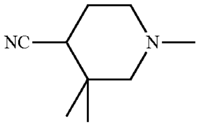 | $CH_3$ | $CH_3$ | $CH_3$ | 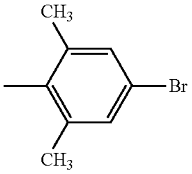 | 143-145*2 (EtOAc/EtOH) |
| 1-335 | 1 | 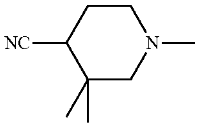 | $CH_3$ | $CH_3$ | H | 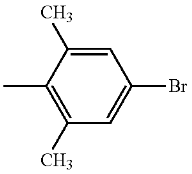 | 172-174*2 (EtOAc/EtOH) |
| 1-336 | 1 | 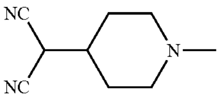 | $CH_3$ | $CH_3$ | $CH_3$ | 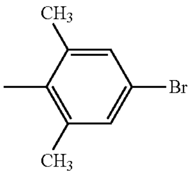 | 168-170 (IPE/hexane) |

TABLE 1*[1]-continued
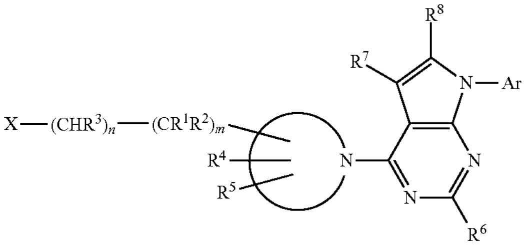
| Com. No. | Ex. No. | 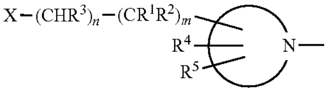 | $R^6$ | $R^7$ | $R^8$ | —Ar | melting point (° C.) (solvent for crystallization) |
|---|---|---|---|---|---|---|---|
| 1-337 | 1 | 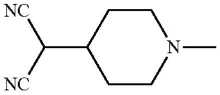 | $CH_3$ | $CH_3$ | H | 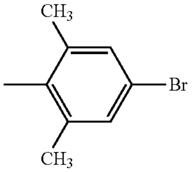 | 164-166 (IPE) |
| 1-338 | 1 | 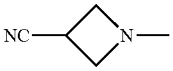 | $CH_3$ | $CH_3$ | $CH_3$ | 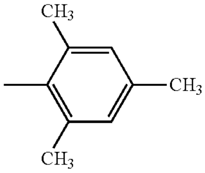 | amorphous |
| 1-339 | 1 | 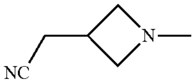 | $CH_3$ | $CH_3$ | H | 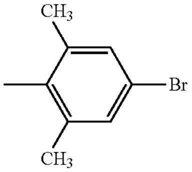 | amorphous |
| 1-340 | 1 | 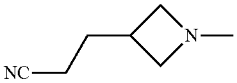 | $CH_3$ | $CH_3$ | $CH_3$ | 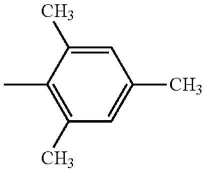 | 148-150 (IPE) |
| 1-341 | 1 | 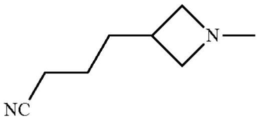 | $CH_3$ | $CH_3$ | $CH_3$ | 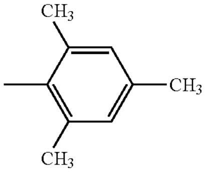 | 183-185 (IPE) |
| 1-342 | 1 | 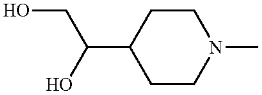 | $CH_3$ | $CH_3$ | $CH_3$ | 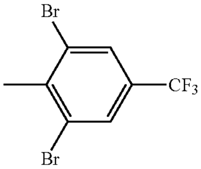 | 221-223 (EtOAc) |
| 1-343 | 1 | 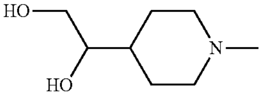 | $CH_3$ | $CH_3$ | H | 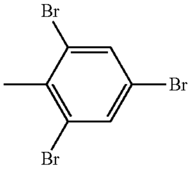 | 205-206 (EtOAc) |

TABLE 1*[1]-continued

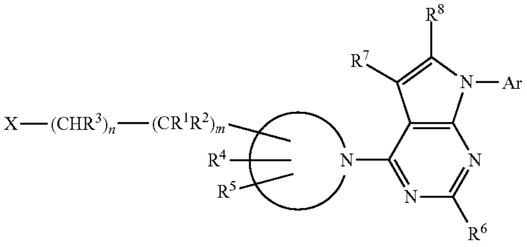

| Com. No. | Ex. No. | 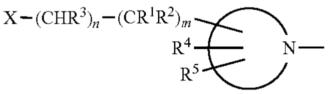 | $R^6$ | $R^7$ | $R^8$ | —Ar | melting point (° C.) (solvent for crystallization) |
|---|---|---|---|---|---|---|---|
| 1-344 | 1 | 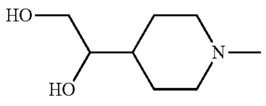 | $CH_3$ | $CH_3$ | H | 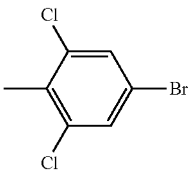 | 203-204 (EtOAc) |
| 1-345 | 1 | 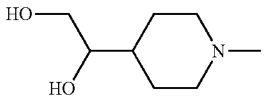 | $CH_3$ | $CH_3$ | H | 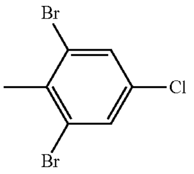 | 196-198 (EtOAc) |
| 1-346 | 1 | 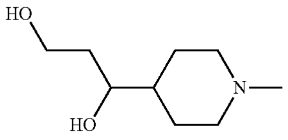 | $CH_3$ | $CH_3$ | $CH_3$ | 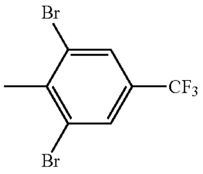 | 234-236 (EtOAc) |
| 1-347 | 1 | 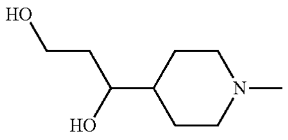 | $CH_3$ | $CH_3$ | H | 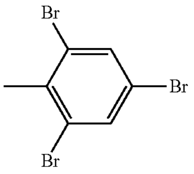 | 202-236 (EtOAc) |
| 1-348 | 1 | 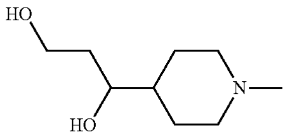 | $CH_3$ | $CH_3$ | H | 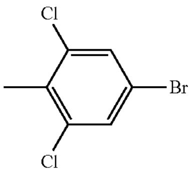 | 187-188 (EtOAc) |
| 1-349 | 1 | 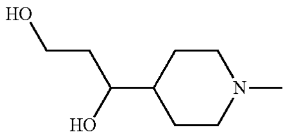 | $CH_3$ | $CH_3$ | H | 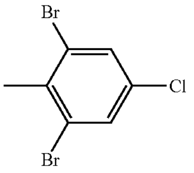 | 200-201 (EtOAc) |

*[1]Com. No. = compound number, Ex. No. = example snumber, solvent for crystallization;

EtOAc = ethyl acetate, EtOH = ehtnaol, IPE = diisopropylether, THF = tetrahydrofuran, IPA = isopropyl alcohol, ACE = acetone, CH3CN = acetonitrile Analytical data of non-crystal compounds, diastereoisomers and optically active compounds are described below.

1-003:

MS (ES, Pos.): 589 $(M+1)^+$, 591 $(M+3)^+$, 593 $(M+5)^+$, 611 (M+Na), 613 $(M+Na+2)^+$, 615 $(M+Na+4)^+$; HPLC retention time: 4.84 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-005:

MS (ES, Pos.): 457 $(M+1)^+$, 459 $(M+3)^+$, 479 $(M+Na)^+$, 481 $(M+Na+2)^+$; HPLC retention time: 9.47 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-011:

MS (ES, Pos.): 393 $(M+1)^+$, 415 $(M+Na)^+$; HPLC retention time: 4.16 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-012:

MS (ES, Pos.): 379 $(M+1)^+$, 401 (M+Na); HPLC retention time: 3.8 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-013:

MS (ES, Pos.): 523 $(M+1)^+$, 525 $(M+3)^+$, 527 $(M+5)^+$, 545 $(M+Na)^+$, 547 $(M+Na+2)^+$, 549 $(M+Na+4)^+$; HPLC retention time: 3.14 and 3.27 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-014:

MS (ES, Pos.): 539 $(M+1)^+$, 541 $(M+3)^+$, 543 $(M+5)^+$, 561 $(M+Na)^+$, 563 $(M+Na+2)^+$, 565 $(M+Na+4)^+$; HPLC retention time: 3.57 and 3.69 min. (Capcell Pak UG120, 4.6 mm×150 mm, Shiseido); Flow rate: 1.0 ml/min; Mobile phase: acetonitrile/0.05M ammonium acetate aqueous solution (80:20); pH of the solvent was adjusted to 7.4 with aqueous ammonia or acetic acid.

1-015:

MS (ES, Pos.): 575 $(M+1)^+$, 577 $(M+3)^+$, 579 $(M+5)^+$; HPLC retention time: 4.05 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-016:

MS (ES, Pos.): 457 $(M+1)^+$, 459 $(M+3)^+$, 479 $(M+Na)^+$, 481 $(M+Na+2)^+$; HPLC retention time: 4.60 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-017 (the Enantiomer of 1-018):

HPLC retention time: 10.0 min. (CHIRAL PAK AD (DAICEL CHEMICAL INDUSTRIES, LTD), 0.46 cm I.D.×25 cm, mobile phase: hexane/IPA=20:1, flow rate: 1.0 mL/min.)

1-018 (the Enantiomer of 1-017):

HPLC retention time: 11.4 min. (CHIRAL PAK AD (DAICEL CHEMICAL INDUSTRIES, LTD), 0.46 cm I.D.×25 cm, mobile phase: hexane/IPA=20:1, flow rate: 1.0 mL/min.)

1-019:

MS (ES, Pos.): 443 $(M+1)^+$, 466 (M+Na); HPLC retention time: 4.27 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-020 (the Enantiomer of 1-021):

HPLC retention time: 9.1 min. (CHIRAL PAK AD (DAICEL CHEMICAL INDUSTRIES, LTD), 0.46 cm I.D.×25 cm, mobile phase: hexane/IPA=20:1, flow rate: 1.0 mL/min.)

1-021 (the Enantiomer of 1-020):

HPLC retention time: 11.0 min. (CHIRAL PAK AD (DAICEL CHEMICAL INDUSTRIES, LTD), 0.46 cm I.D.×25 cm, mobile phase: hexane/IPA=20:1, flow rate: 1.0 mL/min.)

1-022:

MS (ES, Pos.): 439 $(M+1)^+$, 461 $(M+Na)^+$; HPLC retention time: 4.27 and 4.56 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-023:

MS (ES, Pos.): 425 $(M+1)^+$, 447 $(M+Na)^+$; HPLC retention time: 4.16 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-024:

MS (ES, Pos.): 497 $(M+1)^+$, 499 $(M+3)^+$, 519 $(M+Na)^+$, 521 $(M+Na+2)^+$; HPLC retention time: 3.72 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-025:

MS (ES, Pos.): 483 $(M+1)^+$, 485 $(M+3)^+$, 505 $(M+Na)^+$, 507 $(M+Na+2)^+$; HPLC retention time: 3.66 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-026:

MS (ES, Pos.): 421 $(M+1)^+$; HPLC retention time: 5.20 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-027:

MS (ES, Pos.): 409 $(M+1)^+$, 431 $(M+Na)^+$; HPLC retention time: 2.70 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-028:

MS (ES, Pos.): 419 $(M+1)^+$; HPLC retention time: 5.45 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-029:

MS (ES, Pos.): 415 $(M+1)^+$; HPLC retention time: 5.27 mini (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-030:

MS (ES, Pos.): 485 $(M+1)^+$, 487 $(M+3)^+$, 507 $(M+Na)^+$, 509 $(M+Na+2)^+$; HPLC retention time: 8.57 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-031:

MS (ES, Pos.): 471 $(M+1)^+$, 473 $(M+3)^+$, 493 $(M+Na)^+$, 495 $(M+Na+2)^+$; HPLC retention time: 7.71 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-036:

MS (ES, Pos.): 407 $(M+1)^+$, 429 $(M+Na)^+$; HPLC retention time: 4.32 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-037:

MS (ES, Pos.): 415 $(M+Na)^+$; HPLC retention time: 3.98 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-039:

MS (ES, Pos.): 471 $(M+1)^+$, 473 $(M+3)^+$, 493 $(M+Na)^+$, 495 $(M+Na+2)^+$; HPLC retention time: 4.91 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-040:

MS (ES, Pos.): 479 $(M+Na)^+$, 481 $(M+Na+2)^+$; HPLC retention time: 4.46 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-041:

MS (ES, Pos.): 435 $(M+1)^+$; HPLC retention time: 5.56 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-043:

MS (ES, Pos.): 429 $(M+1)^+$; HPLC retention time: 5.47 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-044:

MS (ES, Pos.): 499 $(M+1)^+$, 501 $(M+3)^+$; HPLC retention time: 6.66 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-045:

MS (ES, Pos.): 485 $(M+1)^+$, 487 $(M+3)^+$, 507 $(M+Na)^+$, 509 $(M+Na+2)^+$; HPLC retention time: 6.89 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-056:

MS (ES, Pos.): 415 $(M+1)^+$; HPLC retention time: 4.45 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-057:

MS (ES, Pos.): 485 $(M+1)^+$, 487 $(M+3)^+$; HPLC retention time: 7.54 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-063:

MS (ES, Pos.): 571 (M+Na), 573 $(M+Na+2)^+$, 575 $(M+Na+4)^+$; HPLC retention time: 5.20 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-092:

MS (ES, Pos.): 449 $(M+1)^+$; HPLC retention time: 6.24 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-094:

MS (ES, Pos.): 443 $(M+1)^+$; HPLC retention time: 6.22 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-103:

MS (ES, Pos.): 589 $(M+1)^+$, 591 $(M+3)^+$, 593 (M+5), 611 (M+Na), 613 $(M+Na+2)^+$, 615 $(M+Na+4)^+$; HPLC retention time: 5.01 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-104:

MS (ES, Pos.): 471 $(M+1)^+$, 473 $(M+3)^+$, 493 (M+Na), 495 $(M+Na+2)^+$; HPLC retention time: 6.69 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-105:

MS (ES, Pos.): 457 $(M+1)^+$, 459 $(M+3)^+$, 479 $(M+Na)^+$, 481 $(M+Na+2)^+$; HPLC retention time: 6.01 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-106:

MS (ES, Pos.): 499 $(M+1)^+$, 501 $(M+3)^+$, 521 $(M+Na)^+$, 523 (M+Na+HPLC retention time: 8.06 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-107:

MS (ES, Pos.): 485 $(M+1)^+$, 487 $(M+3)^+$, 507 $(M+Na)^+$, 509 $(M+Na+2)^+$; HPLC retention time: 10.24 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-110:

MS (ES, Pos.): 501 $(M+1)^+$, 503 $(M+3)^+$, 523 $(M+Na)^+$, 525 $(M+Na+2)^+$; HPLC retention time: 4.61 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-114:

MS (ES, Pos.): 613 $(M+Na)^+$, 615 $(M+Na+2)^+$, 617 $(M+Na+4)^+$; HPLC retention time: 2.57 min (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-115:

HPLC retention time: 10.6 mM. (CHIRAL PAK AD (DAICEL CHEMICAL INDUSTRIES, LTD), 0.46 cm I.D.×25 cm, mobile phase: hexane/IPA=20:1, flow rate: 1.0 mL/min.)

1-116:

MS (ES, Pos.): 451 (M+NO % 453 $(M+Na+2)^+$; HPLC retention time: 11.5 min. (CHIRAL PAK AD (DAICEL CHEMICAL INDUSTRIES, LTD), 0.46 cm I.D.×25 cm, mobile phase: hexane/IPA=20:1, flow rate: 1.0 mL/min.)

1-117:

HPLC retention time: 9.3 min. (CHIRAL PAK AD (DAICEL CHEMICAL INDUSTRIES, LTD), 0.46 cm I.D.×25 cm, mobile phase: hexane/IPA=20:1, flow rate: 1.0 mL/min.)

1-118:

MS (ES, Pos.): 429 $(M+1)^+$, 431 $(M+3)^+$; HPLC retention time: 12.1 min. (CHIRAL PAK AD (DAICEL CHEMICAL INDUSTRIES, LTD), 0.46 cm I.D.×25 cm, mobile phase: hexane/IPA=20:1, flow rate: 1.0 mL/min.)

1-125:

MS (ES, Pos.): 388 $(M+1)^+$, 410 $(M+Na)^+$; HPLC retention time: 4.20 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-126:

MS (ES, Pos.): 396 (M+Na); HPLC retention time: 4.40 min. (Capcell Pak UG120, 4.6 mm×150 mm, Shiseido); Flow rate: 1.0 ml/min; Mobile phase: acetonitrile 10.05M ammonium acetate aqueous solution (80:20), pH of the solvent was adjusted to 7.4 with aqueous ammonia or acetic acid.

1-127 (a Diastereoisomer of 1-128):

Rf value 0.55 (developing solvent: hexane/EtOAc=1:1, TLC plate Silica gel 60 $F_{254}$ (Merck)); $^1H$ NMR (300 MHz, $CDCl_3$) δ 1.64-1.82 (1H, m), 1.83-2.03 (2H, m), 2.05-2.18 (1H, m), 2.34 (3H, s), 2.46 (3H, m), 2.53 (3H, s), 2.99-3.12 (1H, m), 3.31-3.70 (3H, m), 3.90-4.02 (1H, m), 6.63 (1H, s), 7.30 (1H, d, J=2.0 Hz), 7.62 (1H, d, J=2.0 Hz); MS (ES, Pos.): 556 (M+Na), 558 (M+Na+2), 560 $(M+Na+4)^4$.

1-128 (a Diastereoisomer of 1-127):

Rf value 0.48 (developing solvent: hexane/EtOAc=1:1, TLC plate Silica gel 60 $F_{254}$ (Merck)); $^1H$ NMR (300 MHz, $CDCl_3$) δ 1.62-1.81 (1H, m), 1.89-2.03 (2H, m), 2.05-2.19 (1H, m), 2.35 (3H, s), 2.46 (3H, d, J=1.2 Hz), 2.53 (3H, s), 3.01-3.13 (1H, m), 3.34-3.70 (3H, m), 3.91-4.02 (1H, m), 6.63 (1H, s), 7.30 (1H, d, J=2.0 Hz), 7.62 (1H, d, J=2.0 Hz); MS (ES, Pos.): 534 $(M+1)^+$, 536 $(M+3)^+$, 538 $(M+5)^+$, 556 $(M+Na)^+$, 558 (M+Na+2), 560 $(M+Na+4)^+$ 1-129:

MS (ES, Pos.): 570 $(M+1)^+$, 572 $(M+3)^+$, 574 $(M+5)^+$; HPLC retention time: 4.46 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-130:

MS (ES, Pos.): 452 $(M+1)^+$, 454 $(M+3)^+$, 474 $(M+Na)^+$, 476 $(M+Na+2)^+$; HPLC retention time: 5.36 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-131:

MS (ES, Pos.): 460 $(M+Na)^+$, 462 $(M+Na+2)^+$; HPLC retention time: 4.87 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-132:

MS (ES, Pos.): 456 $(M+Na)^+$; HPLC retention time: 5.12 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-133:

MS (ES, Pos.): 442 $(M+Na)^+$; HPLC retention time: 4.64 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-138:

MS (ES, Pos.): 500 $(M+Na)^+$, 502 $(M+Na+2)^+$; HPLC retention time: 4.05 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-140:

MS (ES, Pos.): 410 $(M+1)^+$; HPLC retention time: 5.85 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-141:

MS (ES, Pos.): 480 $(M+1)^+$, 482 $(M+3)^+$, 502 $(M+Na)^+$, 504 $(M+Na+2)^+$; HPLC retention time: 7.51 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-142:

MS (ES, Pos.): 466 $(M+1)^+$, 468 $(M+3)^+$, 488 $(M+Na)^+$, 490 $(M+Na+2)^+$; HPLC retention time: 9.01 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-143:

MS (ES, Pos.): 584 $(M+1)^+$, 586 $(M+3)^+$, 588 $(M+5)^+$, 606 $(M+Na)^+$, 608 $(M+Na+2)^+$, 610 $(M+Na+4)^+$; HPLC retention time: 4.48 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-144:

MS (ES, Pos.): 466 $(M+1)^+$, 468 $(M+3)^+$, 488 $(M+Na)^+$, 490 $(M+Na+2)^+$; HPLC retention time: 5.92 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-146:

MS (ES, Pos.): 516 $(M+Na)^+$, 518 $(M+Na+2)^+$; HPLC retention time: 8.63 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-147:

MS (ES, Pos.): 480 $(M+1)^+$, 482 $(M+3)^+$, 502 $(M+Na)^+$, 504 $(M+Na+2)^+$; HPLC retention time: 3.44 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-149:

MS (ES, Pos.): 466 $(M+1)^+$, 468 $(M+3)^+$, 488 $(M+Na)^+$, 490 $(M+Na+2)^+$ 1-168:

MS (ES, Pos.): 444 $(M+1)^+$, 466 $(M+Na)^+$; HPLC retention time: 4.11 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-171:

MS (ES, Pos.): 596 $(M+1)^+$, 598 $(M+3)^+$, 600 $(M+5)^+$, 618 $(M+Na)^+$, 620 $(M+Na+2)^+$, 622 $(M+Na+4)^{4"}$; HPLC retention time: 5.87 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-174:

MS (ES, Pos.): 506 $(M+1)^+$, 508 $(M+3)^+$, 528 $(M+Na)^+$, 530 $(M+Na+2)^+$; HPLC retention time: 5.83 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-179:

MS (ES, Pos.): 474 $(M+Na)^+$, 476 $(M+Na+2)^+$; HPLC retention time: 5.74 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-194:

MS (ES, Pos.): 421 $(M+1)^+$; HPLC retention time: 5.08 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-209:

MS (ES, Pos.): 496 $(M+1)^+$ 1-210:

MS (ES, Pos.): 482 $(M+1)^+$ 1-222:

MS (ES, Pos.): 421 $(M+1)^+$; HPLC retention time: 7.13 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-238:

MS (ES, Pos.): 575 $(M+1)^+$, 577 $(M+3)^+$, 579 $(M+5)^+$ HPLC retention time: 8.6 min. (CHIRAL PAK AD (DAICEL CHEMICAL INDUSTRIES, LTD), 0.46 cm I.D.×25 cm, mobile phase: hexane/IPA=20:1, flow rate: 1.0 mL/min.)

1-239:

MS (ES, Pos.): 575 $(M+1)^+$, 577 $(M+3)^+$, 579 $(M+5)^+$ HPLC retention time: 9.6 min. (CHIRAL PAK AD (DAICEL CHEMICAL INDUSTRIES, LTD), 0.46 cm I.D.×25 cm, mobile phase: hexane/IPA=20:1, flow rate: 1.0 mL/min.)

1-240:

MS (ES, Pos.): 570 $(M+1)^+$, 572 $(M+3)^+$, 574 $(M+5)^+$ HPLC retention time: 13.0 min. (CHIRAL PAK AD (DAICEL CHEMICAL INDUSTRIES, LTD), 0.46 cm I.D.×25 cm, mobile phase: hexane/IPA=100:1, flow rate: 1.0 mL/min.)

1-241:

MS (ES, Pos.): 570 $(M+1)^+$, 572 $(M+3)^+$, 574 $(M+5)^+$ HPLC retention time: 11.9 min. (CHIRAL PAK AD (DAICEL CHEMICAL INDUSTRIES, LTD), 0.46 cm I.D.×25 cm, mobile phase: hexane/IPA=100:1, flow rate: 1.0 mL/min.)

1-267:

MS (ES, Pos.): 438 $(M 1)^+$, 440 $(M+3)^+$, 460 $(M+Na)^+$, 462 $(M+Na+2)^+$; HPLC retention time: 4.43 min. (Capcell Pak UG120, 4.6 mm×150 mm, Shiseido); Flow rate: 1.0 ml/min; Mobile phase: acetonitrile/0.05M ammonium acetate aqueous solution (80:20), pH of the solvent was adjusted to 7.4 with aqueous ammonia or acetic acid.

1-276 (the enantiomer of 1-278):

$[\alpha]_D^{29}$=+7.41 (c 1.00, $CH_3OH$)

1-277 (the enantiomer of 1-279):

HPLC retention time: 6.0 min. (CHIRAL PAK AD (DAICEL CHEMICAL INDUSTRIES, LTD), 0.46 cm I.D.×25 cm, mobile phase: hexane/IPA=8:1, flow rate: 1.0 mL/min.)

1-278 (the enantiomer of 1-276):

$[\alpha]_D^{29}$=−5.90 (c 1.01, $CH_3OH$)

1-279 (the enantiomer of 1-277):

HPLC retention time: 5.5 min. (CHIRAL PAK AD (DAICEL CHEMICAL INDUSTRIES, LTD), 0.46 cm I.D.×25 cm, mobile phase: hexane/IPA=8:1, flow rate: 1.0 mL/min.)

1-280:

$[\alpha]_D^{29}$=−9.30 (c 0.41, $CH_3OH$)

1-281:

$[\alpha]_D^{28}$=−11.2 (c 0.41, $CH_3OH$)

1-282:

$[\alpha]_D^{28}$=−18.0 (c 0.41, $CH_3OH$)

1-283:

$[\alpha]_D^{22}$=−6.6 (c 0.40, $CH_3OH$)

1-284:

$[\alpha]_D^{28}$=−5.5 (c 0.40, $CH_3OH$)

1-302 (the enantiomer of 1-304):

HPLC retention time: 8.4 min. (CHIRAL PAK AD (DAICEL CHEMICAL INDUSTRIES, LTD), 0.46 cm I.D.×25 cm, mobile phase: hexane/IPA=8:1, flow rate: 1.0 mL/min.)

1-303 (the Enantiomer of 1-305):

HPLC retention time: 9.2 min. (CHIRAL PAK AD (DAICEL CHEMICAL INDUSTRIES, LTD), 0.46 cm I.D.×25 cm, mobile phase: hexane/IPA=8:1, flow rate: 1.0 mL/min.)

1-304 (the Enantiomer of 1-302):

HPLC retention time: 8.9 min. (CHIRAL PAK AD (DAICEL CHEMICAL INDUSTRIES, LTD), 0.46 cm I.D.×25 cm, mobile phase: hexane/IPA=8:1, flow rate: 1.0 mL/min.)

1-305 (the Enantiomer of 1-303):

HPLC retention time: 10.6 min. (CHIRAL PAK AD (DAICEL CHEMICAL INDUSTRIES, LTD), 0.46 cm I.D.×25 cm, mobile phase: hexane/IPA=8:1, flow rate: 1.0 mL/min.)

1-306 (the Enantiomer of 1-308):

$[\alpha]_D^{28}$=+5.38 (c 0.81, $CH_3OH$)

1-307 (the Enantiomer of 1-309):

HPLC retention time: 16.6 min. (CHIRAL PAK AD (DAICEL CHEMICAL INDUSTRIES, LTD), (0.46 cm I.D.×25 cm)×2, mobile phase: hexane/IPA=8:1, flow rate: 1.0 mL/min.)

1-308 (the Enantiomer of 1-306):

$[\alpha]_D^{29}$=−7.69 (c 0.80, $CH_3OH$)

1-309 (the enantiomer of 1-307):

HPLC retention time: 17.4 min. (CHIRAL PAK AD (DAICEL CHEMICAL INDUSTRIES, LTD), (0.46 cm I.D.×25 cm)×2, mobile phase: hexane/IPA=8:1, flow rate: 1.0 mL/min.)

1-316:

MS (ES, Pos.): 451 $(M+1)^+$; HPLC retention time: 6.26 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

1-325:

MS (ES, Pos.): 449 $(M+1)^+$; HPLC retention time: 5.78 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

1-338:

MS (ES, Pos.): 360 $(M+1)^+$; HPLC retention time: 6.19 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

1-339:

MS (ES, Pos.): 424 $(M+1)^+$, 426 $(M+3)^+$; HPLC retention time: 5.93 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

*2: HCl salt

*3: a mixture of diastereomers

*4: optically active compound

*5: Crystallized on standing from the compound purified (silica gel column chromatography) and dried.

TABLE 2*1

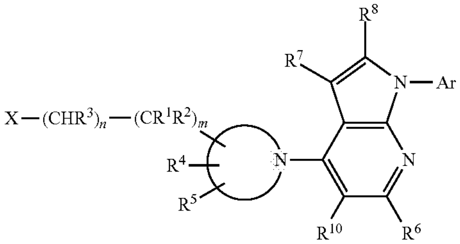

| Com. No. | Ex. No. | 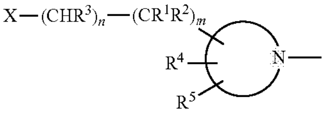 | $R^{10}$ | $R^6$ | $R^7$ | $R^8$ | —Ar | melting point (° C.) (solvent for crystallization) |
|---|---|---|---|---|---|---|---|---|
| 2-001 | 1 | 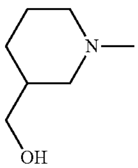 | H | $CH_3$ | $CH_3$ | $CH_3$ | 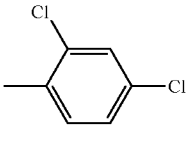 | amorphous |
| 2-002 | 1 | 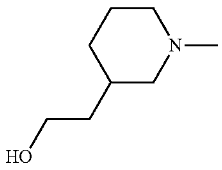 | H | $CH_3$ | $CH_3$ | $CH_3$ | 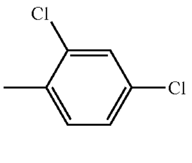 | amorphous |

TABLE 2*1-continued
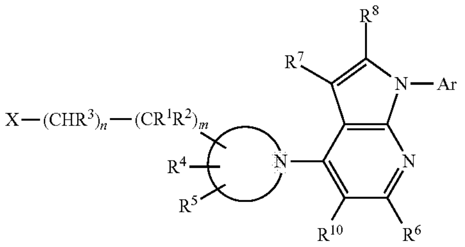
| Com. No. | Ex. No. | 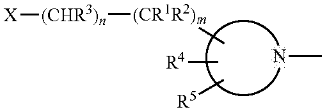 | $R^{10}$ | $R^6$ | $R^7$ | $R^8$ | —Ar | melting point (° C.) (solvent for crystallization) |
|---|---|---|---|---|---|---|---|---|
| 2-003 | 1 | 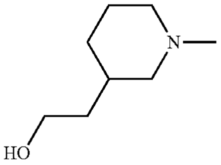 | H | $CH_3$ | $CH_3$ | H | 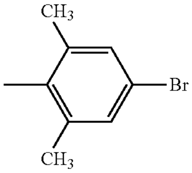 | 119-121*2 (IPE) |
| 2-004 | 1 | 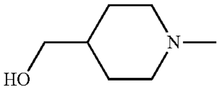 | H | $CH_3$ | $CH_3$ | $CH_3$ | 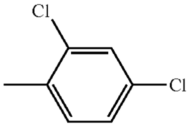 | 200-202*2 (EtOAc) |
| 2-005 | 1 | 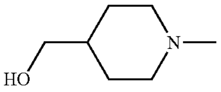 | H | $CH_3$ | $CH_3$ | H | 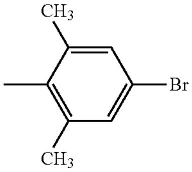 | 202-206*2 (ACE) |
| 2-006 | 1 | 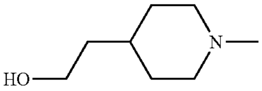 | H | $CH_3$ | $CH_3$ | $CH_3$ | 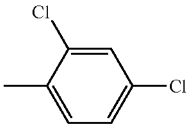 | 228-230*2 (EtOAc) |
| 2-007 | 1 | 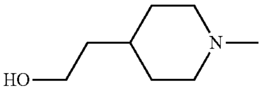 | H | $CH_3$ | $CH_3$ | H | 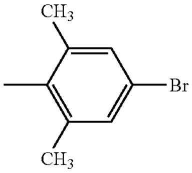 | 218-220*2 (ACE) |
| 2-008 | 1 | 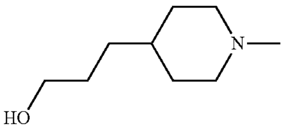 | H | $CH_3$ | $CH_3$ | $CH_3$ | 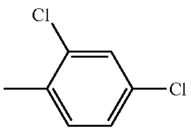 | 179-181*2 (EtOAc/EtOH) |
| 2-009 | 1 | 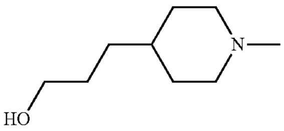 | H | $CH_3$ | $CH_3$ | H | 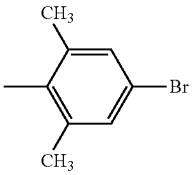 | 204-206*2 (ACE) |

TABLE 2$^{*1}$-continued
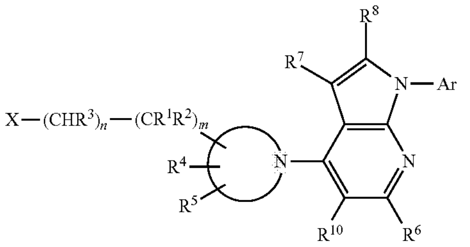
| Com. No. | Ex. No. | 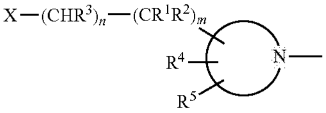 | $R^{10}$ | $R^6$ | $R^7$ | $R^8$ | —Ar | melting point (° C.) (solvent for crystallization) |
|---|---|---|---|---|---|---|---|---|
| 2-010 | 1 | 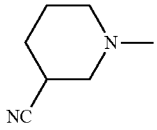 | H | $CH_3$ | $CH_3$ | $CH_3$ | 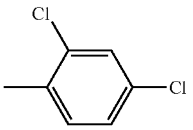 | 146-148$^{*2}$ (EtOAc/EtOH) |
| 2-011 | 1 | 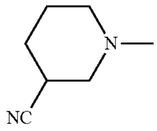 | H | $CH_3$ | $CH_3$ | H | 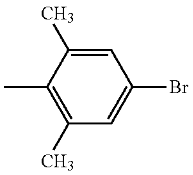 | 108-110$^{*2}$ (IPE) |
| 2-012 | 1 | 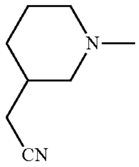 | H | $CH_3$ | $CH_3$ | $CH_3$ | 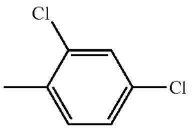 | amorphous |
| 2-013 | 1 | 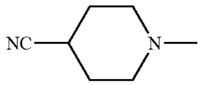 | H | $CH_3$ | $CH_3$ | $CH_3$ | 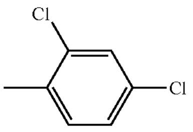 | 163-165$^{*2}$ (EtOAc/EtOH) |
| 2-014 | 1 | 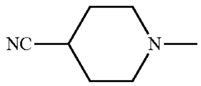 | H | $CH_3$ | $CH_3$ | H | 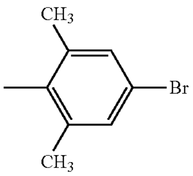 | 179-181$^{*2}$ (ACE) |
| 2-015 | 1 | 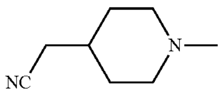 | H | $CH_3$ | $CH_3$ | $CH_3$ | 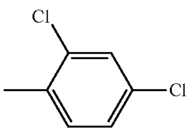 | 149-151$^{*2}$ (EtOAc) |
| 2-016 | 1 | 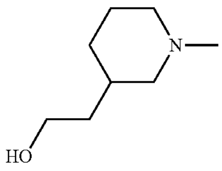 | H | $CH_3$ | $CH_3$ | $CH_3$ | 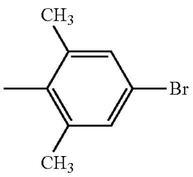 | 125-127$^{*2}$ (MeOH/IPE) |

TABLE 2*1-continued
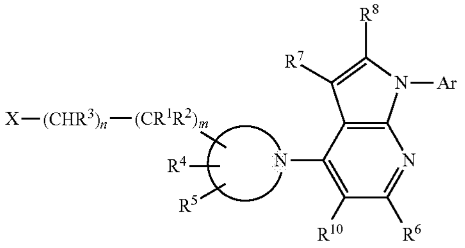
| Com. No. | Ex. No. | 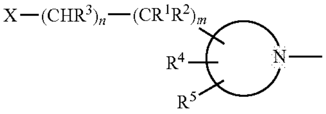 | $R^{10}$ | $R^6$ | $R^7$ | $R^8$ | —Ar | melting point (° C.) (solvent for crystallization) |
|---|---|---|---|---|---|---|---|---|
| 2-017 | 1 | 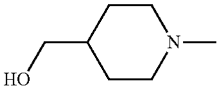 | H | $CH_3$ | $CH_3$ | $CH_3$ | 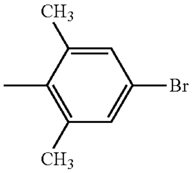 | 172-174*2 (ACE/IPE) |
| 2-018 | 1 | 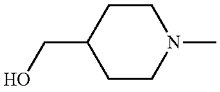 | H | $CH_3$ | $CH_3$ | $CH_3$ | 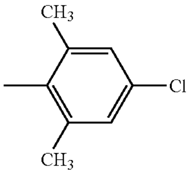 | 133-135*2 (MeOH) |
| 2-019 | 1 | 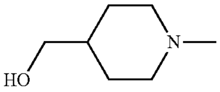 | H | $CH_3$ | $CH_3$ | H | 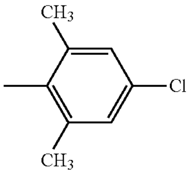 | 207-209*2 (ACE) |
| 2-020 | 1 | 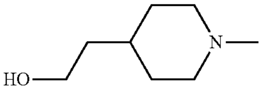 | H | $CH_3$ | $CH_3$ | $CH_3$ | 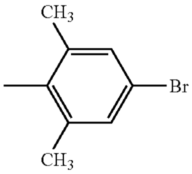 | 130-132*2 (MeOH/IPE) |
| 2-021 | 1 | 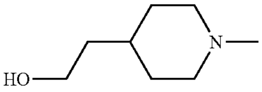 | H | $CH_3$ | $CH_3$ | $CH_3$ | 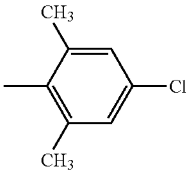 | 124-126*2 (MeOH) |
| 2-022 | 1 | 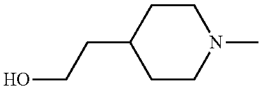 | H | $CH_3$ | $CH_3$ | H | 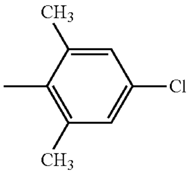 | 110-112*2 (IPE) |

TABLE 2*1-continued
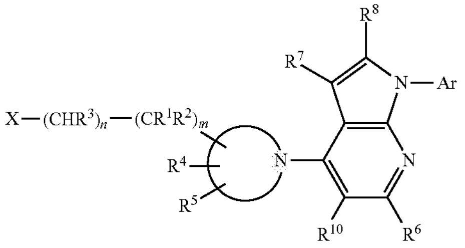
| Com. No. | Ex. No. | 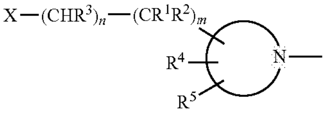 | $R^{10}$ | $R^6$ | $R^7$ | $R^8$ | —Ar | melting point (° C.) (solvent for crystallization) |
|---|---|---|---|---|---|---|---|---|
| 2-023 | 1 | 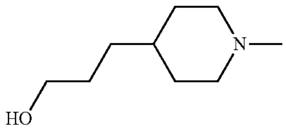 | H | $CH_3$ | $CH_3$ | $CH_3$ | 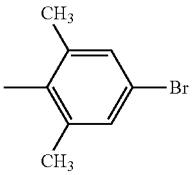 | 132-134*2 (MeOH/IPE) |
| 2-024 | 1 | 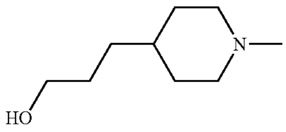 | H | $CH_3$ | $CH_3$ | $CH_3$ | 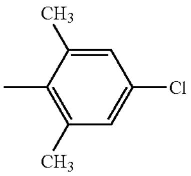 | 130-132*2 (MeOH) |
| 2-025 | 1 | 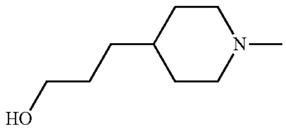 | H | $CH_3$ | $CH_3$ | H | 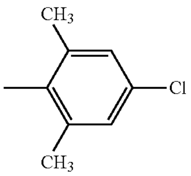 | 200-202*2 (IPA) |
| 2-026 | 1 | 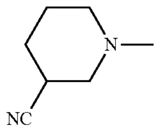 | H | $CH_3$ | $CH_3$ | $CH_3$ | 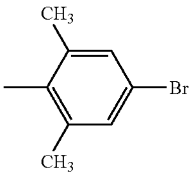 | 122-124*2 (MeOH) |
| 2-027 | 1 | 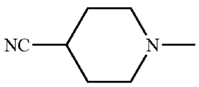 | H | $CH_3$ | $CH_3$ | $CH_3$ | 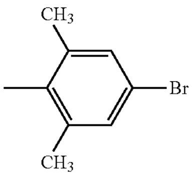 | 198-200*2 (MeOH/IPE) |
| 2-028 | 1 | 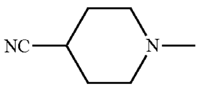 | H | $CH_3$ | $CH_3$ | $CH_3$ | 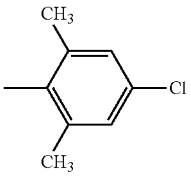 | 124-126*2 (MeOH) |

TABLE 2*1-continued
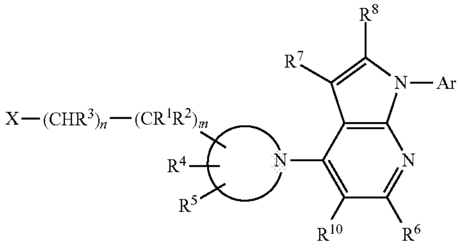
| Com. No. | Ex. No. | 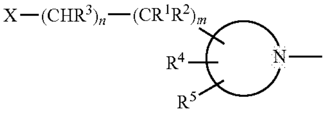 | $R^{10}$ | $R^6$ | $R^7$ | $R^8$ | —Ar | melting point (° C.) (solvent for crystallization) |
|---|---|---|---|---|---|---|---|---|
| 2-029 | 1 | 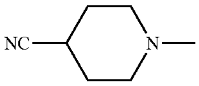 | H | $CH_3$ | $CH_3$ | H | 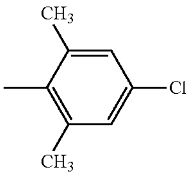 | 184-186*2 (Et2O) |
| 2-030 | 1 | 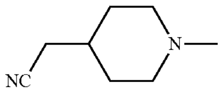 | H | $CH_3$ | $CH_3$ | $CH_3$ | 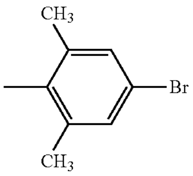 | 138-140*2 (MeOH) |
| 2-031 | 1 | 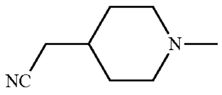 | H | $CH_3$ | $CH_3$ | H | 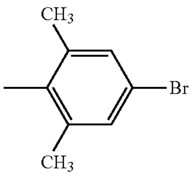 | 157-159*2 (ACE) |
| 2-032 | 1 | 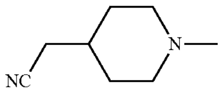 | H | $CH_3$ | $CH_3$ | H | 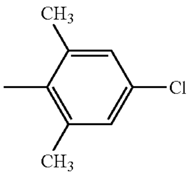 | 154-156*2 (Et2O) |
| 2-033 | 1 | 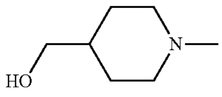 | H | $CH_3$ | $CH_3$ | $CH_3$ | 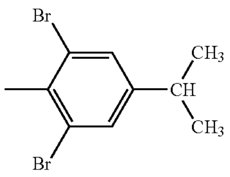 | 167-169*2 (MeOH) |
| 2-034 | 1 | 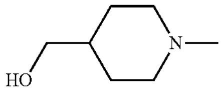 | H | $CH_3$ | $CH_3$ | H | 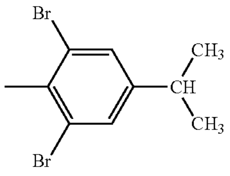 | amorphous*2 |

TABLE 2*[1]-continued
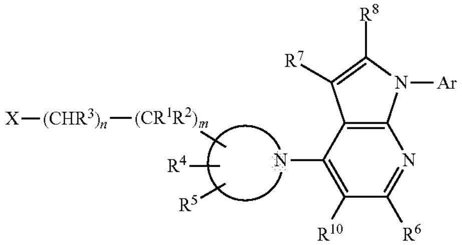
| Com. No. | Ex. No. | 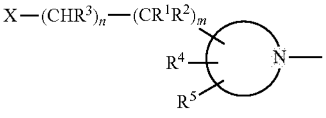 | $R^{10}$ | $R^6$ | $R^7$ | $R^8$ | —Ar | melting point (° C.) (solvent for crystallization) |
|---|---|---|---|---|---|---|---|---|
| 2-035 | 1 | 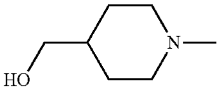 | H | $CH_3$ | $CH_3$ | $CH_3$ | 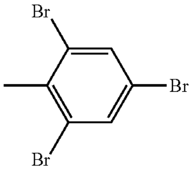 | 223-225*[2] (ACE) |
| 2-036 | 1 | 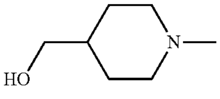 | H | $CH_3$ | $CH_3$ | H | 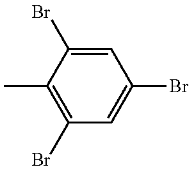 | 236-238*[2] (CH3CN) |
| 2-037 | 1 | 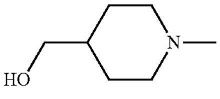 | H | $CH_3$ | $CH_3$ | $CH_3$ | 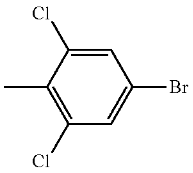 | 228-230*[2] (ACE) |
| 2-038 | 1 | 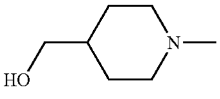 | H | $CH_3$ | $CH_3$ | H | 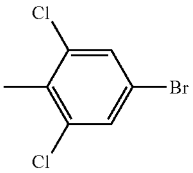 | 230-232*[2] (CH3CN) |
| 2-039 | 1 | 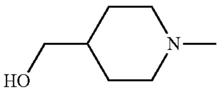 | H | $CH_3$ | $CH_3$ | $CH_3$ | 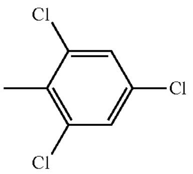 | 218-220*[2] (ACE) |
| 2-040 | 1 | 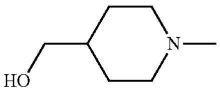 | H | $CH_3$ | $CH_3$ | H | 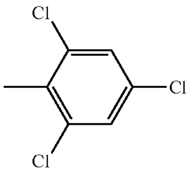 | 232-234*[2] (ACE) |
| 2-041 | 1 | 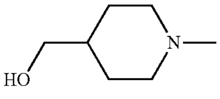 | H | $CH_3$ | $CH_3$ | $CH_3$ | 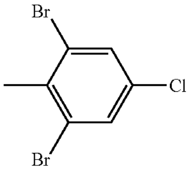 | amorphous*[2] |

TABLE 2*1-continued
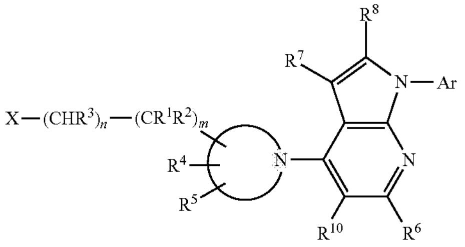
| Com. No. | Ex. No. | 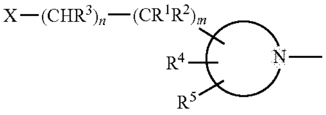 | $R^{10}$ | $R^6$ | $R^7$ | $R^8$ | —Ar | melting point (° C.) (solvent for crystallization) |
|---|---|---|---|---|---|---|---|---|
| 2-042 | 1 | 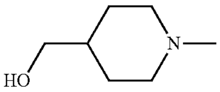 | H | $CH_3$ | $CH_3$ | H | 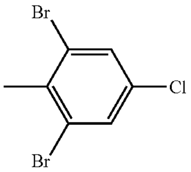 | 241-243*2 (CH3CN) |
| 2-043 | 1 | 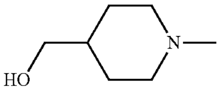 | H | $CH_3$ | $CH_3$ | $CH_3$ | 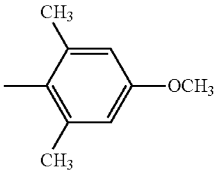 | 218-220*2 (ACE) |
| 2-044 | 1 | 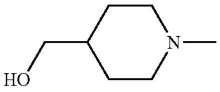 | H | $CH_3$ | $CH_3$ | H | 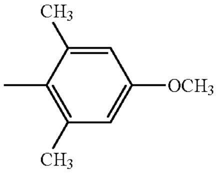 | 182-184*2 (CH3CN) |
| 2-045 | 1 | 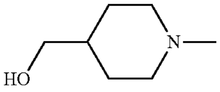 | H | $CH_3$ | $CH_3$ | H | 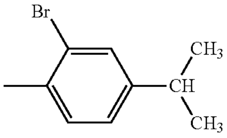 | amorphous*2 |
| 2-046 | 1 | 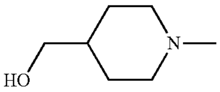 | H | $CH_3$ | $CH_3$ | H | 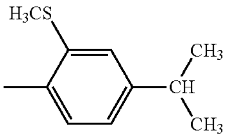 | amorphous*2 |
| 2-047 | 1 | 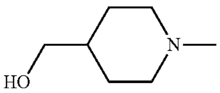 | H | $CH_3$ | $CH_3$ | H | 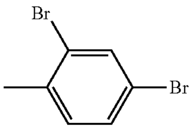 | 198-200*2 (CH3CN) |
| 2-048 | 1 | 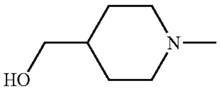 | H | $CH_3$ | $CH_3$ | H | 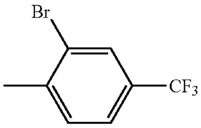 | amorphous*2 |

TABLE 2*1-continued
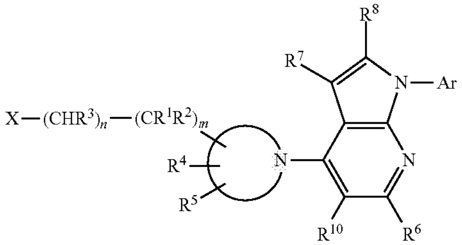
| Com. No. | Ex. No. | 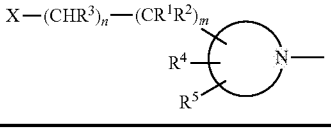 | $R^{10}$ | $R^6$ | $R^7$ | $R^8$ | —Ar | melting point (° C.) (solvent for crystallization) |
|---|---|---|---|---|---|---|---|---|
| 2-049 | 1 | 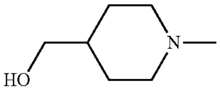 | H | $CH_3$ | $CH_3$ | $CH_3$ | 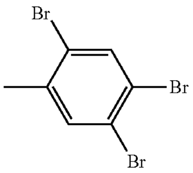 | amorphous*2 |
| 2-050 | 1 | 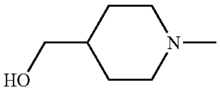 | H | $CH_3$ | $CH_3$ | H | 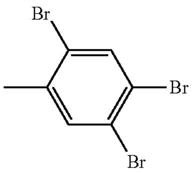 | amorphous*2 |
| 2-051 | 1 | 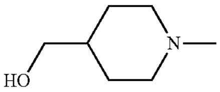 | $CO_2Et$ | $CH_3$ | $CH_3$ | $CH_3$ | 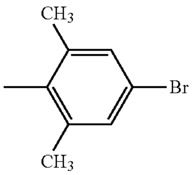 | 169-171 (IPE) |
| 2-052 | 1 | 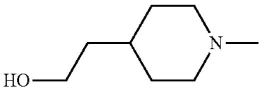 | H | $CH_3$ | $CH_3$ | $CH_3$ | 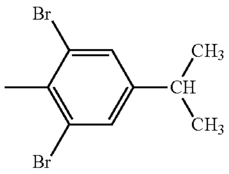 | amorphous*2 |
| 2-053 | 1 | 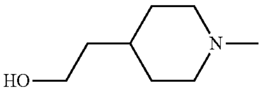 | H | $CH_3$ | $CH_3$ | H | 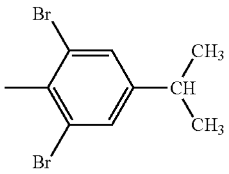 | amorphous*2 |
| 2-054 | 1 | 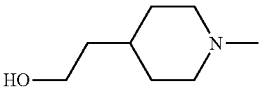 | H | $CH_3$ | $CH_3$ | $CH_3$ | 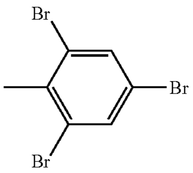 | amorphous*2 |
| 2-055 | 1 | 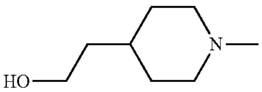 | H | $CH_3$ | $CH_3$ | H | 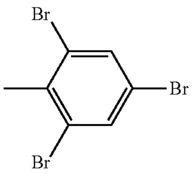 | 215-217*2 (CH3CN) |

TABLE 2*1-continued
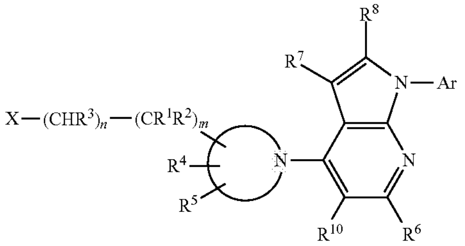
| Com. No. | Ex. No. | 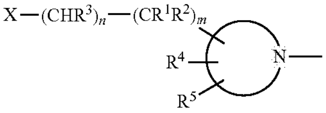 | $R^{10}$ | $R^6$ | $R^7$ | $R^8$ | —Ar | melting point (° C.) (solvent for crystallization) |
|---|---|---|---|---|---|---|---|---|
| 2-056 | 1 | 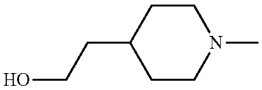 | H | $CH_3$ | $CH_3$ | $CH_3$ | 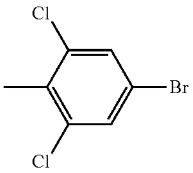 | amorphous*2 |
| 2-057 | 1 | 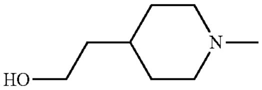 | H | $CH_3$ | $CH_3$ | H | 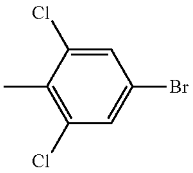 | amorphous*2 |
| 2-058 | 1 | 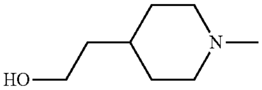 | H | $CH_3$ | $CH_3$ | $CH_3$ | 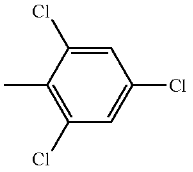 | amorphous*2 |
| 2-059 | 1 | 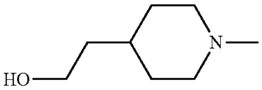 | H | $CH_3$ | $CH_3$ | H | 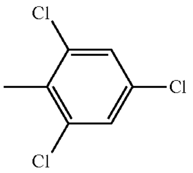 | amorphous*2 |
| 2-060 | 1 | 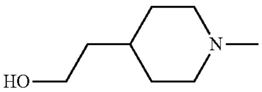 | H | $CH_3$ | $CH_3$ | $CH_3$ | 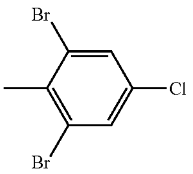 | amorphous*2 |
| 2-061 | 1 | 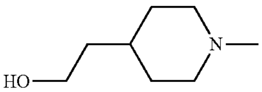 | H | $CH_3$ | $CH_3$ | H | 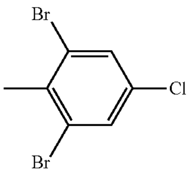 | 210-212*2 (CH3CN) |

TABLE 2*1-continued
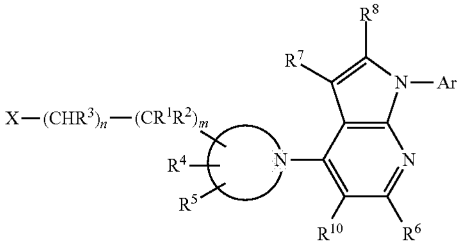
| Com. No. | Ex. No. | 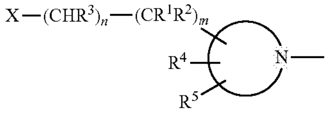 | $R^{10}$ | $R^6$ | $R^7$ | $R^8$ | —Ar | melting point (° C.) (solvent for crystallization) |
|---|---|---|---|---|---|---|---|---|
| 2-062 | 1 | 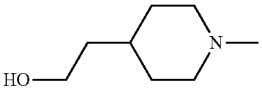 | H | $CH_3$ | $CH_3$ | $CH_3$ | 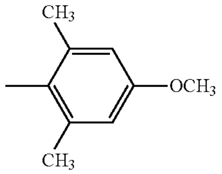 | amorphous*2 |
| 2-063 | 1 | 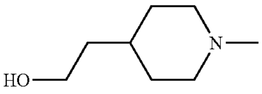 | H | $CH_3$ | $CH_3$ | H | 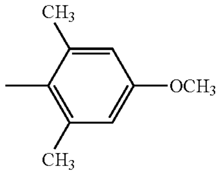 | amorphous*2 |
| 2-064 | 1 | 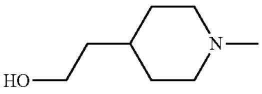 | H | $CH_3$ | $CH_3$ | H | 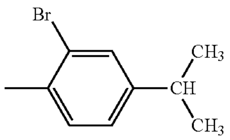 | amorphous*2 |
| 2-065 | 1 | 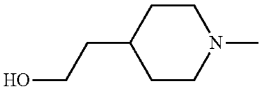 | H | $CH_3$ | $CH_3$ | H | 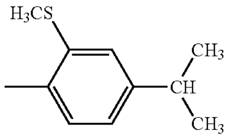 | amorphous*2 |
| 2-066 | 1 | 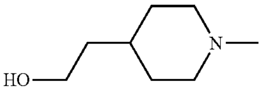 | H | $CH_3$ | $CH_3$ | H | 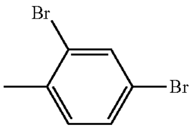 | amorphous*2 |
| 2-067 | 1 | 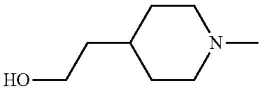 | H | $CH_3$ | $CH_3$ | H | 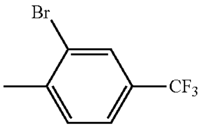 | 113-115*2 (IPE) |
| 2-068 | 1 | 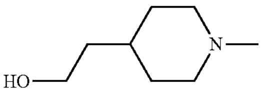 | H | $CH_3$ | $CH_3$ | $CH_3$ | 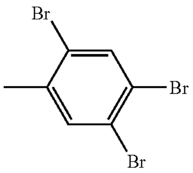 | amorphous*2 |

TABLE 2*1-continued
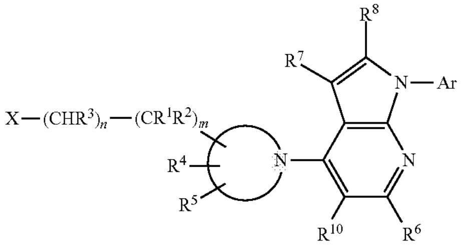
| Com. No. | Ex. No. | 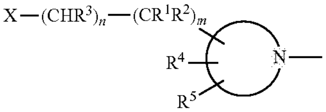 | $R^{10}$ | $R^6$ | $R^7$ | $R^8$ | —Ar | melting point (° C.) (solvent for crystallization) |
|---|---|---|---|---|---|---|---|---|
| 2-069 | 1 | 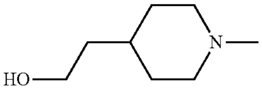 | H | $CH_3$ | $CH_3$ | H | 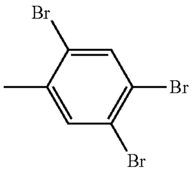 | amorphous*2 |
| 2-070 | 1 | 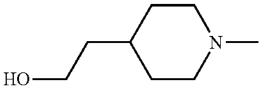 | Br | $CH_3$ | $CH_3$ | H | 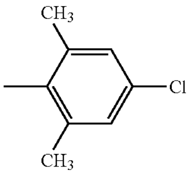 | 216-218*2 (EtOAc/EtOH) |
| 2-071 | 1 | 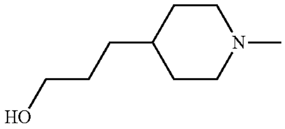 | H | $CH_3$ | $CH_3$ | $CH_3$ | 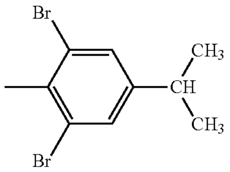 | 127-129*2 (MeOH) |
| 2-072 | 1 | 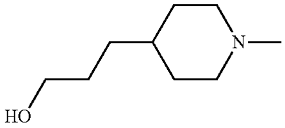 | H | $CH_3$ | $CH_3$ | H | 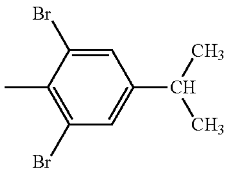 | amorphous*2 |
| 2-073 | 1 | 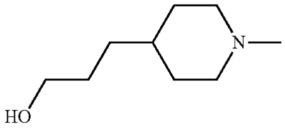 | H | $CH_3$ | $CH_3$ | $CH_3$ | 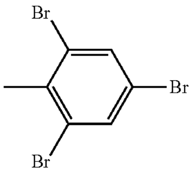 | amorphous*2 |
| 2-074 | 1 | 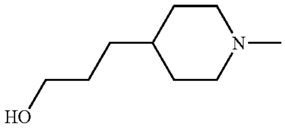 | H | $CH_3$ | $CH_3$ | H | 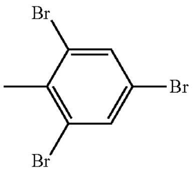 | 215-217*2 (CH3CN) |
| 2-075 | 1 | 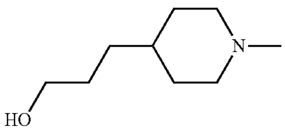 | H | $CH_3$ | $CH_3$ | $CH_3$ | 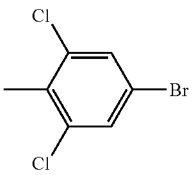 | 202-204*2 (ACE) |

TABLE 2*1-continued
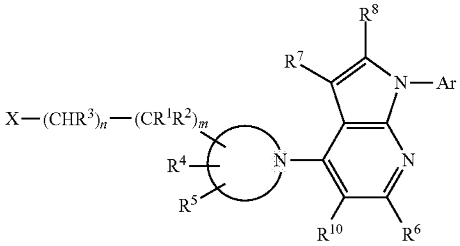
| Com. No. | Ex. No. | 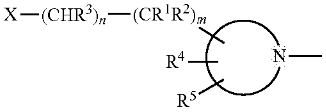 | $R^{10}$ | $R^6$ | $R^7$ | $R^8$ | —Ar | melting point (° C.) (solvent for crystallization) |
|---|---|---|---|---|---|---|---|---|
| 2-076 | 1 | 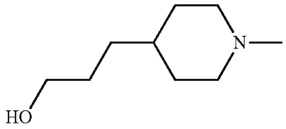 | H | $CH_3$ | $CH_3$ | H | 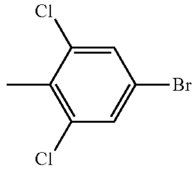 | 197-199*2 (CH3CN) |
| 2-077 | 1 | 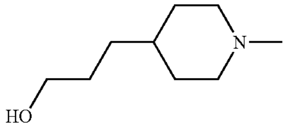 | H | $CH_3$ | $CH_3$ | $CH_3$ | 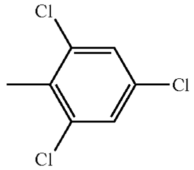 | amorphous*2 |
| 2-078 | 1 | 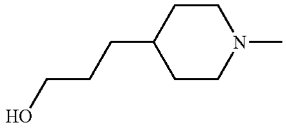 | H | $CH_3$ | $CH_3$ | H | 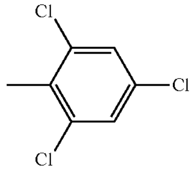 | amorphous*2 |
| 2-079 | 1 | 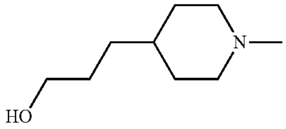 | H | $CH_3$ | $CH_3$ | $CH_3$ | 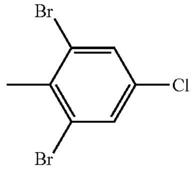 | amorphous*2 |
| 2-080 | 1 | 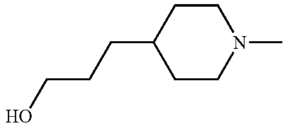 | H | $CH_3$ | $CH_3$ | H | 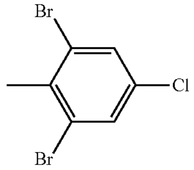 | 212-214*2 (CH3CN) |
| 2-081 | 1 | 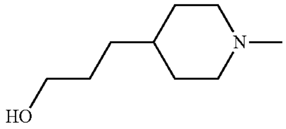 | H | $CH_3$ | $CH_3$ | $CH_3$ | 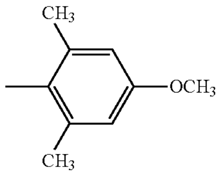 | amorphous*2 |

TABLE 2*1-continued
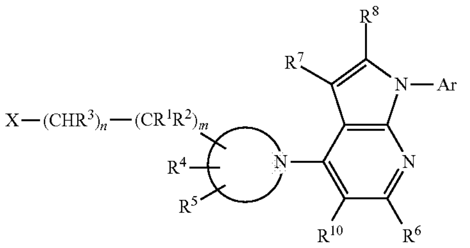
| Com. No. | Ex. No. | 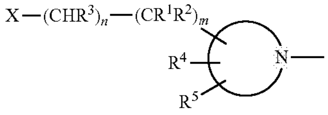 | $R^{10}$ | $R^6$ | $R^7$ | $R^8$ | —Ar | melting point (° C.) (solvent for crystallization) |
|---|---|---|---|---|---|---|---|---|
| 2-082 | 1 | 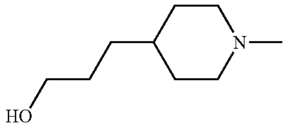 | H | $CH_3$ | $CH_3$ | H | 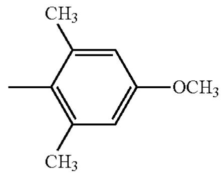 | 178-180*2 (CH3CN) |
| 2-083 | 1 | 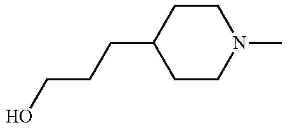 | H | $CH_3$ | $CH_3$ | H | 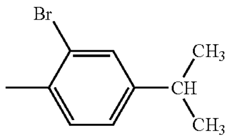 | amorphous*2 |
| 2-084 | 1 | 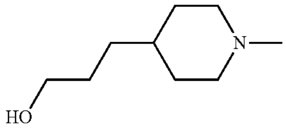 | H | $CH_3$ | $CH_3$ | H | 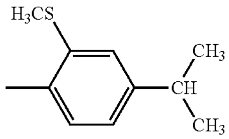 | amorphous*2 |
| 2-085 | 1 | 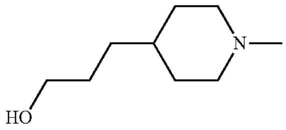 | H | $CH_3$ | $CH_3$ | H | 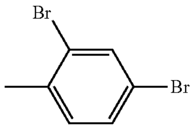 | 201-203*2 (CH3CN) |
| 2-086 | 1 | 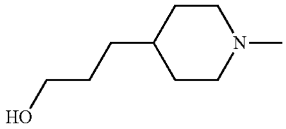 | H | $CH_3$ | $CH_3$ | H | 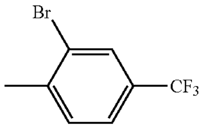 | 192-194*2 (IPE) |
| 2-087 | 1 | 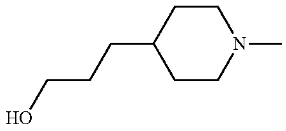 | H | $CH_3$ | $CH_3$ | $CH_3$ | 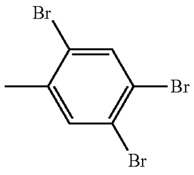 | amorphous*2 |
| 2-088 | 1 | 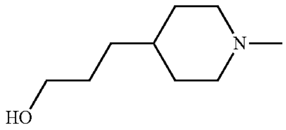 | H | $CH_3$ | $CH_3$ | H | 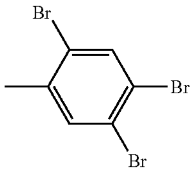 | amorphous*2 |

TABLE 2*1-continued
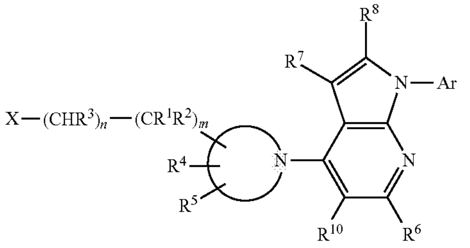
| Com. No. | Ex. No. | 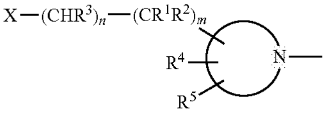 | $R^{10}$ | $R^6$ | $R^7$ | $R^8$ | —Ar | melting point (° C.) (solvent for crystallization) |
|---|---|---|---|---|---|---|---|---|
| 2-089 | 1 | 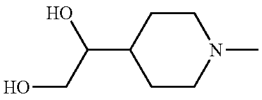 | H | $CH_3$ | $CH_3$ | $CH_3$ | 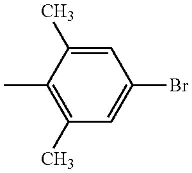 | 153-155*2 (Et2O) |
| 2-090 | 1 | 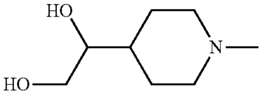 | H | $CH_3$ | $CH_3$ | H | 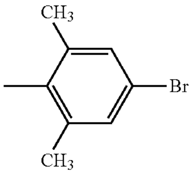 | 215-217*2 (CH3CN) |
| 2-091 | 1 | 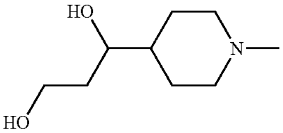 | H | $CH_3$ | $CH_3$ | $CH_3$ | 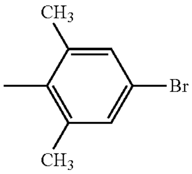 | 208-210*2 (IPE) |
| 2-092 | 1 | 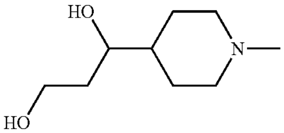 | H | $CH_3$ | $CH_3$ | H | 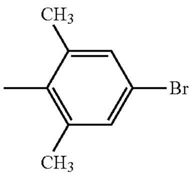 | 207-209*2 (CH3CN) |
| 2-093 | 1 | 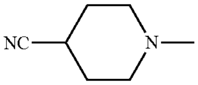 | H | $CH_3$ | $CH_3$ | $CH_3$ | 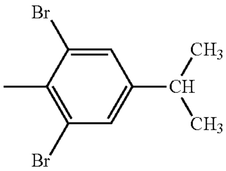 | 130-132*2 (MeOH) |
| 2-094 | 1 | 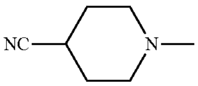 | H | $CH_3$ | $CH_3$ | H | 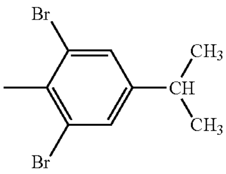 | amorphous*2 |

TABLE $2^{*1}$-continued
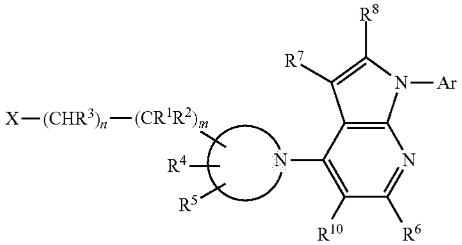
| Com. No. | Ex. No. | 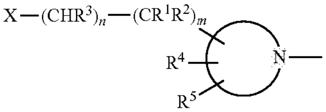 | $R^{10}$ | $R^6$ | $R^7$ | $R^8$ | —Ar | melting point (° C.) (solvent for crystallization) |
|---|---|---|---|---|---|---|---|---|
| 2-095 | 1 | 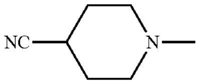 | H | $CH_3$ | $CH_3$ | $CH_3$ | 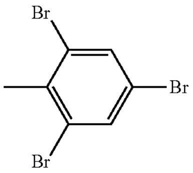 | 236-238$^{*2}$ (ACE) |
| 2-096 | 1 | 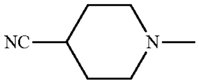 | H | $CH_3$ | $CH_3$ | H | 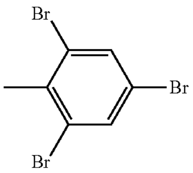 | 226-228$^{*2}$ (Et2O) |
| 2-097 | 1 | 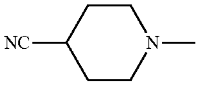 | H | $CH_3$ | $CH_3$ | $CH_3$ | 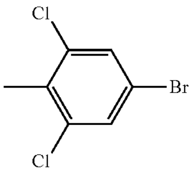 | amorphous$^{*2}$ |
| 2-098 | 1 | 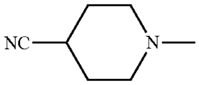 | H | $CH_3$ | $CH_3$ | H | 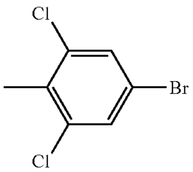 | 225-227$^{*2}$ (Et2O) |
| 2-099 | 1 | 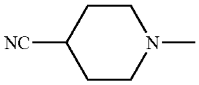 | H | $CH_3$ | $CH_3$ | $CH_3$ | 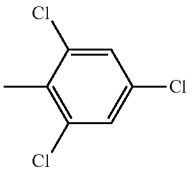 | amorphous |
| 2-100 | 1 | 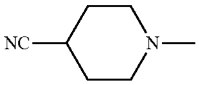 | H | $CH_3$ | $CH_3$ | H | 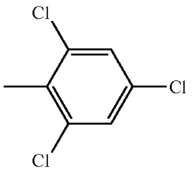 | amorphous$^{*2}$ |
| 2-101 | 1 | 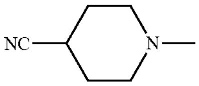 | H | $CH_3$ | $CH_3$ | $CH_3$ | 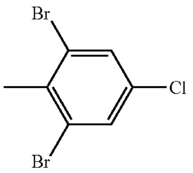 | amorphous$^{*2}$ |

TABLE 2*1-continued
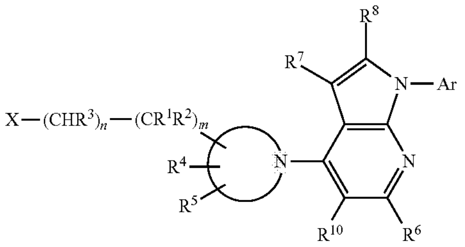
| Com. No. | Ex. No. | 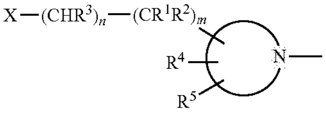 | $R^{10}$ | $R^6$ | $R^7$ | $R^8$ | —Ar | melting point (° C.) (solvent for crystallization) |
|---|---|---|---|---|---|---|---|---|
| 2-102 | 1 | 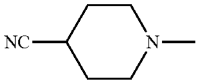 | H | $CH_3$ | $CH_3$ | H | 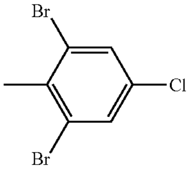 | amorphous*2 |
| 2-103 | 1 | 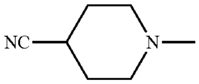 | H | $CH_3$ | $CH_3$ | $CH_3$ | 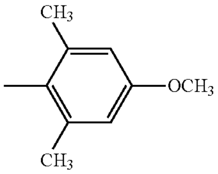 | amorphous*2 |
| 2-104 | 1 | 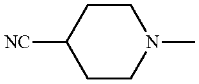 | H | $CH_3$ | $CH_3$ | H | 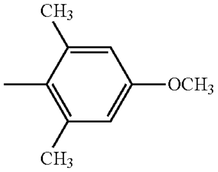 | amorphous*2 |
| 2-105 | 1 | 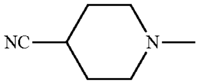 | H | $CH_3$ | $CH_3$ | H | 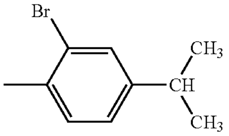 | amorphous*2 |
| 2-106 | 1 | 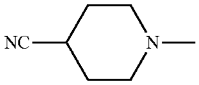 | H | $CH_3$ | $CH_3$ | H | 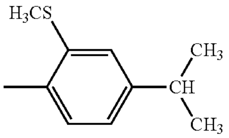 | amorphous*2 |
| 2-107 | 1 | 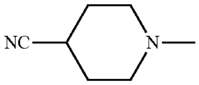 | H | $CH_3$ | $CH_3$ | H | 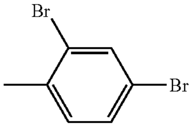 | amorphous*2 |
| 2-108 | 1 | 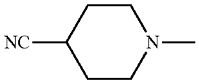 | H | $CH_3$ | $CH_3$ | H | 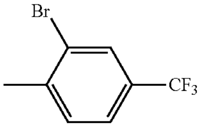 | amorphous*2 |

TABLE 2*1-continued
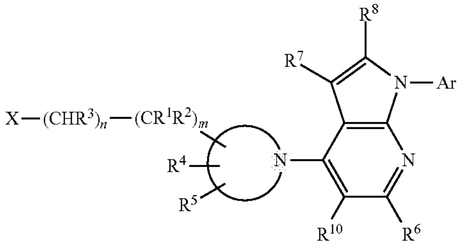
| Com. No. | Ex. No. | 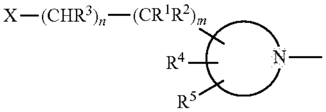 | $R^{10}$ | $R^6$ | $R^7$ | $R^8$ | —Ar | melting point (° C.) (solvent for crystallization) |
|---|---|---|---|---|---|---|---|---|
| 2-109 | 1 | 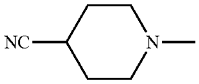 | H | $CH_3$ | $CH_3$ | $CH_3$ | 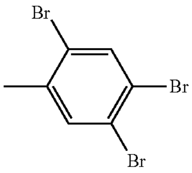 | amorphous*2 |
| 2-110 | 1 | 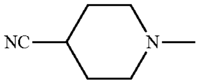 | H | $CH_3$ | $CH_3$ | H | 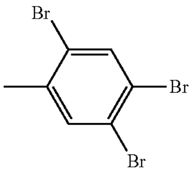 | amorphous*2 |
| 2-111 | 1 | 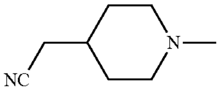 | H | $CH_3$ | $CH_3$ | $CH_3$ | 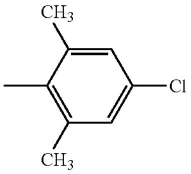 | amorphous*2 |
| 2-112 | 1 | 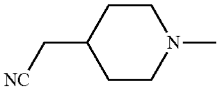 | H | $CH_3$ | $CH_3$ | $CH_3$ | 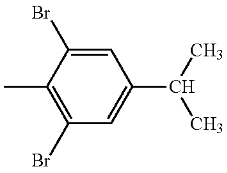 | amorphous*2 |
| 2-113 | 1 | 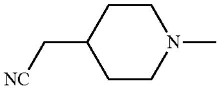 | H | $CH_3$ | $CH_3$ | H | 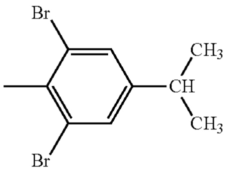 | amorphous*2 |
| 2-114 | 1 | 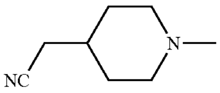 | H | $CH_3$ | $CH_3$ | $CH_3$ | 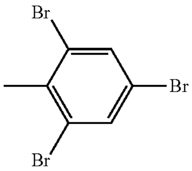 | amorphous*2 |
| 2-115 | 1 | 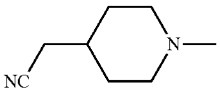 | H | $CH_3$ | $CH_3$ | H | 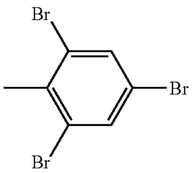 | 217-219*2 (ACE) |

TABLE 2*[1]-continued
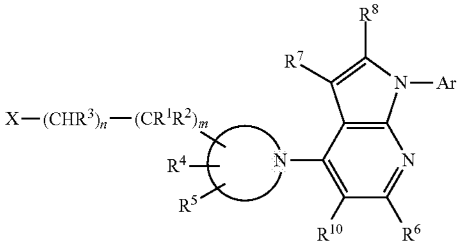
| Com. No. | Ex. No. | 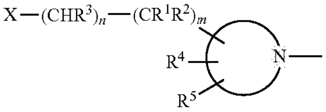 | $R^{10}$ | $R^6$ | $R^7$ | $R^8$ | —Ar | melting point (° C.) (solvent for crystallization) |
|---|---|---|---|---|---|---|---|---|
| 2-116 | 1 | 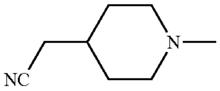 | H | $CH_3$ | $CH_3$ | $CH_3$ | 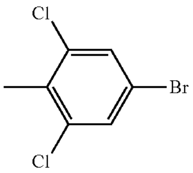 | amorphous*[2] |
| 2-117 | 1 | 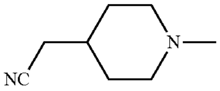 | H | $CH_3$ | $CH_3$ | H | 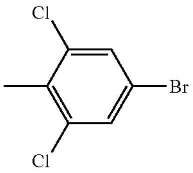 | amorphous*[2] |
| 2-118 | 1 | 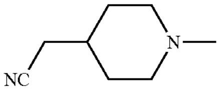 | H | $CH_3$ | $CH_3$ | $CH_3$ | 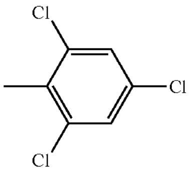 | amorphous*[2] |
| 2-119 | 1 | 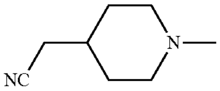 | H | $CH_3$ | $CH_3$ | H | 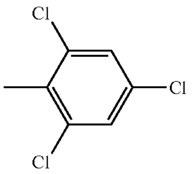 | amorphous*[2] |
| 2-120 | 1 | 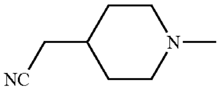 | H | $CH_3$ | $CH_3$ | $CH_3$ | 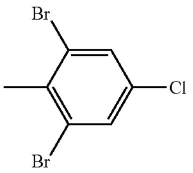 | amorphous*[2] |
| 2-121 | 1 | 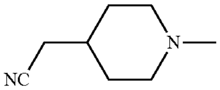 | H | $CH_3$ | $CH_3$ | H | 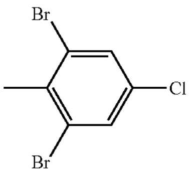 | amorphous*[2] |

TABLE 2*1-continued
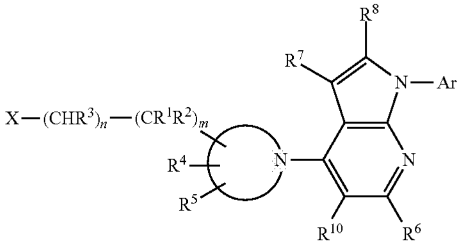
| Com. No. | Ex. No. | 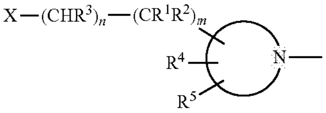 | $R^{10}$ | $R^6$ | $R^7$ | $R^8$ | —Ar | melting point (° C.) (solvent for crystallization) |
|---|---|---|---|---|---|---|---|---|
| 2-122 | 1 | 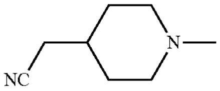 | H | $CH_3$ | $CH_3$ | $CH_3$ | 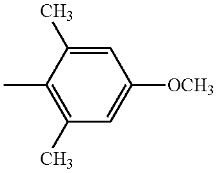 | amorphous*2 |
| 2-123 | 1 | 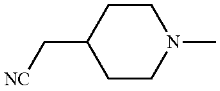 | H | $CH_3$ | $CH_3$ | H | 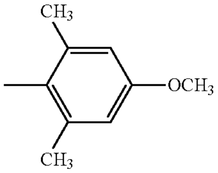 | amorphous*2 |
| 2-124 | 1 | 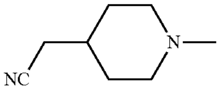 | H | $CH_3$ | $CH_3$ | H | 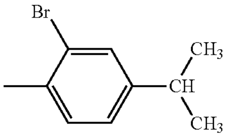 | amorphous*2 |
| 2-125 | 1 | 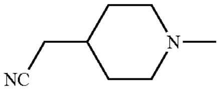 | H | $CH_3$ | $CH_3$ | H | 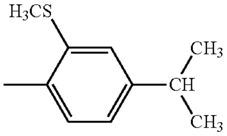 | amorphous*2 |
| 2-126 | 1 | 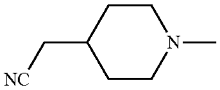 | H | $CH_3$ | $CH_3$ | H | 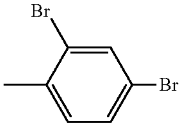 | amorphous*2 |
| 2-127 | 1 | 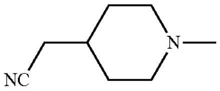 | H | $CH_3$ | $CH_3$ | H | 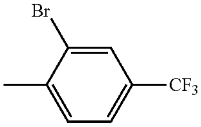 | 212-214*2 (IPE) |
| 2-128 | 1 | 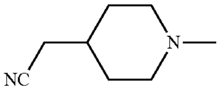 | H | $CH_3$ | $CH_3$ | H | 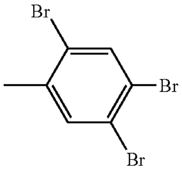 | amorphous*2 |

TABLE 2*[1]-continued

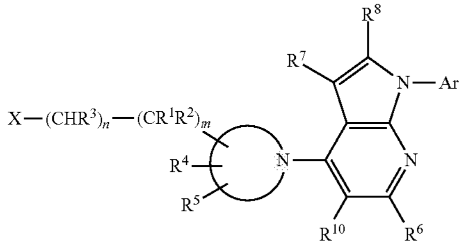

| Com. No. | Ex. No. | 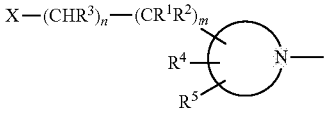 | $R^{10}$ | $R^6$ | $R^7$ | $R^8$ | —Ar | melting point (° C.) (solvent for crystallization) |
|---|---|---|---|---|---|---|---|---|
| 2-129 | 1 | 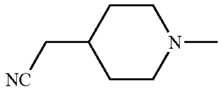 | $CO_2Et$ | $CH_3$ | $CH_3$ | $CH_3$ | 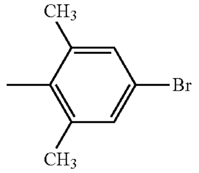 | 176-178 (IPE) |

*[1]Com. No. = compound number, Ex. No. = example number, solvent for crystallization;
ACE = acetone, EtOAc = ethyl acetate, EtOH = ethanol, Et2O = diethylether, IPA = isopropyl alcohol, IPE = diisopropyl ether, MeOH = methanol, CH3CN = acetonitrile Analytical data of non-crystal compounds are described below.

2-001:

MS (ES, Pos.): 418 $(M+1)^+$, 420 $(M+3)^+$, 422 $(M+5)^+$ 2-002:

MS (ES, Pos.): 432 $(M+1)^+$, 434 $(M+3)^+$, 436 $(M+5)^+$ 2-012:

MS (ES, Pos.): 427 $(M+1)^+$ 2-034:

MS (ES, Pos.): 534 $(M+1)^+$, 536 $(M+3)^+$, 538 $(M+5)^+$; HPLC retention time: 6.55 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-041:

MS (ES, Pos.): 540 $(M+1)^+$, 542 $(M+3)^+$, 544 $(M+5)^+$; HPLC retention time: 6.60 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-045:

MS (ES, Pos.): 456 $(M+1)^+$, 458 $(M+3)^+$; HPLC retention time: 6.72 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-046:

MS (ES, Pos.): 424 $(M+1)^+$; HPLC retention time: 6.61 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-048:

MS (ES, Pos.): 482 $(M+1)^+$, 484 $(M+3)^+$; HPLC retention time: 5.67 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-049:

MS (ES, Pos.): 584 $(M+1)^+$, 586 $(M+3)^+$, 588 $(M+5)^+$; HPLC retention time: 6.73 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-050:

MS (ES, Pos.): 570 $(M+1)^+$, 572 $(M+3)^+$, 574 $(M+5)^+$; HPLC retention time: 6.90 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-052:

MS (ES, Pos.): 562 $(M+1)^+$, 564 $(M+3)^+$, 562 $(M+5)^+$; HPLC retention time: 6.81 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-053:

MS (ES, Pos.): 548 $(M+1)^+$, 550 $(M+3)^+$, 552 $(M+5)^+$; HPLC retention time: 6.72 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-054:

MS (ES, Pos.): 598 $(M+1)^+$, 600 $(M+3)^+$, 602 $(M+5)^+$; HPLC retention time: 6.47 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min and reequilibrate with 100% A for 1.5 min)

2-056:

MS (ES, Pos.): 510 $(M+1)^+$, 512 $(M+3)^+$, 514 $(M+5)^+$; HPLC retention time: 6.42 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-057:

MS (ES, Pos.): 496 $(M+1)^+$, 498 $(M+3)^+$, 500 $(M+5)^+$; HPLC retention time: 6.55 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-058:

MS (ES, Pos.): 466 $(M+1)^+$, 468 $(M+3)^+$, 470 $(M+5)^+$; HPLC retention time: 6.82 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-059:

MS (ES, Pos.): 452 $(M+1)^+$, 454 $(M+3)^+$, 456 $(M+5)^+$; HPLC retention time: 6.23 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-060:

MS (ES, Pos.): 554 $(M+1)^+$, 556 $(M+3)^+$, 558 $(M+5)^+$; HPLC retention time: 6.43 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-062:

MS (ES, Pos.): 422 $(M+1)^+$; HPLC retention time: 6.29 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-063:

MS (ES, Pos.): 408 $(M+1)^+$; HPLC retention time: 5.94 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-064:

MS (ES, Pos.): 470 $(M+1)^+$, 472 $(M+3)^+$, HPLC retention time: 6.92 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-065:

MS (ES, Pos.): 438 $(M+1)^+$; HPLC retention time: 6.40 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-066:

MS (ES, Pos.): 506 $(M+1)^+$, 508 $(M+3)^+$, 510 $(M+5)^+$; HPLC retention time: 6.31 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-068:

MS (ES, Pos.): 598 $(M+1)^+$, 600 $(M+3)^+$, 602 $(M+5)^+$; HPLC retention time: 7.11 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-069:

MS (ES, Pos.): 584 $(M+1)^+$, 586 $(M+3)^+$, 588 $(M+5)^+$; HPLC retention time: 7.11 min. (Xterra MS C18 (Waters, Milford, Mass.) 3.5 μm, 4.6×100 mm); Flow rate 1.6 mL/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-072:

MS (ES, Pos.): 562 $(M+1)^+$, 564 $(M+3)^+$, 566 $(M+5)^+$; HPLC retention time: 6.63 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-073:

MS (ES, Pos.): 612 $(M+1)^+$, 614 (M+3) % 616 $(M+5)^+$; HPLC retention time: 6.61 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-077:

MS (ES, Pos.): 480 $(M+1)^+$, 482 $(M+3)^+$, 484 $(M+5)^+$; HPLC retention time: 6.54 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-078:

MS (ES, Pos.): 466 $(M+1)^+$, 468 $(M+3)^+$, 470 $(M+5)^+$; HPLC retention time: 5.95 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-079:

MS (ES, Pos.): 568 $(M+1)^+$, 570 $(M+3)^+$, 572 $(M+5)^+$; HPLC retention time: 6.97 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-081:

MS (ES, Pos.): 436 $(M+1)^+$; HPLC retention time: 6.49 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-083:

MS (ES, Pos.): 484 $(M+1)^+$, 486 $(M+3)^+$; HPLC retention time: 7.09 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-084:

MS (ES, Pos.): 452 $(M+1)^+$; HPLC retention time: 6.55 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% Bin 1 min, 100% B for 1 min. and reequilibrate with 100% A for 1.5 min)

2-087:

MS (ES, Pos.): 612 $(M+1)^+$, 614 $(M+3)^+$, 616 $(M+5)^+$; HPLC retention time: 7.24 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-088:

MS (ES, Pos.): 598 $(M+1)^+$, 600 $(M+3)^+$, 602 $(M+5)^+$; HPLC retention time: 7.21 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-094:

MS (ES, Pos.): 529 $(M+1)^+$, 531 $(M+3)^+$, 533 $(M+5)^+$; HPLC retention time: 6.40 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-097:

MS (ES, Pos.): 491 $(M+1)^+$, 493 $(M+3)^+$, 495 $(M+5)^+$; HPLC retention time: 6.78 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-099:

MS (ES, Pos.): 447 $(M+1)^+$, 449 $(M+3)^+$, 451 $(M+5)^+$; HPLC retention time: 6.73 min. (Xterra MS C18 (Waters, Milford, Mass.) 3.5 μm, 4.6×100 mm); Flow rate 1.6 ml/min.

Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-100:

MS (ES, Pos.): 433 $(M+1)^+$, 435 $(M+3)^+$, 437 $(M+5)^+$; HPLC retention time: 5.70 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-101:

MS (ES, Pos.): 535 $(M+1)^+$, 537 $(M+3)^+$, 539 $(M+5)^+$; HPLC retention time: 6.72 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-102:

MS (ES, Pos.): 521 $(M+1)^+$, 523 $(M+3)^+$, 525 $(M+5)^+$; HPLC retention time: 6.27 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-103:

MS (ES, Pos.): 403 (M+1); HPLC retention time: 6.24 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-104:

MS (ES, Pos.): 389 $(M+1)^+$; HPLC retention time: 5.89 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-105:

MS (ES, Pos.): 451 $(M+1)^+$, 453 (M+3) % HPLC retention time: 6.87 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min, to 100% B in 1 min, 100% B for 1 min. and reequilibrate with 100% A for 1.5 min)

2-106:

MS (ES, Pos.): 419 $(M+1)^+$; HPLC retention time: 6.33 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-107:

MS (ES, Pos.): 487 $(M+1)^+$, 489 $(M+3)^+$, 491 $(M+5)^+$; HPLC retention time: 6.20 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-108:

MS (ES, Pos.): 477 $(M+1)^+$, 479 $(M+3)^+$, 481 $(M+5)^+$; HPLC retention time: 6.21 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-109:

MS (ES, Pos.): 579 $(M+1)^+$, 581 $(M+3)^+$, 583 $(M+5)^+$; HPLC retention time: 7.00 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-110:

MS (ES, Pos.): 565 $(M+1)^+$, 567 $(M+3)^+$, 569 $(M+5)^+$; HPLC retention time: 7.00 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-111:

MS (ES, Pos.): 421 $(M+1)^+$, 423 $(M+3)^+$; HPLC retention time: 6.84 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-112:

MS (ES, Pos.): 557 $(M+1)^+$, 559 $(M+3)^+$, 561 $(M+5)^+$; HPLC retention time: 6.54 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-113:

MS (ES, Pos.): 543 $(M+1)^+$, 545 $(M+3)^+$, 547 $(M+5)^+$; HPLC retention time: 6.69 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-114:

MS (ES, Pos.): 593 $(M+1)^+$, 595 $(M+3)^+$, 597 $(M+5)^+$; HPLC retention time: 6.84 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-116:

MS (ES, Pos.): 505 $(M+1)^+$, 507 $(M+3)^+$, 509 $(M+5)^+$; HPLC retention time: 6.37 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-117:

MS (ES, Pos.): 491 $(M+1)^+$, 493 $(M+3)^+$, 495 $(M+5)^+$; HPLC retention time: 6.52 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-118:

MS (ES, Pos.): 461 (M+1) % 463 $(M+3)^+$, 465 $(M+5)^+$; HPLC retention time: 6.34 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-119:

MS (ES, Pos.): 447 $(M+1)^+$, 449 $(M+3)^+$, 451 $(M+5)^+$; HPLC retention time: 5.79 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-120:

MS (ES, Pos.): 549 $(M+1)^+$, 551 $(M+3)^+$, 553 $(M+5)^+$; HPLC retention time: 6.77 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-121:

MS (ES, Pos.): 535 $(M+1)^+$, 537 $(M+3)^+$, 539 $(M+5)^+$; HPLC retention time: 5.83 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-122:

MS (ES, Pos.): 417 $(M+1)^+$; HPLC retention time: 6.49 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-123:

MS (ES, Pos.): 403 $(M+1)^+$; HPLC retention time: 5.96 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-124:

MS (ES, Pos.): 465 $(M+1)^+$, 467 $(M+3)^+$, HPLC retention time: 6.87 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-125:

MS (ES, Pos.): 433 $(M+1)^+$; HPLC retention time: 6.38 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-126:

MS (ES, Pos.): 501 $(M+1)^+$, 503 $(M+3)^+$, 505 $(M+5)^+$; HPLC retention time: 6.26 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

2-128:

MS (ES, Pos.): 579 $(M+1)^+$, 581 $(M+3)^+$, 583 $(M+5)^+$; HPLC retention time: 6.10 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

*2: HCl salt

TABLE 3*[1]
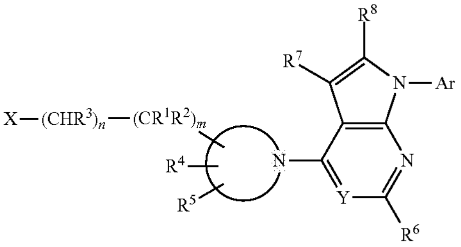
| Com. No. | Ex. No. | 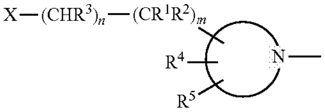 | Y | $R^6$ | $R^7$ | $R^8$ | —Ar | melting point (° C.) (solvent for crystallization) |
|---|---|---|---|---|---|---|---|---|
| 3-001 | 5 | 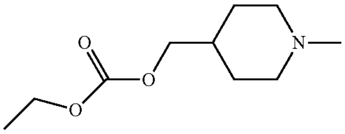 | N | $CH_3$ | $CH_3$ | H | 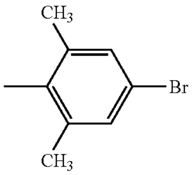 | 151-153 (No solvent) |
| 3-002 | 5 | 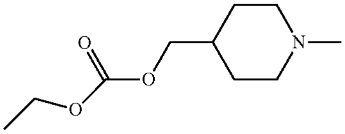 | CH | $CH_3$ | $CH_3$ | H | 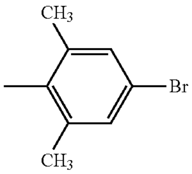 | amorphous |
| 3-003 | 6 | 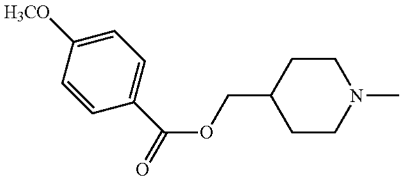 | N | $CH_3$ | $CH_3$ | H | 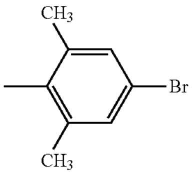 | 142-144 (IPE) |
| 3-004 | 6 | 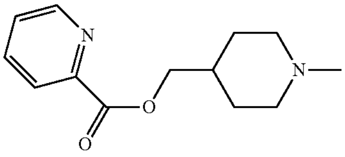 | N | $CH_3$ | $CH_3$ | H | 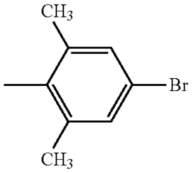 | 143-145 (IPE) |
| 3-005 | 6 | 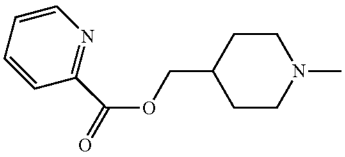 | CH | $CH_3$ | $CH_3$ | H | 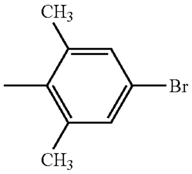 | amorphous |
| 3-006 | 6 | 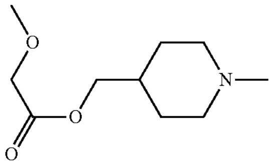 | N | $CH_3$ | $CH_3$ | H | 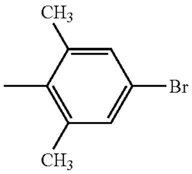 | 131-133 (hexane) |

TABLE 3*[1]-continued
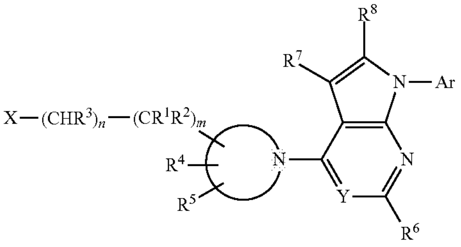
| Com. No. | Ex. No. | 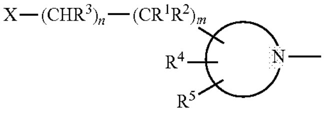 | Y | $R^6$ | $R^7$ | $R^8$ | —Ar | melting point (° C.) (solvent for crystallization) |
|---|---|---|---|---|---|---|---|---|
| 3-007 | 6 | 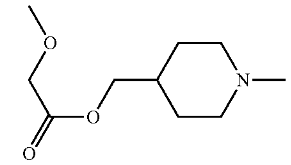 | CH | $CH_3$ | $CH_3$ | H | 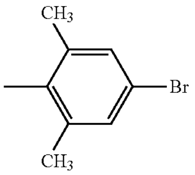 | amorphous |
| 3-008 | 5 | 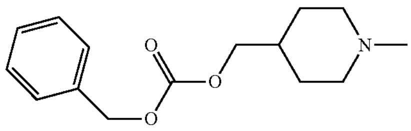 | N | $CH_3$ | $CH_3$ | H | 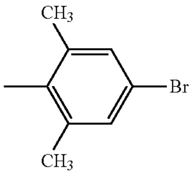 | amorphous |
| 3-009 | 6 | 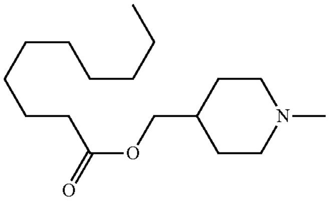 | N | $CH_3$ | $CH_3$ | H | 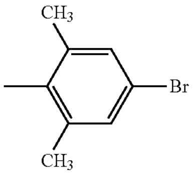 | amorphous |
| 3-010 | 6 | 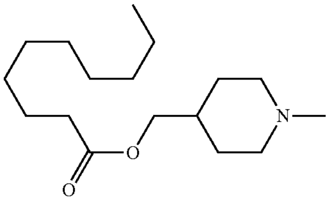 | CH | $CH_3$ | $CH_3$ | $CH_3$ | 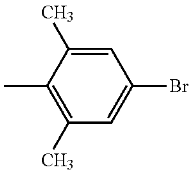 | oil |
| 3-011 | 6 | 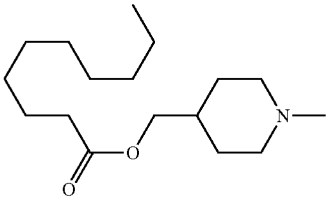 | CH | $CH_3$ | $CH_3$ | H | 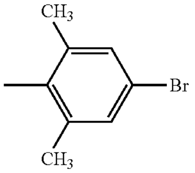 | oil |
| 3-012 | 5 | 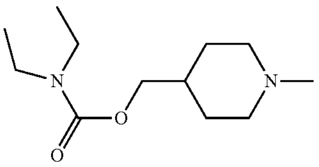 | N | $CH_3$ | $CH_3$ | H | 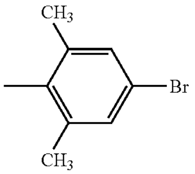 | 110-112 (No solvent) |

TABLE 3*1-continued
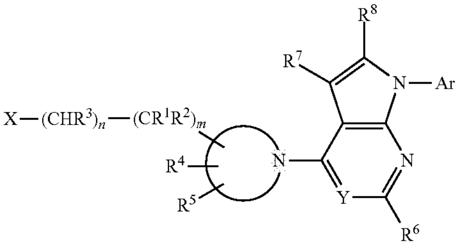
| Com. No. | Ex. No. | 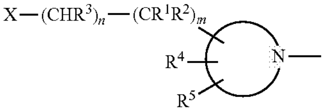 | Y | $R^6$ | $R^7$ | $R^8$ | —Ar | melting point (° C.) (solvent for crystallization) |
|---|---|---|---|---|---|---|---|---|
| 3-013 | 5 | 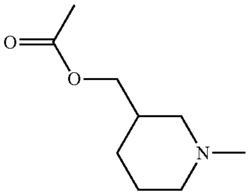 | N | $CH_3$ | $CH_3$ | $CH_3$ | 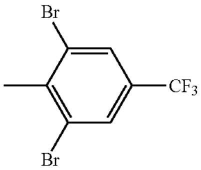 | amorphous |
| 3-014 | 8 | 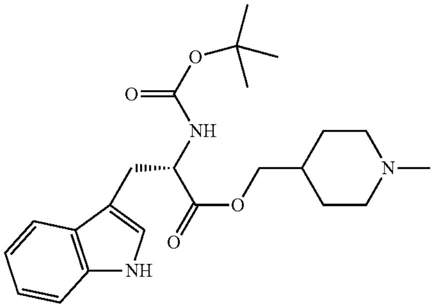 | N | $CH_3$ | $CH_3$ | H | 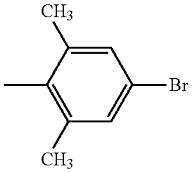 | 205-207*2 (No solvent) |
| 3-015 | 7 | 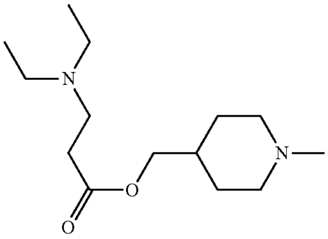 | N | $CH_3$ | $CH_3$ | H | 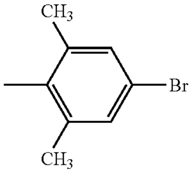 | amorphous |
| 3-016 | 8 | 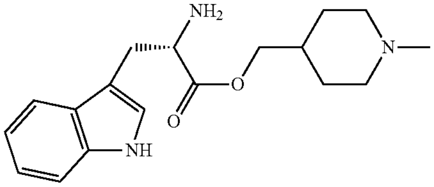 | N | $CH_3$ | $CH_3$ | H | 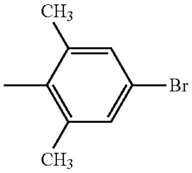 | amorphous*2 |
| 3-017 | 9 | 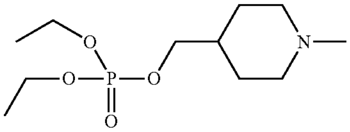 | N | $CH_3$ | $CH_3$ | H | 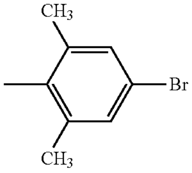 | 94-96 (No solvent) |

TABLE 3*[1]-continued

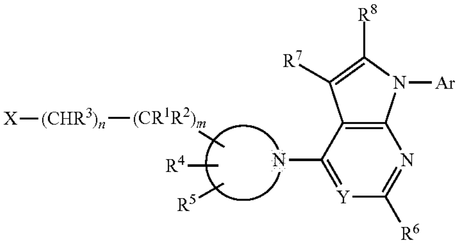

| Com. No. | Ex. No. | 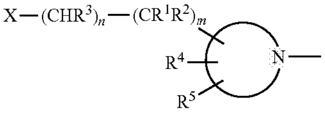 | Y | $R^6$ | $R^7$ | $R^8$ | —Ar | melting point (° C.) (solvent for crystallization) |
|---|---|---|---|---|---|---|---|---|
| 3-018 | 10 | 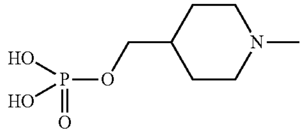 | N | $CH_3$ | $CH_3$ | H | 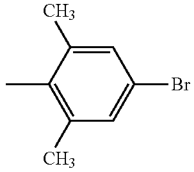 | 215-217*[3] (No solvent) |
| 3-019 | 7 | 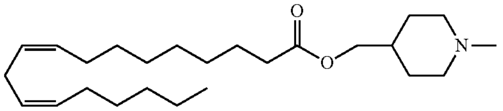 | N | $CH_3$ | $CH_3$ | H | 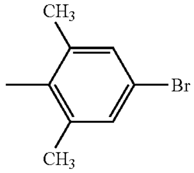 | amorphous |
| 3-020 | 7 | 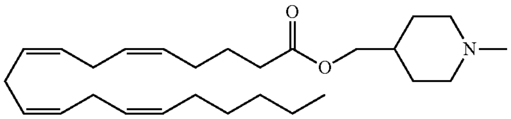 | N | $CH_3$ | $CH_3$ | H | 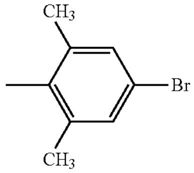 | amorphous |
| 3-021 | 7 | 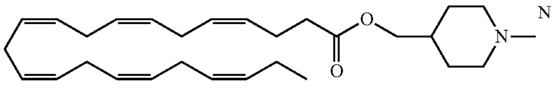 | N | $CH_3$ | $CH_3$ | H | 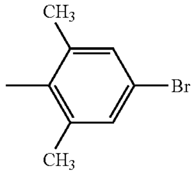 | amorphous |
| 3-022 | 7 | 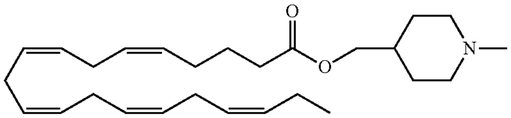 | N | $CH_3$ | $CH_3$ | H | 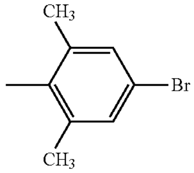 | amorphous |

*[1]Com. No. = compound number, Ex. No. = example number, solvent for crystallization; IPE = diisopropyl ether Analytical data of non-crystal compounds are described below.

3-002:

MS (ES, Pos.): 514 (M+516 (M+3)$^+$; HPLC Retention time: 6.77 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

3-005:

MS (ES, Pos.): 547 (M+1)$^+$, 549 (M+3)$^+$; HPLC Retention time: 7.06 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

3-007:

MS (ES, Pos.): 514 (M+1) % 516 $(M+3)^+$; HPLC Retention time: 7.01 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

3-008:

MS (ES, Pos.): 577 $(M+1)^+$, 579 $(M+3)^+$; HPLC Retention time: 10.89 min. (Xterra MS C18 (Waters, Milford, Mass.) 3.5 μm, 4.6×100 mm); Flow rate 1.2 ml/min. Three mobile phases (mobile phase A 95% 25 mM ammonium acetate+5% acetonitrile; mobile phase B: acetonitrile; mobile phase C: methanol) were employed to run a gradient condition from 30% A, 50% B and 20% C to 50% B and 50% C in 6.5 min., to 100% B in 1 min, 100% B for 1 min. and reequilibrate with 100% A for 1.5 min)

3-009:

MS (ES, Pos.): 597 $(M+1)^+$, 599 $(M+3)^+$; HPLC Retention time: 13.94 min. (Xterra MS C18 (Waters, Milford, Mass.) 3.5 μm, 4.6×100 mm); Flow rate 1.2 ml/min. Three mobile phases (mobile phase A 95% 25 mM ammonium acetate+5% acetonitrile; mobile phase B: acetonitrile; mobile phase C: methanol) were employed to run a gradient condition from 30% A, 50% B and 20% C to 50% B and 50% C in 6.5 min., to 100% B in 1 min, 100% B for 1 min. and reequilibrate with 100% A for 1.5 min)

3-010:

MS No spectrum (decomposition in LC-MS); $^1$H NMR (360 MHz, DMSO-D6) 5 ppm 0.83 (3H, t, J=6.4 Hz), 1.24 (12H, br.s), 1.52 (4H, m), 1.79 (9H, m), 1.93 (3H, s), 2.29 (3H, s), 2.32 (2H, t, J=7.1 Hz), 2.39 (3H, s), 2.68 (2H, t, J=11.3 Hz), 3.46 (2H, d, J=11.7 Hz), 4.00 (2H, d, J=5.9 Hz), 6.45 (1H, s), 7.47 (2H, s)

3-011:

MS (ES, Pos.): 596 $(M+1)^+$, 598 $(M+3)^+$; HPLC Retention time: 6.45 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

3-013:

MS (ES, Pos.): 617 $(M+1)^+$, 619 $(M+3)^+$, 621 $(M+5)^+$; HPLC Retention time: 6.65 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

3-015:

MS (ES, Pos.): 570 $(M+1)^+$, 572 $(M+3)^+$; HPLC Retention time: 7.05 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

3-016:

MS (ES, Pos.): 629 $(M+1)^+$, 631 $(M+3)^+$; HPLC Retention time: 6.86 min. (Xterra MS C18 (Waters, Milford, Mass.) 3.5 μm, 4.6×100 mm); Flow rate 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min)

3-019:

MS (ES, Pos.): 705 $(M+1)^+$, 707 $(M+3)^+$; NMR (300 MHz, $CDCl_3$) 8 ppm 0.89 (3H, t, J=6.7 Hz), 1.17-1.40 (14H, m), 1.42-1.72 (4H, m), 1.81-1.93 (3H, m), 1.92 (6H, s), 2.00-2.07 (4H, m), 2.34 (2H, t, J=7.5 Hz), 2.44 (3H, d, J=1.1 Hz), 2.51 (3H, s), 2.74-2.81 (2H, m), 2.90-3.04 (2H, m), 4.03 (2H, d, J=6.4 Hz), 4.10-4.19 (2H, m), 5.28-5.42 (4H, m), 6.57 (1H, m), 7.30 (2H, s)

3-020:

MS (ES, Pos.): 729 $(M+1)^+$, 731 $(M+3)^+$; $^1$H NMR (300 MHz, $CDCl_3$) δ ppm 0.89 (3H, t, J=6.7 Hz), 1.20-1.40 (6H, m), 1.41-1.53 (2H, m), 1.65-1.80 (2H, m), 1.81-2.00 (3H, m), 1.92 (6H, s), 2.02-2.19 (4H, m), 2.36 (2H, t, J=7.5 Hz), 2.44 (3H, d, J=1.0 Hz), 2.51 (3H, s), 2.77-2.90 (6H, m), 2.92-3.05 (2H, m), 4.03 (2H, d, J=6.4 Hz), 4.05-4.19 (2H, m), 5.28-5.47 (8H, m), 6.57 (1H, m), 7.30 (2H, s)

3-021:

MS (ES, Pos.): 753 $(M+1)^+$, 754 $(M+3)^+$; $^1$H NMR (500 MHz, $CDCl_3$) 8 ppm 0.97 (3H, t, J=7.3 Hz), 1.15-1.40 (1H, m), 1.45-1.55 (2H, m), 1.84-2.00 (3H, m), 1.92 (6H, s), 2.04-2.11 (2H, m), 2.38-2.44 (4H, m), 2.43 (3H, d, J=1.2 Hz), 2.50 (3H, s), 2.77-2.90 (10H, m), 2.94-3.02 (2H, m), 4.04 (2H, d, J=6.7 Hz), 4.09-4.16 (2H, m), 5.27-5.46 (12H, m), 6.57 (1H, m), 7.30 (2H, s)

3-022:

MS (ES, Pos.): 727 $(M+1)^+$, 729 $(M+3)^+$; $^1$H NMR (500 MHz, $CDCl_3$) 8 ppm 0.97 (3H, t, J=7.3 Hz), 1.15-1.40 (1H, m), 1.45-1.55 (2H, m), 1.65-1.80 (2H, m), 1.84-1.98 (2H, m), 1.92 (6H, s), 2.03-2.17 (4H, m), 2.36 (2H, t, J=7.3 Hz), 2.43 (3H, d, J=1.2 Hz), 2.50 (3H, s), 2.77-2.91 (8H, m), 2.94-3.02 (2H, m), 4.04 (2H, d, J=6.7 Hz), 4.09-4.16 (2H, m), 5.28-5.44 (10H, m), 6.57 (1H, m), 7.30 (2H, s)

*2: optically active compound

*3: 1 Na salt

Test Example

CRF Receptor Binding Test

Monkey amygdala membranes were used as a receptor preparation.

$^{125}$I—CRF was used as $^{125}$I-labeled ligand.

Binding reaction using the $^{125}$I-labeled ligand was carried out by the following method described in The Journal of Neuroscience, 7, 88 (1987).

Preparation of Receptor Membranes:

Monkey amygdala was homogenized in 50 mM Tris-HCl buffer (pH 7.0) containing 10 mM $MgCl_2$, 2 mM EDTA and centrifuged at 48,000×g for 20 min, and the precipitate was washed once with Tris-HCl buffer. The washed precipitate was suspended in 50 mM Tris-HCl buffer (pH 7.0) containing 10 mM $MgCl_2$, 2 mM EDTA, 0.1% bovine serum albumin and 100 kallikrein units/ml aprotinin, to obtain a membrane preparation.

CRF Receptor Binding Test:

The membrane preparation (0.3 mg protein/ml), $^{125}$I—CRF (0.2 nM) and a test drug were reacted at 25° C. for 2 hours. After completion of the reaction, the reaction mixture was filtered by suction through a glass filter (GF/C) treated with 0.3% polyethylene imine, and the glass filter was washed three times with phosphate-buffered saline containing 0.01% Triton X-100. After the washing, the radioactivity of the filter paper was measured in a gamma counter.

The amount of $^{125}$I—CRF bound when the reaction was carried out in the presence of 1 μM CRF was taken as the degree of nonspecific binding of $^{125}$I—CRF, and the difference between the total degree of $^{125}$I—CRF binding and the degree of nonspecific $^{125}$I—CRF binding was taken as the degree of specific $^{125}$I—CRF binding. An inhibition curve was obtained by reacting a definite concentration (0.2 nM) of $^{125}$I—CRF with various concentrations of each test drug under the conditions described above. A concentration of the test drug at which binding of $^{125}$I—CRF is inhibited by 50% ($IC_{50}$) was determined from the inhibition curve.

As a result, it was found that compounds 1-003, 1-004, 1-005, 1-007, 1-008, 1-009, 1-010, 1-013, 1-014, 1-016, 1-018, 1-019, 1-021, 1-032, 1-038, 1-039, 1-040, 1-046, 1-050, 1-051, 1-052, 1-053, 1-054, 1-056, 1-057, 1-058, 1-059, 1-060, 1-061, 1-062, 1-063, 1-064, 1-067, 1-068, 1-072, 1-073, 1-074, 1-077, 1-078, 1-087, 1-088, 1-089, 1-090, 1-091, 1-097, 1-098, 1-099, 1-103, 1-104, 1-105, 1-112, 1-117, 1-118, 1-120, 1-121, 1-122, 1-123, 1-125, 1-126, 1-127, 1-128, 1-129, 1-130, 1-131, 1-132, 1-133, 1-135, 1-141, 1-142, 1-143, 1-144, 1-145, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-172, 1-173, 1-176, 1-177, 1-178, 1-179, 1-181, 1-183, 1-184, 1-188, 1-195, 1-208, 1-213, 1-235, 1-236, 1-237, 1-243, 1-245, 1-251, 1-257, 1-262, 1-264, 1-278, 1-280, 1-283, 1-284, 1-285, 1-286, 1-287, 1-288, 1-302, 1-304, 1-306, 1-308, 1-319, 1-320, 1-332, 1-333, 1-336, 1-337, 2-002, 2-003, 2-004, 2-005, 2-006, 2-007, 2-008, 2-009, 2-010, 2-011, 2-012, 2-013, 2-014, 2-015, 2-016, 2-017, 2-018, 2-019, 2-020, 2-021, 2-022, 2-023, 2-024, 2-025, 2-026, 2-027, 2-028, 2-029, 2-030, 2-031, 2-032, 2-033, 2-034, 2-035, 2-036, 2-037, 2-038, 2-039, 2-040, 2-041, 2-042, 2-043, 2-044, 2-045, 2-046, 2-047, 2-048, 2-049, 2-050, 2-052, 2-053, 2-054, 2-055, 2-056, 2-057, 2-058, 2-059, 2-060, 2-061, 2-062, 2-063, 2-064, 2-065, 2-066, 2-068, 2-069, 2-070, 2-071, 2-072, 2-073, 2-074, 2-075, 2-076, 2-077, 2-078, 2-079, 2-080, 2-081, 2-082, 2-084, 2-087, 2-088, 2-089, 2-090, 2-091, 2-092, 2-093, 2-094, 2-095, 2-096, 2-097, 2-098, 2-099, 2-100, 2-101, 2-102, 2-103, 2-104, 2-105, 2-106, 2-107, 2-108, 2-109, 2-110, 2-111, 2-112, 2-113, 2-114, 2-115, 2-116, 2-117, 2-118, 2-119, 2-120, 2-121, 2-122, 2-123, 2-124, 2-125, 2-126, 2-127, 2-128, 3-001, 3-004, 3-006, 3-007, 3-008, 3-009, 3-015 and 3-018 can be exemplified as typical compounds having an $IC_{50}$ value of 50 nM or less.

Effect of the Invention

According to the present invention, compounds having a high affinity for CRF receptors have been provided. These compounds are effective against diseases in which CRF is considered to be involved, such as depression, anxiety, Alzheimer's disease, Parkinson's disease, Huntington's chorea, eating disorder, hypertension, gastric diseases, drug dependence, epilepsy, cerebral infarction, cerebral ischemia, cerebral edema, cephalic external wound, inflammation, immunity-related diseases, alopecia, irritable bowel syndrome, sleep disorders, epilepsy, dermatitides, schizophrenia, etc.

The invention claimed is:

1. A pyrrolopyridine compound substituted with a cyclic amino group represented by the following formula [I]:

[I]

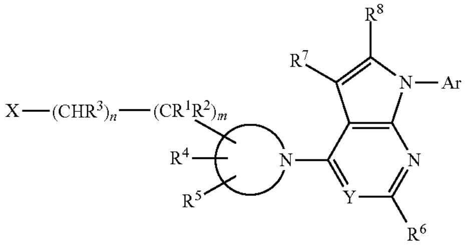

(wherein the cyclic amino group is represented by the following formula [II]:

[II]

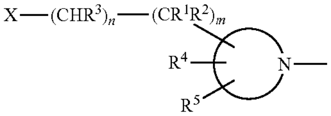

in which the cyclic amino group is a 3- to 8-membered saturated cyclic amine or a 3- to 8-membered saturated cyclic amine bridged with $C_{3-8}$alkylene or $C_{1-3}$alkylene-O—$C_{3-8}$alkylene between any different two carbon atoms of the cyclic amine, which cyclic amine is substituted with a group represented by —$(CR^1R^2)_m(CHR^3)_n$X, $R^4$ and $R^5$ independently on the same or different carbon atoms of the cyclic amine;

X is cyano, hydroxy or —$OR^9$;

Y is $CR^{10}$;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4, and 5;

n is 0 or 1;

with the proviso that when X is hydroxy or $OR^9$, and n is 0, then m is an integer elected from 1, 2, 3, 4 and 5;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy or —$N(R^{11})R^{12}$;

$R^7$ and $R^8$ are the same or different, and independently are hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —$N(R^{11a})R^{12a}$, —$CO_2R^{13}$, cyano, nitro, $C_{1-5}$alkylthio, trifluoromethyl or trifluoromethoxy;

$R^9$ is $C_{1-24}$acyl, $C_{1-10}$alkoxycarbonyl, aryl-$C_{1-5}$alkyloxycarbonyl, —CO—O—$CHR^{14}$—O—CO—$R^{15}$, —P(═O)($OR^{14a}$)$OR^{15a}$, —CO—$(CH_2)_p$—$(CHR^{16})_q$$NR^{17}R^{18}$, arylcarbonyl or heteroarylcarbonyl, wherein each said acyl, aryl and heteroaryl is unsubstituted or substituted with $C_{1-5}$alkoxy, and $C_{1-24}$acyl optionally includes one to six double bonds;

$R^{10}$ is hydrogen, $C_{1-5}$alkyl, halogen, cyano or —($CO_2R^{19}$;

Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —$CO_2R^{19a}$, —C(═O)$R^{19a}$, —$CONR^{11b}R^{12b}$, —OC(═O)$R^{19a}$, —$NR^{11b}CO_2R^{19a}$, —$S(O)_rNR^{11b}R^{12b}$, hydroxy-$C_{2-5}$alkylamino-$C_{2-5}$alkoxy, trifluoromethyl, trifluoromethoxy, difluoromethoxy, fluoromethoxy, methylenedioxy, ethylenedioxy and —N($R^{20}$)$R^{21}$:

$R^{11}$ and $R^{12}$ are the same or different, and independently are hydrogen, $C_{1-5}$alkyl, $C_{3-8}$cycloalkyl or $C_{3-8}$cycloalkyl-$C_{1-5}$alkyl;

$R^{11a}$ and $R^{12a}$ are the same or different, and independently are hydrogen, $C_{1-5}$alkyl, $C_{3-8}$cycloalkyl or $C_{3-8}$cycloalkyl-$C_{1-5}$alkyl;

$R^{11b}$ and $R^{12b}$ are the same or different, and independently are hydrogen, $C_{1-5}$alkyl, $C_{3-8}$cycloalkyl or $C_{3-8}$alkyl-$C_{1-5}$alkyl;

$R^{13}$ is hydrogen, $C_{1-5}$alkyl, $C_{3-8}$cycloalkyl, $C_{3-8}$cycloalkyl-$C_{1-5}$alkyl, $C_{1-5}$alkoxy-$C_{1-5}$alkyl, $C_{3-8}$-cycloalkyoxy-$C_{1-5}$alkyl or phenyl;

$R^{14}$ and $R^{15}$ are the same or different, and independently are hydrogen, $C_{1-5}$alkyl or aryl-$C_{1-5}$alkyl;

$R^{14a}$ and $R^{15a}$ are the same or different, and independently are hydrogen, $C_{1-5}$alkyl or aryl-$C_{1-5}$alkyl;

$R^{16}$ is hydrogen, $C_{1-5}$alkyl, aryl, heteroaryl, aryl-$C_{1-5}$alkyl, heteroaryl-$C_{1-5}$alkyl, hydroxy-$C_{1-5}$alkyl, hydroxycarbonyl-$C_{1-5}$alkyl, hydroxyphenyl-$C_{1-5}$alkyl, $C_{1-5}$alkoxy-$C_{1-5}$alkyl, amino-$C_{1-5}$alkyl, guanidine-$C_{1-5}$alkyl, mercapto-$C_{1-5}$alkyl, $C_{1-5}$alkylthio-$C_{1-5}$alkyl or aminocarbonyl, $C_{1-5}$alkyl;

$R^{17}$ and $R^{18}$ are the same or different, and independently are hydrogen, $C_{1-5}$alkyl, $C_{3-8}$cycloalkyl, $C_{3-8}$cycloalkyl-$C_{1-5}$alkyl, $C_{1-10}$acyl, $C_{1-10}$alkoxycarbonyl or aryl-$C_{1-3}$alkyloxycarbonyl;

or $R^{16}$ and $R^{17}$ are taken together to form —$CH_2$—, —$CH_2CH_2$—, —$CH_2CH_2CH_2$— or —$CH_2CH_2CH_2CH_2$—;

p is an integer selected from 0, 1, 2, 3, 4 and 5;

q is 0 or 1;

$R^{19}$ is hydrogen or $C_{1-5}$alkyl;

$R^{19a}$ is hydrogen or $C_{1-5}$alkyl;

r is 1 or 2;

$R^{20}$ and $R^{21}$ are the same or different, and independently are hydrogen or $C_{1-5}$alkyl), racemic or non-racemic mixtures of stereoisomers thereof or N-oxide thereof, or pharmaceutically acceptable salts thereof.

2. The pyrrolopyridine compound substituted with the cyclic amino group according to claim 1, which is a compound represented by the following formula [III]:

[III]

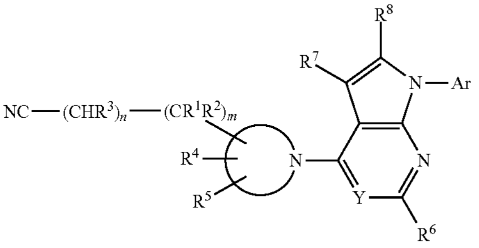

(wherein the cyclic amino group is represented by the following formula [IV]:

[IV]

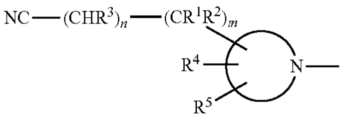

in which the cyclic amino group is a 3- to 8-membered saturated cyclic amine or a 3- to 8-membered saturated cyclic amine bridged with $C_{1-5}$alkylene or $C_{1-4}$alkylene-O—$C_{1-4}$-alkylene between any different two carbon atoms of the cyclic amine, which cyclic amine is substituted with a group represented by —$CR^1R^2)_m$—$(CHR^3)_n$—CN, $R^4$ and $R^5$ independently on the same or different carbon atoms of the cyclic amine;

Y is $CR^{10}$;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4 and 5;

n is 0 or 1;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy or —N($R^{11}$)$R^{12}$;

$R^7$ and $R^8$ are the same or different, and independently are hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —N($R^{11a}$)$R^{12a}$. —$CO_2R^{13}$, cyano, nitro, $C_{1-5}$alkylthio, trifluoromethyl or trifluoromethoxy;

$R^{10}$ is hydrogen, $C_{1-5}$alkyl, halogen, cyano or —$CO_2R^{19}$;

Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl $C_{1-5}$alkylsulfonyl, cyano, nitro, hydroxy, —$CO_2R^{19a}$, —C(═O)$R^{19a}$, —$CONR^{11b}R^{12b}$, —OC(═O)$R^{19a}$, —$NR^{11b}CO_2R^{19a}$, —$S(O)_rNR^{11b}R^{12b}$, hydroxy-$C_{2-5}$alkylamino-$C_{2-5}$alkoxy, trifluoromethyl, trifluoromethoxy, difluoromethoxy, fluoromethoxy, methylenedioxy, ethylenedioxy and —N($R^{20}$)$R^{21}$;

$R^{11}$ and $R^{12}$ are the same or different, and independently are hydrogen, $C_{1-5}$alkyl, $C_{3-8}$cycloalkyl or $C_{3-8}$cycloalkyl-$C_{1-5}$alkyl;

$R^{11a}$ and $R^{12a}$ are the same or different, and independently are hydrogen, $C_{1-5}$alkyl, $C_{3-8}$cycloalkyl or $C_{3-8}$cycloalkyl-$C_{1-5}$alkyl;

$R^{11b}$ and $R^{12b}$ are the same or different, and independently are hydrogen, $C_{1-5}$alkyl, $C_{3-8}$cycloalkyl or $C_{3-8}$cycloalkyl-$C_{1-5}$alkyl;

$R^{13}$ is hydrogen, $C_{1-5}$alkyl, $C_{3-8}$cycloalkyl, $C_{3-8}$cycloalkyl-$C_{1-5}$alkyl, $C_{1-5}$alkoxy-$C_{1-5}$alkyl, $C_{3-8}$cycloalkyloxy-$C_{1-5}$alkyl or phenyl;

$R^{19}$ is hydrogen or $C_{1-5}$alkyl;

$R^{19a}$ is hydrogen or $C_{1-5}$alkyl;

r is 1 or 2;

$R^{20}$ and $R^{21}$ are the same or different, and independently are hydrogen or $C_{1-5}$alkyl), racemic or non-racemic mixtures of stereoisomers thereof, or pharmaceutically acceptable salts thereof.

3. The pyrrolopyridine compound substituted with the cyclic amino group according to claim 2 represented by formula [III], wherein n is 0; $R^1$, $R^2$, $R^4$ and $R^5$ are hydrogen; $R^{10}$ is hydrogen or halogen; and the cyclic amino group, m, $R^6$, $R^7$, $R^8$ and Ar are as defined in claim 2; racemic or non-racemic mixtures of stereoisomers thereof, or pharmaceutically acceptable salts thereof.

4. The pyrrolopyridine compound substituted with the cyclic amino group according to claim 2 represented by formula [III], wherein the cyclic amino group is a 4- to 7-membered saturated cyclic amine; m is an integer selected from 0, 1, 2 and 3; n is 0; $R^1$, $R^2$, $R^4$ and $R^5$ are hydrogen; $R^6$ is methyl; $R^7$ and $R^8$ are the same or different, and independently are hydrogen or $C_{1-5}$alkyl; $R^{10}$ is hydrogen or halogen; and Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N($R^{20}$)$R^{21}$ (wherein $R^{20}$ and $R^{21}$ are the same or different, and independently are hydrogen or $C_{1-3}$alkyl); racemic or non-racemic mixtures of stereoisomers thereof, or pharmaceutically acceptable salts thereof.

5. The pyrrolopyridine compound substituted with the cyclic amino group according to claim 2 represented by formula [III], wherein the cyclic amino group is a 6-membered saturated cyclic amine; m is 0 or 1; n is 0; $R^1$, $R^2$, $R^4$ and $R^5$ are hydrogen; $R^6$ is methyl: $R^7$ and $R^8$ are the same or different, and independently are hydrogen or methyl; $R^{10}$ is hydrogen; and Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino; racemic or non-racemic mixtures of stereoisomers thereof, or pharmaceutically acceptable salts thereof.

6. The pyrrolopyridine compound substituted with the cyclic amino group according to claim 1, which is a compound represented by the following formula [V]:

[V]

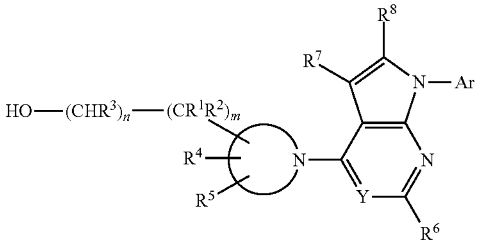

(wherein the cyclic amino group is represented by the following formula [VI]:

[VI]

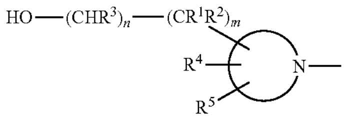

in which the cyclic amino group is a 3- to 8-membered saturated cyclic amine or a 3- to 8-membered saturated cyclic amine bridged with $C_{1-5}$alkylene or $C_{1-4}$alkylene-O—$C_{1-4}$alkylene between any different two carbon atoms of the cyclic amine, which cyclic amine is substituted with a group represented by —($CR^1R^2$)$_m$—($CHR^3$)$_n$—OH, $R^4$ and $R^5$ independently on the same or different carbon atoms of the cyclic amine;

Y is $CR^{10}$;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4 and 5;

n is 0 or 1;

with the proviso that when n is 0, m is an integer selected from 1, 2, 3, 4 and 5;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy or —N($R^{11}$)$R^{12}$;

$R^7$ and $R^8$ are the same or different, and independently are hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —N($R^{11a}$)$R^{12a}$, $CO_2R^{13}$,cyano, nitro, $C_{1-5}$alkylthio, trifluoromethyl or trifluoromethoxy;

$R^{10}$ is hydrogen, $C_{1-5}$alkyl, halogen, cyano or —$CO_2R^{19}$;

Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —CO—$R^{19a}$, —C(═O)$R^{19a}$, —CONR$^{11b}$R$^{12b}$, —OC(═O)$R^{19a}$, —NR$^{11b}$CO$_2$R$^{19a}$, —S(O)$_r$NR$^{11b}$R$^{12b}$, hydroxy-$C_{2-5}$alkylamino-$C_{2-5}$alkoxy, trifluoromethyl, trifluoromethoxy, difluoromethoxy, fluoromethoxy, methylenedioxy, ethylenedioxy and —N($R^{20}$)$R^{21}$;

$R^{11}$ and $R^{12}$ are the same or different, and independently are hydrogen, $C_{1-5}$alkyl, $C_{3-8}$cycloalkyl or $C_{3-8}$cycloalkyl-$C_{1-5}$alkyl;

$R^{11a}$ and $R^{12a}$ are the same or different, and independently are hydrogen, $C_{1-5}$alkyl, $C_{3-8}$cycloalkyl, or $C_{3-8}$cycloalkyl-$C_{1-5}$alkyl;

$R^{11b}$ and $R^{12b}$ are the same or different, and independently are hydrogen, $C_{1-5}$alkyl, $C_{3-8}$cycloalkyl or $C_{3-8}$cycloalkyl-$C_{1-5}$alkyl;

$R^{13}$ is hydrogen, $C_{1-5}$alkyl, $C_{3-8}$cycloalkyl, $C_{3-8}$cycloalkyl-$C_{1-5}$alkyl, $C_{1-5}$alkoxy-$C_{1-5}$alkyl, $C_{3-8}$cycloalkyloxy-$C_{1-5}$alkyl or phenyl;

$R^{19}$ is hydrogen or $C_{1-5}$alkyl;

$R^{19a}$ is hydrogen or $C_{1-5}$alkyl;

r 1 or 2;

$R^{20}$ and $R^{21}$ are the same or different, and independently are hydrogen or $C_{1-5}$alkyl), racemic or non-racemic mixtures of stereoisomers thereof, or pharmaceutically acceptable salts thereof.

7. The pyrrolopyridine compound substituted with the cyclic amino group according to claim 6 represented by formula [V], wherein m is an integer selected from 1, 2, 3, 4 and 5; n is 0; $R^1$, $R^2$, $R^4$ and $R^5$ are hydrogen; $R^{10}$ is hydrogen or halogen; and the cyclic amino group, $R^6$, $R^7$, $R^8$ and Ar are as defined in claim 6; racemic or non-racemic mixtures of stereoisomers thereof, or pharmaceutically acceptable salts thereof.

8. The pyrrolopyridine compound substituted with the cyclic amino group according to claim 6 represented by formula [V], wherein the cyclic amino group is a 4- to 7-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or $C_{1-5}$alkyl; $R^{10}$ is hydrogen or halogen; and Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N($R^{20}$)$R^{21}$ (wherein $R^{20}$ and $R^{21}$ are the same or different, and independently are hydrogen or $C_{1-3}$alkyl); racemic or non-racemic mixtures of stereoisomers thereof, or pharmaceutically acceptable salts thereof.

9. The pyrrolopyridine compound substituted with the cyclic amino group according to claim 6 represented by formula [V], wherein the cyclic amino group is a 6-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or methyl; $R^{10}$ is hydrogen; and Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluromethyl, trifluoromethoxy and dimethylamino; racemic or non-racemic mixtures of stereoisomers thereof, or pharmaceutically acceptable salts thereof.

10. The pyrrolopyridine compound substituted with the cyclic amino group according to claim 6 represented by formula [V], wherein m is 1; n is 0; $R^1$ is $C_{1-5}$alkyl or hydroxy-$C_{1-5}$alkyl; $R^2$, $R^4$ and $R^5$ are hydrogen; $R^{10}$ is hydrogen or halogen; and the cyclic amino group, $R^6$, $R^7$, $R^8$ and Ar are as defined in claim 6; racemic or non-racemic mixtures of stereoisomers thereof, or pharmaceutically acceptable salts thereof.

11. The pyrrolopyridine compound substituted with the cyclic amino group according to claim 6 represented by formula [V], wherein m is 1; n is 0; the cyclic amino group is a 4- to 7-membered saturated cyclic amine; $R^1$ is $C_{1-5}$alkyl or hydroxy-$C_{1-5}$alkyl; $R^2$, $R^4$ and $R^5$ are hydrogen; $R^6$ is methyl; $R^7$ and $R^8$ are the same or different, and independently are hydrogen or $C_{1-5}$alkyl; $R^{10}$ is hydrogen or halogen; and Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl); racemic or non-racemic mixtures of stereoisomers thereof, or pharmaceutically acceptable salts thereof.

12. The pyrrolopyridine compound substituted with the cyclic amino group according to claim 6 represented by formula [V], wherein m is 1; n is 0; the cyclic amino group is a 6-membered saturated cyclic amine; $R^1$ is $C_{1-5}$alkyl or hydroxy-$C_{1-5}$alkyl; $R^2$, $R^4$ and $R^5$ are hydrogen; $R^6$ is methyl; $R^7$ and $R^8$ are the same or different, and independently are hydrogen or methyl; $R^{10}$ is hydrogen; and Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino; racemic or non-racemic mixtures of stereoisomers thereof, or pharmaceutically acceptable salts thereof.

13. The pyrrolopyridine compound substituted with the cyclic amino group according to claim 6 represented by formula [V], wherein m is an integer selected from 1, 2, 3, 4 and 5; n is 0; $R^1$, $R^2$ and $R^5$ are hydrogen; $R^4$ is cyano; $R^{10}$ is hydrogen or halogen; and the cyclic amino group, $R^6$, $R^7$, $R^8$ and Ar are as defined in claim 6, wherein a group represented by —$(CR^1R^2)_m$—$(CHR^3)_n$—OH and $R^4$ are substituted on the same carbon atom of the cyclic amine; racemic or non-racemic mixtures of stereoisomers thereof, or pharmaceutically acceptable salts thereof.

14. The pyrrolopyridine compound substituted with the cyclic amino group according to claim 6 represented by formula [V], wherein the cyclic amino group is a 4- to 7-membered saturated cyclic amine; m is an integer selected from 1, 2 and 3; n is 0; $R^1$, $R^2$ and $R^5$ are hydrogen; $R^4$ is cyano; $R^6$ is methyl; $R^7$ and $R^3$ are the same or different, and independently are hydro en or $C_{1-5}$alkyl; $R^{10}$ is hydrogen or halogen; and Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{20})R^{21}$ (wherein $R^{20}$ and $R^{21}$ are the same or different, and independently are hydrogen or $C_{1-3}$alkyl), wherein a group represented by —$(CR^1R^2)_m$—$(CHR^3)_n$—OH and $R^4$ are substituted on the same carbon atom of the cyclic amine; racemic or non-racemic mixtures of stereoisomers thereof, or pharmaceutically acceptable salts thereof.

15. The pyrrolopyridine compound substituted with the cyclic amino group according to claim 6 represented by formula [V], wherein the cyclic amino group is a 6-membered saturated cyclic amine; m is an integer selected from 1, 2 and 3; n is 0; $R^1$, $R^2$ and $R^5$ are hydrogen; $R^4$ is cyano; $R^6$ is methyl; $R^7$ and $R^8$ are the same or different, and independently are hydrogen or methyl; $R^{10}$ is hydrogen; and Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino, wherein a group represented by —$(CR^1R^2)_m$—$(CHR^3)_n$—OH and $R^4$ are substituted on the same carbon atom of the cyclic amine; racemic or non-racemic mixtures of stereoisomers thereof, or pharmaceutically acceptable salts hereof.

16. The pyrrolopyridine compound substituted with the cyclic amino group according to claim 1, which is a compound represented by the following formula [VII]:

[VII]

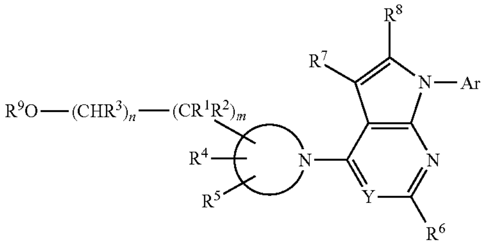

(wherein the cyclic amino group is represented by the following formula [VII]:

[VIII]

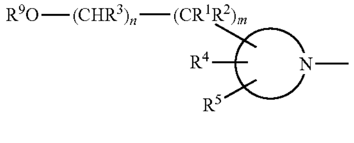

in which the cyclic amino group is a 3- to 8-membered saturated cyclic amine or a 3- to 8-membered saturated cyclic amine bridged with $C_{1-5}$alkylene or $C_{1-4}$alkylene-O—$C_{1-4}$alkylene between any different two carbon atoms of the cyclic amine, which cyclic amine is substituted with a group represented by —$(CR^1R^2)_m$—$(CHR^3)_n OR^9$, $R^4$ and $R^5$ independently on the same or different carbon atoms of the cyclic amine;

Y is $CR^{10}$;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{3-5}$alkoxy, $C_{1-5}$alkyl or hydroxy-$C_{1-5}$alkyl;

m an integer selected from 0, 1, 2, 3, 4 and 5;

n is 0 or 1;

with the proviso that when n is 0, m is an integer selected from 1, 2, 3, 4 and 5;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy or —N($R^{11}$)$R^{12}$;

$R^7$ and $R^8$ are the same or different, and independently are hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —N($R^{11a}$)$R^{12a}$, —$CO_2R^{13}$, cyano, nitro, $C_{1-5}$alkylthio, trifluoromethyl or trifluoromethoxy;

$R^9$ is $C_{1-24}$acyl, $C_{1-10}$alkoxycarbonyl, aryl-$C_{1-5}$alkyloxycarbonyl, —CO—O—$CHR^{14}$—O—CO—$R^{15}$, —P(═O)($OR^{14a}$)$OR^{15a}$, —CO—$(CH_2)_p$—$(CHR^{16})_q$—$NR^{17}R^{18}$, arylcarbonyl or heteroarylcarbonyl, wherein each said acyl, aryl and heteroaryl is unsubstituted or substituted with $C_{1-5}$alkoxy, and $C_{1-24}$acyl optionally includes one to six double bonds;

$R^{10}$ is hydrogen, $C_{1-5}$alkyl, halogen, cyano or —$CO_2R^{19}$;

Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —$CO_2R^{19a}$, —C(═O)$R^{19a}$, —$CONR^{11b}R^{12b}$, —OC(═O)$R^{19a}$, —$NR^{11b}CO_2R^{19a}$, —$S(O)_rNR^{11b}R^{12b}$, hydroxy-$C_{2-5}$alkylamino-$C_{2-5}$alkoxy, trifluoromethyl, trifluoromethoxy, difluoromethoxy, fluoromethoxy, methylenedioxy, ethylenedioxy and —N($R^{20}$)$R^{21}$;

$R^{11}$ and $R^{12}$ are the same or different, and independently are hydrogen, $C_{1-5}$alkyl, $C_{3-8}$cycloalkyl or $C_{3-8}$cycloalkyl-$C_{1-5}$alkyl;

$R^{11a}$ and $R^{12a}$ are the same or different, and independently are hydrogen, $C_{1-5}$alkyl, $C_{3-8}$cycloalkyl or $C_{3-8}$cycloalkyl-$C_{1-5}$alkyl;

$R^{11b}$ and $R^{12b}$ are the same or different, and independently are hydrogen, $C_{1-5}$alkyl, $C_{3-8}$cycloalkyl or $C_{3-8}$cycloalkyl-$C_{1-5}$alkyl;

$R^{13}$ is hydrogen, $C_{1-5}$alkyl, $C_{3-8}$cycloalkyl, $C_{3-8}$cycloalkyl-$C_{1-5}$alkyl, $C_{1-5}$alkoxy-$C_{1-5}$alkyl, $C_{3-8}$cycloalkyloxy-$C_{1-5}$alkyl or phenyl;

$R^{14}$ and $R^{15}$ are the same or different, and independently are hydrogen, $C_{1-5}$alkyl or aryl-$C_{1-5}$alkyl;

$R^{14a}$ and $R^{15a}$ are the same or different, and independently are hydrogen, $C_{1-5}$alkyl or aryl-$C_{1-5}$alkyl;

$R^{16}$ is hydrogen, $C_{1-5}$alkyl, aryl, heteroaryl, aryl-$C_{1-5}$alkyl, heteroaryl-$C_{1-5}$alkyl, hydroxy-$C_{1-5}$alkyl, hydroxycarbonyl-$C_{1-5}$alkyl, hydroxyphenyl-$C_{1-5}$alkyl, $C_{1-5}$alkoxy-$C_{1-5}$alkyl, amino-$C_{1-5}$alkyl, guanidino-$C_{1-3}$alkyl, mercapto-$C_{1-5}$alkyl, $C_{1-5}$alkylthio-$C_{1-5}$alkyl or aminocarbonyl-$C_{1-5}$alkyl;

$R^{17}$ and $R^{18}$ are the same or different, and independently are hydrogen, $C_{1-5}$alkyl, $C_{3-8}$cycloalkyl, $C_{3-8}$cycloalkyl-$C_{1-5}$alkyl, $C_{1-10}$acyl, $C_{1-10}$alkoxycarbonyl and aryl-$C_{1-5}$alkyloxycarbonyl, or $R^{16}$ and $R^{17}$ are taken together to form —$CH_2$—, —$CH_2CH_2$—, —$CH_2CH_2CH_2$— or —$CH_2CH_2CH_2CH_2$—;

p is an integer selected from 0, 1, 2, 3, 4 and 5;

q is 0 or 1;

$R^{19}$ is hydrogen or $C_{1-5}$alkyl;

$R^{19a}$ is hydrogen or $C_{1-5}$alkyl;

r is 1 or 2;

$R^{20}$ and $R^{21}$ are the same or different, and independently are hydrogen or $C_{1-5}$alkyl), racemic or non-racemic mixtures of stereoisomers thereof, or pharmaceutically acceptable salts thereof.

17. The pyrrolopyridine compound substituted with the cyclic amino group according to claim 16 represented by formula [VII], wherein m is an integer selected from 1, 2, 3, 4 and 5; n is 0; $R^1$, $R^2$, $R^4$ and $R^5$ are hydrogen; and the cyclic amino group, $R^6$, $R^7$, $R^8$, $R^9$, $R^{10}$ and Ar are as defined in claim 16; racemic or non-racemic mixtures of stereoisomers thereof, or pharmaceutically acceptable salts thereof.

18. The pyrrolopyridine compound substituted with the cyclic amino group according to claim 16 represented by formula [VII], wherein the cyclic amino group is a 4- to 7-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or $C_{1-5}$alkyl; $R^{10}$ is hydrogen or halogen, and Ar is phenyl or pyridyl which phenyl or pyridyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N($R^{20}$)$R^{21}$ (wherein $R^{20}$ and $R^{21}$ are the same or different, and independently are hydrogen or $C_{1-5}$alkyl); $R^9$ is as defined in claim 16; racemic or non-racemic mixtures of stereoisomers thereof, or pharmaceutically acceptable salts thereof.

19. The pyrrolopyridine compound substituted with the cyclic amino group according to claim 16 represented by formula [VII], wherein the cyclic amino group is it 6-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or methyl; $R^{10}$ is hydrogen; and Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino; $R^9$ is as defined in claim 16; racemic or non-racemic mixtures of stereoisomers thereof, or pharmaceutically acceptable salts thereof.

20. The pyrrolopyridine compound represented by formula [I] according to claim 1, which compound is selected from the group consisting of 2-{1-[1-(2,4-dichloro-phenyl-2,3,6-trimethyl-1H-pyrrolo[2,3-b]pyridin-4-yl]piperidin-3-yl}-ethanol, 2-{1-[1-(4-bromo-2,6-dimethyl-phenyl)-3,6-dimethyl-1H-pyrrolo[2,3-b]pyridin-4-yl]-piperidin-3-yl}-ethanol, {1-[1-(2,4-dichloro-phenyl)-2,3,6-trimethyl-1H-pyrrolo[2,3-b]pyridin-4-yl]piperidin-4-yl}-methanol, {1-[1-(4-bromo-2,6-dimethyl-phenyl)-3,6-dimethyl-1H-pyrrolo[2,3-b]pyridin-4-yl]-piperidin-4-yl}-methanol, 2-{1-[1-(2,4-dichloro-phenyl)-2,3,6-trimethyl-1H-pyrrolo[2,3-b]pyridin-4-yl]-piperidin-4-yl}ethanol, 2-{1-[1-(4-bromo-2,6-dimethyl-phenyl)-3,6-dimethyl-1H-pyrrolo[2,3-b]pyridin-4-yl]-piperidin-4-yl}-ethanol, 3-{1-[1-(2,4-dichloro-phenyl)-2,3,6-trimethyl-1H-pyrrolo[2,3-b]pyridin-4-yl]-piperidin-4-yl}-propan-1-ol, 3-{1-[1-(4-bromo-2,6-dimethyl-phenyl-3,6-dimethyl-1H-pyrrolo[2,3-b]pyridin-4-yl]-piperidin-4-yl}-propan-1-ol, 1-[1-(2,4-dichloro-phenyl)-2,3,6-trimethyl-1H-pyrrolo[2,3-b]pyridin-4-yl]-piperidine-3-carbonitrile, 1-[1-(4-bromo-2,6-dimethyl-phenyl-3,6-dimethyl-1H-pyrrolo[2,3-b]pyridin-4-yl]-piperidine-3-carbonitrile, {1-[1-(2,4-dichloro-phenyl)-2,3,6-trimethyl-1H-pyrrolo[2,3-b]pyridin-4-yl]-piperidin-3-yl}-acetonitrile, 1-[1-(2,4-dichloro-phenyl)-2,3,6-trimethyl-1H-pyrrolo[2,3-b]pyridin-4-yl]-piperidine-4-carbonitrile, 1-[1-(4-bromo-2,6-dimethyl-phenyl)-3,6-dimethyl-1H-pyrrolo[2,3-b]pyridin-4-yl]-piperidine-4-carbonitrile,

[1-[1-(2,4-dichloro-phenyl)-2,3,6-trimethyl-1H-pyrrolo[2,3-b]pyridin-4-yl]-piperidin-4-yl]-acetonitrile, 2-{1-[1-(4-bromo-2,6-dimethyl-phenyl)-2,3,6-trimethyl-1H-pyrrolo[2,3-b]pyridin-4-yl]-piperidin-3-yl}-ethanol, {1-[1-(4-bromo-2,6-dimethyl-phenyl)-2,3,6-trimethyl-1H-pyrrolo[2,3-b]pyridin-4-yl]-piperidin-4-yl}-methanol, {1-[1-(4-chloro-2,6-dimethyl-phenyl)-2,3,6-trimethyl-1H-pyrrolo[2,3-b]pyridin-4-yl]-piperidin-4-yl}methanol, {1-[1-(4-chloro-2,6-dimethyl-phenyl)-3,6-dimethyl-1H-pyrrolo[2,3-b]pyridin-4-yl]-piperidin-4-yl}-methanol, 2-{1-[1-(4 bromo-2,6 dimethyl-phenyl)-2,3,6-trimethyl-1H-pyrrolo[2,3-b]pyridin-4-yl]-piperidin-4-yl}-ethanol, 2-{1-[1-(4-chloro-2,6-dimethyl-phenyl)-2,3,6-trimethyl-1H-pyrrolo[2,3-b]pyridin-4-yl]-piperidin-4-yl}-ethanol, 2-{1-[1-(4-chloro-2,6-dimethyl-phenyl)-3,6-dimethyl-1H-pyrrolo[2,3-b]pyridin-4-yl]-piperidin-4-yl}-ethanol, 3-{1-[1-(4-bromo-2,6-dimethyl-phenyl)-2,3,6-trimethyl-1H-pyrrolo[2,3-b]pyridin-4-yl]-piperidin-4-yl}-propan-1-ol, 3-{1-[1-(4-chloro-2,6-dimethyl-phenyl)-2,3,6-trimethyl-1H-pyrrolo[2,3-b]pyridin-4-yl]-piperidin-4-yl}-propan-1-ol, 3-{1-[1-(4-chloro-2,6-dimethyl-phenyl)-3,6-dimethyl-1H-pyrrolo[2,3-b]pyridin-4-yl]-piperidin-4-yl}-propan-1-ol, 1-[1-(4-bromo-2,6-dimethyl-phenyl)-2,3,6-trimethyl-1H-pyrrolo[2,3-b]pyridin-4-yl]-piperidine-3-carbonitrile, 1-[1-(4-bromo-2,6-dimethyl-phenyl)-2,3,6-trimethyl-1H-pyrrolo[2,3-b]pyridin-4-yl]-piperidine-4-carbonitrile, 1-[1-(4-chloro-2,6-dimethyl-phenyl)-2,3,6-trimethyl-1H-pyrrolo[2,3-b]pyridin-4-yl]-piperidine-4-carbonitrile, 1-[1-(4-chloro-2,6-dimethyl-phenyl)-3,6-dimethyl-1H-pyrrolo[2,3-b]pyridin-4-yl]-piperidine-4-carbonitrile, {1-[1-(4-bromo-2,6-dimethyl-phenyl)-2,3,6-trimethyl-1H-pyrrolo[2,3-b]pyridin-4-yl]-piperidin-4-yl}-acetonitrile, {1-[1-(4-bromo-2,6-dimethyl-phenyl)-3,6-dimethyl-1H-pyrrolo[2,3-b]pyridin-4-yl]-piperidin-4-yl}-acetonitrile, {1-[1-(4-chloro-2,6-dimethyl-phenyl-3,6-dimethyl-1H-pyrrolo[2,3-b]pyridin-4-yl]-piperidin-4-yl}-acetonitrile, {1-[1-(2,6-dibromo-4-isopropyl-phenyl)-2,3,6-trimethyl-1H-pyrrolo[2,3-b]pyridin-4-yl]-piperidin-4-yl}-methanol, {1-[1-(2,6-dibromo-4-isopropyl-phenyl-3,6-dimethyl-1H-pyrrolo[2,3-b]pyridin-4-yl]-piperidin-4-yl}-methanol, {1-[2,3,6-trimethyl-1-(2,4,6-tribromo-phenyl)-1H-pyrrolo[2,3-b]pyridin-4-yl]-piperidin-4-yl}-methanol, {1-[3,6-dimethyl-1-(2,4,6-tribromo-phenyl)-1H-pyrrolo[2,3-b]pyridin-4-yl]-piperidin-4-yl}-methanol, {1-[1-(4-bromo-2,6-dichloro-phenyl)-2,3,6-trimethyl-1H-pyrrolo[2,3-b]pyridin-4-yl]-piperidin-4-yl}-methanol, {1-[1-(4-bromo-2,6-dichloro-phenyl)-3,6-dimethyl-1H-pyrrolo[2,3-b]pyridin-4-yl]-piperidin-4-yl}-methanol, {1-[2,3,6-trimethyl-1-(2,4,6-trichloro-phenyl)-1H-pyrrolo[2,3-b]pyridin-4-yl]-piperidin-4-yl}-methanol, {1-[3,6-dimethyl-1-(2,4,6-trichloro-phenyl)-1H-pyrrolo[2,3-b]pyridin-4-yl]-piperidin-4-yl}-methanol, {1-[1-(2,6-dibromo-4-chloro-phenyl)-2,3,6-trimethyl-1H-pyrrolo[2,3-b]pyridin-4-yl]-piperidin-4-yl}-methanol, {1-[1-(2,6-dibromo-4-chloro-phenyl)-3,6-dimethyl-1H-pyrrolo[2,3-b]pyridin-4-yl]-piperidin-4-yl}-methanol, {1-[1-(4-methoxy-2,6-dimethyl-phenyl)-2,3,6-trimethyl-1H-pyrrolo[2,3-b]pyridin-4-yl]-piperidin-4-yl}-methanol, {1-[1-(4-methoxy-2,6-dimethyl-phenyl)-3,6-dimethyl-1H-pyrrolo[2,3-b]pyridin-4-yl]-piperidin-4-yl}-methanol, {1-[1-(2-bromo-4-isopropyl-phenyl)-3,6-dimethyl-1H-pyrrolo[2,3-b]pyridin-4-yl]-piperidin-4-yl}-methanol, {1-[1-(4-isopropyl-2-methylsulfanyl-phenyl)-3,6-dimethyl-1H-pyrrolo[2,3-b]pyridin-4-yl]-piperidin-4-yl}-methanol, {1-[1-(2,4-dibromo-phenyl)-3,6-dimethyl-1H-pyrrolo[2,3-b]pyridin-4-yl]-piperidin-4-yl}-methanol, {1-[1-(2-bromo-4-trifluoromethyl-phenyl)-3,6-dimethyl-1H-pyrrolo[2,3-b]pyridin-4-yl]-piperidin-4-yl}-methanol, {1-[2,3,6-trimethyl-1-(2,4,5-tribromo-phenyl)-1H-pyrrolo[2,3-b]pyridin-4-yl]-piperidin-4-yl}-methanol, {1-[3,6-dimethyl-1-(2,4,5-tribromo-phenyl)-1H-pyrrolo[2,3-b]pyridin-4-yl]-piperidin-4-yl}-methanol, 2-{1-[1-(2,6-dibromo-4-isopropyl-phenyl)-2,3,6-trimethyl-1H-pyrrolo[2,3-b]pyridin-4-yl]-piperidin-4-yl}-ethanol, 2-{1-[1-(2,6-dibromo-4-isopropyl-phenyl)-3,6-trimethyl-1H-pyrrolo[2,3-b]pyridin-4-yl]-piperidin-4-yl}-ethanol, 2-{1-[2,3,6-trimethyl-1-(2,4,6-tribromo-phenyl)-1H-pyrrolo[2,3-b]pyridin-4-yl]-piperidin-4-yl}-ethanol, 2-{1-[3,6-dimethyl-1-(2,4,6-tribromo-phenyl)-1H-pyrrolo[2,3-b]pyridin-4-yl]-piperidin-4-yl}-ethanol, 2-{1-[1-(4-bromo-2,6-dichloro-phenyl)-2,3,6-trimethyl-1H-pyrrolo[2,3-b]pyridin-4-yl]-piperidin-4-yl}-ethanol, 2-{1-[1-(4-bromo-2,6-dichloro-phenyl)-3,6-dimethyl-1H-pyrrolo[2,3-b]pyridin-4-yl]-piperidin-4-yl}-ethanol, 2-{1-[2,3,6-trimethyl-1-(2,4,6-trichloro-phenyl)-1H-pyrrolo[2,3-b]pyridin-4-yl]-piperidin-4-yl}-ethanol, 2-{1-[3,6-dimethyl-1-(2,4,6-trichloro-phenyl)-1H-pyrrolo[2,3-b]pyridin-4-yl]-piperidin-4-yl}-ethanol, 2-{1-[1-(2,6-dibromo-4-chloro-phenyl)-2,3,6-trimethyl-1H-pyrrolo[2,3-b]pyridin-4-yl]-piperidin-4-yl}-ethanol, 2-{1-[1-(2,6-dibromo-4-chloro-phenyl-3,6-dimethyl-1H-pyrrolo[2,3-b]pyridin-4-yl]-piperidin-4-yl}-ethanol, 2-{1-[1-(4-methoxy-2,6-dimethyl-phenyl)-2,3,6-trimethyl-1H-pyrrolo[2,3-b]pyridin-4-yl]-piperidin-4-yl}-ethanol, 2-{1-[1-(4-methoxy-2,6-dimethyl-phenyl)-3,6-dimethyl-1H-pyrrolo[2,3-b]pyridin-4-yl]-piperidin-4-yl}-ethanol, 2-{1-[1-(2-bromo-4-isopropyl-phenyl)-3,6-dimethyl-1H-pyrrolo[2,3-b]pyridin-4-yl]-piperidin-4-yl}-ethanol, 2-{1-[1-(4-isopropyl-2-methylsulfanyl-phenyl)-3,6-dimethyl-1H-pyrrolo[2,3-b]pyridin-4-yl]-piperidin-4-yl}-ethanol,
2-{1-[1-(2,4-dibromo-phenyl)-3,6-dimethyl-1H-pyrrolo[2,3-b]pyridin-4-yl]-piperidin-4-yl}-ethanol,
2-{1-[2,3,6-trimethyl-1-(2,4,5-tribromo-phenyl)-1H-pyrrolo[2,3-b]pyridin-4-yl]-piperidin-4-yl}-ethanol,
2-{1-[3,6-dimethyl-1-(2,4,5-tribromo-phenyl)-1H-pyrrolo[2,3-b]pyridin-4-yl]-piperidin-4-yl}-ethanol,
2-{1-[5-bromo-1-(4-chloro-2,6-dimethyl-phenyl)-3,6-dimethyl-1H-pyrrolo[2,3-b]pyridin-4-yl]-piperidin-4-yl}-ethanol,
3-{1-[1-(2,6-dibromo-4-isopropyl-phenyl)-2,3,6-trimethyl-1H-pyrrolo[2,3-b]pyridin-4-yl]-piperidin-4-yl}-propan-1-ol,
3-{1-[1-(2,6-dibromo-4-isopropyl-phenyl)-3,6-dimethyl-1H-pyrrolo[2,3-b]pyridin-4-yl]-piperidin-4-yl}-propan-1-ol,
3-{1-[2,3,6-trimethyl-1-(2,4,6-tribromo-phenyl)-1H-pyrrolo[2,3-b]pyridin-4-yl]-piperidin-4-yl}-propan-1-ol,
3-{1-[3,6-dimethyl-1-(2,4,6-tribromo-phenyl)-1H-pyrrolo[2,3-b]pyridin-4-yl]-piperidin-4-yl}-propan-1-ol,
3-{1-[1-(4-bromo-2,6-dichloro-phenyl)-2,3,6-trimethyl-1H-pyrrolo[2,3-b]pyridin-4-yl]-piperidin-4-yl}-propan-1-ol,
3-{1-[1-(4-bromo-2,6-dichloro-phenyl)-3,6-dimethyl-1H-pyrrolo[2,3-b]pyridin-4-yl]-piperidin-4-yl}-propan-1-ol,
3-{1-[2,3,6-trimethyl-1-(2,4,6-trichloro-phenyl)-1H-pyrrolo[2,3-b]pyridin-4-yl]-piperidin-4-yl}-propan-1-ol,
3-{1-[3,6-dimethyl-1-(2,4,6-trichloro-phenyl)-1H-pyrrolo[2,3-b]pyridin-4-yl]-piperidin-4-yl}-propan-1-ol.
3-{1-[1-(2,6-dibromo-4-chloro)-phenyl)-2,3,6-trimethyl-1H-pyrrolo[2,3-b]pyridin-4-yl]-piperidin-4-yl}-propan-1-ol,
3-{1-[1-(2,6-dibromo-4-chloro-phenyl)-3,6-dimethyl-1H-pyrrolo[2,3-b]pyridin-4-yl]-piperidin-4-yl}-propan-1-ol,
3-{1-[1-(4-methoxy-2,6-dimethyl-phenyl)-2,3,6-trimethyl-1H-pyrrolo[2,3-b]pyridin-4-yl]-piperidin-4-yl}-propan-1-ol,
3-{1-[1-(4-methoxy-2,6-dimethyl-phenyl)-3,6-dimethyl-1H-pyrrolo[2,3-b]pyridin-4-yl]-piperidin-4-yl}-propan-1-ol,
3-{1-[1-(4-isopropyl-2-methylsulfanyl-phenyl)-3,6-dimethyl-1H-pyrrolo[2,3-b]pyridin-4-yl]-piperidin-4-yl}-propan-1-ol,
3-{1-[2,3,6-trimethyl-1-(2,4,5-tribromo-phenyl)-1H-pyrrolo[2,3-b]pyridin-4-yl]-piperidin-4-yl}-propan-1-ol,
3-{1-[3,6-dimethyl-1-(2,4,5-tribromo-phenyl)-1H-pyrrolo[2,3-b]pyridin-4-yl]-piperidin-4-yl}-propan-1-ol,
1-{1-[1-(4-bromo-2,6-dimethyl-phenyl)-2,3,6-trimethyl-1H-pyrrolo[2,3-b]pyridin-4-yl]-piperidin-4-yl}-ethane-1,2-diol,
1-{1-[1-(4-bromo-2,6-dimethyl-phenyl)-3,6-dimethyl-1H-pyrrolo[2,3-b]pyridin-4-yl]-piperidin-4-yl}-ethane-1,2-diol,
1-{1-[1-(4-bromo-2,6-dimethyl-phenyl)-2,3,6-trimethyl-1H-pyrrolo[2,3-b]pyridin-4-yl]-piperidin-4-yl}-propane-1,3-diol,
1-{1-[1-(4-bromo-2,6-dimethyl-phenyl)-3,6-dimethyl-1H-pyrrolo[2,3-b]pyridin-4-yl]-piperidin-4-yl}-propane-1,3-diol,
1-[1-(2,6-dibromo-4-isopropyl-phenyl)-2,3,6-trimethyl-1H-pyrrolo[2,3-b]pyridin-4-yl]-piperidine-4-carbonitrile,
1-[1-(2,6-dibromo-4-isopropyl-phenyl)-3,6-dimethyl-1H-pyrrolo[2,3-b]pyridin-4-yl]-piperidine-4-carbonitrile,
1-[2,3,6-trimethyl-1-(2,4,6-tribromo-phenyl)-1H-pyrrolo[2,3-b]pyridin-4-yl]-piperidine-4-carbonitrile,
1-[3,6-dimethyl-1-(2,4,6-tribromo-phenyl)-1H-pyrrolo[2,3-b]pyridin-4-yl]-piperidine-4-carbonitrile,
1-[1-(4-bromo-2,6-dichloro-phenyl)-2,3,6-trimethyl-1H-pyrrolo[2,3-b]pyridin-4-yl]-piperidine-4-carbonitrile,
1-[1-(4-bromo-2,6-dichloro-phenyl)-3,6-dimethyl-1H-pyrrolo[2,3-b]pyridin-4-yl]-piperidine-4-carbonitrile,
1-[2,3,6-trimethyl-1-(2,4,6-trichloro-phenyl)-1H-pyrrolo[2,3-b]pyridin-4-yl]-piperidine-4-carbonitrile,
1-[3,6-dimethyl-1-(2,4,6-trichloro-phenyl)-1H-pyrrolo[2,3-b]pyridin-4-yl]-piperidine-4-carbonitrile,
1-[1-(2,6-dibromo-4-chloro-phenyl)-2,3,6-trimethyl-1H-pyrrolo[2,3-b]pyridin-4-yl]-piperidine-4-carbonitrile,
1-[1-(2,6-dibromo-4-chloro-phenyl)-3,6-dimethyl-1H-pyrrolo[2,3-b]pyridin-4-yl]-piperidine-4-carbonitrile,
1-[1-(4-methoxy-2,6-dimethyl-phenyl)-2,3,6-trimethyl-1H-pyrrolo[2,3-b]pyridin-4-yl]-piperidine-4-carbonitrile,
1-[1-(4-methoxy-2,6-dimethyl-phenyl)-3,6-dimethyl-1H-pyrrolo[2,3-b]pyridin-4-yl]-piperidine-4-carbonitrile,
1-[1-(2-bromo-4-isopropyl-phenyl)-3,6-dimethyl-1H-pyrrolo[2,3-b]pyridin-4-yl]-piperidine-4-carbonitrile,
1-[1-(4-isopropyl-2-methylsulfanyl-phenyl)-3,6-dimethyl-1H-pyrrolo[2,3-b]pyridin-4-yl]-piperidine-4-carbonitrile,
1-[1-(2,4-dibromo-phenyl)-3,6-dimethyl-1H-pyrrolo[2,3-b]pyridin-4-yl]-piperidine-4-carbonitrile,
1-[1-(2-bromo-4-trifluoromethyl-phenyl)-3,6-dimethyl-1H-pyrrolo[2,3-b]pyridin-4-yl]-piperidine-4-carbonitrile,
1-[2,3,6-trimethyl-(2,4,5-tribromo-phenyl)-1H-pyrrolo[2,3-b]pyridin-4-yl]-piperidine-4-carbonitrile,
1-[3,6-dimethyl-1-(2,4,5-tribromo-phenyl)-1H-pyrrolo[2,3-b]pyridin-4-yl]-piperidine-4-carbonitrile,
{1-[1-(4-chloro-2,6-dimethyl-phenyl)-2,3,6-trimethyl-1H-pyrrolo[2,3-b]pyridin-4-yl]-piperidin-4-yl}-acetonitrile,
{1-[1-(2,6-dibromo-4-isopropyl-phenyl)-2,3,6-trimethyl-1H-pyrrolo[2,3-b]pyridin-4-yl]-piperidin-4-yl}-acetonitrile,
{1-[1-(2,6-dibromo-4-isopropyl-phenyl)-3,6-dimethyl-1H-pyrrolo[2,3-b]pyridin-4-yl]-piperidin-4-yl}-acetonitrile,
{1-[2,3,6-trimethyl-1-(2,4,6-tribromo-phenyl)-1H-pyrrolo[2,3-b]pyridin-4-yl]-piperidin-4-yl}-acetonitrile,
{1-[3,6-dimethyl-1-(2,4,6-tribromo-phenyl)-1H-pyrrolo[2,3-b]pyridin-4-yl]-piperidin-4-yl}-acetonitrile,
{1-[1-(4-bromo-2,6-dichloro-phenyl)-2,3,6-trimethyl-1H-pyrrolo[2,3-b]pyridin-4-yl]-piperidin-4-yl}-acetonitrile,
{1-[1-(4-bromo-2,6-dichloro-phenyl)-3,6-dimethyl-1H-pyrrolo[2,3-b]pyridin-4-yl]-piperidin-4-yl}-acetonitrile,
{1-[2,3,6-trimethyl-1-(2,4,6-trichloro-phenyl)-1H-pyrrolo[2,3-b]pyridin-4-yl]-piperidin-4-yl}-acetonitrile,
{1-[3,6-dimethyl-1-(2,4,6-trichloro-phenyl)-1H-pyrrolo[2,3-b]pyridin-4-yl]-piperidin-4-yl}-acetonitrile,
{1-[1-(2,6-dibromo-4-chloro-phenyl)-2,3,6-trimethyl-1H-pyrrolo[2,3-b]pyridin-4-yl]-piperidin-4-yl}-acetonitrile,
{1-[1-(2,6-dibromo-4-chloro-phenyl)-3,6-dimethyl-1H-pyrrolo[2,3-b]pyridin-4-yl]-piperidin-4-yl}-acetonitrile, {1-[1-(4-methoxy-2,6-dimethyl-phenyl-2,3,6-trimethyl-1H-pyrrolo[2,3-b]pyridine-4-yl]-piperidin-4-yl}-acetonitrile, {1-[1-(4-methoxy-2,6-dimethyl-phenyl)-3,6-dimethyl-1H-pyrrolo[2,3-b]pyridin-4-yl]-piperidin-4-yl}-acetonitrile, {1-[1-(2-bromo-4-isopropyl-phenyl)-3,6-dimethyl-1H-pyrrolo[2,3-b]pyridin-4-yl]-piperidin-4-yl}-acetonitrile, {1-[1-(4-isopropyl-2-methylsulfanyl-phenyl)-3,6-dimethyl-1H-pyrrolo[2,3-b]pyridin-4-yl]-piperidin-4-yl}-acetonitrile, {1-[1-(2,4-dibromo-phenyl)-3,6-dimethyl-1H-pyrrolo[2,3-b]pyridin-4-yl]-piperidin-4-yl}-acetonitrile, {1-[1-(2-bromo)-4-trifluoromethyl-phenyl-3,6-dimethyl-1H-pyrrolo[2,3-b]pyridin-4-yl]-piperidin-4-yl}-acetonitrile, {1-[3,6-dimethyl-1-(2,4,5-tribromo-phenyl)-1H-pyrrolo[2,3-b]pyridin-4-yl]-piperidin-4-yl}-acetonitrile, and methoxy-acetic acid 1-[1-(4-bromo-2,6-dimethyl-phenyl)-3,6-dimethyl-1H-pyrrolo[2,3-b]pyridin-4-yl]-piperidin-4-ylmethyl ester, racemic or non-racemic mixtures of stereoisomers thereof, or pharmaceutically acceptable salts thereof.

21. A pharmaceutical composition comprising the pyrrolopyridine compound substituted with a cyclic amino group, or a pharmaceutically acceptable salt thereof according to claim 1, an active ingredient, and a pharmaceutically acceptable carrier.

* * * * *